US009644240B2

(12) United States Patent
de Rijk et al.

(10) Patent No.: US 9,644,240 B2
(45) Date of Patent: May 9, 2017

(54) DISEASE SUSCEPTIBILITY

(75) Inventors: Rolandus Hendrikus de Rijk, Leidschendam (NL); Melanie Diane Klok, Amsterdam (NL); Edo Ronald de Kloet, te Tienhoven (NL)

(73) Assignee: Leiden University, Leiden (NL)

( * ) Notice: Subject to any disclaimer, the term of this patent is extended or adjusted under 35 U.S.C. 154(b) by 467 days.

(21) Appl. No.: 13/503,424

(22) PCT Filed: Oct. 21, 2010

(86) PCT No.: PCT/EP2010/006430
§ 371 (c)(1),
(2), (4) Date: Apr. 23, 2012

(87) PCT Pub. No.: WO2011/047856
PCT Pub. Date: Apr. 28, 2011

(65) Prior Publication Data
US 2012/0208195 A1    Aug. 16, 2012

(30) Foreign Application Priority Data

Oct. 22, 2009 (EP) .................................... 09252465
Sep. 10, 2010 (GB) .................................... 1015071.2

(51) Int. Cl.
*C12Q 1/68* (2006.01)
(52) U.S. Cl.
CPC ..... *C12Q 1/6883* (2013.01); *C12Q 2600/136* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 5,445,934 A     8/1995  Fodor

FOREIGN PATENT DOCUMENTS

JP      2005110606 A    4/2005
WO      WO95/22058      8/1995

OTHER PUBLICATIONS

Kuningas et al. Neuropsychopharmacology (2007) 32, 1295-1301.*
Kunigas et al. Neuropsychopharmacology (2007) 32, 1295-1301.*
Lambert et al. Posted on Aug. 26, 2010 by Christophe Lambert on http://blog.goldenhelix.com, two pages.*
Langford et al The American Statistician, Nov. 2001, vol. 55,No. 4, pp. 322-325.*
Sotos et al. 2009 Statistics Education Research Journal 8(2)33-55.*
Zill Molecular Psychiatry (2004) 9, 1030-1036.*
Pal et al TheProstate 69:1548^ 1556 (2009).*
Wall. Nature Reviews, vol. 4, Aug. 2003, pp. 587-597.*
Van Rossum (Biol Psychiatry 2006;59:681-688).*
DeRijk et al. (European Journal of Pharmacoloty 585 (2008) 492-501.*
Sullivan et al. (Molecular Psychiatry (2009) 14, 359-375; doi:10.1038/mp.2008.125; published online Dec. 9, 2008).*
Ambroggi Fre'de'ric et al. (2009) "Stress and addiction: glucocorticoid receptor in dopaminoceptive neurons facilitates cocaine seeking," Nataure Neuroscience, 12(3):247-249.
Arnold, Leslie (2009) "Strategies for Managing Fibromyalgia," The American Journal of Medicine, 122:S31-S43.
Arriza, Jeffrey et al, (1987) "Cloning of Human Mineralocorticoid Receptor Complementary DNA: Structural and Functional Kinship with the Glucocorticoid Receptor" Science, 237:268-275.
Avat, Emanuela et al. (2001) "Mineralocorticoid Receptor Blockade by Canrenoate increases Both Spontaneous and Stimulated Adrenal Function in Humans" The Journal of Clinical Endocrinology & Metabolism, 86(7):3176-3181.
Barrett, J.C. et al. (2005) "Haploview: analysis and visualization of LD and haplotype maps" Bioinformatics, 21(2):263-265.
Berger, Stefan et al. (2006) "Loss of the limbic mineralocorticoid receptor impairs behavioral plasticity" Proceedings of the National Academy of Sciences (PNAS), 103(1):195-200.
Binder, Elisabeth et al. (2008) "Association of FKBP5 Polymorphisms and Childhood Abuse With Risk of Posttraumatic Stress Disorder Symptoms in Adults" The Journal of the American Medical Association (JAMA), 299(11):1291-1305.
Brinks, Vera et al. (2007) "Differential MR/GR Activation inMice Results in Emotional States Beneficial or Impairing for Cognition" Neural Plasticity, Article ID 90163:1-11.
Caraci, Filippo et al. (2010) "Depression and Alzheimer's disease: Neurobiological links and common pharmacological targets" European Journal of Pharmacology, 626:64-71.
Carver, Charles et al. (2010) "Personality and Coping" Annual Review Psychology; 61:679-704.
Carver, Charles et al. (1993) "How Coping Mediates the Effect of Optimism on Distress: A Study of Women With Early Stage Breast Cancer" Journal of Personality and Social Psychology, 65(2):375-390.
Casren Maija et al. (1995) "Regulation of Rat Mineralocorticoid Receptor Expression in Neurons by Progesterone" Endocrinology, 136(9):3800-3806.

(Continued)

*Primary Examiner* — Juliet Switzer
(74) *Attorney, Agent, or Firm* — Lisa V. Mueller; Michael Best & Friedrich LLP

(57) ABSTRACT

Provided herein is a method of assessing the susceptibility of a subject to, or aiding the diagnosis of, an anxiety disorder or depression, the method including determining whether the subject has a haplotype including rs3216799, rs6814934, rs7658048, rs2070950 and rs2070951 with respective alleles '+CT, 'C', 'T', 'C' and 'C'. Also provided is a kit of parts or solid substrate for use in assessing the susceptibility of a subject to an anxiety disorder or depression, the kit including or the solid substrate having attached thereto one or more nucleic acid molecules that hybridize selectively to a genomic region encompassing any two or more SNPs selected from the group consisting of rs3216799, rs6814934, rs7658048, rs2070950 and rs2070951, and/or that hybridize selectively to a genomic region encompassing two or more polymorphic sites in linkage disequilibrium with any one or more SNPs selected from rs3216799, rs6814934, rs7658048, rs2070950 and rs2070951.

2 Claims, 28 Drawing Sheets

(56) References Cited

OTHER PUBLICATIONS

Figure 1:
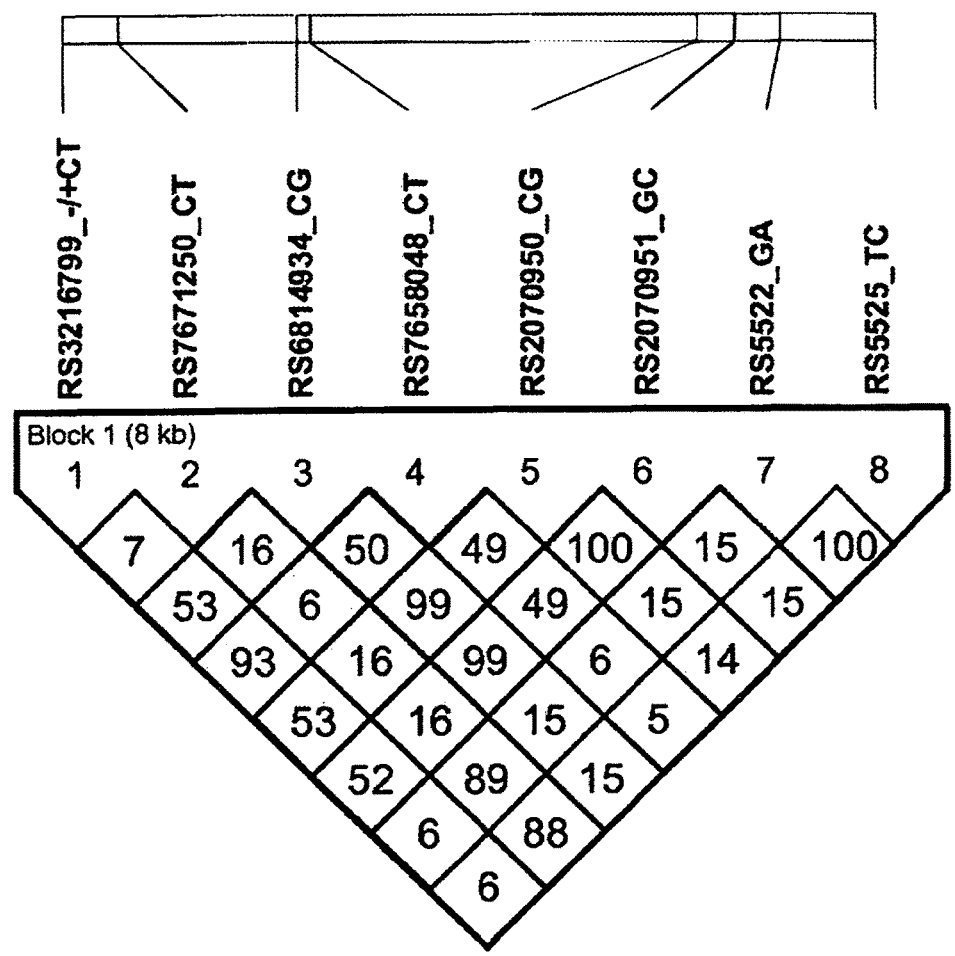

Conrad, Cheryl et al. (1997) "The effects of Type I and Type II corticosteroid receptor agonists on exploratory behavior and spatial memory in the Y-maze" Brain Research, 759:76-83.
Datson, Nicole et al. (2008) "Central corticosteroid actions: Search for gene targets" European Journal of Pharmacology, 583:272-289.
De Beurs, Edwin et al, (2005) "Stability and change of emotional functioning in late life: modelling of vulnerability profiles" Journal of Affective Disorders, 84:53-62.
De Kloet, E. Ronald et al. (1998) "Brain Corticosteroid Receptor Balance in Health and Disease" Endocrine Reviews, 19(3):269-301.
De Kloet, E. Ronald et al. (2000) "Brain mineralocorticoid receptors and centrally regulated functions" Kidney International, 57:1329-1336.
DeRijk Roel et al. (2011) "Mineralocortcoid Receptor Gene Variants as Determinants of HPA Axis Regulation and Behavior" Endocrine Development, 20:137-148.
DeRijk, Roel et al. (2008) "Corticosteroid receptor-gene variants: Modulators of the stress-response and implications for mental health" European Journal of Pharmacology, 585:492-501.
DeRijk, Roel (2009) "Single Nucteotide Polymorphisms Related to HPA Axis Reactivity" Neuroimmunomodulation, 16:340-352.
DeRijk, Roel et at. (2008) "Corticosteroid receptor polymorphisms: Determinants of vulnerability and resilience" European Journal of Pharmacolody, 583:303-311.
DeRijk, Roel et al. (2006) "A Common Polymorphism in the Mineralocorticoid Receptor Modulates Stress Responsiveness" The Journal of Clinical Endocrinology & Metabolism, 91(12):5083-5089.
Eekelen, J. A. M. van et al. (1991) "The Effect of Aging on Stress Responsiveness and Central Corticosteriod Receptors in the Brown Norway Rat" Neurobiology of Aging, 13:159-170.
Egede, Leonard et al. (2010) "Diabetes and depression: Global perspectives" Diabetes Research and Clinical Practice, 87:302-312.
Everson, Susan et al. (1996) "Hopelessness and Risk of Mortality and Incidence of Myocardial Infarction and Cancer" Psychosomatic Medicine, 58:113-121.
Femandes-Rosa, Fa'bio et al. (2011) "Mineralocorticoid Receptor Mutations Differentially Affect Individual Gene Expression Profiles in Pseudohypoaldosteronism Type 1" The Journal of Clinical Endocrinology & Metabolism, 96(3):E519—E527.
Geers, Andrew et al. (2009) "Dispositional Optimism and Engagement: The Moderating Influence of Goal Prioritization" Journal of Personality and Social Psychology, 96(4):913-932.
Giltay, Erik et al. (2006) "Dispositional Optimism and the Risk of Cardiovascular Death" Archives of Internal Medicine, 166:431-436.
Giltay, Erik et al. (2004) "Dispositional Optimism and All-Cause and Cardiovascular Mortality in a Prospective Cohort of Elderly Dutch Men and Women" Archives of General Psychiatry, 61:1126-1135.
Giltay, Erik et al. (2006) "Dispositional optimism and the risk of depressive symptoms during 15 years of follow-up: The Zutphen Elderly Study" Journal of Affective Disorders, 91:45-52.
Holmbeck, Signe et al. (1998) "High-resolution Solution Structure of the Retinoid X Receptor DNA-binding Domain" Journal of Molecular Biology, 281:271-284.
Hombergh, Carla E. J. Van Den et al. (1995) "Physical Activities of Noninstitutionalized Dutch Elderly and Characteristics of Inactive Elderly" Medicine and Science in Sports and Exercise, pp. 334-339.
Isaacowitz, Derek (2005) "The Gaze of the Optimist" Personality and Social Psychology Bulietin, 31:407-413.
Jacobs, Kenneth et al. (1988) "The thermal stability of oligonucleotide duplexes is sequence independent in tetraalkylammonium salt solutions: application to identifying recombinant DNA clones" Nucleic Acids Research, 16(10):4637-4650.
Joels, Marian et al. (2007) "The coming out of the brain mineralocorticoid receptor" Trends in Neuroscience (TINS), 573:1-7.

Keck, Martin et al. (2008)"Combined Effects of Exonic Polymorphisms in CRHR1 and AVPR1B Genes in a Case/Control Study for Panic Disorder" American Journal of Medical Genetics Part B (Neuropsychiatric Genetics), 147B:1196-1204.
Klok, Melanie et al. (2010) "Decreased expression of mineralocorticoid receptor mRNA and its splice variants in postmortem brain regions of patients with major depressive disorder" Journal of Psychiatric Research, pp. 1-8.
Kick, Melanie et al. (2010) "Common functional mineralocorticoid receptor polymorphisms modulate the cortisol awakening response: Interaction with SSRIs" Psychoneuroendocrinology (PNEC),1849:1-11.
Klok, Melanie et al. (2011) "A common and functional mineralocorticoid receptor haplotype enhances optimism and protects against depression in females" Translational Psychiatry, 1(e62):1-8.
Kohler, G et al. (1975) "Continuous Cultures of Fused Cells Secreting Antibody of Predefined Specificity" Nature, 256:495-497.
Kudielka, Brigitte et al. (2005) "Sex differences in HPA axis reponses to stress: a review" Biological Psychology, 69:112-132.
Kumsta, Robert et al. (2007) "Sex Specific Associations between Common Glucocorticoid Receptor Gene Variants and Hypothalamus-Pituitary-Adrenal Axis Responses to Psychosocial Stress" Biological Psychiatry, 62:863-869.
Kuningas, Maris et al. (2007) "Mental Performance in Old Age Dependent on Cortisol and Genetic Variance in the Mineralocorticoid and Glucocorticoid Receptors" Neuropsychopharmacology, 32:1295-1301.
Lai, Julian C. L. et al. (2005) "Optimism, positive affectivity, and salivary cortisol" British Journal of Health Psychology, 10:467-484.
Lang, U. A. (2008) "Gender-dependent Association of a Functional NGF Polymorphism with Anxiety-related Personality Traits" Pharmacopsychiatry, 41:196-199.
Lupien Sonia J. et al. (2002) "The modulatory effects of corticosteroids on cognition: studies in young human populations" Psychoneuroendocrinology, 27:401-416.
Montgomery Stuart et al. (1979) "A New Depession Scale Designed to be Sensitive to Change" Britsh Journal of Psychiatry, 134:382-389.
Nes, Lise S. et al. (2006) "Dispositonal Optimism and Coping: A Meta-Analytic Review" Personality and Social Psychology Review, 19(3):235-251.
Oitzl, Melly et al. (1992) "Selective Corticosteroid Antagonists Modulate Specific Aspects of Spatial Orientation Learning" Behavioral Neuroscience, 106(1):62-71.
Otte, Christian et al. (2007) "Blockade of the Mineralocorticoid Receptor in Healthy Men: Effects on Experimentally Induced Panic Symptoms, Stress Hormones, and Cognition" Neuropsychopharmacology, 32:232-238.
Penninx, Brenda W. J. H. et al. (2008) "The Netherlands Study of Depression and Anxiety (NESDA): rationale, objectives and methods" The International Journal of Methods in Psychiatric Research, 17(3):121-140.
Plomin. Robert et al. (1992) "Optimism, Pessimism and Mental Health: A Twin/Adoption Analysis" Personality and Individual Differences, 13(8):921-930.
Quinkler, M. et al. (2002) "Agonistic and antagonistic properties of progesterone metabolites at the human mineralocorticoid receptor" European Journal of Endocrinology, 146:789-800.
Rozeboom, Arron et al. (2007) "Mineralocorticoid receptor overexpression in forebrain decreases anxiety-like behavior and alters the stress response in mice" Proceedings of the National Academy of Sciences (PNAS), 104(11):4688-4693.
Saiki, Randall et al.(1988) "Primer-Directed Enzymatic Amplification of DNA with a Thermostable DNA Polymerase" Science, 239:487-491.
Scheier, Michael et al. (1992) "The Effects of Optimism on Psychological and Physical Well-Being: Theoretical Overview and Empirical Update" Cognitive Therapy and Research, 16(2):201-228.
Schmidt, M et al. (2003) "The postnatal development of the hypothalamic-pituitary-adrenal axis in the mouse" International Journal of Developmental Neuroscience, 21:125-132.

(56) References Cited

OTHER PUBLICATIONS

Schmit David et al. (2008) "Why Can't a Man Be More Like a Woman? Sex Differences in Big Five Personality Traits Across 55 Cultures" Journal of Personality and Social Psychology, 94(1):168-182.

Scheier, Michael et al. (1986) "Coping With Stress: Divergent Strategies of Optimists and Pessimists" Journal of Personality and Social Psychology, 51(6):1257-1264.

Scheier, Michael et al. (1985) "Optimism, Coping. And Health: Assessment and Implications of Generalized Outcome Expectancies" Health Psychology, 4(3):219-247.

Scheier, Michael et al. (1994) "Distinguishing Optimism From Neuroticism (and Trait Anxiety, Self-Mastery. and Self-Esteem): A Reevaluation of the Life Orientation Test" Journal of Personality and Social Psychology, 67(6):1063-1078.

Sher, Yelizaveta et al. (2010) "The Impact of Depression in Heart Disease" Current Psychiatry Reports, 12:255-264.

Southwick Steven et al. (2005) "The Psychobiology of Depression and Resilence to Stress: Implications for Prevention and Treatment" The Annual Review of Clinical Psychology, 1:255-91.

Staner, Luc (2010) "Comorbidity of insomnia and depression" Sleep Medicine Reviews, 14:35-46.

Steptoe, Andrew et al. (2007) "Neuroendocrine and Inflammatory Factors Associated with Positive Affect in Healthy Men and Women" American Journal of Epidemiology, 167(1):96-102.

Tapper, W. et al. (2005) "A map of the human genome in linkage disequilibrium units" Proceedings of the National Academy of Sciences (PNAS), 102(33):11835-11839.

Turner, Barbara (1997) "Influence of Gonadal Steroids on Brain Corticosteroid Receptors: A Minireview" Neurochemical Research, 22(11):1375-1385.

Uhr, Manfred et al. (2008) "Polymorphisms in the Drug Transporter Gene ABCB1 Predict Antidepressant Treatment Response in Depression" Neuron, 57:203-209.

Urani, Alexandre et al. (2005) "Mutant mouse models of depression: Candidate genes and current mouse lines" Neuroscience and Biobehavioral Reviews, 29:805-828.

Uzun, Suzana et al. (2009) "Depressive Disorders and Comorbidity: Somatic Illness vs. Side Effect" Psychiatria Danubina, 21(3):391-398.

Van der Does, Willem (2002) "Cognitive reactivity to sad mood: structure and validity of a new measure" Behaviour Research and Therapy, 40:105-120.

Van Leeuwen, Nienke et al. (2010) "Functional mineralocorticoid receptor (MR) gene variation influences the cortisol awakening response after dexamethasone" Psychoneuroendocrinology, 35:339-349.

Van Leeuwen, Nienke et al. (2010) "The Functonal c.-2G<C Variant of the Mineralocorticoid Receptor Modulates Blood Pressure, Renin, and Aldosterone Levels" Hypertension, 56:995-1002.

Van Leeuwen, Nienke et al. (2011) "Human mineralocorticoid receptor (MR) gene haplotypes modulate MR expression and transactivation: Implication for the stress response" Psychoneuroendocrinology, 36:699-709.

Vickers, Kristin et al. (2000) "Dispositional optimism as a predictor of depressive symptoms over time" Personality and Individual Differences, 28:259-272.

Walker, G. Terrance et al. (1992)"Strand displacement amplification-an isothermal, in vitro DNA amplification technique" Nucleic Acids Research, 20(7):1691-1696.

Winter, Greg et al. (1994) "Making Antibodies by Phage Display Technology" The Annual Review of Immunology, 12:433-455.

Wolf, Oliver et al. (2002) "Endogenous Estradiol and Testosterone Levels Are Associated with Cognitive Performance in Older Women and Men" Hormones and Behavior, 41:259-266.

Wu. Q. et al. (2009) "Depression and low bone mineral density: a meta-analysis of epidemiologic studies" Osteoporosis International, 20:1309-1320.

Wu at, Stefan et al. (2009) "Sex-specific association between the 5-HTT gene-linked polymorphic region and basal cortisol secretion" Psychoneuroendocrinology, 34:972-982.

Yang, Jun et al. (2009) "The mineralocorticoid receptor and its coregulators" Journal of Molecular Endocrinology, 43:53-64.

Zennaro, Maria-Christina et al. (2004) "Mineralocorticoid resistance" Endocrinology and Metabolism, 15(6):264-270.

Ziera, Tim et al. (2009) "Cnksr3 is a direct mineralocorticoid receptor target gene and plays a key role in the regulation of the epithelial sodium channel" The FASEB Journal, 23:3936-3946.

\* cited by examiner

Figure 3
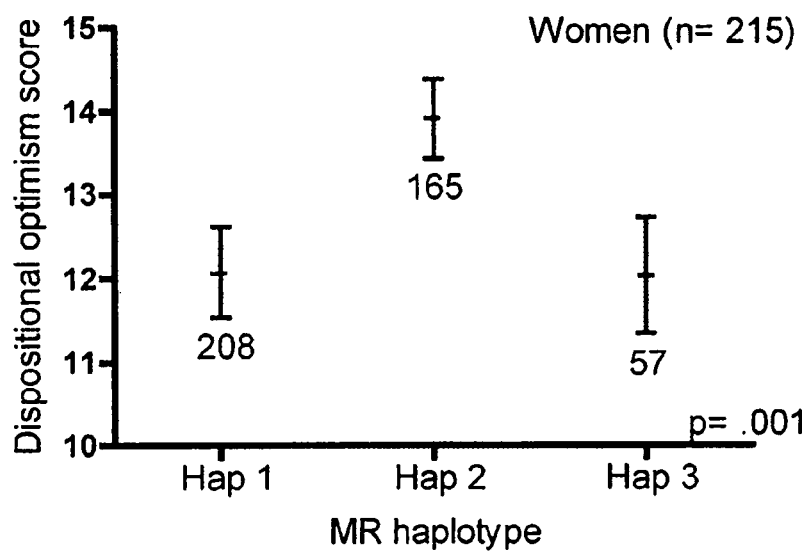
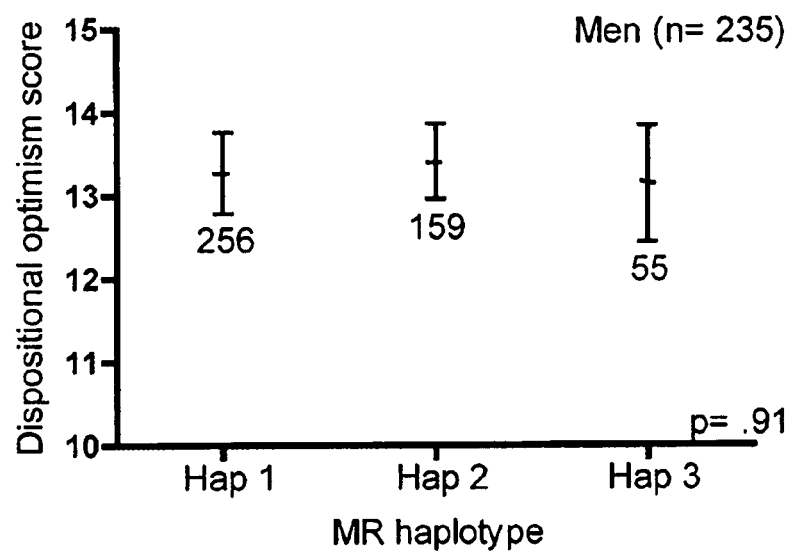

Figure 4 www.enseml.org

>chromosome:NCBI36:4:149585973

```
GGGGGTGGGGCAGAGGCGCGGCGAGCCCGAGAGGGGCGGGGAGAGGAGCAGCCTGGCGGG      P2
GTGGGCAGCCGAGGAGCAGGAAAAGAAAACTTTTCCCTCCCGCCCCCCGCGCGAGGTCCC
CAGCCCTCGCCTCCCCCCGCAGGTGGGAACTGCACCTGAAGCCGGGCGCGAGGTCAGGGC
CGGACTTTGGAGGGCTGCGGGCAGGGCTGAAGGGGGTGCGTGCATTTGGGCTCAGTTTTC      rs9992256
CTTTGGCCTCCAGGTTGTCAGTGGCCGTAGTGGGAGGGCGGCTGCCGGCGCCCCTGCCCG      C/T
TTTCCCACCCGCGGGTGGCCGGACGCGGTGCCGCCTCCTCCCGCTCGTGAGGGCGTGACC
CGGGGAGGGGGGCGCAGGCTCCCCCTGCGACCGCCCCCTCACACACGCGCTCGGCCGCCG      SNP x C/T
GAGCTGTCACCGGCCACCCAGGGCCCGGGGAGGGGGCGCGGAGAGTGGCGCTGCGGAGCG      149585620
GCGGGCGCGGGATCCTCCTGCCGGACTTCCCGGCTCCCAGGGACGCCGCTGTCAACGCCG      -8158 (in
AGCGGACGCGCAGCCCCGGGAGAGGGGCCCGCCAGAGGCCCGGCCGCCGCCGCTGGGGGC      relation to
GGGCGGGTGCCCGCGTCCCCCTCTGCGCGATTTGGCGCCGCTGCCTCGCCGCCTCTTGTA      first ATG)
GGGTAACAGCACTATTGCTCTACCCACCGTCAGCAGGGCGACTGCCACTGCCGGGATTAT      rs5520
CATCCTCTCCATCCTCACCGCCGATCAGCCAATATTGGACTTGCTGGTGGCGGCGGCAGC      G/C
AGCGGCGGCGGGAGTCTAGCCGTTCCCCTTCCCCCGCCCCAGCCTCCCCACCATGTCCTA      Exon 1β
GAAAAGGTGAGTGCAGCGACAGTCACTTTGCGCTGACAGCGGCGAGAGGGGGTCCGGAGA
GCGCAGGGGCGGCCCCGGGCAAGGCAGGTTGCGCGCCCAGGGCAGAGGGCGCGGGTTGGC
GAGCGGAGGTGGGATGCGGGCAGGAGACGAGTTGCCCGCTGGCGGCCCTGGGGCAAGGGT
GCTGGGTGGCGGGCGAGTGATCGCGGCGGCTGCCCCTGCACGGTTCTAACCTAGATTTTG
CAAGAAGCTGAGATCCAGGGCAAGACCGGCCCTCCTCAAAGGAGATAAAAACTTAGTAA{-/CT}A
AGAGACACGTCCATTCCTTTAATAATGAATAATTCGGCAACGCTTGCGGAGCCGCCGCCG
CCTCGCGTGCCCAGGCTCTAGGTCCGGGACTCCCCTTGCTCCGCCCGCCGCCCGCGCTC      rs32167799
TGCCGACGTGAGATCGATGCCCAGTTCGCTGGGCCGGGAGAGTGCGCGTGACGGTGGGCC      -/CT
CCGCGGGAAAGTTGGGACGCTCGGCGGGGACTCCTGGCTGCGGGGACGCCGGGGGCAGCT
CCAAGCTGGGGACCGAGGGGCATTAGAGTCTGGGGTCAGGACCAGCTCGCGGCGCTGCCG
CTGTCGCCCCTATCTCCAGGGAGTTCCTGACTGGAGCGGCTGAGAGTTCAAGTCTCAGCC
CTGGGTTAGGGGTCCGGAATCCCGGAGCTTAACTAACTGTTAAGGAGAGGAGGGGCCTTT      rs2248038
GGGCACAGGGTGTCCCCCGGTCCCCGCCTCGGGCTTTGGCGGGCGCGAAGCGAGGGTGA      G/A
GGCGGGAGGCCGCACAGCTGCCGCCGCCGGGCTGCGGGTCGCCGAGGGCCGGGGGACCAG
ATTTAGGTGTATACGTCACTGATGCTGACTCCGGGCCAGCGGGGAGCCTAAAACGGGGCC
TTACATGAGAAGCCTAAAAGTCCTTAGAAATCAAAGTTAGGAACCCCATCCTTTTGCTTA      rs7671250
GTAACTGCAGCATTTGGGTGGGCGGGAGGAGAATCGAGGAGGGGGCGGTTGGAGGGAAAC      C/T
CGAAATTTCTTCATGCAGACAACCGATCCTTAGAAAACAGTTTGGTTCCTTCCCCCCTCC
TGTCTGTTTCTCCCACTTATGTGACCCACCCCCTCCACCCATTATAACGTGAATATCCTC
GATGGTAAGCTTGCTTTCAAATTGAACTAGTGGAAAAATCCAATACTAAAGTAGTAAGTA
CAGTGACAAAATTATAAGGAAGTAGAGGAGCAGCTCTTGACCCTGCCACTTCTTTCATTT
ATCTTTCTCTCTCTCTCTTTTTTTTTTTTTTTTTTTTTTTTTTGGTGTTAGGGG
TCTAAGGGATGGGAGGAAAGCTGTGTTTAAAGGGTTTTTCCAGCACGGTTAAAACAACTA
AATTCAAATCGAGTGAACGTGATCGTCTTGCTCGCTGGCAGCGAAGGCTGCTGCTGCTCT
GCTGAGAGGTAACTCTGGAGACAGTGGAAAGGGCTGGGAGAGGAACCTCGAGGGTCGGG      P1
TGAAGCCCACCCAGAGTCCTCCCCGCGCGCGGACGCTGTTGGGCGGCGCCAGGGTCTGGG
CTGCAGCTCACCTGGAGCTGCAGGTGGAGAGCGTGAGGGGACGACACTTTGCTCGCGGAA
AAACCGACTTCTTCCGCGTCAGCACACTTTTCACATCTCTCCAGATATCCTGGGGTCGGT
CAGAAGGAGAGCAGGGTGGACGTAAGCAAGTTTGGGCGGCCGAGCGATGGGGGTGGGGG
CAGCGTGCGGAGGCCGCCTGATGTAGCCACCGCCCGGCACCCCAAGCTCCCGCCGCGGCT
GCGGCTTTAAGGAAGCTGCCGAGTCCAGGCTGTGTCGCAGCAACTTTGTATCAGTCATGT
CGCCCGCCTGGTGACTGACAGCCTGGATTGTCCAATAAGAAGCCCGCCTGACCCGTGCGG
CGTGGAGCCTTGCTTCTTCGGGCCAATAGGAAGGGTTCAGGGGGGCGGGATAGCAACC
TGAACTTTATCTGGACATGTGACCCGCTTTTAAAAGGGCCAGCCCTCCAGCTGGCCCACT
CCCCCTCCGGGCTTTCGCCCGCCCTCTCTCCCTCCCTTTTTGCCCGCCCTGGCCCTGCC
CCTGCCCCTGCCCCCTCCTCTCAGCCCCTCCGCGCCCGGGGTGTCATTGGGCCCGGGAGA
CGGGAGCCAACTTCAGGCTGCTCAGAGGAAGCCCGTGCAGTCAGTCACCTGGGTGCAAGA
```

Figure 4 (Contd.)

```
GCGTTGCTGCCTCGGGCTCTCCCGCTGCAGGGAGAGCGGCACTCGCTGGCCTGGATGTGG
TTGGATTTAGGGGGGCTCCGCAGCAGGGGTTTCGTGGCGGTGGCAAGCGCTGCAACAGGT          Exon 1α
AGACGGCGAGAGACGGACCCCGGCCGAGGCAGGTGTGTAGGGGCGCGCGGCGGGGCACCG
CTTGCCGTGCTCGGCGTGCGGCCGCGGCGCGGGAGCGTGCACTTTGCAGGGAGAAGTGGC
TGCGTAATCCGGAGGCACAGTCAGTATGGTGCTGTGTGCTTGTTGTTTGTTTTGGTTTT
CCACTTTTCTCCCCCTTTGGCCGCCAGAGGACTATTTTGGGAAAGTTTGGCCACTTTGGA
TAAATGCCCTCTAACTAGCAGCTTTTAACTGCCTTTGGCAGTGGGAGGTCTACCACCCTT
CCCTTTACCCAAAGATGAATTTCGGATCATTTTCCCTGTACAATTTTTAAAGGACGTTTG
AATAATATTTCTTTCCTTTATCAATTGCGGACGCTCCCAAATCTCAGCCGGAGGTGTAGC
GCATAAGGGCAGTTGAAGGAGATATAGATCCTAATAGATCCTGTATAAAAGGGGCTCTGG         rs6814934
AAATTCGTGCATTTCCCGTTCGCTAGCATTCGCGAAACTCTTGAGACAGGCTACGCTTCC         C/G
TATGGCATCAGTTGGAATTTTAAGGGCAAGGGAGAAGGGGACGAAGCTTCTTTTGGTGGC         rs7658048
ATCCTTACTCTGCTACTGAATTTTAGGTGCGTGGCTTTGCCTACTCAATTTAAAAGACC          C/T
AGGTTTAAATAATAATGGTTTATGGCACCATCAGTTTTAATTATTTATTATGACATAGGA
GTTAGGAAAACTTTTGATAGCAGACGAGCTTTTGAAACCGCCGAATTTTAAAGGCACCAA
ATTGCTTCCTAACATTTTGTATTGCCATTTCTCAGGTGCTGTTATTGATGATATTTACA
TAGTAATGATAACAGCATTCTCCATCTGTGAAGTCCTGCTGTGAAGTTTAAATTTTATGT
TTGACATCGTGGCAGCTATCATGGAAAAGCTTGAGAGGAGAAGTTTTAAAAAATAATTTA
AAGTGGAGCTTTTTCCTTTAAGGGAGGCATAGTTTTGTTGGCGATTTTGGAAAGATCA
GGTGGCTCGGTAAATTAGGTGAGTGAATAGAAATCAGGTGTGCTCAGTTCTAACTGGTTC         Intron 1
TCCCGCTCTCTCAGGTGACCTTGGGCAGATTTCTATCATTTACCTCATCTATAAAGAGA
GGAACATAATAGTTATGTAGTGGGAATGACAAAAAATAGTTACATATAGTGAACTTTTA
CAACTATGCAGTCTATAGATGATTGTGAGATTCTTAAGCTTAGTCTTTAAAGTGCCATC
TTATAGTCAAATAAATATAAAAAAGATGCCTTTTCTATCATTTCCATCATGATGAGATTG
GGTTTTGGGGGTTACTAAAAGTGAAAGTGTTTCCAGATAAAATACAAATTCGCAAGGATC
TTTGTTAATATTCCCGAAAAAAGTACTTCTTTATGGAAAAGGGCAATTTAACACAGACTG
TAAAACGTAAAACTTTAAGGTTTTCCTTTGTGAAAACAGCATTTCTTTTGTGTTTGAGAG
CATATGTATGGCTTAAAGTAGCACCTCCACCAGTGCTTTTCCTTTAGTGAATTTTTTTT
GTGTTTTGGGGCGAGGCCCATTTGCATGAAAATTAAAAGTTCATAATGTTTTTGCATTT
GTCCTAAGAGAATCTTTGGTATGGTTTCCATTGTGAGGCAGGCAAGCCTGATTTTGTTA
GTTAGATTTGTATACCTCTATCTGCTTCATTTTATACTTTAGTAACATAAACTTTTTCTT
TATCCTCTAGATATTAAGTTCTATGAGGATCATATTCATCGACTAGTATTTTCAGTATTC
ACTAGTTAGTACAGGTTGACTGAAATTCTGCTCAAGCCATGGTCATTGTGCCAGTTGCAA
AAAGATAACCTCTGCTTCCTGGATGACATAGTAAATAAATTCCTAACTGGACCCATTTGT
TTACAGAAAAGACTAATTAAAAATACTAGGGAGACTCAAAATATTTCAATAATGCTATTTG
AAAAATATCTGATCTTAAAAAAATGTTTGTGTAGAAGCCGTGCAGATGCTAGATGTCTTG
TATTCTTTTGTGTTTGACTATTGCCAATCTGTATTGTTTCCTTTGTTGAGAGGTGCATTA
GGTTGGTAGATGAGAATACCTTAAACAAAGTAATTTAGATTTCAGCAAAGCCTTTTGCAA
ATTCCTTAATGAGACTCCTGTCAATAATGTGGTGAAACACAGCCTATTTTATGTTATTAA
GGGAGTTCAAGGTTAGCCAAACAGGACTTGGAAAGTTGTGATCAGCTGTATGATGTTAGC
TGGTAAGGTGCTACCTTGTCCAGGGCTTTAAGACTGTCTTTGGTACCCATCATCTCCAGT
ATAGATTCTCTTCAGGTCTTCCGTAGCCTCACAAATGTGGGATATGGTTCTTGCTTTAGG
GCAGAGTGCCGAAAAGTGCAGAATCTTAGTAGATGTTCTTTGAGAAAAAGGTGGAGTGGT
CAAATTATTTGAGGAATGCTGGATTAAAAAGTAAACAGAATCTCCCAGAGGTTTTGATAT
GCAAATTTATATAGGGAAATTTCAAAAAAGCCAAGAGTGGACCGCCCTTCCCAAAAGACA
ATTTGGAGAATGGGTTTTGGAGAGGGGTCTGGGTGGGGGTCCCCTTCAGACACGGGACAG
AGAGCCCTCTTGACTATGACCAGGAAGAGAATGAGGCTATGTGAGTGACGCAGAGTGTGC
CAGTGAAGGCCTTCAGGTAAAGCTGTTGAGACAAGAGTAACTTCCAGGCATCTGGTTAGA
TGGTGGTGCAGTTTGCCAAGAGAGCGAATGTGAATTTGGGGGTGTGGGGGGAGAGATG
TGCAGAAAGTGTTCAGTTTTGAATACAAATAGACATATTTATTGTGTTGTTTAATGGATT
TGGATCTGAACCATTTATACCTTAGCTATATAGTAATTTATCTTTAGTATGGGGAAGACA
AAATATTCTTAGGTAGAAATAGAAGCAGCATATAATATTTACTGCTATTTTCAATACAT
AGCTATGACTAAATGGTTTTTTAGTAAAGCATAAAAGGCCAGTCTTAGCTATTTGGATCC
CAATTCACTGTTTTTAGTTTAGTTTTCTATCAGCTTTTACTTGGCTTTCATCCACACCA
```

Figure 4 (Contd.)

```
AACATTTTGGCTGGAATTACTATTAATAGATAACTACCTCAACCTTTGTAATTTTATTTA
TTTTCTACTGTTTTGTGATTGATTTTTGATTAGGAATTCATAGGATGTTCTTTAAGTGAA
AACATACTACATAATTGGTAGATTTTAATGTTTGGAAATTGAGCATTGATATTATAATAG
TTGAAAATTTTTCAATGTATCCACTTGGGATACTGTAGTGAAATTGATCATTTCTGCCC
TTTGAGAAGGTAAACTCTAGTGTAAAAACACAGAAAAGTAAGAGGTAATTATAATACTTG
GACAATTTGGACATTAAATTTCTTCATAGGGCTTTGTGCTATCTAATGCAAATTTATTTA
TGAGTCCAGCTAAGATTTATCTAATGCAAATTTATTTAGTAGCATTATTTTTCAATGTTA
ATACATATTCTGTAACAAAAGGACTTCGTGTTTTTTGTTTTTTTTAAATGAAGGGAAGG
TAGGCAGGGTGGAGATAGTGACAAAGAGGGGAAAGGATGAGAGGCCAAAAATAAAACTTG
TGTATAGAATGGCAGAAACAGCATCTTTTAGATCAGGACTTTTTTGGGCCATAGATTGT
TTACAGACTTTGAAATGTTTGAAAAATGCATAATACAGATTTTAGGAGTTTTAAAATACT
AAAATGTAAAAATAAAATTTTACTGTGAGTGAGTTAATTTCCTTTAAGATATGTTTCTTT
ACAGTGGTGGTTGTCAGCCAAGGGTGATTTTGCCCCCCATGGGCATTTGGTAATGTCTGG
AGACATTTTCAGTTGTCACAACTGGGGAGGTGGAATGCTACTGGCATCTAGTGGGTAGGG
GTTAGGGATACTGCTAAACGCCTTAGCAATGCATTATTGACCTCCACAACTAAGAATTAT
CAGGCCCAAAATGTCAATGTGCCAAGATTGAGAAACTGTATAGAGAGAGACTTGCGATCA
AATTGCAGCTCCAACACTTGGTTGTGTGTCTGGTGCCTCAGTTTTCACACTTGTATTATT
TGGATAATACTTTTATCAGTCATTCAGGGTTGTGTGTAAGGATAAATGAATTAATATATG
CAAGAAGCTTGCAATACTGCATTAAATTATATGGGTAAGAATTATATCAATATAGCCTAT
TATGAAGATTCTGTCTGTGAAGTAAATTGATCTATAGAGCGCATGGATATGGTTATATAT
CTGAAACAACCTGGTGGGTTGCTTGAGGATGGGGATTGTGTCTCTTTTGTTTATCACTGC
CTGTTCACTGACTGGTCTAAGGCCAAGGGTGTAGCAGGCACTTGGTAAATATTGTTGAAT
GAATGAATGAATGCTTAAATTTTCGGGGCTCCTCTCAAAAGTCACCATTTACCATTGAGA
GTAAACATTTCTGGTTGTTGGCAGTCGTTCTAGCAGAGGTACCACTGGTACCATGCACAG
GTCAGGGTGCATGTCAAAGTCCTTGCCAGTACTGAAATACAGAGAAGACACCAGTCATTC
CTGAATTGTCATACAGCCCTTCTGAGATATGGACCATCTTTATCAGAATGTATAGATCTT
TTCAGAACTGACATTAAATTATCTTCATCACTAATCTAAAGAGAGTCTTACTTTTAAAAA
AATCAAAAATTATTTTTCCTATGATAATTCACTTGGTATGTTTATGTTTGGAAAGAGTAA
CTTTAATTACATTTCCATATTGTTTTTAACAAGGCCATGAATTAAATATGGAAGGCAGCT    rs2070949
TCTATATGATCCAAAGACTCCAAAGGCATTGGAGTCAAAAGATTTAGATTTAAACCCAAC    A/T
TTTGTCACCATGTCTTTGACTTTGGGCAAGCCACCCACTTCACTAAGTCCTCAGTTACCT    rs2070950
TTTTTTGCCTGCCTTAATAATTCCCAGGATTACTTTGAATATCTAATAAGTTAACATTTG    G/C
TAAATATTTTTTGCAGACTCTAAAGACTGTATTATAGCAAACATGTTACTTTTATTTAGA
TCCAAAACAGTTTTATATGATCGCTTCTCTTGTTCTGACATCTCGACAAGCTGTAGTCAA
TACTCTGTTATGTCAGCATCCAAAAGGTAACAGTTTTAAATTAGCTAGAAATGTTGCTC
ATAATAAGTAGAATATGTTTTGTGGCTTAGCAAATGCAATTTTAGAATGTCTTTTAGAGT
AATATTGCTATAACTGACTCTAATTTTTTAATGTAAATTTATTTGTTAGCGATGGAGACC    rs2070951
AAAGGCTACCACAGTCTCCCTGAAGGTCTAGATATGGAAAGACGGTGGGGTCAAGTTTCT    G/C
CAGGCTGTGGAGCGTTCTTCCCTGGGACCTACAGAGAGGACCGATGAGAATAACTACATG
GAGATTGTCAACGTAAGCTGTGTTTCCGGTGCTATTCCAAACAACAGTACTCAAGGAAGC
AGCAAAGAAAAACAAGAACTACTCCCTTGCCTTCAGCAAGACAATAATCGGCCTGGGATT
TTAACATCTGATATTAAAACTGAGCTGGAATCTAAGGAACTTTCAGCAACTGTAGCTGAG
TCCATGGGTTTATATATGGATTCTGTAAGAGATGCTGACTATTCCTATGAGCAGCAGAAC
CAACAAGGAAGCATGAGTCCAGCTAAGATTTATCAGAATGTTGAACACGCCCTTGAGATCA
TTTATGTCTGACTCTGGGAGCTCCGTGAATGGTGGCGTCATGCGCGCCGTTGTTAAAAGC    rs5522
CCTATCATGTGTCATGAGAAAAGCCCGTCTGTTTGCAGCCCTCTGAACATGACATCTTCG    A/G
GTTTGCAGCCCTGCTGGAATCAACTCTGTGTCCTCCACCACAGCCAGCTTTGGCAGTTTT
CCAGTGCACAGCCCAATCACCCAGGGAACTCCTCTGACATGCTCCCCTAATGTTGAAAAT
CGAGGCTCCAGGTCGCACAGCCCTGCACATGCTAGCAATGTGGGCTCTCCTCTCTCAAGT
CCGTTAAGTAGCATGAAATCCTCAATTTCCAGCCCTCCAAGTCACTGCAGTGTAAAATCT    Exon 2
CCAGTCTCCAGTCCCAATAATGTCACTCTGAGATCCTCTGTGTCTAGCCCTGCAAATATT
AACAACTCAAGGTGCTCTGTTTCCAGCCCTTCGAACACTAATAACAGATCCACGCTTTCC
AGTCCGGCAGCCAGTACTGTGGGATCTATCTGTAGCCCTGTAAACAATGCCTTCAGCTAC
```

Figure 4 (Contd.)

```
ACTGCTTCTGGCACCTCTGCTGGATCCAGTACATTGCGGGATGTGGTTCCCAGTCCAGAC
ACGCAGGAGAAAGGTGCTCAAGAGGTCCCTTTTCCTAAGACTGAGGAAGTAGAGAGTGCC
ATCTCAAATGGTGTGACTGGCCAGCTTAATATTGTCCAGTACATAAAACCAGAACCAGAT
GGAGCTTTTAGCAGCTCATGTCTAGGAGGAAATAGCAAAATAAATTCGGATTCTTCATTC
TCAGTACCAATAAAGCAAGAATCAACCAAGCATTCATGTTCAGGCACCTCTTTTAAAGGG
AATCCAACAGTAAACCCGTTTCCATTTATGGATGGCTCGTATTTTCCTTTATGGATGAT
AAAGACTATTATTCCCTATCAGGAATTTTAGGACCACCTGTGCCCGGCTTTGATGGTAAC
TGTGAAGGCAGCGGATTCCCAGTGGGTATTAAACAAGAACCAGATGATGGGAGCTATTAC           rs5525
CCAGAGGCCAGCATCCCTTCCTCTGCTATTGTTGGGGTGAATTCAGGTGGACAGTCCTTC           C/T
CACTACAGGATTGGTGCTCAAGGTACAATATCTTTATCACGATCGGCTAGAGACCAATCT
TTCCAACACCTGAGTTCCTTTCCTCCTGTCAATACTTTAGTGGAGTCATGGAAATCACAC
GGCGACCTGTCGTCTAGAAGAAGTGATGGGTATCCGGTCTTAGAATACATTCCAGAAAAT
GTATCAAGGTAAGTTGGTTTTCTCCATTTTTTGGAAGTCATGGCTTTATACATGTTGAA
GGTTAGCATTATCTTTACAGTTGATAAATTTAAACACATTTCAGATTACTGTTTTAAGGA
TGGTCATATGTTGCTCCACTTTGCATGTTGATATAATGTTATTTTTTGAAGTAGAGGGA
AAAAGCATTCTTAAAATGTCTTAGAAAATATCTGCATTGATTTTGAAGGGGCATATGTAG
GTGTCCCGCACTCCCCATTTCCTGTTTAGGTGTTCGGAAAATTTATGTTTTACTGCCAG
TTACTATTGTAAATACAGTAATTTAGCAGACCAGTACTAGATTTTTTTCCTTTAGCTGT
TTGCCGGTTTACTAAAATTGCTTTAAGTTAGTTTATTTGTGGTCTTAGTCCTTTTTTTA
TTATGGCTTTCTTTATTAATCATCACTTCATCGGTTGTGAAAGCTAAAATTGAATCCTGT
ATCTGTTACCCACAGGCTTCCCTCCCTTCTGCCCTTTTCTAAGTAGGTTAATTATATGAA                         Intron 2
AGTTGTGGTTTTTCAATACAAATAAATCATTTCCTTAACTGTGAGAGCTTTTAAAGACT
CAGCATATCTAAAATTACTAAGTGGACAATCTTGCTTTCTTACTTATATTGGAAGTGAAA
TATGTCACTGCAGTTTTGAATTGGTATATTTATAACTTTTCAGATCTGCAAGAAGACATA
TTTTATTTACTGTAAAATATCTCTTGGCTTTCCTTGTTGCAGATAGCATGTTGTATATAT
TTAGAAAAAACAAGGAAGAGGTTTTAGATATGACTATAAAGGGTGGTTCTAAGTTATACA
GTGAATACTTGGATTGGACTTTGCTTCAGTACTGTTTTATTACATGGTTGTGATAAATT
ATTCCTTTATGGACTATATAAAGAATAGATTTCCTTAGTATAGTTCATTCCTTTGGCATC
CAGAACTATGTGGATAGTTTCCTTTATTTCATTAAAAATTATTTTGTGGGAATATGTCC
ATCCCATTAACAGGATATAGGGTTTACATGTATTGCTGTGGCTTTCTCTTATTCTATTTT
TTTCCAAACCAAAAGCAAAAACTTTATGTATTCTTCTTATTGTCATTGCCTCAAACCTTG
CTTTTCTTGCTTATGGAAGCAAACATTTCATAAAGGATACATTTTATAGTTTCCCCACA
GCATGAACTATTTAATCATATTCTGATGCTGTCTCTTAAATTATAAGTTCTAACACAAGT
CATGAGATAGCATGGCTGCCATCAGAACCAAATTGAGCATGTGTTTTACTGCTAGTGCTT
TGCTTTACTTTTAGAGAAGGACTTTTTTCATGTGTTGTGAATATTTTTGTAAATGATGTT
TTTAGTGAGCTGGTATGAGGTAGTATAGCCTGGTAGTTAACAGCATAACTGGTTGAAATC
CCAACTCTGCTACTTAATTGTTTAGTTTTCTCAACTGTATAAGGGGATTAAATAGTACCC
ATCTCAAAGGTAGTTAAGACAATTTAAATGAGATAATTTATGAGAAATACTTTGAATTCC
TTCCAGTATGTTAGTATGCATTGTATATGTTTTGCTATTATGAAATTGTTTTATAATTTT
TAGTTTTCATATTTTTAGTTTTCTTTTCTTCATTGTATGAAATTCCACAGAATCTTATA
AAGAAATACTTAAAATATTTAAGCACTTGTTAAAGTAAATATTTGATAATCTCTTATGAT
TAAACTCATATTTTAAAAATGATTATGCACTATACCTTTGTTATTACAGTTCTATTTATG
CTTTTTTATTTTTGAAAACTATTGCTTTGAGTAATGATGTTTCTGGTAGAAATATTACAG
ATGCAGTAAGCTCAAATGATTGTCTCTTATGTTTGTTCTATATCCCTATTTCTACTATTT           rs11730626
TAAATGTAGTTTTCATGCTCCACTCAAGAAGCCCTCCTGATGGTCCAATGACCCGTGCAT           G/A
AGCCTTAGACATGTTAGTATGAATTAGTGACCTTGAGCCTATCCTGCATTCATAGGCACA
GGAAGCATTGTCTTGTGTCTCCTCTTGAGTATTCCAAAATTCCTTATGTATTTGTTAATA
CAGTCAACAGGGATTCATTCTGCTTATATACATACTAGTTTTGTGCCAGCTAAATTTCCT           rs11099695
AAAAACTTTAAAGCTTTAACGTGATTTGATATCTCTTATAGATTAATGATTCTTTACAGC           T/C
TTTTCTTGGTGAATACTATCCAAACCTATTTGTTTTGATGATTACCAGAGTAAAAGCTCA
AGGATCAGAGGAAATTTAGTTGTTTTCTAGAGTTCAGTCTACATGTTATAATATTTAAT
TTAACCTTGTCCAAGTATCATCCTTAGTCTCTTATTTTGAACAAAAAACCCAACCTTTTT
GCCTATTTCTTAAAATATGATGATAACTCATTTCAGGGAATGTTGAATAGGTTAATGAAT           rs11929719
TAAATATCATAAAGGATCAAGGCAGTGTATACTGCTTCTAGGTTAATAGTATCCTTCAT           T/C
```

Figure 4 (Contd.)

```
CATTAGGTTGAACCTTGAACTGCAGTATTTTCTGGTAGATGTCAAATCATGGTTTGAGGG
TTCCTGAGACCTTTTCAAGGAAGTTCACACAGTCAGAAATCATGCTTTGTTAAAATATCC
ACCCAAAATGGAACACAGATCAATGGATTTTGATATAATCTTGTATGAAAATTTCACTGA
TGTTGTTTCAGATTCCACATTGAAACTAACCTTTAAGGAACTATTCAGTGTTATTTTTCA
GTATAGTATCAAAGATTCATATCTACAATTATCTGAAATGACCATTAAAATATTCTTCCC
CTTTCCCAACAACATATCTATATGAGATGAGATTTTCTCTATGTACTTGAAGAAAAACAT
AGCACCACACGTAGCAATGAAATCCAGCAGTCTTCTATTAAGTGTGACAGTAGTCTTGC
AAAAATGTTAAACAGTGCCACTCTTCTCACTAAGGATTTTTGTTTGGGGAAATATTGTTT
CATAAACAGTTTTCATATTGTTTATGTTAATATGCAATCACTTATTTTTAAATGATTTTA
AAACATTTGTTTTAATTTTTAATTTAAACTAATTTAATATTAGTTTTAATTTTTAACTTA
AATAATTTAATTTTAGTTTTAATTTCCAATACAGTAGCAATAACTGTAACTCACATAAAC
AAATGCTCTTTGGGATCCTTCATACTTTTTAAGAATGAAAAGGAGTTCTGAGATCCAGAA
GCTGAGAACTGCTGGTCTGTTCTCTTCTATACACGCTTTGGAGGTTAATGAAGAAAGAAG
ACATTACATTATTTGTATTAGTGTTACTGAATATTATTTTGAGGAAGGAGTGTTCTATTC    rs2172002
AAATAGGAAAAATGATTCTTGCTCAGGTTAATTTTTTAAACTGACAGAAATGAGTAATGG    T/C
CTGTGAGGTGTGTGTTGTCTTTATTTCAGTCTGTGGGCATTCAGTGAGAGTGGTGACGAA
AGTCATCTGTTAATAATTTCCAGTGAATGGATTGTCTGAGCACCAAATTGTAAAGTAAAT    rs4835519
TATGACAAAGCTAAATGTAAAGCCCTTAGAATGGACGCCGGACCTAGTTGTGTCAGGTGG    A/G
ATTAGAACTCCCCTGTCTGCTTGGACATCAACAAAACCGCTCTGAGCCTCAGTTTCTTCA
TTTTAAAGTGATTAAGTTGAACTAATCATTTTGCTGATCACTAATGTGCCCCAAGAGCTG
CCAGTGTAATTTCCTTTGAAGAATCAAAATAGAGTATCCTTTAACATACTTGCTAATTTA
GTTTCAAGTATTTTGTATACTCAAGTCTAGCTTCATGGTTTTCAGGGTAGTCTGGGGAGA
AAAATATCATTTCCATTTACCATTTTAAAGTAAAAATGAGGAGGGGCGATCTATGATTTT
ACTTGAAAAGAGGAGCAGTTGTGTTTTTTAAAACCAGATTTAAAGAAAAAATAAACTCT
GAAACTTACTATGAATTCCTTGTTCTTCTTATTTATACAATTCCTCATGGAAACAGGGCA
TTTCTGTTGACATAACACTGGCTGTTTATGGCGATAGTCATAGTCACTTTGATAGCATCA
TAACACAGGGCTAACATTGACTTAGACTTTTAAATGTAAAGTTTACTATTTCAAAGGGCA
TATTCTGGTAGGTTACAAGAACAGTAATTAGGATTTATCTTAATATGTGCTGATTTTTTT
TCACGATAGAATGAAACAGTTTAGTAAATAACCTATATTTATTCTTTTATTTTTCAATTG
CCCCTGAAGTTTCCTTGAAACTCACATTATATGACAAACCAAACATCAGAATTCGGGGAG
TTTGTGACAAAGTTTGCCCTTTTACTAAACTTTCAATATAAACAGTTGAGAAGGAAATAT
TTCCATGTAATGCAATGTCTGAAAGAATGGTAGGGTGTGTGTCTGAGAGAGAGAGAGTGT
ATTGGTGCTTACTCTAATACATAAATCCATTACAGCATTGCTTAGGTCATTTGGGAATGA
AAACATGTAACTTTCTTTTACTTATTATTTGTCTCATAATATTTTGATTTTGAAATTGCT
AATGTACCTAGAATTTCACCAGGTAAATATTTTAAATATTTTTGTAAATTATTTTAAAAT
GAGAGTTGTTTCTCCTGATATTCATTTTCATTCGCTTATATTTCTGGGAAGAGTGGTGA
TAATAAAAAAATTAAGTGTTTTATAATACACAAATCACTATGTACAGTGTACTTTTGTGA
GTTTCATTTTTAAACATCACAAATATCGTAGGTTTATATGTCAGTATGTCTGCCTCTTAT
CATCTAAAATATTGGTTTATTATTTACATCATACTTTAAAAATGATGCTGAGATAAAAGC
CATGGTTTCAGTTAGATAACCTCAAATTATTCCACTTAATGCAATTTTCATACCGGTGAC
ATACTACGGACTTAGACTTTTGAATGTAAAGTTCTTACTATGGAGATATTACTTATAGAT
TTGATATTCCATGTTGCCTTTTGCAATATTGAAATTCTAGGTGTGTCTGACCTTTTCTGT
CCTTGGAATGTTACAGTAATAGCAGATGTTATATTGATCACCACTAATTTAGGAGCAACA
CTTTGCTTCTCTTCATACTTTGATGTCATTATGTTTTCTGCAAAGTAGTACTTTTTCT
TCACTTTCAGCTGTTGCTTTAGTTTTGTACTGTTCATTTGCTGATAAAATATACCCCCA
CTGCTAAATAATATCATTTGTTTCGTTTACTAAATTCAAATTGAGAGAAAATATTA
GCTTCTTGATTACATTTAAATATAGCCATTAACTTGGATATCTTTGATGACATTCCAACA
TTTATTAATGAAAACCGAGGAAAAATAAAAGCATGTTAAATGGATAGCGTCTTCATTTTA
AACATTAGGGTCTCTGGTTTTAAACTTGTGAAGTATAGGATTTGTTTTAGTTTTAAGAG
TTTTATTTTGTTCCTTATATAGTAAGGTGGTGATGAAGTTAAAATGTAATTACATATAAG
CACTTGTTAATTTATGCTCTAGAAACTTCTGGATTTATGATTTGTTAGTGGTATGGCTAAG
GCCAAAATTTTTATGTAGAAAAGTGGTGGAAATTGTTTGTATTTTGTGCTAGAAATAGAA
AACTGTAGTTTAAGGAAGGAAACAGGACAAAAAAAAGTAATTTGAATGCTTAAAAAGTTA
ATACCTTAGGGAGGGAGTATGAGATAATAGCTGGCCATCTGGATTCATAACTGTGGCTAT
GACTTAATTTCATTTCTGATGAATACTTCATTGGTATGTAACGAATATTCACCTTATATA
```

Figure 5 (Contd.)

| # | Name | Position | ObsHET | PredHET | HWpval | %Geno | FamTrio | MendErr | MAF | Alleles | Rating |
|---|---|---|---|---|---|---|---|---|---|---|---|
| 57 | rs4635799 | 1495699... | 0.45 | 0.477 | 0.8179 | 100.0 | 30 | 0 | 0.392 | T:C | ✓ |
| 58 | rs17024718 | 1495702... | 0.0 | 0.0 | 1.0 | 100.0 | 30 | 0 | 0.0 | C:C | ✓✓ |
| 59 | rs6817925 | 1495707... | 0.017 | 0.017 | 1.0 | 100.0 | 30 | 0 | 0.0080 | C:T | ✓ |
| 60 | rs4835519 | 1495722... | 0.51 | 0.498 | 1.0 | 85.6 | 18 | 0 | 0.471 | T:C | ✓ |
| 61 | rs2172002 | 1495724... | 0.145 | 0.165 | 0.7227 | 92.2 | 23 | 0 | 0.091 | T:C | ✓ |
| 62 | rs6831307 | 1495724... | 0.0 | 0.0 | 1.0 | 98.9 | 29 | 0 | 0.0 | G:G | |
| 63 | rs11929719 | 1495732... | 0.492 | 0.498 | 1.0 | 97.8 | 28 | 0 | 0.466 | A:G | ✓ |
| 64 | rs11099695 | 1495735... | 0.483 | 0.499 | 0.9633 | 100.0 | 30 | 0 | 0.475 | A:G | ✓ |
| 65 | rs11730626 | 1495737... | 0.2 | 0.206 | 1.0 | 100.0 | 30 | 0 | 0.117 | T:C | ✓ |
| 66 | rs5529 | 1495757... | 0.0 | 0.0 | 1.0 | 100.0 | 30 | 0 | 0.0 | A:A | ✓ |
| 67 | rs5527 | 1495758... | 0.0 | 0.0 | 1.0 | 100.0 | 30 | 0 | 0.0 | A:A | ✓✓ |
| 68 | rs5526 | 1495758... | 0.0 | 0.0 | 1.0 | 100.0 | 30 | 0 | 0.0 | G:G | ✓✓ |
| 69 | rs5525 | 1495759... | 0.2 | 0.206 | 1.0 | 100.0 | 30 | 0 | 0.117 | G:A | ✓✓ |
| 70 | rs12509135 | 1495760... | 0.0 | 0.0 | 1.0 | 91.1 | 22 | 0 | 0.0 | G:G | |
| 71 | rs5523 | 1495761... | 0.0 | 0.0 | 1.0 | 100.0 | 30 | 0 | 0.0 | A:A | |
| 72 | rs5522 | 1495769... | 0.2 | 0.206 | 1.0 | 100.0 | 30 | 0 | 0.117 | A:G | ✓✓ |
| 73 | rs13306591 | 1495770... | 0.0 | 0.0 | 1.0 | 100.0 | 30 | 0 | 0.0 | G:G | |
| 74 | rs2070951 | 1495774... | 0.45 | 0.477 | 0.8179 | 100.0 | 30 | 0 | 0.392 | C:G | |
| 75 | rs2070950 | 1495778... | 0.45 | 0.477 | 0.8179 | 100.0 | 30 | 0 | 0.392 | C:G | |
| 76 | rs2070949 | 1495779... | 0.45 | 0.483 | 0.7385 | 100.0 | 30 | 0 | 0.408 | A:T | |
| 77 | rs12643841 | 1495779... | 0.0 | 0.0 | 1.0 | 96.7 | 27 | 0 | 0.0 | A:A | |
| 78 | rs6822758 | 1495781... | 0.0 | 0.0 | 1.0 | 92.2 | 24 | 0 | 0.0 | A:A | |
| 79 | rs10028821 | 1495781... | 0.0 | 0.0 | 1.0 | 100.0 | 30 | 0 | 0.0 | G:G | |
| 80 | rs6823133 | 1495782... | 0.0 | 0.0 | 1.0 | 98.9 | 29 | 0 | 0.0 | C:C | |
| 81 | rs7658048 | 1495821... | 0.483 | 0.499 | 0.9633 | 100.0 | 30 | 0 | 0.475 | G:A | |
| 82 | rs2248038 | 1495844... | 0.2 | 0.206 | 1.0 | 100.0 | 30 | 0 | 0.117 | A:G | |
| 83 | rs10213471 | 1495899... | 0.217 | 0.243 | 0.6395 | 100.0 | 30 | 0 | 0.142 | G:A | |

Figure 5 (Contd.)

rs7658048 = SNP# 81
rs2070950 = SNP# 75
rs2070951 = SNP# 74
rs5522 = SNP# 72
rs5525 = SNP# 69

The other SNPs in this haplotype bin 2, SNPs 60-82, are related to/in LD with our SNPs Based on studies in other Dutch cohorts we know that also the following SNPs are linked to our SNPs:

rs9992256 C/T, rs5520, rs5521, rs17485227 A/G

B.

| Haplotype | rs9992256 | rs5520 | rs3216799 | rs2248038 | rs7671250 | rs6814934 | rs7658048 | rs2070949 | rs2070950 | rs2070951 | rs5522 | rs5525 | rs11730626 | rs11099695 | rs11929719 | rs2172002 | rs4835519 | Haplotype freq. |
|---|---|---|---|---|---|---|---|---|---|---|---|---|---|---|---|---|---|---|
| 1 | T | C | G | - | A | T | G | C | A | G | G | A | C | A | C | C | T | G | .52 |
| 2 | C | T | C | C | T | A | T | C | T | C | A | C | A | T | T | T | A | .36 |
| 3 | C | C | G | - | G | C | C | C | A | C | C | G | T | T | C | A | .12 |

(novel SNP, no rs number for rs5520)

Figure 6
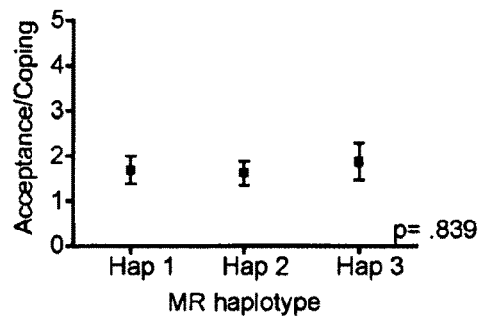
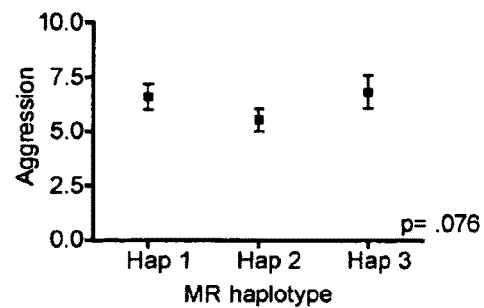
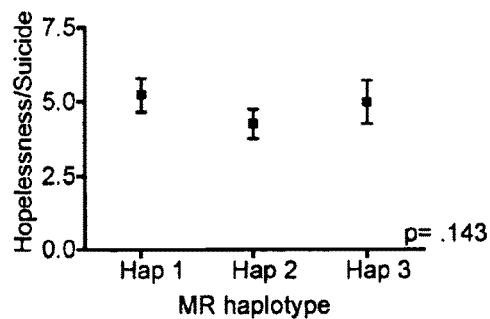
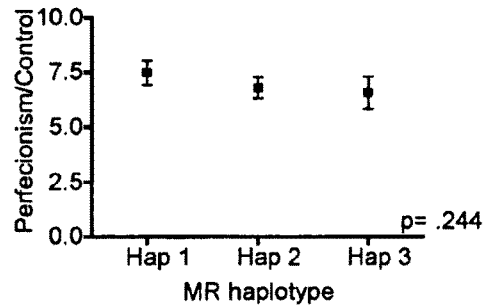
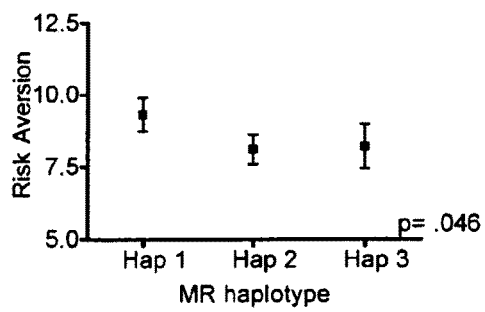
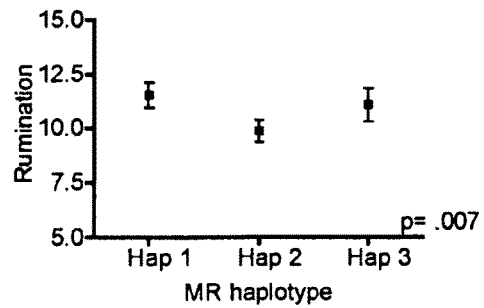
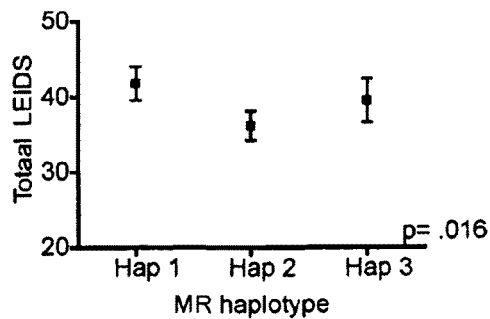

Figure 8
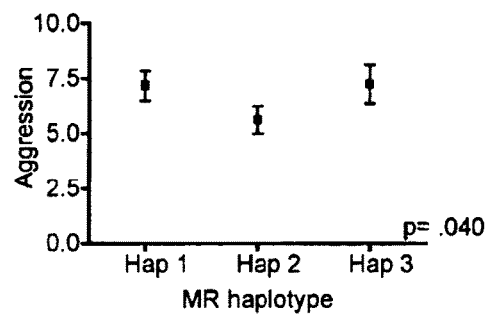
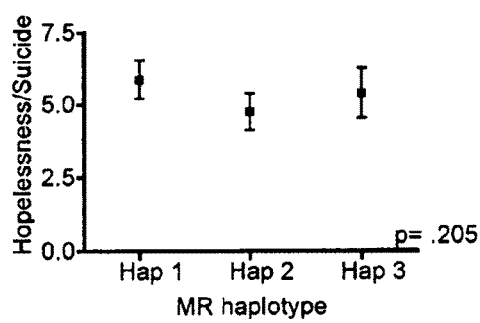
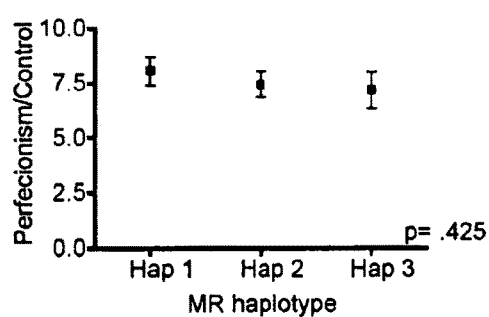
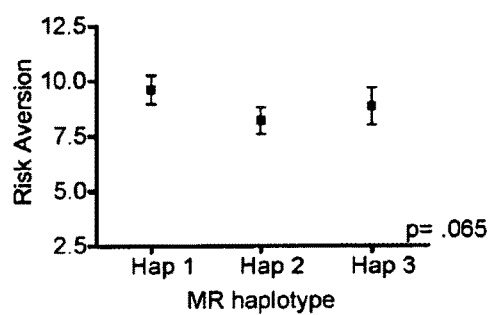
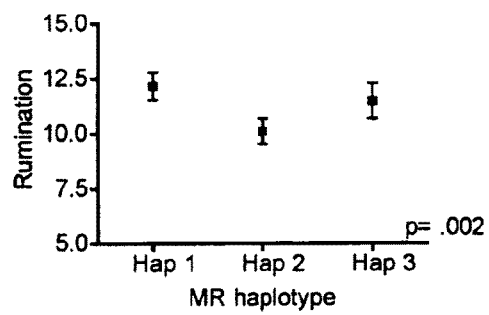
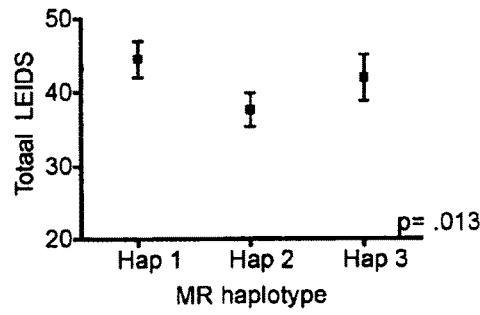

Figure 10
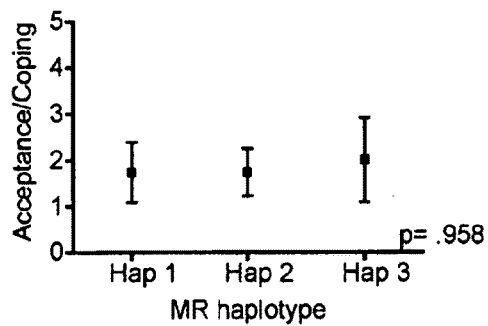
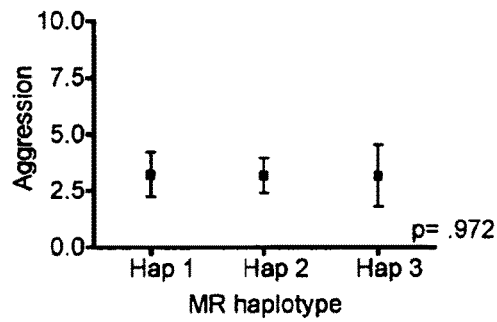
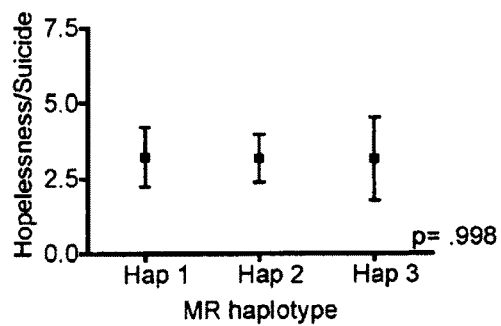
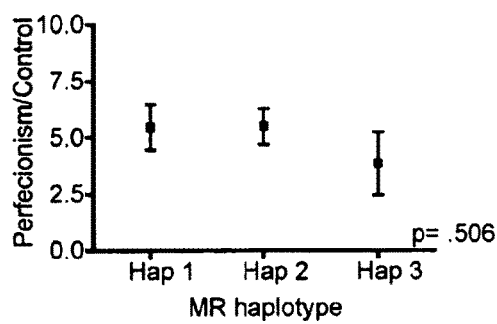
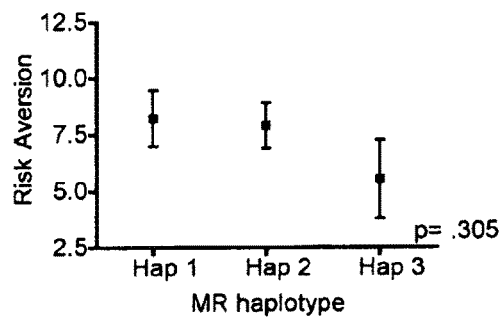
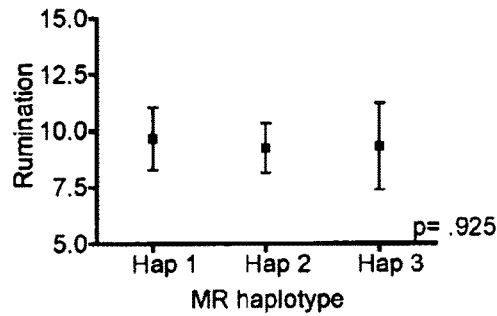
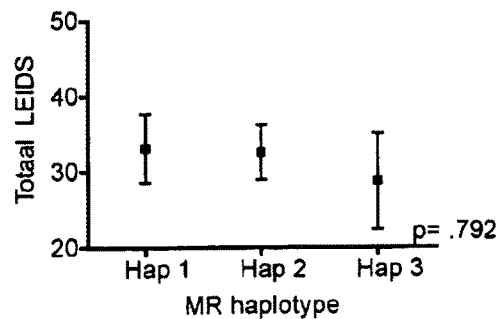

0.5 * 10⁵ M17 cells/well

6x 200 ng Hap-pGL3B
100 ng pGL3B
100 ng pGL3C
10 ng pGL4.74
1 ul lipo 48 hrs incubation

| Comparison of hap 1-3 | | | | |
|---|---|---|---|---|
| One-way analysis of variance | | | | |
| P value | P<0.0001 | | | |
| Bonferroni's Multiple Comparison Test | Mean Diff. | t | P value | 95% CI of diff |
| Hap 1 vs Hap 2 | -0.8008 | 4.079 | P < 0.01 | -1.330 to -0.2720 |
| Hap 1 vs Hap 3 | 0.6655 | 3.390 | P < 0.05 | 0.1366 to 1.194 |
| Hap 2 vs Hap 3 | 1.466 | 7.469 | P < 0.001 | 0.9375 to 1.995 |

Figure 19 hMR cDNA (NR3C2)

rs2070951 G51/C49 — ATG-start

Part of Exon1α

```
                                    smid - cggcgagagacg
          gaccccggcc gaggcag g ATG gaaagacg gtgggtcaa gtttctcagg cgtggagcgt
      301 tcttccctgg gacctacaga gaggaccgat gagaataact acatggagat tgtcaacgta
      361 agctgtgttt ccggtgctat tccaaacaac agtactcaag gaagcagcaa agaaaaacaa
      421 gaactactcc cttgccttca gcaagacaat aatcggcctg ggattttaac atctgatatt
Exon2 481 aaaactgagc tggaatctaa ggaactttca gcaactgtag ctgagtccat gggtttatat
      541 atggattctg taagagatgc tgactattcc tatgagcagc agaaccaaca aggaagcatg
      601 agtccagcta agatttatca gaatgttgaa cagctggtga aatttacaa aggaaatggc
      661 catcgtcctt ccactctaag ttgtgtgaac acgcccttga gatcatttat gtctgactct
      721 gggagctccg tgaatggtgg cgtcatgcgc gcc ttgtta aaagccctat catgtgtcat   rs5522 A80/G2
      781 gagaaaagcc cgtctgtttg cagccctctg aacatgacat cttcggtttg cagccctgct
      841 ggaatcaact ctgtgtcctc caccacagcc agctttggca gttttccagt gcacagccca
      901 atcacccagg gaactcctct gacatgctcc cctaatgctg aaaatcgagg ctccagtcg
      961 cacagccctg cacatgctag caatgtgggc tctcctctct caagtccgtt aagtagcatg
     1021 aaatcctcaa tttccagccc tccaagtcac tgcagtgtaa aatctccagt ctccagtccc
     1081 aataatgtca ctctgagatc ctctgtgtct agccctgcaa atattaacaa ctcaaggtgc
     1141 tctgtttcca gcccttcgaa cactaataac agatccacgc tttccagtcc ggcagccagt
     1201 actgtgggat ctatctgtag ccctgtaaac aatgccttca gctacactgc ttctggcacc
     1261 tctgctggat ccagtacatt gcgggatgtg gttcccagtc cagacacgca ggagaaaggt
     1321 gctcaagagg tccctttcc taagactgag gaagtagaga gtgccatctc aaatggtgtg
     1381 actggccagc ttaatattgt ccagtacata aaaccagaac cagatggagc ttttagcagc
     1441 tcatgtctag gaggaaatag caaaatcaaat tcggattctt cattctcagt accaataaag
     1501 caagaatcaa ccaagcattc atgttcaggc acctcttta aagggaatcc aacagtaaac
     1561 ccgttctcctc ttatgatgg ctcgtatttt tccttttatgg atgataaaga ctattattcc
     1621 ctatcaggaa ttttaggacc acctgtgccc ggctttgatg gtaactgtga aggcagcgga   rs5525 C80/T2
     1681 ttcccagtgg gtattaaaca agaaccagat ga gggagct attacccaga ggccagcatc
     1741 ccttcctctg ctattgttgg ggtgaattca ggtggacagt ccttccacta caggattggt
     1801 gctcaaggta caatatcttt atcacgatcg gctagagacc aatctttcca acacctgagt
     1861 tccttcctc ctgtcaatac tttagtggag tcatggaaat cacacgacga cctgtcgtct
     1921 agaagaagtg atgggtatcc ggtcttagaa tacattccag aaaatgtatc aagctctact
Exon3 1981 ttacgaagtg tttctactgg atcttcaaga cccttcaaaaa tatgtttggt gtgtggggat
     2041 gaggcttcag gatgccatta tggggtagtc acctgtggca gctgcaaagt ttcttcaaa
     2101 agagcagtgg aag ggcaaca caactattta tgtgctggaa gaaatgattg catcattgat
Exon4 2161 aagattcgac gaaagaattc tcctgcttca agacttcaga aatgtcttca agctggaatg
     2221 aatttaggag cacgaaagtc aaagaagttg ggaaagttaa aaggattca cgaggagcag
     2281 ccacagcagc agcagccccc accccacacc ccaccccgc aaagcccaga ggaagggaca
     2341 acgtacatcg ctcctgcaaa agaaccctcg gtcaacacag cactggttcc tcagctctcc
     2401 acaatctcac gagcgctcac accttcccc gttatggtcc ttgaaaacat tgaacctgaa
Exon5 2461 attgtatatg caggctatga cagctcaaaa ccagatacag ccgaaaatct gctctccacg
     2521 ctcaaccgct tagcaggcaa acagatgatc caagtcgtga agtgggcaa gtacttcca
     2581 g gatttaaaaa acttgcctct tgaggaccaa attaccctaa tccagtattc ttggatgtgt
Exon6 2641 ctatcatcat ttgccttgag ctggagatcg tacaaacata cgaacagcca atttctctat
     2701 tttgcaccag acctagtctt taatga gag aagatgcatc agtctgccat gtatgaacta
Exon7 2761 tgccagggga tgcaccaaat cagccttcag ttcgttcgac tgcagctcac ctttgaagaa
     2821 tacaccatca tgaaagtttc gctgctacta agcacaa ttc caaaggatgg cctcaaaagc
     2881 caggctgcat ttgaagaaat gaggacaaat tacatcaaag aactgaggaa gatggtaact
Exon8 2941 aagtgtccca acaattctgg gcagagctgg cagaggttct accaactgac caagctgctg
     3001 gactccatgc atgac tggt gagcgacctg ctggaattct gcttctacac cttccgagag
     3061 tcccatgcgc tgaaggtaga gttccccgca atgctggtgg agatcatcag cgaccagctg
     3121 cccaaggtgg agtcggggaa cgccaacgcc ctctacttcc accgaag cg ctgcccgct
Exon9 (part) 3181 gcccagaaga actttgcctt aagtttccct gtgttgttcc acacccagaa ggactcccaa
     3241 aaacctgttt ttaacatgtg atggttgatt cacacttgtt caacagtttc tcaagtttaa
     3301 agtcatgtca gaggtttgga gccgggaaag ctgtttttcc gtggatttgg cgagaccaga
     3361 gcagtctgaa ggattcccca cctccaatcc cccagcgctt agaaacatgt tcctgttcct
     3421 cgg - plasmid
```

Figure 20

| | | |
|---|---|---|
| 1 | METKGYHSLP | EGLDMERRWG |
| 21 | QVSQAVERSS | LGPTERTDEN |
| 41 | NYMEIVNVSC | VSGAIPNNST |
| 61 | QGSSKEKQEL | LPCLQQDNNR |
| 81 | PGILTSDIKT | ELESKELSAT |
| 101 | VAESMGLYMD | SVRDADYSYE |
| 121 | QQNQQGSMSP | AKIYQNVEQL |
| 141 | VKFYKGNGHR | PSTLSCVNTP |
| 161 | LRSFMSDSGS | SVNGGVMRAI (→V) |
| 181 | VKSPIMCHEK | SPSVCSPLNM |
| 201 | TSSVCSPAGI | NSVSSTTASF |
| 221 | GSFPVHSPIT | QGTPLTCSPN |
| 241 | AENRGSRSHS | PAHASNVGSP |
| 261 | LSSPLSSMKS | SISSPPSHCS |
| 281 | VKSPVSSPNN | VTLRSSVSSP |
| 301 | ANINNSRCSV | SSPSNTNNRS |
| 321 | TLSSPAASTV | GSICSPVNNA |
| 341 | FSYTASGTSA | GSSTLRDVVP |
| 361 | SPDTQEKGAQ | EVPFPKTEEV |
| 381 | ESAISNGVTG | QLNIVQYIKP |
| 401 | EPDGAFSSSC | LGGNSKINSD |
| 421 | SSFSVPIKQE | STKHSCSGTS |
| 441 | FKGNPTVNPF | PFMDGSYFSF |
| 461 | MDDKDYYSLS | GILGPPVPGF |
| 481 | DGNCEGSGFP | VGIKQEPDDG |
| 501 | SYYPEASIPS | SAIVGVNSGG |
| 521 | QSFHYRIGAQ | GTISLSRSAR |
| 541 | DQSFQHLSSF | PPVNTLVESW |
| 561 | KSHGDLSSRR | SDGYPVLEYI |
| 581 | PENVSSSTLR | SVSTGSSRPS |
| 601 | KICLVCGDEA | SGCHYGVVTC |
| 621 | GSCKVFFKRA | VEGQHNYLCA |
| 641 | GRNDCIIDKI | RRKNCPACRL |

SEQUENCE LISTING

```
<160> NUMBER OF SEQ ID NOS: 13

<210> SEQ ID NO 1
<211> LENGTH: 16080
<212> TYPE: DNA
<213> ORGANISM: Homo sapiens
<220> FEATURE:
<221> NAME/KEY: variation
<222> LOCATION: (231)..(231)
<223> OTHER INFORMATION: where c is replaced with t
<220> FEATURE:
<221> NAME/KEY: variation
<222> LOCATION: (354)..(354)
<223> OTHER INFORMATION: where c is replaced with t
<220> FEATURE:
<221> NAME/KEY: variation
<222> LOCATION: (615)..(615)
<223> OTHER INFORMATION: where g is replaced with c
<220> FEATURE:
<221> NAME/KEY: variation
<222> LOCATION: (1140)..(1140)
<223> OTHER INFORMATION: where a is replaced with cta
<220> FEATURE:
<221> NAME/KEY: variation
<222> LOCATION: (1525)..(1525)
<223> OTHER INFORMATION: where g is replaced with a
```

```
<220> FEATURE:
<221> NAME/KEY: variation
<222> LOCATION: (1744)..(1744)
<223> OTHER INFORMATION: where c is replaced with t
<220> FEATURE:
<221> NAME/KEY: variation
<222> LOCATION: (3655)..(3655)
<223> OTHER INFORMATION: where c is replaced with g
<220> FEATURE:
<221> NAME/KEY: variation
<222> LOCATION: (3780)..(3780)
<223> OTHER INFORMATION: where c is replaced with t
<220> FEATURE:
<221> NAME/KEY: variation
<222> LOCATION: (8020)..(8020)
<223> OTHER INFORMATION: where a is replaced with t
<220> FEATURE:
<221> NAME/KEY: variation
<222> LOCATION: (8152)..(8152)
<223> OTHER INFORMATION: where c is replaced with g
<220> FEATURE:
<221> NAME/KEY: variation
<222> LOCATION: (8510)..(8510)
<223> OTHER INFORMATION: where c is replaced with g
<220> FEATURE:
<221> NAME/KEY: variation
<222> LOCATION: (9049)..(9049)
<223> OTHER INFORMATION: where g is replaced with a
<220> FEATURE:
<221> NAME/KEY: variation
<222> LOCATION: (10008)..(10008)
<223> OTHER INFORMATION: where t is replaced with c
<220> FEATURE:
<221> NAME/KEY: variation
<222> LOCATION: (12235)..(12235)
<223> OTHER INFORMATION: where g is replaced with a
<220> FEATURE:
<221> NAME/KEY: variation
<222> LOCATION: (12385)..(12385)
<223> OTHER INFORMATION: where t is replaced with c
<220> FEATURE:
<221> NAME/KEY: variation
<222> LOCATION: (12764)..(12764)
<223> OTHER INFORMATION: where t is replaced with c
<220> FEATURE:
<221> NAME/KEY: variation
<222> LOCATION: (13562)..(13562)
<223> OTHER INFORMATION: where c is replaced with t
<220> FEATURE:
<221> NAME/KEY: variation
<222> LOCATION: (13755)..(13755)
<223> OTHER INFORMATION: where a is replaced with g

<400> SEQUENCE: 1
gggggtgggg cagaggcgcg gcgagcccga gaggggcggg gagaggagca gcctggcggg      60
gtgggcagcc gaggagcagg aaaagaaaac ttttccctcc cgcccccgc gcgaggtccc      120 cagccctcgc ctccccccgc aggtgggaac tgcacctgaa gccgggcgcg aggtcagggc     180
cggactttgg agggctgcgg gcagggctga aggggtgcg tgcatttggg ctcagttttc      240
ctttggcctc caggttgtca gtggccgtag tgggagggcg gctgccggcg cccctgcccg     300
tttcccaccc gcgggtggcc ggacgcggtg ccgcctcctc ccgctcgtga gggcgtgacc     360
cggggagggg ggcgcaggct cccctgcga ccgcccctc acacacgcgc tcggccgccg       420
gagctgtcac cggccaccca gggcccgggg aggggggcgcg gagagtggcg ctgcggagcg    480
gcgggcgcgg gatcctcctg ccggacttcc cggctcccag ggacgccgct gtcaacgccg    540
agcggacgcg cagccccggg agaggggccc gccagaggcc cggccgccgc cgctgggggc    600
gggcgggtgc ccgcgtcccc ctctgcgcga tttggcgccg ctgcctcgcc gcctcttgta     660
gggtaacagc actattgctc tacccaccgt cagcagggcg actgccactg ccgggattat     720
```

```
catcctctcc atcctcaccg ccgatcagcc aatattggac ttgctggtgg cggcggcagc    780
agcggcggcg ggagtctagc cgttcccctt cccccgcccc agcctcccca ccatgtccta    840
gaaaaggtga gtgcagcgac agtcactttg cgctgacagc ggcgagaggg ggtccggaga    900 gcgcagggc ggccccgggc aaggcaggtt gcgcgcccag ggcagagggc gcgggttggc    960
gagcggaggt gggatgcggg caggagacga gttgcccgct ggcggccctg gggcaagggt   1020
gctgggtggc gggcgagtga tcgcggcggc tgcccctgca cggttctaac ctagattttg   1080
caagaagctg agatccaggg caagaccggc cctcctcaaa ggagataaaa acttagtaaa   1140
agagacacgt ccattccttt aataatgaat aattcggcaa cgcttgcgga gccgccgccg   1200
cctcgcgtgc ccaggctcta ggtccgggac tccccttgct cccgcccgcc gcccgcgctc   1260
tgccgacgtg agatcgatgc ccagttcgct gggccgggag agtgcgcgtg acggtgggcc   1320
ccgcgggaaa gttgggacgc tcggcgggga ctcctggctg cggggacgcc ggggggcagct  1380 ccaagctggg gaccgagggg cattagagtc tggggtcagg accagctcgc ggcgctgccg   1440
ctgtcgcccc tatctccagg gagttcctga ctggagcggc tgagagttca agtctcagcc   1500
ctgggttagg ggtccggaat cccggagctt aactaactgt taaggagagg aggggccttt   1560
gggcacaggg tgtcccccgg tccccgcct cgggctttgg cgggcgcgaa gcgagggtga    1620
ggcgggaggc cgcacagctg ccgccgccgg gctgcgggtc ccgagggcc ggggaccag     1680 atttaggtgt atacgtcact gatgctgact ccggccagc ggggagccta aaacggggcc    1740
ttacatgaga agcctaaaag tccttagaaa tcaaagttag gaaccccatc cttttgctta   1800
gtaactgcag catttgggtg ggcgggagga gaatcgagga ggggcggtt ggagggaaac    1860 cgaaatttct tcatgcagac aaccgatcct tagaaaacag tttggttcct tccccctcc    1920 tgtctgtttc tcccacttat gtgacccacc cctccaccc attataacgt gaatatcctc    1980
gatggtaagc ttgctttcaa attgaactag tggaaaaatc caatactaaa gtagtaagta   2040
cagtgacaaa attataagga agtagaggag cagctcttga ccctgccact tctttcattt   2100
atctttctct ctctctcttt tttttttttt tttttttttt tttttttttg gtgttagggg   2160
tctaagggat gggaggaaag ctgtgtttaa agggttttc cagcacggtt aaaacaacta    2220
aattcaaatc gagtgaacgt gatcgtcttg ctcgctggca gcgaaggctg ctgctgctct   2280
gctgagaggt aactctggag acagtggaaa ggggctggga gaggaacctc gagggtcggg   2340
tgaagcccac ccagagtcct ccccgcgcgc ggacgctgtt gggcggcgcc agggtctggg   2400
ctgcagctca cctggagctg caggtggaga gcgtgagggg acgacacttt gctcgcggaa   2460
aaaccgactt cttccgcgtc agcacacttt tcacatctct ccagatatcc tggggtcggt   2520
cagaaggaga gcagggtgga cgtaagcaag tttgggcgg ccgagcgatg ggggtggggg    2580
cagcgtgcgg aggccgcctg atgtagccac cgcccggcac cccaagctcc cgccgcggct   2640
gcggctttaa ggaagctgcc gagtccaggc tgtgtcgcag caactttgta tcagtcatgt   2700
cgcccgcctg gtgactgaca gcctggattg tccaataaga agcccgcctg acccgtgcgg   2760
cgtggagcct tgcttctctt cgggccaata ggaagggttc agggggggcgg gatagcaacc   2820 tgaactttat ctggacatgt gacccgcttt taaaagggcc agcctccag ctggcccact     2880 ccccctccgg gctttcgccc gccctctctc cctcccttt tgcccgccc tggccctgcc     2940 cctgcccctg ccccctcctc tcagcccctc cgcgcccggg gtgtcattgg gcccgggaga   3000
cgggagccaa cttcaggctg ctcagaggaa gcccgtgcag tcagtcacct gggtgcaaga   3060
gcgttgctgc ctcgggctct cccgctgcag ggagagcggc actcgctggc ctggatgtgg   3120
```

```
ttggatttag gggggctccg cagcagggt ttcgtggcgg tggcaagcgc tgcaacaggt      3180
agacggcgag agacggaccc cggccgaggc aggtgtgtag gggcgcgcgg cggggcaccg      3240
cttgccgtgc tcggcgtgcg gccgcggcgc gggagcgtgc actttgcagg gagaagtggc      3300
tgcgtaatcc ggaggcacag tcagtatggt gctgtgtgct tgttgttttg ttttggtttt      3360
ccacttttct ccccctttgg ccgccagagg actattttgg gaaagtttgg ccactttgga      3420
taaatgccct ctaactagca gcttttaact gcctttggca gtgggaggtc taccacccttt     3480
cccttttaccc aaagatgaat ttcggatcat tttccctgta caatttttaa aggacgtttg     3540
aataatattt cttccttta tcaattgcgg acgctcccaa atctcagccg gaggtgtagc       3600
gcataagggc agttgaagga gatatagatc ctaatagatc ctgtataaaa ggggctctgg     3660
aaattcgtgc atttcccgtt cgctagcatt cgcgaaactc ttgagacagg ctacgcttcc     3720
tatggcatca gttggaattt taagggcaag ggagaagggg acgaagcttc ttttggtggc      3780
atccttactc tgctactgaa ttttaggtgc gtggctttgc ctactcaatt taaaaagacc       3840
aggtttaaat aataatggtt tatggcacca tcagttttaa ttatttatta tgacatagga      3900
gttaggaaaa cttttgatag cagacgagct tttgaaaccg ccgaattta aaggcaccaa        3960
attgcttcct aacattttgt attgccattt ctctaggtgc tgttattgat gatatttaca       4020
tagtaatgat aacagcattc tccatctgtg aagtcctgct gtgaagttta aattttatgt       4080
ttgacatcgt ggcagctatc atggaaaagc ttgagaggag aagttttaaa aataatttta      4140
aagtggagct ttttccttta agggaggcat agttttgttt ggcgattttt ggaaagatca      4200
ggtggctcgg taaattaggt gagtgaatag aaatcaggtg tgctcagttc taactggttc      4260
tcccgctctc tcaggtgacc ttgggcagat ttctatcatt tacctcatct ataaaagaga      4320
ggaacataat agttatgtag tggggaatga caaaaaatag ttacatatag tgaacttta       4380
caactatgca gtctatagat gattgtgaga ttcttaagct ttagtcttta aagtgccatc      4440
ttatagtcaa ataaatataa aaaagatgcc ttttctatca tttccatcat gatgagattg      4500
ggttttgggg gttactaaaa gtgaaagtgt ttccagataa aatacaaatt cgcaaggatc      4560
tttgttaata ttcccgaaaa aagtacttct ttatggaaaa gggcaattta acacagactg      4620
taaaacgtaa aacttaagg tttttccttg tgaaaacagc atttcttttg tgtttgagag       4680
catatgtatg gcttaaagta gcacctccac cagtgctttt cctttagtga attttttttt      4740
gtgttttggg gcgaggccca tttgcatgaa aattaaaagt tcataatgtt ttttgcattt      4800
gtcctaagag aatctttggt atggtttcca ttgtgaggca ggcaagcctg attttgtta       4860
gttagatttg tatacctcta tctgcttcat tttatacttt agtaacataa acttttctt       4920
tatcctctag atattaagtt ctatgaggat catattcatc gactagtatt ttcagtattc      4980
actagttagt acaggttgac tgaaattctg ctcaagccat ggtcattgtg ccagttgcaa      5040
aaagataacc tctgcttcct ggatgacata gtaaataaat tcctaactgg acccatttgt      5100
ttacagaaaa gactaattaa aatactaggg agactcaaaa tatttcaata atgctatttg     5160
aaaaatatct gatcttaaaa aaatgttgt gtagaagccg tgcagatgct agatgtcttg      5220
tattcttttg tgtttgacta ttgccaatct gtattgtttc ctttgttgag aggtgcatta      5280
ggttggtaga tgagaatacc ttaaacaaag taatttagat ttcagcaaag ccttttgcaa      5340
attccttaat gagactcctg tcaataatgt ggtgaaacac agcctatttt atgttattaa      5400
gggagttcaa ggttagccaa acaggacttg gaaagttgtg atcagctgta tgatgttagc      5460
```

```
tggtaaggtg ctaccttgtc cagggcttta agactgtctt tggtacccat catctccagt    5520
atagattctc ttcaggtctt ccgtagcctc acaaatgtgg gatatggttc ttgctttagg    5580
gcagagtgcc gaaaagtgca gaatcttagt agatgttctt tgagaaaaag gtggagtggt    5640
caaattattt gaggaatgct ggattaaaaa gtaaacagaa tctcccagag gttttgatat    5700
gcaaatttat ataggaaatt ttcaaaaaag ccaagagtgg accgcccttc ccaaaagaca    5760
atttggagaa tgggttttgg agaggggtct gggtggggt ccccttcaga cacgggacag     5820
agagccctct tgactatgac caggaagaga atgaggctat gtgagtgacg cagagtgtgc    5880
cagtgaaggc cttcaggtaa agctgttgag acaagagtaa cttccaggca tctggttaga    5940
tggtggtgca gtttgccaag agagcgaatg tgaatttggg ggtgtgtggg gggagagatg    6000
tgcagaaagt gttcagtttt gaatacaaat agacatattt attgtgttgt ttaatggatt    6060
tggatctgaa ccatttatac cttagctata tagtaattta tctttagtat ggggaagaca    6120
aaatattctt aggtagaaat agaagcagca tataatattt actgctattt ttcaatacat    6180
agctatgact aaatggtttt ttagtaaagc ataaaaggcc agtcttagct atttggatcc    6240
caattcactg ttttttagtt tagttttcta tcagctttta cttggctttc atccacacca    6300
aacattttgg ctgaattac tattaataga taactacctc aacctttgta atttatttta     6360
ttttctactg ttttgtgatt gattttttgat taggaattca taggatgttc tttaagtgaa   6420
aacatactac ataattggta gatttttaatg tttggaaatt gagcattgat attataatag   6480
ttgaaaattt tttcaatgta tccacttggg atactgtagt gaaattgatc atttctgccc    6540
tttgagaagg taaactctag tgtaaaaaca cagaaaagta agaggtaatt ataatacttg    6600
gacaatttgg acattaaatt tcttcatagg gctttgtgct atctaatgca aatttattta    6660
tgagtccagc taagattttat ctaatgcaaa tttatttagt agcattattt ttcaatgtta   6720
atacatattc tgtaacaaaa ggacttcgtg ttttttgttt ttttttaaat gaagggaagg    6780
taggcagggt ggagatagtg acaaagaggg gaaaggatga gaggccaaaa ataaaacttg    6840
tgtatagaat ggcagaaaca gcatcttta gatcaggact ttttttgggc catagattgt     6900
ttacagactt tgaaatgttt gaaaaatgca taatacagat tttaggagtt ttaaaatact    6960
aaaatgtaaa aataaaattt tactgtgagt gagttaattt cctttaagat atgtttcttt    7020
acagtggtgg ttgtcagcca agggtgattt tgccccccat gggcatttgg taatgtctgg    7080
agacattttc agttgtcaca actggggagg tggaatgcta ctggcatcta gtgggtaggg    7140
gttagggata ctgctaaacg ccttagcaat gcattattga cctccacaac taagaattat    7200
caggcccaaa atgtcaatgt gccaagattg agaaactgta tagagagaga cttgcgatca    7260
aattgcagct ccaacacttg gttgtgtgtc tggtgcctca gttttcacac ttgtattatt    7320
tggataatac ttttatcagt cattcagggt tgtgtgtaag gataaatgaa ttaatatatg    7380
caagaagctt gcaatactgc attaaattat atgggtaaga attatatcaa tatagcctat    7440
tatgaagatt ctgtctgtga agtaaattga tctatagagc gcatggatat ggttatatat    7500
ctgaaacaac ctggtgggtt gcttgaggat ggggattgtg tctcttttgt ttatcactgc    7560
ctgttcactg actggtctaa ggccaagggt gtagcaggca cttggtaaat attgttgaat    7620
gaatgaatga atgcttaaat tttcggggct cctctcaaaa gtcaccattt accattgaga    7680
gtaaacattt ctggttgttg gcagtcgttc tagcagaggt accactggta ccatgcacag    7740
gtcagggtgc atgtcaaagt ccttgccagt actgaaatac agagaagaca ccagtcattc    7800
ctgaattgtc atacagccct tctgagatat ggaccatctt tatcagaatg tatagatctt    7860
```

| | |
|---|---|
| ttcagaactg acattaaatt atcttcatca ctaatctaaa gagagtctta ctttttaaaaa | 7920 |
| aatcaaaaat tattttttcct atgataattc acttggtatg tttatgtttg gaaagagtaa | 7980 |
| ctttaattac atttccatat tgttttttaac aaggccatga attaaatatg gaaggcagct | 8040 |
| tctatatgat ccaaagactc caaaggcatt ggagtcaaaa gatttagatt taaacccaac | 8100 |
| tttgtcacca tgtctttgac tttgggcaag ccacccactt cactaagtcc tcagttacct | 8160 |
| ttttttgcct gccttaataa ttcccaggat tactttgaat atctaataag ttaacatttg | 8220 |
| taaatatttt ttgcagactc taaagactgt attatagcaa acatgttact tttatttaga | 8280 |
| tccaaaacag ttttatatga tcgcttctct tgttctgaca tctcgacaag ctgtagtcaa | 8340 |
| tactctgtta tgtcagcatc caaaaggta acagttttaa attagctaga aatgttgctc | 8400 |
| ataataagta gaatatgttt tgtggcttag caaatgcaat tttagaatgt cttttagagt | 8460 |
| aatattgcta taactgactc taatttttta atgtaaattt atttgttagc gatggagacc | 8520 |
| aaaggctacc acagtctccc tgaaggtcta gatatggaaa gacggtgggg tcaagtttct | 8580 |
| caggctgtgg agcgttcttc cctgggacct acagagagga ccgatgagaa taactacatg | 8640 |
| gagattgtca acgtaagctg tgtttccggt gctattccaa acaacagtac tcaaggaagc | 8700 |
| agcaaagaaa aacaagaact actcccttgc cttcagcaag acaataatcg gcctgggatt | 8760 |
| ttaacatctg atattaaaac tgagctggaa tctaaggaac tttcagcaac tgtagctgag | 8820 |
| tccatgggtt tatatatgga ttctgtaaga gatgctgact attcctatga gcagcagaac | 8880 |
| caacaaggaa gcatgagtcc agctaagatt tatcagaatg ttgaacagct ggtgaaattt | 8940 |
| tacaaaggaa atggccatcg tccttccact ctaagttgtg tgaacacgcc cttgagatca | 9000 |
| tttatgtctg actctgggag ctccgtgaat ggtggcgtca tgcgcgccgt tgttaaaagc | 9060 |
| cctatcatgt gtcatgagaa aagcccgtct gtttgcagcc ctctgaacat gacatcttcg | 9120 |
| gtttgcagcc ctgctggaat caactctgtg tcctccacca cagccagctt tggcagtttt | 9180 |
| ccagtgcaca gcccaatcac ccagggaact cctctgacat gctcccctaa tgttgaaaat | 9240 |
| cgaggctcca ggtcgcacag ccctgcacat gctagcaatg tgggctctcc tctctcaagt | 9300 |
| ccgttaagta gcatgaaatc ctcaatttcc agccctccaa gtcactgcag tgtaaaatct | 9360 |
| ccagtctcca gtcccaataa tgtcactctg agatcctctg tgtctagccc tgcaaatatt | 9420 |
| aacaactcaa ggtgctctgt ttccagcccct tcgaacacta ataacagatc cacgctttcc | 9480 |
| agtccggcag ccagtactgt gggatctatc tgtagccctg taaacaatgc cttcagctac | 9540 |
| actgcttctg gcacctctgc tggatccagt acattgcggg atgtggttcc cagtccagac | 9600 |
| acgcaggaga aaggtgctca agaggtccct tttcctaaga ctgaggaagt agagagtgcc | 9660 |
| atctcaaatg gtgtgactgg ccagcttaat attgtccagt acataaaacc agaaccagat | 9720 |
| ggagcttttta gcagctcatg tctaggagga aatagcaaaa taaattcgga ttcttcattc | 9780 |
| tcagtaccaa taaagcaaga atcaaccaag cattcatgtt caggcacctc ttttaaaggg | 9840 |
| aatccaacag taaacccgtt tccatttatg gatggctcgt attttttcctt tatggatgat | 9900 |
| aaagactatt attccctatc aggaatttta ggaccacctg tgcccggctt tgatggtaac | 9960 |
| tgtgaaggca gcggattccc agtgggtatt aaacaagaac cagatgatgg gagctattac | 10020 |
| ccagaggcca gcatcccttc ctctgctatt gttggggtga attcaggtgg acagtccttc | 10080 |
| cactacagga ttggtgctca aggtacaata tcttttatcac gatcggctag agaccaatct | 10140 |
| ttccaacacc tgagttcctt tcctcctgtc aatactttag tggagtcatg gaaatcacac | 10200 |

```
ggcgacctgt cgtctagaag aagtgatggg tatccggtct tagaatacat tccagaaaat   10260
gtatcaaggt aagttggttt tctccatttt tttggaagtc atggctttat acatgttgaa   10320
ggttagcatt atctttacag ttgataaatt taaacacatt tcagattact gttttaagga   10380
tggtcatatg ttgctccact ttgcatgttg atataatgtt atttttttga agtagaggga   10440
aaaagcattc ttaaaatgtc ttagaaaata tctgcattga ttttgaaggg gcatatgtag   10500
gtgtcccgca ctccccattt cctgttttag gtgttcggaa atttatgtt ttactgccag    10560 ttactattgt aaatacagta atttagcaga ccagtactag atttttttc ctttagctgt     10620 ttgccggttt actaaaattg ctttaagtta gtttatttgt ggtcttagtc ctttttttta    10680
ttatggcttt ctttattaat catcacttca tcggttgtga aagctaaaat tgaatcctgt   10740
atctgttacc cacaggcttc cctcccttct gcccttttct aagtaggtta attatatgaa   10800
agttgtggtt tttcaataca aataaatcat ttccttaact gttgagagct tttaaagact   10860
cagcatatct aaaattacta agtggacaat cttgctttct tacttatatt ggaagtgaaa   10920
tatgtcactg cagttttgaa ttggtatatt tataactttt cagatctgca agaagacata   10980
ttttatttac tgtaaaatat ctcttggctt tccttgttgc agatagcatg ttgtatatat    11040
ttagaaaaaa caaggaagag gttttagata tgactataaa gggtggttct aagttataca   11100
gtgaatactt ggattggact ttgcttcagt actgttttta ttacatggtt gtgataaatt    11160
attcctttat ggactatata aagaatagat ttccttagta tagttcattc ctttggcatc    11220
cagaactatg tggatagttt cctttatttc attaaaaatt attttgtggg gaatatgtcc    11280
atcccattaa caggatatag ggtttacatg tattgctgtg gctttctctt attctatttt    11340
tttccaaacc aaaagcaaaa actttatgta ttcttcttat tgtcattgcc tcaaaccttg   11400
cttttcttgc ttatggaagc aaacatttca taaaggatac atttttatag tttccccaca    11460
gcatgaacta tttaatcata ttctgatgct gtctcttaaa ttataagttc taacacaagt   11520
catgagatag catggctgcc atcagaacca aattgagcat gtgttttact gctagtgctt   11580
tgctttactt ttagagaagg acttttttca tgtgttgtga atattttgt aaatgatgtt    11640 tttagtgagc tggtatgagg tagtatagcc tggtagttaa cagcataact ggttgaaatc    11700
ccaactctgc tacttaattg tttagttttc tcaactgtat aaggggatta aatagtaccc    11760
atctcaaagg tagttaagac aatttaaatg agataattta tgagaaatac tttgaattcc    11820
ttccagtatg ttagtatgca ttgtatatgt tttgctatta tgaaattgtt ttataatttt    11880
tagttttcat attttagtt ttcttttct tcattgtatg aaattccaca gaatcttata       11940
aagaaatact taaatatttt aagcacttgt taaagtaaat atttgataat ctcttatgat    12000
taaactcata ttttaaaaat gattatgcac tataccttg ttattacagt tctatttatg     12060 ctttttatt tttgaaaact attgctttga gtaatgatgt ttctggtaga aatattacag     12120
atgcagtaag ctcaaatgat tgtctcttat gttgttccta tatccctatt tctactatt     12180 taaatgtagt tttcatgctc cactcaagaa gccctcctga tggtccaatg acccgtgcat   12240
agccttagac atgttagtat gaattagtga ccttgagcct atcctgcatt cataggcaca   12300
ggaagcattg tcttgtgtct cctcttgagt attccaaaat tccttatgta tttgttaata    12360
cagtcaacag ggattcattc tgcttatata catactagtt ttgtgccagc taaatttcct   12420
aaaaacttta aagctttaac gtgatttgat atctcttata gattaatgat tctttacagc   12480
ttttcttggt gaatactatc caaacctatt tgttttgatg attaccagag taaaagctca   12540
aggatcagag gaaatttagt tgttttttcta gagttcagtc tacatgttat aatatttaat   12600
```

```
ttaaccttgt ccaagtatca tccttagtct cttattttga acaaaaaacc caaccttttt   12660
gcctatttct taaaatatga tgataactca tttcagggaa tgttgaatag gttaatgaat   12720
taaatatcat aaaggatcaa ggcagtgtat actgcttcta ggtttaatag tatccttcat   12780
cattaggttg aaccttgaac tgcagtattt tctggtagat gtcaaatcat ggtttgaggg   12840
ttcctgagac cttttcaagg aagttcacac agtcagaaat catgctttgt taaaatatcc   12900
acccaaaatg aacacagat caatggattt tgatataatc ttgtatgaaa atttcactga    12960
tgttgtttca gattccacat tgaaactaac ctttaaggaa ctattcagtg ttattttca    13020 gtatagtatc aaagattcat atctacaatt atctgaaatg accattaaaa tattcttccc   13080 cttttcccaac aacatatcta tatgagatga gattttctct atgtacttga agaaaaacat  13140
agcaccacac gtagcaatga aaatccagca gtcttctatt aagtgtgaca gtagtcttgc   13200
aaaaatgtta aacagtgcca ctcttctcac taaggatttt tgtttgggga aatattgttt   13260
cataaacagt tttcatattg tttatgttaa tatgcaatca cttattttta aatgattta    13320 aaacatttgt tttaattttt aatttaaact aatttaatat tagtttaat tttaactta     13380 aataatttaa ttttagtttt aatttccaat acagtagcaa taactgtaac tcacataaac   13440
aaatgctctt tgggatcctt catactttt aagaatgaaa aggagttctg agatccagaa    13500
gctgagaact gctggtctgt tctcttctat acacgctttg gaggttaatg aagaaagaag   13560
acattacatt atttgtatta gtgttactga atattatttt gaggaaggag tgttctattc   13620
aaataggaaa aatgattctt gctcaggtta attttttaaa ctgacagaaa tgagtaatgg   13680
ctgtgaggtg tgtgttgtct ttatttcagt ctgtgggcat tcagtgagag tggtgacgaa   13740
agtcatctgt taataatttc cagtgaatgg attgtctgag caccaaattg taaagtaaat   13800
tatgacaaag ctaaatgtaa agcccttaga atggacgccg gacctagttg tgtcaggtgg   13860
attagaactc ccctgtctgc ttggacatca acaaaaccgc tctgagcctc agtttcttca   13920 tttttaaagtg attaagttga actaatcatt ttgctgatca ctaatgtgcc ccaagagctg   13980
ccagtgtaat ttccttgaa gaatcaaaat agagtatcct ttaacatact tgctaattta    14040
gtttcaagta ttttgtatac tcaagtctag cttcatggtt ttcagggtag tctggggaga   14100
aaaatatcat ttccatttac cattttaaag taaaaatgag gaggggcgat ctatgatttt   14160
acttgaaaag aggagcagtt gtgttttttt aaaaccagat ttaaagaaaa aataaactct   14220
gaaacttact atgaattcct tgttcttctt atttatacaa ttcctcatgg aaacagggca   14280
tttctgttga cataacactg gctgtttatg gcgatagtca tagtcactt gatagcatca     14340 taacacaggg ctaacattga cttagacttt taaatgtaaa gtttactatt tcaagggca    14400 tattctggta ggttacaaga acagtaatta ggatttatct taatatgtgc tgatttttt    14460 tcacgataga atgaaacagt ttagtaaata acctatattt attcttttat ttttcaattg   14520
cccctgaagt ttccttgaaa ctcacattat atgacaaacc aaacatcaga attcggggag   14580
tttgtgacaa agtttgccct tttactaaac tttcaatata aacagttgag aaggaaatat   14640
ttccatgtaa tgcaatgtct gaaagaatgg tagggtgtgt gtctgagaga gagagagtgt   14700
attggtgctt actctaatac ataaatccat tacagcattg cttaggtcat ttgggaatga   14760
aaacatgtaa cttctcttta cttattattt gtctcataat attttgattt tgaaattgct   14820
aatgtaccta gaatttcacc aggtaaatat tttaaatatt tttgtaaatt attttaaaat   14880
gagagttgtt tctcctgata ttcattttc attcgcttat atttctggga agagtggtga   14940
```

-continued

```
taataaaaaa attaagtgtt ttataataca caaatcacta tgtacagtgt acttttgtga    15000
gtttcatttt taaacatcac aaatatcgta ggtttatatg tcagtatgtc tgcctcttat    15060
catctaaaat attggtttat tatttacatc atactttaaa aatgatgctg agataaaagc    15120
catggtttca gttagataac ctcaaattat tccacttaat gcaattttca taccggtgac    15180
atactacgga cttagacttt tgaatgtaaa gttcttacta tggagatatt acttatagat    15240
ttgatattcc atgttgcctt ttgcaatatt gaaattctag gtgtgtctga ccttttctgt    15300
ccttggaatg ttacagtaat agcagatgtt atattgatca ccactaattt aggagcaaca    15360
ctttgcttct cttcatactt tgatgtcatt atgttttttct gcaaagtagt actttttttct   15420 tcactttcag ctgttgcttt agttttgtac tgttcatttg ctgataaaaa tatacccccca   15480 ctgctaaata atatatcatt ttgtttcgtt tactaaaattc aaattgagag aaaaatatta    15540
gcttcttgat tacatttaaa tatagccatt aacttggata tctttgatga cattccaaca   15600
tttattaatg aaaaccgagg aaaaataaaa gcatgttaaa tggatagcgt cttcattta    15660 aacattaggg tctctggttt taaacttgtg aagtatagga tttgttttta gtttaagag    15720 ttttattttg ttccttatat agtaaggtgg tgatgaagtt aaaatgtaat tacatataag    15780
cacttgttaa tttatgctct agaaacttct ggatttatga ttgttagtgg tatggctaag   15840
gccaaaattt ttatgtagaa aagtggtgga aattgtttgt attttgtgct agaaatagaa    15900
aactgtagtt taaggaagga aacaggacaa aaaaaagtaa tttgaatgct taaaaagtta    15960 atacccttagg gagggagtat gagataaatag ctggccatct ggattcataa ctgtggctat   16020 gacttaatttt catttctgat gaatacttca ttggtatgta acgaatattc accttatata   16080
```

<210> SEQ ID NO 2
<211> LENGTH: 11
<212> TYPE: DNA
<213> ORGANISM: Homo sapiens

<400> SEQUENCE: 2
gagggtgtga c                                                          11

<210> SEQ ID NO 3
<211> LENGTH: 13
<212> TYPE: DNA
<213> ORGANISM: Homo sapiens

<400> SEQUENCE: 3
tgagggtgtg acc                                                        13

<210> SEQ ID NO 4
<211> LENGTH: 14
<212> TYPE: DNA
<213> ORGANISM: Homo sapiens

<400> SEQUENCE: 4
gtgagggtgt gacc                                                       14

<210> SEQ ID NO 5
<211> LENGTH: 16
<212> TYPE: DNA
<213> ORGANISM: Homo sapiens

<400> SEQUENCE: 5
cgtgagggtg tgaccc                                                     16

-continued

```
<210> SEQ ID NO 6
<211> LENGTH: 18
<212> TYPE: DNA
<213> ORGANISM: Homo sapiens

<400> SEQUENCE: 6
tcgtgagggt gtgacccg                                                  18

<210> SEQ ID NO 7
<211> LENGTH: 15
<212> TYPE: DNA
<213> ORGANISM: Rattus norvegicus

<400> SEQUENCE: 7
tgtacaggat gttct                                                     15

<210> SEQ ID NO 8
<211> LENGTH: 3195
<212> TYPE: DNA
<213> ORGANISM: Homo sapiens

<400> SEQUENCE: 8
cggcgagaga cggaccccgg ccgaggcagg gatggaaaga cggtggggtc aagtttctca      60
ggcgtggagc gttcttccct gggacctaca gagaggaccg atgagaataa ctacatggag     120
attgtcaacg taagctgtgt ttccggtgct attccaaaca cagtactca aggaagcagc      180 aaagaaaaac aagaactact cccttgcctt cagcaagaca ataatcggcc tgggatttta     240
acatctgata ttaaaactga gctggaatct aaggaacttt cagcaactgt agctgagtcc     300
atgggtttat atatggattc tgtaagagat gctgactatt cctatgagca gcagaaccaa     360
caaggaagca tgagtccagc taagatttat cagaatgttg aacagctggt gaaattttac     420
aaaggaaatg ccatcgtcc ttccactcta agttgtgtga cacgcccctt gagatcattt      480
atgtctgact ctgggagctc cgtgaatggt ggcgtcatgc gcgccattgt taaaagccct     540
atcatgtgtc atgagaaaag cccgtctgtt tgcagccctc tgaacatgac atcttcggtt     600
tgcagccctg ctggaatcaa ctctgtgtcc tccaccacag ccagctttgg cagttttcca     660
gtgcacagcc caatcaccca gggaactcct ctgacatgct cccctaatgc tgaaaatcga     720
ggctccaggt cgcacagccc tgcacatgct agcaatgtgg gctctcctct ctcaagtccg     780
ttaagtagca tgaaatcctc aatttccagc cctccaagtc actgcagtgt aaaatctcca     840
gtctccagtc caataatgt cactctgaga tcctctgtgt ctagccctgc aaatattaac     900
aactcaaggt gctctgtttc agcccttcg aacactaata acagatccac gctttccagt     960
ccggcagcca gtactgtggg atctatctgt agccctgtaa acaatgcctt cagctacact    1020
gcttctggca cctctgctgg atccagtaca ttgcgggatg tggttcccag tccagacacg    1080
caggagaaag gtgctcaaga ggtcccttt cctaagactg aggaagtaga gagtgccatc    1140
tcaaatggtg tgactggcca gcttaatatt gtccagtaca taaaaccaga accagatgga    1200
gcttttagca gctcatgtct aggaggaaat agcaaaataa attcggattc ttcattctca    1260
gtaccaataa agcaagaatc aaccaagcat tcatgttcag gcacctcttt taagggaat    1320 ccaacagtaa acccgtttcc atttatggat ggctcgtatt tttccttat ggatgataaa    1380 gactattatt ccctatcagg aattttagga ccacctgtgc ccggctttga tggtaactgt    1440
gaaggcagcg gattcccagt gggtattaaa caagaaccag atgacgggag ctattaccca    1500
gaggccagca tcccttcctc tgctattgtt ggggtgaatt caggtggaca gtccttccac    1560
```

-continued

```
tacaggattg gtgctcaagg tacaatatct ttatcacgat cggctagaga ccaatctttc    1620
caacacctga gttcctttcc tcctgtcaat actttagtgg agtcatggaa atcacacggc    1680
gacctgtcgt ctagaagaag tgatgggtat ccggtcttag aatacattcc agaaaatgta    1740
tcaagctcta ctttacgaag tgtttctact ggatcttcaa gaccttcaaa aatatgtttg    1800
gtgtgtgggg atgaggcttc aggatgccat tatggggtag tcacctgtgg cagctgcaaa    1860
gttttcttca aaagagcagt ggaagggcaa cacaactatt tatgtgctgg aagaaatgat    1920
tgcatcattg ataagattcg acgaaagaat tgtcctgctt gcagacttca gaaatgtctt    1980
caagctggaa tgaatttagg agcacgaaag tcaagaagt tgggaaagtt aaaagggatt     2040
cacgaggagc agccacagca gcagcagccc ccaccccac ccccaccccc gcaaagccca     2100
gaggaaggga caacgtacat cgctcctgca aagaacccct cggtcaacac agcactggtt    2160
cctcagctct ccacaatctc acgagcgctc acccttccc ccgttatggt ccttgaaaac     2220
attgaacctg aaattgtata tgcaggctat gacagctcaa aaccagatac agccgaaaat    2280
ctgctctcca cgctcaaccg cttagcaggc aaacagatga tccaagtcgt gaagtgggca    2340
aaggtacttc caggatttaa aaacttgcct cttgaggacc aaattacccct aatccagtat   2400
tcttggatgt gtctatcatc atttgccttg agctggagat cgtacaaaca tacgaacagc    2460
caatttctct attttgcacc agacctagtc tttaatgaag agaagatgca tcagtctgcc    2520
atgtatgaac tatgccaggg gatgcaccaa atcagccttc agttcgttcg actgcagctc    2580
acctttgaag aatacaccat catgaaagtt ttgctgctac taagcacaat tccaaaggat    2640
ggcctcaaaa gccaggctgc atttgaagaa atgaggacaa attacatcaa gaactgaggg    2700
aagatggtaa ctaagtgtcc caacaattct gggcagagct ggcagaggtt ctaccaactg    2760
accaagctgc tggactccat gcatgacctg gtgagcgacc tgctggaatt ctgcttctac    2820
accttccgag agtcccatgc gctgaaggta gagttccccg caatgctggt ggagatcatc    2880
agcgaccagc tgcccaaggt ggagtcgggg aacgccaagc cgctctactt ccaccggaag    2940
tgactgcccg ctgcccagaa gaactttgcc ttaagtttcc ctgtgttgtt ccacacccag    3000
aaggacccaa gaaaacctgt ttttaacatg tgatggttga ttcacacttg ttcaacagtt    3060
tctcaagttt aaagtcatgt cagaggtttg gagccgggaa agctgttttt ccgtggattt    3120
ggcgagacca gagcagtctg aaggattccc cacctccaat cccccagcgc ttagaaacat    3180
gttcctgttc ctcgg                                                    3195
```

<210> SEQ ID NO 9
<211> LENGTH: 660
<212> TYPE: PRT
<213> ORGANISM: Homo sapiens
<220> FEATURE:
<221> NAME/KEY: SITE
<222> LOCATION: (180)..(180)
<223> OTHER INFORMATION: Isoleucine is replaced with Valine

<400> SEQUENCE: 9

```
Met Glu Thr Lys Gly Tyr His Ser Leu Pro Glu Gly Leu Asp Met Glu
1               5                   10                  15

Arg Arg Trp Gly Gln Val Ser Gln Ala Val Glu Arg Ser Ser Leu Gly
            20                  25                  30

Pro Thr Glu Arg Thr Asp Glu Asn Asn Tyr Met Glu Ile Val Asn Val
        35                  40                  45

Ser Cys Val Ser Gly Ala Ile Pro Asn Asn Ser Thr Gln Gly Ser Ser
    50                  55                  60
```

```
Lys Glu Lys Gln Glu Leu Leu Pro Cys Leu Gln Gln Asp Asn Asn Arg
 65                  70                  75                  80

Pro Gly Ile Leu Thr Ser Asp Ile Lys Thr Glu Leu Glu Ser Lys Glu
                 85                  90                  95

Leu Ser Ala Thr Val Ala Glu Ser Met Gly Leu Tyr Met Asp Ser Val
            100                 105                 110

Arg Asp Ala Asp Tyr Ser Tyr Glu Gln Gln Asn Gln Gln Gly Ser Met
        115                 120                 125

Ser Pro Ala Lys Ile Tyr Gln Asn Val Glu Gln Leu Val Lys Phe Tyr
    130                 135                 140

Lys Gly Asn Gly His Arg Pro Ser Thr Leu Ser Cys Val Asn Thr Pro
145                 150                 155                 160

Leu Arg Ser Phe Met Ser Asp Ser Gly Ser Ser Val Asn Gly Gly Val
                165                 170                 175

Met Arg Ala Ile Val Lys Ser Pro Ile Met Cys His Glu Lys Ser Pro
            180                 185                 190

Ser Val Cys Ser Pro Leu Asn Met Thr Ser Ser Val Cys Ser Pro Ala
        195                 200                 205

Gly Ile Asn Ser Val Ser Thr Thr Ala Ser Phe Gly Ser Phe Pro
    210                 215                 220

Val His Ser Pro Ile Thr Gln Gly Thr Pro Leu Thr Cys Ser Pro Asn
225                 230                 235                 240

Ala Glu Asn Arg Gly Ser Arg Ser His Ser Pro Ala His Ala Ser Asn
                245                 250                 255

Val Gly Ser Pro Leu Ser Ser Pro Leu Ser Ser Met Lys Ser Ser Ile
            260                 265                 270

Ser Ser Pro Pro Ser His Cys Ser Val Lys Ser Pro Val Ser Ser Pro
        275                 280                 285

Asn Asn Val Thr Leu Arg Ser Ser Val Ser Ser Pro Ala Asn Ile Asn
290                 295                 300

Asn Ser Arg Cys Ser Val Ser Ser Pro Ser Asn Thr Asn Asn Arg Ser
305                 310                 315                 320

Thr Leu Ser Ser Pro Ala Ala Ser Thr Val Gly Ser Ile Cys Ser Pro
                325                 330                 335

Val Asn Asn Ala Phe Ser Tyr Thr Ala Ser Gly Thr Ser Ala Gly Ser
            340                 345                 350

Ser Thr Leu Arg Asp Val Val Pro Ser Pro Asp Thr Gln Glu Lys Gly
        355                 360                 365

Ala Gln Glu Val Pro Phe Pro Lys Thr Glu Glu Val Glu Ser Ala Ile
    370                 375                 380

Ser Asn Gly Val Thr Gly Gln Leu Asn Ile Val Gln Tyr Ile Lys Pro
385                 390                 395                 400

Glu Pro Asp Gly Ala Phe Ser Ser Cys Leu Gly Gly Asn Ser Lys
                405                 410                 415

Ile Asn Ser Asp Ser Ser Phe Ser Val Pro Ile Lys Gln Glu Ser Thr
            420                 425                 430

Lys His Ser Cys Ser Gly Thr Ser Phe Lys Gly Asn Pro Thr Val Asn
        435                 440                 445

Pro Phe Pro Phe Met Asp Gly Ser Tyr Phe Ser Phe Met Asp Asp Lys
    450                 455                 460

Asp Tyr Tyr Ser Leu Ser Gly Ile Leu Gly Pro Pro Val Pro Gly Phe
465                 470                 475                 480
```

Asp Gly Asn Cys Glu Gly Ser Gly Phe Pro Val Gly Ile Lys Gln Glu
                485                 490                 495

Pro Asp Asp Gly Ser Tyr Tyr Pro Glu Ala Ser Ile Pro Ser Ser Ala
            500                 505                 510

Ile Val Gly Val Asn Ser Gly Gly Gln Ser Phe His Tyr Arg Ile Gly
        515                 520                 525

Ala Gln Gly Thr Ile Ser Leu Ser Arg Ser Ala Arg Asp Gln Ser Phe
    530                 535                 540

Gln His Leu Ser Ser Phe Pro Pro Val Asn Thr Leu Val Glu Ser Trp
545                 550                 555                 560

Lys Ser His Gly Asp Leu Ser Ser Arg Arg Ser Asp Gly Tyr Pro Val
                565                 570                 575

Leu Glu Tyr Ile Pro Glu Asn Val Ser Ser Ser Thr Leu Arg Ser Val
            580                 585                 590

Ser Thr Gly Ser Ser Arg Pro Ser Lys Ile Cys Leu Val Cys Gly Asp
        595                 600                 605

Glu Ala Ser Gly Cys His Tyr Gly Val Val Thr Cys Gly Ser Cys Lys
    610                 615                 620

Val Phe Phe Lys Arg Ala Val Glu Gly Gln His Asn Tyr Leu Cys Ala
625                 630                 635                 640

Gly Arg Asn Asp Cys Ile Ile Asp Lys Ile Arg Arg Lys Asn Cys Pro
                645                 650                 655

Ala Cys Arg Leu
            660

<210> SEQ ID NO 10
<211> LENGTH: 26
<212> TYPE: DNA
<213> ORGANISM: Artificial Sequence
<220> FEATURE:
<223> OTHER INFORMATION: Primer for mutating MR-2G/C (rs2070951)

<400> SEQUENCE: 10
ggccgaggca gcgatggaga ccaaag                                    26

<210> SEQ ID NO 11
<211> LENGTH: 26
<212> TYPE: DNA
<213> ORGANISM: Artificial Sequence
<220> FEATURE:
<223> OTHER INFORMATION: Primer for mutating MR-2G/C (rs2070951)

<400> SEQUENCE: 11
cgctgcctcg gccctttggt ctccat                                    26

<210> SEQ ID NO 12
<211> LENGTH: 33
<212> TYPE: DNA
<213> ORGANISM: Artificial Sequence
<220> FEATURE:
<223> OTHER INFORMATION: Primer for mutating MRI180V (rs5522)

<400> SEQUENCE: 12
ggcgtcatgc gcgccgttgt taaaagcccc tat                            33

<210> SEQ ID NO 13
<211> LENGTH: 32
<212> TYPE: DNA
<213> ORGANISM: Artificial Sequence
<220> FEATURE:
<223> OTHER INFORMATION: Primer for mutating MRI180V (rs5522)

```
<400> SEQUENCE: 13
atagggcttt taacaacggc gcgcatgacg cc                                    32
```

DISEASE SUSCEPTIBILITY

CROSS-REFERENCE TO RELATED APPLICATIONS

This application is a United States national stage of PCT Patent Application No. PCT/EP2010/006430, filed 21 Oct. 2010, which claims priority to Great Britain Patent Application No. GB1015071.2 filed Sep. 10, 2010 and European Patent Application No. EP09252465.1 filed Oct. 22, 2009, all of which are fully incorporated herein by reference to the extent not inconsistent herewith.

The present invention relates to a method of determining disease susceptibility. In particular, it relates to a method of determining susceptibility to an anxiety disorder or depression. It also relates to a method of selecting an agent that modulates an activity of the mineralocorticoid receptor.

Anxiety disorders are common psychiatric disorders which can be classified into the following categories: substance-induced anxiety disorder, generalised anxiety, panic disorder, acute stress disorder, post-traumatic stress disorder, adjustment disorder with anxious features, social phobia, obsessive-compulsive disorder and specific phobias (American Psychiatric Association. *Diagnostic and Statistical Manual of Mental Disorders*. 4th ed. Text Revision. Washington, D.C.: American Psychiatric Association; 2000). Generally, the disorders are chronic conditions which may be present from an early age or they may be initiated by a particular event. The disorders are often triggered by periods of high stress and are frequently accompanied by physiological symptoms such as headache, sweating, muscle spasms, palpitations and hypertension, which may lead to fatigue or even exhaustion.

Anxiety disorders are commonly comorbid with other mental health diseases. Of particular note, depression is believed to occur in as many as 60% of people with anxiety disorders (Cameron, 2007 Psychiatric Times 24(14)). Major depression is among the most important mental health problems and affects 1-3% of elderly people, whereas 8-25% have minor depression. Depressive symptoms are associated with future impairments in mobility and functioning, and with higher medical costs (Giltay et al, 2006 *J Aff Disord* 91: 45-52).

The impact of comorbid anxiety and depression is substantial. As demonstrated by the Global Burden of Disease study, neuropsychiatric disorders accounted for more than 13% of all medical disability worldwide and for more than 27% of all noncommunicable disease in 2005 (Cameron, 2007 Psychiatric Times 24(14)). Depression alone produced 10% to 12% of all disability from noncommunicable disease and approximately 5% of all disability (noncommunicable, communicable, injury). Thus, comorbid anxiety and depression may account for as much as 2% to 4% of all medical disability worldwide. In addition, depression (and, thus, comorbid depression and anxiety) is associated with other psychiatric and nonpsychiatric medical conditions (eg, cardiovascular disease, diabetes, HIV/AIDS, maternal and reproductive-related syndromes, and psychosomatic illnesses), with their resulting socioeconomic costs. Taken together, it is clearly important to establish risk factors of anxiety disorders and depression, and particularly ones which do not rely of the subjectiveness of questionnaire based diagnoses.

Further, many patients suffering from anxiety disorders and depression show insufficient treatment responses, and treatment efficacy among patients is very diverse. Moreover, serious side effects may occur before a treatment response observed, which may itself take months. Thus, there is also need for a biomarker that predicts treatment efficacy of anxiety disorders and depression.

Studies conducted by the present inventors have now identified particular variants in the mineralocorticoid receptor (MR) gene that may be used to predict susceptibility to an anxiety disorder or depression, and also treatment efficacy. In one study of 450 elderly subjects, the inventors demonstrated an association between each of five single nuclear polymorphisms (SNPs) in the MR gene, and dispositional optimism, a stable personality trait believed to confer resilience against depression (Plomin et al, 1992, *Person individ Diff* 13(8):921-930; and Giltay et al, 2006, *J Aff Disord* 91:45-52). An association between a haplotype comprising these SNPs and each of dispositional optimism and anxiety (Hospital anxiety and depression scale; HADS-A) was also found. In a second study of 154 students, the inventors correlated the presence of the same haplotype with reduced symptoms of depression.

The listing or discussion of an apparently prior-published document in this specification should not necessarily be taken as an acknowledgement that the document is part of the state of the art or is common general knowledge.

A first aspect of the invention provides a method of assessing the susceptibility of a subject to an anxiety disorder or depression, the method comprising genotyping any one or more single nucleotide polymorphisms (SNPs) selected from the group consisting of rs3216799, rs6814934, rs7658048, rs2070950 and rs2070951, and/or one or more polymorphic sites which are in linkage disequilibrium with any one or more SNPs selected from the group consisting of rs3216799, rs6814934, rs7658048, rs2070950 and rs2070951, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more '+CT', 'C', 'T', 'C' and 'C' alleles of the one or more SNPs.

By 'assessing the susceptibility of a subject to an anxiety disorder or depression' we include the meaning of assessing the risk of development of an anxiety disorder or depression in a subject. However, it will be appreciated that the method may also be useful in aiding diagnosis of an anxiety disorder or depression.

By 'anxiety disorder' we include any of substance-induced anxiety disorder, generalised anxiety, panic disorder, acute stress disorder, post-traumatic stress disorder, adjustment disorder with anxious features, social phobia, obsessive-compulsive disorder or specific phobias.

The SNPs rs3216799, rs6814934, rs7658048, rs2070950 and rs2070951 reside within the human mineralocorticoid receptor (MR) gene. The human MR gene is disclosed in GenBank Accession No NC_000004.11 and the sequence of a particular variant of the gene, the position of various SNPs including rs3216799, rs6814934, rs7658048, rs2070950 and rs2070951, and their possible alleles, are given in FIG. 4 (SEQ ID No: 1).

Preferably, one or more of rs3216799, rs6814934, rs7658048, rs2070950 and rs2070951 are genotyped, for example, two or more, three or more, four or more, or all five of rs3216799, rs6814934, rs7658048, rs2070950 and rs2070951 are genotyped.

In addition to rs3216799, rs6814934, rs7658048, rs2070950 and rs2070951 which the inventors have shown are individually associated with dispositional optimism, it will be appreciated that polymorphic sites in linkage disequilibrium with one or more of these SNPs are also useful in assessing the susceptibility of a subject to an anxiety disorder or depression. Thus, the invention includes genotyping one or more polymorphic sites which are in linkage disequilibrium with any one or more of rs3216799, rs6814934, rs7658048, rs2070950 and rs2070951, either instead of or in addition to genotyping one or more of rs3216799, rs6814934, rs7658048, rs2070950 and rs2070951. By 'polymorphic sites in linkage disequilibrium" we include one or more base pairs or other structural features of the nucleic acid (such as an insertion or deletion or repeat sequence) that are in linkage disequilibrium with any one or more of rs3216799, rs6814934, rs7658048, rs2070950 and rs2070951. Typically, the polymorphic sites are SNPs; however, they may be an insertion, a deletion, a microsatellite or an inversion or a combination of these. It is appreciated that the polymorphic sites disclosed herein may or may not be causative. Polymorphic sites which are not causative but which are in linkage disequilibrium with any one of more of rs3216799, rs6814934, rs7658048, rs2070950 and rs2070951 may be used as proxy markers.

In one embodiment, the one or more polymorphic sites in linkage disequilibrium with rs3216799, rs6814934, rs7658048, rs2070950 and rs2070951 are polymorphic sites within the MR gene itself or within the vicinity of the MR gene and form part of the promoter or regulatory architecture. Thus, it will be appreciated that the one or more polymorphic sites may correspond to polymorphic sites within the nucleotide sequence provided in FIG. 4 (SEQ ID No: 1).

Figure 2:
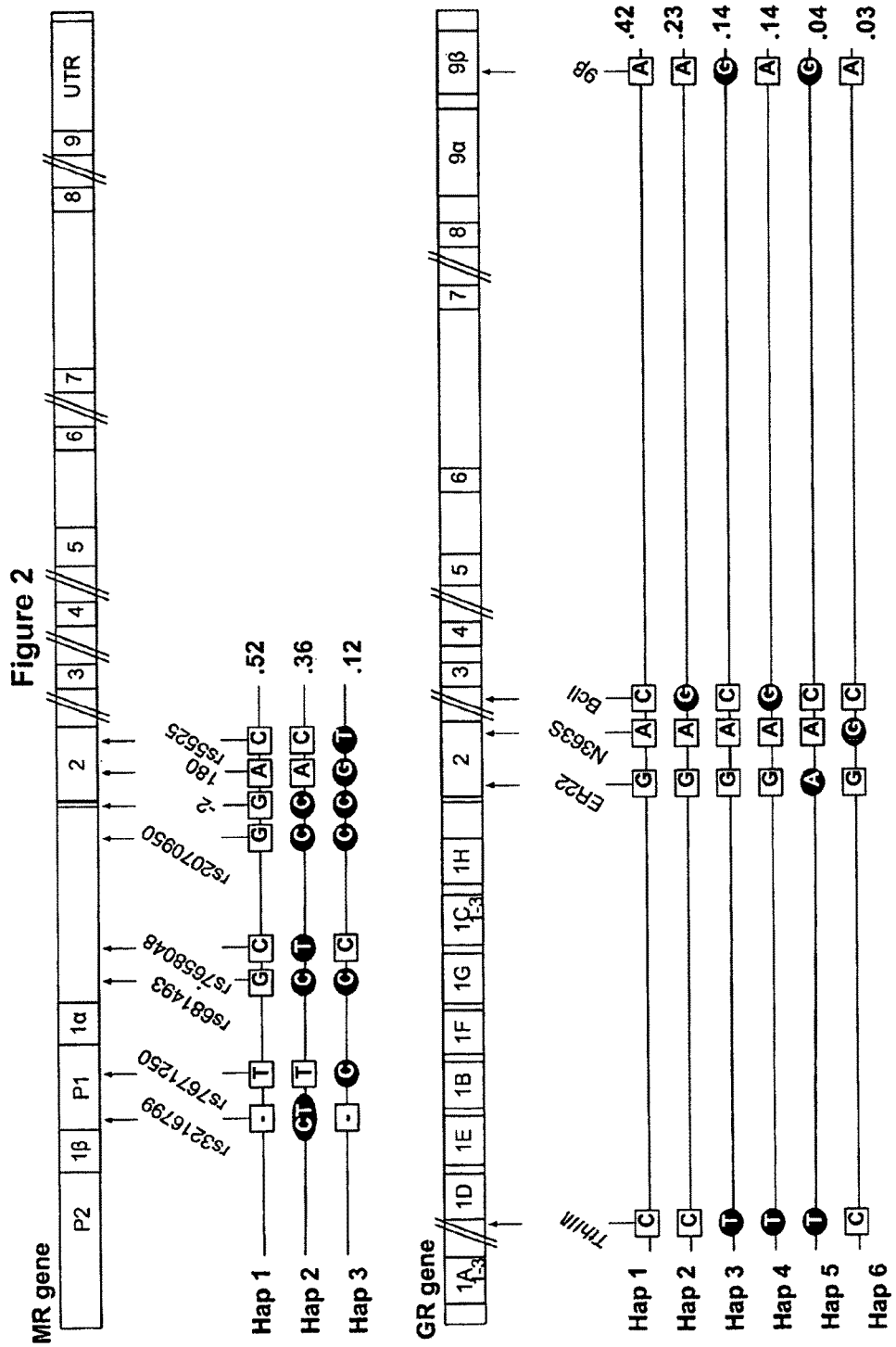

For example, the inventors have identified a haplotype comprising eight SNPs within the MR gene that is associated with dispositional optimism and reduced symptoms of depression (see haplotype 2 of MR gene in FIG. 2). The haplotype includes rs3216799, rs6814934, rs7658048, rs2070950 and rs2070951, as well as rs5522, rs5525 and rs7671250. Thus in a particular embodiment, the one or more polymorphic sites in linkage disequilibrium with rs3216799, rs6814934, rs7658048, rs2070950 and rs2070951 may be selected from the group consisting of rs5522, rs5525 and rs7671250 present on the same haplotype. Preferably one or more of rs3216799, rs6814934, rs7658048, rs2070950 and rs2070951 are genotyped, and one or more of rs5522, rs5525 and rs7671250 are genotyped, for example two or more, or all three of rs5522, rs5525 and rs7671250 may be genotyped. In an embodiment, all of rs3216799, rs6814934, rs7658048, rs2070950, rs2070951, rs5522, rs5525 and rs7671250 are genotyped. As seen in Example 1, the SNPs rs3216799, rs6814934, rs7658048, rs2070950, rs2070951, rs5522, rs5525 and rs7671250 with respective alleles '+CT', 'C', 'T', 'C', 'C', 'A', 'C' and 'T' reside together on haplotype 2 in the MR gene. Therefore, in an embodiment each of rs3216799, rs6814934, rs7658048, rs2070950, rs2070951, rs5522, rs5525 and rs7671250 are genotyped and reduced susceptibility is indicated when their respective alleles are '+CT', 'C', 'T', 'C', 'C', 'A', 'C' and 'T'.

Figure 5:
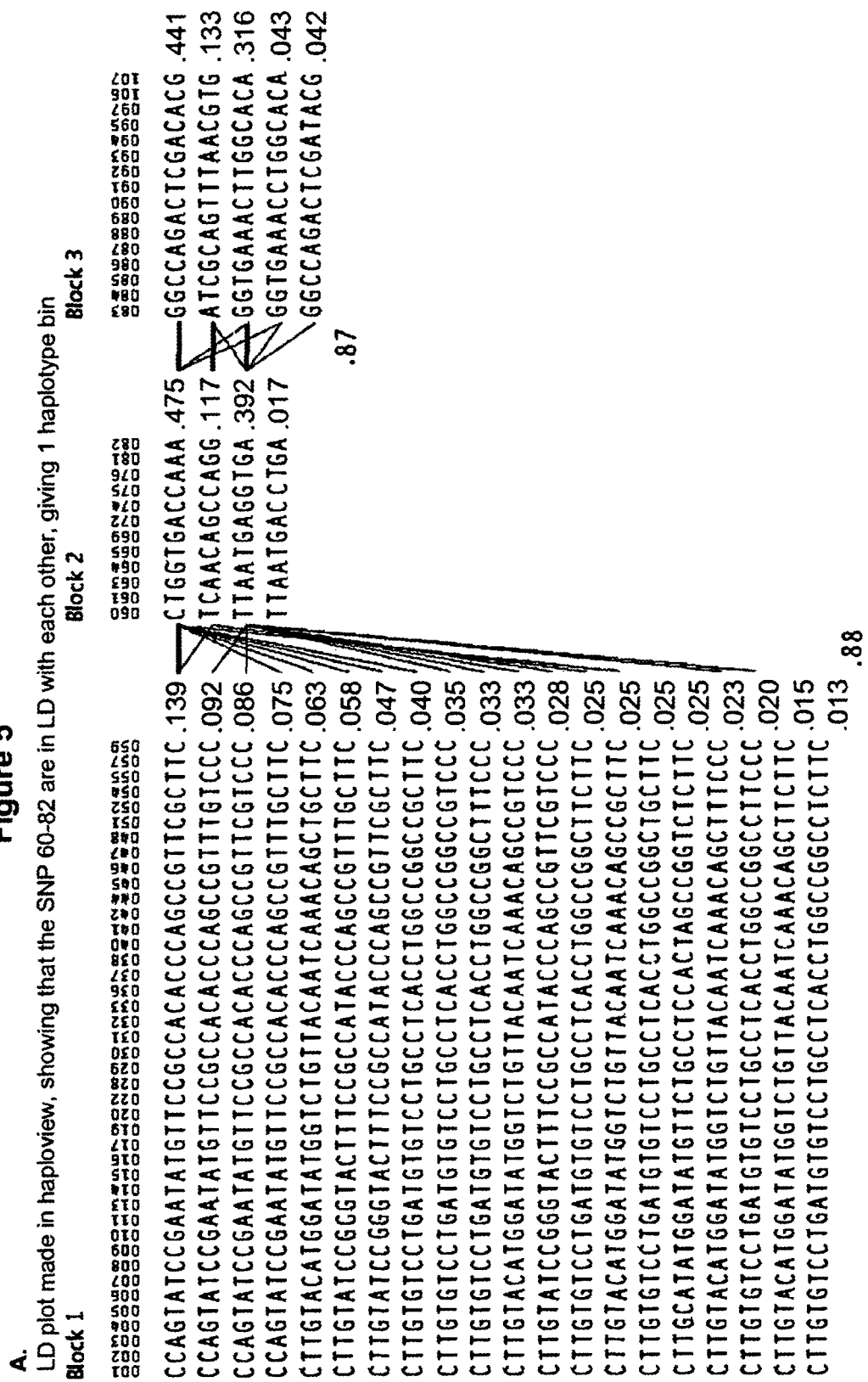

As illustrated in FIG. 5, the inventors have identified a further haplotype (haplotype 2A) that comprises the eight SNP alleles in haplotype 2 in addition to a further 10 SNPs. Haplotype 2A comprises rs3216799, rs6814934, rs7658048, rs2070950 and rs2070951, as well as rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4. Thus in a particular embodiment, the one or more polymorphic sites in linkage disequilibrium with rs3216799, rs6814934, rs7658048, rs2070950 and rs2070951 may be selected from the group consisting of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4 present on the same haplotype. Preferably one or more of rs3216799, rs6814934, rs7658048, rs2070950 and rs2070951 are genotyped, and one or more of (eg at least 2, 3, 4, 5, 6, 7, 8, 9, 10, 11 or 12 or more, or all 13 of) rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4 are genotyped. In an embodiment each of rs3216799, rs6814934, rs7658048, rs2070950, rs2070951, rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4 are genotyped and reduced susceptibility is indicated when their respective alleles are '+CT', 'C', 'T', 'C', 'C', 'A', 'C', 'T', 'A', 'T', 'T', 'T', 'A', 'T', 'C', 'C', 'A' and 'T'.

An analysis of the HapMap database (http://hapmap.ncbi.nlm.nih.gov/) by the inventors (see FIG. 5) has identified the following polymorphic sites as being in linkage disequilibrium with one or more of rs3216799, rs6814934, rs7658048, rs2070950 and rs2070951: rs4835519, rs2172002, rs11929719, rs11099695, rs11730626 and rs2070949. Further studies in other Dutch cohorts conducted by the inventors have also identified rs2248038, rs9992256, rs5520, and SNP x at position 149585620 in the MR gene as numbered in FIG. 4 as being linked to one or more of rs3216799, rs6814934, rs7658048, rs2070950 and rs2070951.

Accordingly, in another embodiment, the one or more polymorphic sites in linkage disequilibrium with any one or more of rs3216799, rs6814934, rs7658048, rs2070950 and rs2070951, may be selected from the group consisting of rs7671250, rs5522, rs5525, rs4835519, rs2172002, rs11929719, rs11099695, rs11730626, rs2070949, rs2248038, rs9992256, rs5520, and SNP x at position 149585620 in the MR gene as numbered in FIG. 4. For example, the one or more polymorphic sites may correspond to at least 2, 3, 4, 5, 6, 7, 8, 9, 10, 11, 12 or all, 13, of rs7671250, rs5522, rs5525, rs4835519, rs2172002, rs11929719, rs11099695, rs11730626, rs2070949, rs2248038, rs9992256, rs5520, and SNP x at position 149585620 in the MR gene as numbered in FIG. 4. It will be appreciated that any one or more of these polymorphic sites may be genotyped alone or in combination with any one or more of rs3216799, rs6814934, rs7658048, rs2070950 and rs2070951. When any of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4 are genotyped, reduced susceptibility is indicated when their respective alleles are 'A', 'C', 'T', 'A', 'T', 'T', 'A', 'T', 'C', 'C', 'A' and 'T', which are in linkage disequilibrium with the respective '+CT', 'C', 'T', 'C' and 'C' alleles of rs3216799, rs6814934, rs7658048, rs2070950 and rs2070951.

It will be appreciated that the one or more polymorphic sites in linkage disequilibrium with one or more of rs3216799, rs6814934, rs7658048, rs2070950 and rs2070951, may be within a genomic region encompassing the MR gene, rather than, or in addition to, being within the MR gene itself. Thus, in humans, where the MR gene resides on chromosome 4, the one or more polymorphic sites may be a site anywhere on chromosome 4 that is in linkage disequilibrium with one or more of rs3216799, rs6814934, rs7658048, rs2070950 and rs2070951. For example, the one or more polymorphic sites may be within 500 kb or within 100 kb or within 50 kb, or within 40 kb, or within 30 kb, or within 20 kb, or within 10 kb, or within 5 kb of the MR gene. This may be measured from the 5' end of the first exon of the gene going in the 5' direction and from the 3' end of the last exon in the gene going in the 3' direction. Variation may be found within the exons or within the introns or in regulatory regions of the genes such as the promoter region.

Further polymorphic sites that are in linkage disequilibrium with one or more of rs3216799, rs6814934, rs7658048, rs2070950 and rs2070951, or any other SNP, may be determined, for example, by using relevant data from linkage disequilibrium maps of the human genome (when the subject is human) which have been created using HapMap data (see Tapper et al (2005) *Proc. Natl. Acad. Sci. USA* 102, 11835-11839 for methodology).

The inventors have associated each of the respective '+CT', 'C', 'T', 'C' and 'C' alleles of rs3216799, rs6814934, rs7658048, rs2070950 and rs2070951 with dispositional optimism. Thus it will be appreciated that reduced susceptibility to an anxiety disorder or depression is indicated when the alleles of the one or more SNPs are identified as being respectively one or more of '+CT', 'C', 'T', 'C' and 'C'. Similarly, when genotyping one or more polymorphic sites in linkage disequilibrium with one or more of rs3216799, rs6814934, rs7658048, rs2070950 and rs2070951, it will be appreciated that reduced susceptibility to an anxiety disorder or depression is indicated when the alleles of the polymorphic sites are those which are in linkage disequilibrium with the '+CT', 'C', 'T', 'C' and 'C' alleles of respective SNPs rs3216799, rs6814934, rs7658048, rs2070950 and rs2070951. For example, when genotyping one or more of rs5522, rs5525 and rs7671250, reduced susceptibility is indicated when the allele is found to be respectively 'A', 'C' and 'T', which are in linkage disequilibrium with the '+CT', 'C', 'T', 'C' and 'C' alleles of respective SNPs rs3216799, rs6814934, rs7658048, rs2070950 and rs2070951, and which together form a haplotype. Similarly, when genotyping one or more of rs4835519, rs2172002, rs11929719, rs11099695, rs11730626, rs2070949, rs9992256, rs5520, rs2248038 and SNP x at position 149585620 in the MR gene as numbered in FIG. 4, reduced susceptibility is indicated when their respective alleles are 'A', 'T', 'T', 'T', 'A', 'T', 'C', 'C', 'A' and 'T', which are in linkage disequilibrium with the respective '+CT', 'C', 'T', 'C' and 'C' alleles of rs3216799, rs6814934, rs7658048, rs2070950 and rs2070951.

Although the inventors have found that rs3216799, rs6814934, rs7658048, rs2070950 and rs2070951 with respective alleles '+CT', 'C', 'T', 'C' and 'C' are individually associated with dispositional optimism, it is appreciated that SNP alleles generally occur in combination as haplotypes. Thus, in a particularly preferred embodiment, genotyping any one or more single nucleotide polymorphisms (SNPs) selected from the group consisting of rs3216799, rs6814934, rs7658048, rs2070950 and rs2070951, and/or one or more polymorphic sites which are in linkage disequilibrium with any one or more SNPs selected from the group consisting of rs3216799, rs6814934, rs7658048, rs2070950 and rs2070951, is used to determine whether the subject has a haplotype comprising rs3216799, rs6814934, rs7658048, rs2070950 and rs2070951 with respective alleles '+CT', 'C', 'T', 'C' and 'C'.

Accordingly, the invention provides a method of assessing the susceptibility of a subject to an anxiety disorder or depression, the method comprising determining whether the subject has a haplotype comprising rs3216799, rs6814934, rs7658048, rs2070950 and rs2070951 with respective alleles '+CT', 'C', 'T', 'C' and 'C', or a haplotype that is genetically equivalent thereto.

As discussed above and in Examples 1 and 2, the inventors have investigated associations between variants of the MR gene and each of dispositional optimism and depression. Haplotype reconstruction identified three main haplotypes shown in FIG. 2 (haplotypes 1, 2, and 3) with different allelic combinations of the same SNPs.

By 'haplotype 1' we include the meaning of a haplotype comprising SNPs rs3216799, rs6814934, rs7658048, rs2070950, rs2070951, rs5522, rs5525 and rs7671250 with respective alleles '−CT', 'G', 'C', 'G', 'G', 'A', 'C' and 'T'.

By 'haplotype 2' we include the meaning of a haplotype comprising SNPs rs3216799, rs6814934, rs7658048, rs2070950, rs2070951, rs5522, rs5525 and rs7671250 with respective alleles '+CT', 'C', 'T', 'C', 'C', 'A', 'C' and 'T'.

By 'haplotype 3' we include the meaning of a haplotype comprising SNPs rs3216799, rs6814934, rs7658048, rs2070950, rs2070951, rs5522, rs5525 and rs7671250 with respective alleles '−CT', 'C', 'C', 'C', 'C', 'G', 'T' and 'C'.

Haplotype 2 comprises rs3216799, rs6814934, rs7658048, rs2070950 and rs2070951 with respective alleles '+CT', 'C', 'T', 'C' and 'C', and the inventors have associated this haplotype with both dispositional optimism and reduced symptoms of depression. Thus, in a preferred embodiment, the haplotype comprising rs3216799, rs6814934, rs7658048, rs2070950 and rs2070951 with respective alleles '+CT', 'C', 'T', 'C' and 'C', is 'haplotype 2' comprising rs3216799, rs6814934, rs7658048, rs2070950, rs2070951, rs5522, rs5525 and rs7671250 with respective alleles '+CT', 'C', 'T', 'C', 'C', 'A', 'C' and 'T'. It will be appreciated that the presence of haplotype 2 in the DNA of a subject may be used as an indicator that the subject has reduced susceptibility to an anxiety disorder or depression.

It will be understood that one or more further polymorphic sites may be in linkage disequilibrium with the alleles of the SNPs in haplotypes 1, 2 or 3, and so one or more further polymorphic sites (eg SNPs) may reside on the same haplotype. For example, FIG. 5B shows that each of haplotypes 1, 2 and 3 defined above are part of haplotypes comprising further SNPs (giving rise to haplotypes 1A, 2A and 3A respectively).

By 'haplotype 1A', we include the meaning of a haplotype comprising SNPs rs9992256, SNP x at position 149585620 in the MR gene as numbered in FIG. 4, rs5520, rs3216799, rs2248038, rs7671250, rs6814934, rs7658048, rs2070949, rs2070950, rs2070951, rs5522, rs5525, rs17730626, rs11099695, rs11929719, rs2172002 and rs4835519 with respective alleles 'T', 'C', 'G', '−', 'A', 'T', 'G', 'C', 'A', 'G', 'G', 'A', 'C', 'A', 'C', 'C', 'T' and 'C' (see FIG. 5B).

By 'haplotype 2A', we include the meaning of a haplotype comprising SNPs rs9992256, SNP x at position 149585620 in the MR gene as numbered in FIG. 4, rs5520, rs3216799, rs2248038, rs7671250, rs6814934, rs7658048, rs2070949, rs2070950, rs2070951, rs5522, rs5525, rs17730626, rs11099695, rs11929719, rs2172002 and rs4835519 with respective alleles 'C'. 'T', 'C', '+CT', 'A', 'T', 'C', 'T', 'T', 'C', 'C', 'A', 'C', 'A', 'T', 'T', 'T' and 'A' (see FIG. 5B).

By 'haplotype 3A' we include the meaning of a haplotype comprising SNPs rs9992256, SNP x at position 149585620 in the MR gene as numbered in FIG. 4, rs5520, rs3216799, rs2248038, rs7671250, rs6814934, rs7658048, rs2070949, rs2070950, rs2070951, rs5522, rs5525, rs17730626, rs11099695, rs11929719, rs2172002 and rs4835519 with respective alleles 'C', 'C', 'G', '–', 'G', 'C', 'C', 'C', 'A', 'C', 'C', 'G', 'T', 'G', 'T', 'T', 'C' and 'A' (see FIG. 5B).

Haplotype 2A comprises rs3216799, rs6814934, rs7658048, rs2070950 and rs2070951 with respective alleles '+CT', 'C', 'T', 'C' and 'C', and so in a preferred embodiment, the haplotype comprising rs3216799, rs6814934, rs7658048, rs2070950 and rs2070951 with respective alleles '+CT', 'C', 'T', 'C' and 'C', is 'haplotype 2A' comprising SNPs rs9992256, SNP x at position 149585620 in the MR gene as numbered in FIG. 4, rs5520, rs3216799, rs2248038, rs7671250, rs6814934, rs7658048, rs2070949, rs2070950, rs2070951, rs5522, rs5525, rs17730626, rs11099695, rs11929719, rs2172002 and rs4835519 with respective alleles 'C', 'T', 'C', '+CT', 'A', 'T', 'C', 'T', 'T', 'C', 'C', 'A', 'C', 'A', 'T', 'T', 'T' and 'A'. It will be appreciated that the presence of haplotype 2A in the DNA of a subject may be used as an indicator that the subject has reduced susceptibility to an anxiety disorder or depression.

Since the inventors' haplotype reconstruction of the MR gene variants identified only three main haplotypes (eg haplotypes 1-3 or haplotypes 1A-3A), it is appreciated that the presence of 'haplotype 2' or 'haplotype 2A' may be determined by genotyping only two of the SNPs within the haplotype, for example, so as to distinguish 'haplotype 2' or 'haplotype 2A', from 'haplotype 1' or 'haplotype 1A', or from 'haplotype 3' or 'haplotype 3A'. For example, genotyping rs6814934 and rs7658048, or genotyping rs2070951 and rs5522, or genotyping rs9992256 and rs5520 may be used to distinguish between the presence of 'haplotype 2A' as opposed to 'haplotype 1A' or haplotype 3A'. Taking the combination of rs2070951 and rs5522 as a particular example; if a chromosome contains haplotype 1A then the genotype results will be G and A respectively; if the chromosome contains haplotype 2A then the genotype results will be C and A respectively; and if the chromosome contains haplotype 3A then the genotype results will be C and G respectively. Any particular combination of two SNPs may be selected for genotyping in order to distinguish between haplotypes 1-3 by reference to FIG. 2, or to distinguish between haplotypes 1A-3A by reference to FIG. 5B. However, it is appreciated that it may be desirable to genotype more than two SNPs.

Thus in one embodiment, the method comprises genotyping two or more of (eg at least 3, 4, 5, 6, 7 or all 8 of) rs3216799, rs6814934, rs7658048, rs2070950, rs2070951, rs5522, rs5525 and rs7671250. In this way, at least two SNPs may be genotyped in order to distinguish between each of haplotypes 1-3.

In another embodiment, the method comprises genotyping two or more of (eg at least 3, 4, 5, 6, 7, 8, 9, 10, 11, 12, 13, 14, 15, 16, 17 or all 18 of) rs9992256, SNP x at position 149585620 in the MR gene as numbered in FIG. 4, rs5520, rs3216799, rs2248038, rs7671250, rs6814934, rs7658048, rs2070949, rs2070950, rs2070951, rs5522, rs5525, rs17730626, rs11099695, rs11929719, rs2172002 and rs4835519. In this way, at least two SNPs may be genotyped in order to distinguish between each of haplotypes 1A-3A.

The inventors have identified a further MR haplotype, defined herein as haplotype 4; however its frequency in vivo is rare. Nonetheless, it is appreciated that at least two SNPs may be genotyped in order to distinguish any of haplotypes 1-3 from haplotype 4.

By 'haplotype 4' we include the meaning of a haplotype comprising SNPs rs2070951 and rs5522 with respective alleles 'G' and 'G'.

As mentioned above with respect to haplotypes 1-3, it will be understood that one or more further polymorphic sites may be in linkage disequilibrium with the alleles of the SNPs in haplotype 4, and so one or more further polymorphic sites (eg SNPs) may reside on the same haplotype.

As well as genotyping the SNPs within a haplotype to determine whether or not that haplotype is present, it is appreciated that one or more polymorphic sites that are in linkage disequilbrium with (and so act as a tag of) that haplotype may be genotyped. Thus, the methods of the invention may involve genotyping one or more polymorphic sites that are in linkage disequilbrium with a haplotype comprising rs3216799, rs6814934, rs7658048, rs2070950 and rs2070951 with respective alleles '+CT', 'C', 'T', 'C' and 'C', such as haplotype 2 or haplotype 2A above, in order to determine whether that particular haplotype is present.

By 'genotyping', we include the meaning of determining the genotype of at least one of the SNPs described herein. In this way, the particular base or allele of a polymorphic site (eg SNP) becomes known. It is appreciated that by 'genotyping' we include the direct determination of a particular base or allele of a polymorphic site, as well as an indirect indicator of a particular base or allele of a polymorphic site.

It will be appreciated that genotyping any one or more of the polymorphic sites (eg SNPs) described above conveniently comprises contacting a sample of nucleic acid from the subject with one or more nucleic acid molecules that hybridise selectively to a genomic region encompassing any one or more of the polymorphic sites (eg SNPs).

By 'hybridising selectively to a genomic region encompassing' any 'one or more SNPs' or 'one or more polymorphic sites', we include the meaning of a nucleic acid molecule hybridising to one allele of a polymorphic site (eg SNP) but not to the other allele of that polymorphic site (eg SNP). Thus, whether or not a given nucleic acid hybridises to a genomic region encompassing a polymorphic site (eg SNP) can be used as an indicator of which allele is present at that site.

It will be appreciated that a given nucleic acid molecule may hybridise selectively to more than one polymorphic site (eg SNP), for example a given nucleic molecule may hybridise selectively to polymorphic sites that are in close proximity to each other.

The sample of nucleic acid from the subject may be any suitable sample and includes genomic DNA, RNA and cDNA. Genomic DNA is preferred because most SNPs are in non-translated regions, but for the avoidance of doubt and where the context permits it, the sample also includes cDNA and mRNA. The sample of nucleic acid may be obtained in any suitable way, for example from a blood sample or from a mouthwash or from a buccal swab or other tissue sample. The sample of nucleic acid which is analysed may be a sample obtained from the subject. However, typically, the sample of nucleic acid which is analysed is one which has been amplified from the immediate sample obtained from the subject. For example, polymerase chain reaction (PCR), or other in vitro amplification techniques such as the ligase chain reaction (LCR), may conveniently be used to amplify the sample. Thus it will be appreciated that the sample of nucleic acid from the subject may be subjected to a nucleic acid amplification before contacting with one or more nucleic acid molecules that hybridise selectively to any one or more of the SNPs described above, such as those selected from the group consisting of rs3216799, rs6814934, rs7658048, rs2070950 and rs2070951, and/or to one or more polymorphic sites which are in linkage disequilibrium with any one or more SNPs selected from the group consisting of rs3216799, rs6814934, rs7658048, rs2070950 and rs2070951.

As is explained in more detail below, the one or more nucleic acid molecules that hybridise selectively to the a genomic region encompassing any one or more of the SNPs described above, such as those selected from the group consisting of rs3216799, rs6814934, rs7658048, rs2070950 and rs2070951, and/or a genomic region encompassing one or more polymorphic sites which are in linkage disequilibrium with any one or more SNPs selected from the group consisting of rs3216799, rs6814934, rs7658048, rs2070950 and rs2070951, may be, for example, a PCR primer which is used to amplify a genomic region containing a polymorphic site (eg an SNP), or may be a nucleic acid which is able to hybridise at or close to a polymorphic site (eg an SNP) and be used to determine the nucleic acid sequence variant(s) at the polymorphic site. When the subject is a human, it will be appreciated that the genomic region corresponds to the nucleic acid of chromosome 4.

By "selectively hybridising" we include the meaning that the nucleic acid molecule has sufficient nucleotide sequence similarity with the said genomic DNA or cDNA or mRNA that it can hybridise under highly stringent conditions. As is well known in the art, the stringency of nucleic acid hybridisation depends on factors such as length of nucleic acid over which hybridisation occurs, degree of identity of the hybridising sequences and on factors such as temperature, ionic strength and CG or AT content of the sequence. Thus, any nucleic acid which is capable of selectively hybridising as said is useful in the practice of the invention. It is preferred that the nucleic acid which selectively hybridises, selectively hybridises to the MR gene, preferably the human MR gene.

An example of a typical hybridisation solution when a nucleic acid is immobilised on a nylon membrane and the probe nucleic acid is 500 bases or base pairs is:
6×SSC (saline sodium citrate)
0.5% sodium dodecyl sulphate (SDS)
100 µg/ml denatured, fragmented salmon sperm DNA The hybridisation is performed at 68° C. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of sodium citrate in 800 ml of H$_2$O. Adjust the pH to 7.0 with a few drops of a 10 N solution of NaOH. Adjust the volume to 1 liter with H$_2$O. Dispense into aliquots. Sterilize by autoclaving.

An example of a typical hybridisation solution when a nucleic acid is immobilised on a nylon membrane and the probe is an oligonucleotide of between 15 and 50 bases is:
3.0 M trimethylammonium chloride (TMACl)
0.01 M sodium phosphate (pH 6.8)
1 mm EDTA (pH 7.6)
0.5% SDS
100 µg/ml denatured, fragmented salmon sperm DNA
0.1% nonfat dried milk The optimal temperature for hybridisation is usually chosen to be 5° C. below the T$_i$ for the given chain length. T$_i$ is the irreversible melting temperature of the hybrid formed between the probe and its target sequence. Jacobs et al (1988) *Nucl. Acids Res.* 16, 4637 discusses the determination of T$_i$s. The recommended hybridization temperature for 17-mers in 3 M TMACl is 48-50° C.; for 19-mers, it is 55-57° C.; and for 20-mers, it is 58-66° C.

Nucleic acids which can selectively hybridise to the said DNA (such as human DNA) include nucleic acids which have >95% sequence identity, preferably those with >98%, more preferably those with >99% sequence identity, for example 100% sequence identity, over at least a portion of the nucleic acid with the said DNA or cDNA. As is well known, mammalian (such as human) genes usually contain introns such that, for example, a mRNA or cDNA derived from a gene within the said human DNA would not match perfectly along its entire length with the said human DNA but would nevertheless be a nucleic acid capable of selectively hybridising to the said human DNA. Thus, the invention specifically includes nucleic acids which selectively hybridise to a cDNA but may not hybridise to an MR gene, or vice versa. For example, nucleic acids which span the intron-exon boundaries of the MR gene may not be able to selectively hybridise to the MR cDNA respectively.

"Nucleic acid which selectively hybridises" is typically nucleic acid which will amplify DNA from the said region of DNA by any of the well known amplification systems such as those described in more detail below, in particular the polymerase chain reaction (PCR). Suitable conditions for PCR amplification include amplification in a suitable 1× amplification buffer:
10× amplification buffer is 500 mM KCl; 100 mM Tris.Cl (pH 8.3 at room temperature); 15 mM MgCl$_2$; 0.1% gelatin.

A suitable denaturing agent or procedure (such as heating to 95° C.) is used in order to separate the strands of double-stranded DNA.

Suitably, the annealing part of the amplification is between 37° C. and 60° C., preferably 50° C.

Various methods are known in the art for genotyping polymorphic sites, including SNPs, in the method of the invention.

For example, methods of determining polymorphic sites within a nucleic acid may involve sequencing of DNA at one or more of the relevant positions within the relevant region, including direct sequencing; direct sequencing of PCR-amplified products; differential hybridisation of an oligonucleotide probe designed to hybridise at the relevant positions within the relevant region (conveniently this uses immobilised oligonucleotide probes in, so-called, "chip" systems which are well known in the art); denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; heteroduplex analysis; selective DNA amplification using oligonucleotides; fluorescent in-situ hybridisation (FISH) of interphase chromosomes; ARMS-PCR (Amplification Refractory Mutation System-PCR) for specific mutations; cleavage at mismatch sites in hybridised nucleic acids (the cleavage being chemical or enzymatic); SSCP single strand conformational polymorphism or DGGE (discontinuous or denaturing gradient gel electrophoresis); analysis to detect mismatch in annealed normal/mutant PCR-amplified DNA; and protein truncation assay (translation and transcription of exons—if a mutation introduces a stop codon a truncated protein product will result). Other methods may be employed such as detecting changes in the secondary structure of single-stranded DNA resulting from changes in the primary sequence, for example, using the cleavase I enzyme. This system is commercially available from GibcoBRL, Life Technologies, 3 Fountain Drive, Inchinnan Business Park, Paisley PA4 9RF, Scotland. SNP changes may also be detected by DNA high resolution melt assays or by the Taqman assay system (see Heid et al (1996) *Genome Res.* 6, 986-994).

It will be appreciated that the methods of the invention may also be carried out on "DNA chips". Such "chips" are described in U.S. Pat. No. 5,445,934 (Affymetrix; probe arrays), WO 96/31622 (Oxford; probe array plus ligase or polymerase extension), and WO 95/22058 (Affymax; fluorescently marked targets bind to oligomer substrate, and location in array detected); all of these are incorporated herein by reference.

Detailed methods of mutation detection are described in "Laboratory Protocols for Mutation Detection" 1996, ed. Landegren, Oxford University Press on behalf of HUGO (Human Genome Organisation).

It is preferred if RFLP is used for the detection of fairly large (≥500 bp) deletions or insertions which may be in linkage disequilibrium with any one or more of rs3216799, rs6814934, rs7658048, rs2070950 and rs2070951. Southern blots may be used for this embodiment of the invention.

PCR amplification of smaller regions (for example up to 300 bp) to detect small changes greater than 3-4 by insertions or deletions may be preferred. Amplified sequence may be analysed on a sequencing gel, and small changes (minimum size 3-4 bp) can be visualised. Suitable primers are designed as herein described.

In addition, using either Southern blot analysis or PCR, restriction enzyme variant sites may be detected. For example, for analysing variant sites in genomic DNA restriction enzyme digestion, gel electrophoresis, Southern blotting, and hybridisation specific probe (for example any suitable fragment derived from the MR cDNA or gene) may be used. For example, for analysing variant sites using PCR DNA amplification, restriction enzyme digestion, gel detection by ethidium bromide, silver staining or incorporation of radionucleotide or fluorescent primer in the PCR may be used.

Other suitable methods include the development of allele specific oligonucleotides (ASOs) for specific mutational events.

Primers which are suitable for use in a polymerase chain reaction (PCR; Saiki et al (1988) *Science* 239, 487-491) are preferred.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991)*Nature* 350, 91-92 and AIDS (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

The methods of the invention may make use of a difference in restriction enzyme cleavage sites caused by mutation. A non-denaturing gel may be used to detect differing lengths of fragments resulting from digestion with an appropriate restriction enzyme.

An "appropriate restriction enzyme" is one which will recognise and cut one polymorphic sequence and not another polymorphic sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which match (i.e. hybridise to) either one polymorphic site or the other polymorphic site but not both. Whether amplified DNA is produced will then indicate whether one or the other allele is present.

Any of the above methods may be employed in the method of the invention. In a particularly preferred embodiment, the genotyping may be carried out using a Sequenom Mass ARRAY iPLEX assay (Sequenom, San Diego, Calif., USA) or the like, as described in Example 1. In this assay, after amplification by PCR, a primer extension is used to introduce allele specific mass differences for a given SNP which can be detected using mass spectrometry.

Typically, the subject is a human subject, and preferably a female human subject. In this case, the one or more polymorphic sites in linkage disequilibrium with one or more of rs3216799, rs6814934, rs7658048, rs2070950 and rs2070951, or with any of the SNPs in haplotype 2 or haplotype 2A, would be within the human MR gene or in a genomic region encompassing the human MR gene (ie chromosome 4).

The method of the invention may comprise analysing a further genetic locus of the subject associated with an anxiety disorder or depression. Other genetic loci which have been associated with an anxiety disorder or depression in humans include the glucocorticoid receptor (GR) gene (eg any one or more of rs6195, rs6196, rs6189, rs6190, rs41423247, rs6198, rs10052957, rs10482605, rs1866388, rs2918419 and rs860458, may be genotyped—see DeRijk NIM 16, pp 340-352, 2009), a heat shock protein gene such as FKBP 5 (eg any one or more of rs9296158, rs3800373, rs1360780 and rs9470080 may be genotyped—see Binder JAMA 299, pp 1291-1305, 2008), the P-glycoprotein (P-gp) gene (eg any one or more of rs2032583 and rs2235015 may be genotyped—see Uhr et al Neuron 57, pp 203-209, 2008), the Corticotropin Releasing hormone Receptor 1 gene (CRHR1; eg rs878886 may be genotyped) or the Vasopressin 1B Receptor gene (AVPR1B; eg rs28632197 may be genotyped, see Keck et al, AJ Med Gen Part B, NeuroPsychi Res, 147B(7):1196-204, 2008). Thus, an analysis at any one or more of these loci may be carried out in addition to the analysis of the one or more polymorphic sites (eg SNPs) described above, such as those selected from the group consisting of rs3216799, rs6814934, rs7658048, rs2070950 and rs2070951, and/or the one or more polymorphic sites which are in linkage disequilibrium with any one or more SNPs selected from the group consisting of rs3216799, rs6814934, rs7658048, rs2070950 and rs2070951.

It will be appreciated that with current technology multiple mutations may be identified in a subject, for example from a single DNA sample. The skilled person may readily use the information contained herein to genotype not only the polymorphic sites (eg SNPs) described above that the inventors have associated with dispositional optimism and anxiety, but also one or more additional genetic loci as mentioned above. As is discussed below, the invention therefore also includes kits of parts and DNA chips which are specifically designed to be useful in assessing a subject's susceptibility to an anxiety disorder or depression.

It will be appreciated that it may be desirable to obtain data on other risk factors for an anxiety disorder or depression, in addition to the genotyping methods described above. Thus, in one embodiment, one or more of the age, sex, body mass index (BMI), smoking status, childhood trauma, or stress status (eg chronic or acute) of the subject is considered.

The data produced from carrying out the methods of the invention may conveniently be recorded on a data carrier. Thus, the invention includes a method of recording data concerning the susceptibility of a subject to an anxiety disorder or depression using any of the methods of the invention and recording the results on a data carrier. Typically, the data are recorded in an electronic form and the data carrier may be a computer, a disk drive, a memory stick, a CD or DVD or floppy disk or the like.

Information recorded on the data carrier may include the name, date of birth, age, sex and smoking status of the subject, as well as genotype information obtained using the methods of the invention.

A second aspect of the invention provides a use of one or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 for assessing the susceptibility of a subject to an anxiety disorder or depression, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more 'C', 'T', 'C' and 'C' alleles of the one or more SNPs.

In an embodiment, the one or more polymorphic sites (eg SNPs) which are in linkage disequilibrium with any one or more SNPs selected form the group consisting of rs3216799, rs6814934, rs7658048, rs2070950 and rs2070951, are SNPs selected from the group consisting of rs5522, rs5525, rs7671250, rs4835519, rs2172002, rs11929719, rs11099695, rs11730626, rs2070949, rs2248038, rs9992256, rs5520, and SNP x at position 149585620 in the MR gene as numbered in FIG. 4. Reduced susceptibility is indicated when the respective alleles of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4, are 'A', 'C', 'T', 'A', 'T', 'T', 'T', 'A', 'T', 'C', 'C', 'A' and 'T'.

In this aspect of the invention and in the third, fourth, fifth and sixth aspects of the invention described below, it will be appreciated that the any one or more nucleic acid molecules may hybridise selectively to one allele of a polymorphic site (eg SNP) but not to the other allele of that polymorphic site (eg SNP). In this way, it can readily be determined which allele of a particular polymorphic site (eg SNP) is present depending upon whether the nucleic acid molecule binds or not.

A third aspect of the invention provides one or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 for use in assessing the susceptibility of a subject to an anxiety disorder or depression, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more '+CT', 'C', 'T', 'C' and 'C' alleles of the one or more SNPs.

In an embodiment, the one or more polymorphic sites (eg SNPs) which are in linkage disequilibrium with any one or more SNPs selected form the group consisting of rs3216799, rs6814934, rs7658048, rs2070950 and rs2070951, are SNPs selected from the group consisting of rs5522, rs5525, rs7671250, rs4835519, rs2172002, rs11929719, rs11099695, rs11730626, rs2070949, rs2248038, rs9992256, rs5520, and SNP x at position 149585620 in the MR gene as numbered in FIG. 4. Reduced susceptibility is indicated when the respective alleles of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4, are 'A', 'C', 'T', 'A', 'T', 'T', 'T', 'A', 'T', 'C', 'C', 'A' and 'T'.

It will be appreciated that the one or more nucleic acid molecules in the second and third aspects of the invention may be ones that can be used to determine whether a subject has a haplotype comprising rs3216799, rs6814934, rs7658048, rs2070950 and rs2070951, including any of the particular haplotypes disclosed herein such as haplotype 2 or 2A.

A fourth aspect of the invention provides a use of one or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 in the manufacture of a reagent for assessing the susceptibility of a subject to an anxiety disorder or depression, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more '+CT', 'C', 'T', 'C' and 'C' alleles of the one or more SNPs.

In an embodiment, the one or more polymorphic sites (eg SNPs) which are in linkage disequilibrium with any one or more SNPs selected form the group consisting of rs3216799, rs6814934, rs7658048, rs2070950 and rs2070951, are SNPs selected from the group consisting of rs5522, rs5525, rs7671250, rs4835519, rs2172002, rs11929719, rs11099695, rs11730626, rs2070949, rs2248038, rs9992256, rs5520, and SNP x at position 149585620 in the MR gene as numbered in FIG. 4. Reduced susceptibility is indicated when the respective alleles of rs5522, rs5525, rs7671250, rs4835519, rs2172002, rs11929719, rs11099695, rs11730626, rs2070949, rs9992256, rs5520, rs2248038 and SNP x are 'A', 'C', 'T', 'A', 'T', 'T', 'T', 'A', 'T', 'C', 'C', 'A' and 'T'.

A fifth aspect of the invention provides a kit of parts for use in assessing the susceptibility of a subject to an anxiety disorder or depression, the kit comprising one or more nucleic acid molecules that hybridise selectively to a genomic region encompassing any two or more SNPs selected from the group consisting of rs3216799, rs6814934, rs7658048, rs2070950 and rs2070951 (eg with respective alleles '+CT', 'C', 'T', 'C' and 'C'), and/or that hybridise selectively to a genomic region encompassing two or more polymorphic sites in linkage disequilibrium with any one or more SNPs selected from the group consisting of rs3216799, rs6814934, rs7658048, rs2070950 and rs2070951 (eg with respective alleles '+CT', 'C', 'T', 'C' and 'C'). For example, the kit of parts may comprise one or more nucleic acid molecules that hybridise selectively to a genomic region encompassing any two or more SNPs selected from the group consisting of rs3216799, rs6814934, rs7658048, rs2070950 and rs2070951, and/or one or more nucleic acid molecules that hybridise selectively to a genomic region encompassing two or more polymorphic sites in linkage disequilibrium with any one or more SNPs selected from the group consisting of rs3216799, rs6814934, rs7658048, rs2070950 and rs2070951.

Typically, the kit of parts comprises two or more nucleic acid molecules (eg, three or more, or four or more, or five or more nucleic acid molecules) that hybridise selectively to a genomic region encompassing two or more SNPs (eg, three or more, or four or more, or five SNPs) selected from the group consisting of rs3216799, rs6814934, rs7658048, rs2070950 and rs2070951 and/or that hybridise selectively to a genomic region encompassing two or more polymorphic sites (eg three or more, or four or more, or five or more) in linkage disequilibrium with any one or more SNPs selected from the group consisting of rs3216799, rs6814934, rs7658048, rs2070950 and rs2070951.

It is appreciated that the kit of parts contains reagents which are able to be used to determine the genotype of any two or more SNPs (eg three or more, four or more or all five SNPs) selected from the group consisting of rs3216799, rs6814934, rs7658048, rs2070950 and rs2070951, and/or two or more (eg three or more, four or more, or five or more) polymorphic sites in linkage disequilibrium with any one or more SNPs selected from the group consisting of rs3216799, rs6814934, rs7658048, rs2070950 and rs2070951. Thus, the kit of parts may be used to determine whether a subject has a haplotype comprising rs3216799, rs6814934, rs7658048, rs2070950 and rs2070951 with respective alleles '+CT', 'C', 'T', 'C' and 'C', such as haplotype 2 or 2A described above. Conveniently, the kit contains PCR primers which are able to amplify a genomic region encompassing any two or more SNPs (eg three or more, four or more or all five SNPs) selected from the group consisting of rs3216799, rs6814934, rs7658048, rs2070950 and rs2070951, and/or two or more (eg three or more, four or more, or five or more) polymorphic sites in linkage disequilibrium with any one or more SNPs selected from the group consisting of rs3216799, rs6814934, rs7658048, rs2070950 and rs2070951. Conveniently, the kit contains nucleic acid molecules, such as oligonucleotide probes, which can be used to determine the genotype of two or more (eg three or more, four or more or all five SNPs) SNPs selected from the group consisting of rs3216799, rs6814934, rs7658048, rs2070950 and rs2070951 and/or two or more (eg three or more, four or more, or five or more) polymorphic sites in linkage disequilibrium with any one or more SNPs selected from the group consisting of rs3216799, rs6814934, rs7658048, rs2070950 and rs2070951.

In one embodiment, the two or more polymorphic sites in linkage disequilibrium with any one or more SNPs selected from the group consisting of rs3216799, rs6814934, rs7658048, rs2070950 and rs2070951, are two or more of (eg all three of) the SNPs selected from the group consisting of rs5522, rs5525 and rs7671250. Thus, the kit of parts may comprise one or more nucleic acid molecules that selectively hybridise to a genomic region encompassing two or more SNPs selected from the group consisting of rs5522, rs5525 and rs7671250 (eg with respective alleles 'A', 'C' and 'T').

In another embodiment, the two or more polymorphic sites in linkage disequilibrium with any one or more SNPs selected from the group consisting of rs3216799, rs6814934, rs7658048, rs2070950 and rs2070951, are two or more of (eg at least 2, 3, 4, 5, 6, 7, 8, 9, 10, 11 or 12, or all of) the SNPs selected from the group consisting of rs5522, rs5525, rs7671250, rs4835519, rs2172002, rs11929719, rs11099695, rs11730626, rs2070949, rs2248038, rs9992256, rs5520, and SNP x at position 149585620 in the MR gene as numbered in FIG. 4. Thus, the kit of parts may comprise one or more nucleic acid molecules that selectively hybridise to a genomic region encompassing two or more of (eg at least 2, 3, 4, 5, 6, 7, 8, 9, 10, 11 or 12, or all 13, of) the SNPs selected from the group consisting of rs5522, rs5525, rs7671250, rs4835519, rs2172002, rs11929719, rs11099695, rs11730626, rs2070949, rs2248038, rs9992256, rs5520 and SNP x at position 149585620 in the MR gene as numbered in FIG. 4. Preferably, the two or more polymorphic sites in linkage disequilibrium with any one or more SNPs selected from the group consisting of rs3216799, rs6814934, rs7658048, rs2070950 and rs2070951, are two or more of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4, with respective alleles 'A', 'C', 'T', 'A', 'T', 'T', 'T', 'A', 'T', 'C', 'C', 'A' and 'T', which are in linkage disequilibrium with the respective CT', 'C', 'T', 'C' and 'C' alleles of rs3216799, rs6814934, rs7658048, rs2070950 and rs2070951.

In a further embodiment, the kit of parts further comprises or consists of a nucleic acid molecule that hybridises selectively to a further genetic locus associated with an anxiety disorder, such as the GR gene (eg the nucleic acid may hybridise selectively to any of rs6195, rs6196, rs6189, rs6190, rs41423247, rs6198, rs10052957, rs10482605, rs1866388, rs2918419 and rs860458—see DeRijk NIM 16, pp 340-352, 2009), a heat shock protein gene such as FKBP 5 (eg the nucleic acid may hybridise selectively to any of rs9296158, rs3800373, rs1360780 and rs9470080—see Binder JAMA 299, pp 1291-1305, 2008), the P-glycoprotein (P-gp) gene (eg the nucleic acid may hybridise selectively to rs2032583 or rs2235015—see Uhr et al Neuron 57, pp 203-209, 2008), the Corticotropin Releasing hormone Receptor 1 gene (CRHR1; eg the nucleic acid may hybridise selectively to rs878886) or the Vasopressin 1B Receptor gene (AVPR1B; eg the nucleic acid may hybridise selectively to rs28632197, see Keck et al, AJ Med Gen Part B, NeuroPsychi Res, 147B(7):1196-204, 2008).

The invention also includes a kit of parts for use in assessing the susceptibility of a subject to an anxiety disorder or depression, the kit comprising or consisting of one or more nucleic acid molecules that hybridise selectively to a genomic region encompassing any one or more SNPs selected from the group consisting of rs3216799, rs6814934, rs7658048, rs2070950 and rs2070951 (eg with respective alleles '+CT', 'C', 'T', 'C' and 'C'), and that hybridise selectively to a genomic region encompassing one or more polymorphic sites in linkage disequilibrium with any one or more SNPs selected from the group consisting of rs3216799, rs6814934, rs7658048, rs2070950 and rs2070951 (eg with respective alleles '+CT', 'C', 'T', 'C' and 'C'). For example, the kit of parts may comprise one or more nucleic acid molecules that hybridise selectively to a genomic region encompassing any one or more SNPs selected from the group consisting of rs3216799, rs6814934, rs7658048, rs2070950 and rs2070951, and one or more nucleic acid molecules that hybridise selectively to a genomic region encompassing one or more polymorphic sites in linkage disequilibrium with any one or more SNPs selected from the group consisting of rs3216799, rs6814934, rs7658048, rs2070950 and rs2070951. Preferences for the one or more polymorphic sites in linkage disequilibrium with any one or more SNPs selected from the group consisting of rs3216799, rs6814934, rs7658048, rs2070950 and rs2070951 include those described above.

In one embodiment, the kit of parts consists of only the nucleic acid molecules that hybridise as said.

It will be appreciated that the kit of parts of the invention may comprise or consist of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 different nucleic acid molecules. By different we mean that the nucleic acid molecules have different hybridisation selectivities (eg they may hybridise selectively to different polymorphic sites).

It is also appreciated that the one or more nucleic acid molecules of the kit of parts may hybridise selectively to a region of genome at or close to the given polymorphic sites (eg SNPs).

Typically, the kit of parts of the invention comprises or consists of less than 100 different nucleic acid molecules, eg less than 95, 90, 85, 80, 75, 70, 65, 60, 55, 50, 45, 40, 35, 30, 25, 20, 15 or 10 different nucleic acid molecules.

Typically, the one or more nucleic acid molecules of the kit of parts are less than 100 bases in length, such as less than 90, 80, 70, 60, 50, 40 or 30 bases. For example, the one or more nucleic acid molecules may be between 10 and 30 bases in length, such as 11, 12, 13, 14, 15, 16, 17, 18, 19, 20, 21, 22, 23, 24, 25, 26, 27, 28 or 29 bases in length.

A sixth aspect of the invention provides a solid substrate for use in assessing the susceptibility of a subject to an anxiety disorder or depression, the solid substrate having attached thereto one or more nucleic acid molecules that hybridise selectively to a genomic region encompassing any two or more SNPs selected from the group consisting of rs3216799, rs6814934, rs7658048, rs2070950 and rs2070951 (eg with respective alleles '+CT', 'C', 'T', 'C' and 'C'), and/or that hybridise selectively to a genomic region encompassing two or more polymorphic sites in linkage disequilibrium with any one or more SNPs selected from the group consisting of rs3216799, rs6814934, rs7658048, rs2070950 and rs2070951 (eg with respective alleles '+CT', 'C', 'T', 'C' and 'C'). For example, the solid substrate may have attached thereto one or more nucleic acid molecules that hybridise selectively to a genomic region encompassing any two or more SNPs selected from the group consisting of rs3216799, rs6814934, rs7658048, rs2070950 and rs2070951, and/or one or more nucleic acid molecules that hybridise selectively to a genomic region encompassing two or more polymorphic sites in linkage disequilibrium with any one or more SNPs selected from the group consisting of rs3216799, rs6814934, rs7658048, rs2070950 and rs2070951.

Typically, solid substrate has attached thereto two or more nucleic acid molecules (eg, three or more, or four or more, or five or more nucleic acid molecules) that hybridise selectively to a genomic region encompassing two or more SNPs (eg, three or more, or four or more, or five SNPs) selected from the group consisting of rs3216799, rs6814934, rs7658048, rs2070950 and rs2070951 and/or that hybridise selectively to a genomic region encompassing two or more polymorphic sites (eg three or more, or four or more, or five or more) in linkage disequilibrium with any one or more SNPs selected from the group consisting of rs3216799, rs6814934, rs7658048, rs2070950 and rs2070951.

It is appreciated that the solid substrate may be used to determine whether a subject has a haplotype comprising rs3216799, rs6814934, rs7658048, rs2070950 and rs2070951 with respective alleles '+CT', 'C', 'T', 'C' and 'C', such as haplotype 2 or 2A described above.

The solid substrate with one or more nucleic acids attached thereto may be a DNA chip or a microarray.

In one embodiment, the solid substrate has only the nucleic acid molecules that hybridise as said attached thereto.

Conveniently, the solid substrate has attached thereto nucleic acid molecules, such as oligonucleotide probes, which can be used to determine the genotype of two or more (eg three or more, four or more or all five SNPs) SNPs selected from the group consisting of rs3216799, rs6814934, rs7658048, rs2070950 and rs2070951 and/or two or more (eg three or more, four or more, or five or more) polymorphic sites in linkage disequilibrium with any one or more SNPs selected from the group consisting of rs3216799, rs6814934, rs7658048, rs2070950 and rs2070951.

In one embodiment, the two or more polymorphic sites in linkage disequilibrium with any one or more SNPs selected from the group consisting of rs3216799, rs6814934, rs7658048, rs2070950 and rs2070951, are two or more of (eg all three of) the SNPs selected from the group consisting of rs5522, rs5525 and rs7671250. Thus, the solid substrate may have attached thereto one or more nucleic acid molecules that selectively hybridise to a genomic region encompassing two or more SNPs selected from the group consisting of rs5522, rs5525 and rs7671250 (eg with respective alleles 'A', 'C' and 'T').

In another embodiment, the two or more polymorphic sites in linkage disequilibrium with any one or more SNPs selected from the group consisting of rs3216799, rs6814934, rs7658048, rs2070950 and rs2070951, are two or more of (eg at least 2, 3, 4, 5, 6, 7, 8, 9, 10, 11 or 12, or all 13 of) the SNPs selected from the group consisting of rs5522, rs5525, rs7671250, rs4835519, rs2172002, rs11929719, rs11099695, rs11730626, rs2070949, rs10028821, rs2248038, rs9992256, rs5520, and SNP x at position 149585620 in the MR gene as numbered in FIG. 4. Thus, the solid substrate may have attached thereto one or more nucleic acid molecules that selectively hybridise to a genomic region encompassing two or more of (eg at least 2, 3, 4, 5, 6, 7, 8, 9, 10, 11 or 12, or all 13 of) the SNPs selected from the group consisting of rs5522, rs5525, rs7671250, rs4835519, rs2172002, rs11929719, rs11099695, rs11730626, rs2070949, rs2248038, rs9992256, rs5520, and SNP x at position 149585620 in the MR gene as numbered in FIG. 4. Preferably, the two or more polymorphic sites in linkage disequilibrium with any one or more SNPs selected from the group consisting of rs3216799, rs6814934, rs7658048, rs2070950 and rs2070951, are two or more of rs5522, rs5525, rs7671250, rs4835519, rs2172002, rs11929719, rs11099695, rs11730626, rs2070949, rs9992256, rs5520, rs2248038 and SNP x at position 149585620 in the MR gene as numbered in FIG. 4, with respective alleles 'A', 'C', 'T', 'A', 'T', 'T', 'T', 'A', 'T', 'C', 'C', 'A' and 'T', which are in linkage disequilibrium with the respective CT', 'C', 'T', 'C' and 'C' alleles of rs3216799, rs6814934, rs7658048, rs2070950 and rs2070951.

In a further embodiment, the solid substrate has attached thereto a nucleic acid molecule that hybridises selectively to a further genetic locus associated with an anxiety disorder, such as the GR gene (eg the nucleic acid may hybridise selectively to any of rs6195, rs6196, rs6189, rs6190, rs41423247, rs6198, rs10052957, rs10482605, rs1866388, rs2918419 and rs860458—see DeRijk NIM 16, pp 340-352, 2009), a heat shock protein gene such as FKBP 5 (eg the nucleic acid may hybridise selectively to any of rs9296158, rs3800373, rs1360780 and rs9470080—see Binder JAMA 299, pp 1291-1305, 2008), the P-glycoprotein (P-gp) gene (eg the nucleic acid may hybridise selectively to rs2032583 or rs2235015—see Uhr et al Neuron 57, pp 203-209, 2008), the Corticotropin Releasing hormone Receptor 1 gene (CRHR1; eg the nucleic acid may hybridise selectively to rs878886) or the Vasopressin 1B Receptor gene (AVPR1B; eg the nucleic acid may hybridise selectively to rs28632197, see Keck et al, AJ Med Gen Part B, NeuroPsychi Res, 147B(7):1196-204, 2008).

The invention also includes a solid substrate for use in assessing the susceptibility of a subject to an anxiety disorder or depression, the solid substrate having attached thereto one or more nucleic acid molecules that hybridise selectively to a genomic region encompassing any one or more SNPs selected from the group consisting of rs3216799, rs6814934, rs7658048, rs2070950 and rs2070951 (eg with respective alleles '+CT', 'C', 'T', 'C' and 'C'), and that hybridise selectively to a genomic region encompassing one or more polymorphic sites in linkage disequilibrium with any one or more SNPs selected from the group consisting of rs3216799, rs6814934, rs7658048, rs2070950 and rs2070951 (eg with respective alleles '+CT', 'C', 'T', 'C' and 'C'). Preferences for the one or more polymorphic sites in linkage disequilibrium with any one or more SNPs selected from the group consisting of rs3216799, rs6814934, rs7658048, rs2070950 and rs2070951 include those described above.

It will be appreciated that the solid substrate of the invention may have attached thereto at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 different nucleic acid molecules.

It is also appreciated that the one or more nucleic acid molecules of the solid substrate may hybridise selectively to a region of genome at or close to the given polymorphic sites.

Typically, the solid substrate of the invention has attached thereto less than 100 different nucleic acid molecules, eg less than 95, 90, 85, 80, 75, 70, 65, 60, 55, 50, 45, 40, 35, 30, 25, 20, 15 or 10 different nucleic acid molecules.

Typically, the one or more nucleic acid molecules of the solid substrate are less than 100 bases in length, such as less than 90, 80, 70, 60, 50, 40 or 30 bases. For example, the one or more nucleic acid molecules may be between 10 and 30 bases in length, such as 11, 12, 13, 14, 15, 16, 17, 18, 19, 20, 21, 22, 23, 24, 25, 26, 27, 28 or 29 bases in length.

It will be appreciated that the methods of the invention, and the uses, kits and solid substrates (eg DNA chips) described herein, may be used to determine the optimal therapy (eg pharmaco- or cognitive) for an anxiety disorder or depression. For example, clinical studies may be conducted in which treatment efficacy in patients is stratified according to genotype. In this way, the methods, uses, kits and solid substrates (eg DNA chips) of the invention may be useful in selecting subjects who may benefit from particular treatments for combating an anxiety disorder or depression.

It will be appreciated that the methods, uses, kits and solid substrates (eg DNA chips) may also find uses in selecting cohorts of subjects for clinical trials.

A seventh aspect of the invention provides a method of combating an anxiety disorder or depression in a subject, the method comprising assessing the susceptibility of a subject to an anxiety disorder or depression according to the method of the first aspect of the invention and depending upon the outcome of the assessment treating the subject.

By 'combating' we include the meaning that the invention can be used to alleviate symptoms of the disorder (ie palliative use) or to prevent the disorder or to treat the disorder.

In one embodiment, treating the subject comprises administering any one or more of an anti-depressant, an anti-convulsant, a beta-blocker, cortisol, a cortisol agonist, a cortisol antagonist, or an agent that modulates MR-expression to the subject. Examples of agents that modulate MR-expression include antidepressants such as tricyclic antidepressants (TCAs) and selective serotonin reuptake inhibitor (SSRIs), which have been shown to increase MR expression (de Koet, DeRijk, Meijer, Clinical Practice article 08). Further examples include ACTH (adrenocorticotrophic hormone) which has been shown to increase MR expression in an animal model; steroids (both natural and synthetic); progesterone; and estrogen. It will be appreciated that by the terms 'cortisol agonist' and 'cortisol antagonist', we include the meaning of the terms 'MR agonist' and 'MR antagonist' respectively. Thus, treating the subject may comprise administering an MR agonist or an MR antagonist, i.e. any agent that is capable of modulating MR activity, examples of which are provided below.

In animal models, acute and chronic stress is known to change MR expression, and it is possible that cognitive behavioural therapy and exercise affect MR expression. Thus, it is appreciated that treating the subject may comprise treating with a cognitive behavioural therapy or exercise regime.

The invention provides a compound for use in combating an anxiety disorder or depression in a subject who has been assessed as having, or having an increased likelihood of developing, an anxiety disorder or depression according to the first aspect of the invention, the compound being selected from an anti-depressant, an anti-convulsant, a beta-blocker, cortisol or an agent that modulates MR-expression.

The invention provides a use of a compound in the manufacture of a medicament for combating an anxiety disorder or depression in a subject who has been assessed as having, or having an increased likelihood of developing, an anxiety disorder or depression according to the first aspect of the invention, the compound being selected from an anti-depressant, an anti-convulsant, a beta-blocker, cortisol or an agent that modulates MR-expression.

Preferences for the subject are as defined above with respect to the first aspect of the invention. Preferably, the subject is a female human.

An eighth aspect of the invention provides an isolated polynucleotide comprising an MR gene sequence having a polymorphic site (eg SNP) at position 149585620 as numbered in FIG. 4 (see position represented by SNP x in FIG. 4 which is 8158 nucleotides before the translation start site (first ATG)). Preferably the polynucleotide has a 'T' allele at position 149585620 as numbered in FIG. 4, which the inventors have shown resides on a haplotype comprising rs3216799, rs6814934, rs7658048, rs2070950 and rs2070951 with respective alleles 'C', 'T', 'C' and 'C'.

In one embodiment, the polynucleotide comprises the sequence GAGGG[T]GTGAC (SEQ ID No: 2), wherein the T in square brackets corresponds to the base at position 149585620 as numbered in FIG. 4, or a sequence with at least 70% sequence identity to the sequence GAGGG[T]GTGAC (SEQ ID No: 2), for example at least 75% or 80% or 85% or 90% sequence identity to the sequence GAGGG[T]GTGAC (SEQ ID No: 2), which has a 'T' at position 149585620 as numbered in FIG. 4.

For example, the polynucleotide may comprise any of the sequences TGAGGG[T]GTGACC (SEQ ID No: 3), GTGAGGG[T]GTGACC (SEQ ID No: 4), CGTGAGGG[T]GTGACCC (SEQ ID No: 5) or TCGTGAGGG[T]GTGACCCG (SEQ ID No: 6), or the sequence in FIG. 4 wherein the base at position 149585620 as numbered in FIG. 4 is a 'T', or a sequence with at least 60%, 65%, 70%, 75%, 80%, 85%, 90%, 95%, 96%, 97%, 98% or 99% sequence identity to any of said sequences.

Preferably, the MR gene sequence is a human MR gene sequence.

A ninth aspect of the invention provides an isolated polynucleotide that selectively hybridises to the polymorphic site at position 149585620 as numbered in FIG. 4. For example, the polynucleotide may hybridise to one allele of the polymorphic site (eg SNP) but not to the other allele of the polymorphic site (eg SNP) at position 149585620 as numbered in FIG. 4. Thus, whether or not the polynucleotide hybridises to a genomic region encompassing the polymorphic site at position 149585620 as numbered in FIG. 4 can be used as an indicator of which allele is present at that site.

Typically, the polynucleotides of the eighth and ninth aspects of the invention are less than 1000 kb in length, for example no more than 900 kb, 800 kb, 700 kb, 600 kb, 500 kb, 450 kb, 400 kb, 350 kb, 300 kb, 250 kb, 200 kb, 150 kb, 100 kb, 50 kb, 40 kb, 30 kb, 20 kb, 10 kb, 9 kb, 8 kb, 7 kb, 6 kb, 5 kb, 4 kb, 3 kb, 2 kb or 1 kb in length. In further embodiments, such polynucleotides are no more than 950 b, 900 b, 850 b, 800 b, 750 b, 700 b, 650 b, 600 b, 550 b, 500 b, 450 b, 400 b, 350 b, 300 b, 250 b, 200 b, 150 b or 100 b bases in length, such as less than 90, 80, 70, 60, 50, 40 or 30 bases. For example, the polynucleotides may be between 10 and 30 bases in length, such as 11, 12, 13, 14, 15, 16, 17, 18, 19, 20, 21, 22, 22, 23, 24, 25, 26, 27, 28 or 29 bases in length. Typically, the polynucleotides of the eight and ninth aspects of the invention are genomic DNA or cDNA.

It is appreciated that the polynucleotides of the eighth and ninth aspects of the invention may be primers or probes, for example for use in the above methods, kits and solid substrates, to determine whether a subject has a particular allele (eg 'T') at the polymorphic site at position 149585620 as numbered in FIG. 4. Accordingly, the invention provides a polynucleotide according to the eighth or ninth aspect of the invention for use in assessing the susceptibility of a subject to anxiety disorder, wherein reduced susceptibility is indicated when the allele of the polymorphic site at position 149585620 as numbered in FIG. 4 is 'T'.

The invention also provides a polynucleotide according to the ninth aspect of the invention for use in assessing the susceptibility of a subject to an anxiety disorder or depression, wherein reduced susceptibility is indicated when the allele of the polymorphic site at position 149585620 as numbered in FIG. 4 is 'T'.

The invention provides a use of a polynucleotide according to the ninth aspect of the invention in the manufacture of a reagent for assessing the susceptibility of a subject to an anxiety disorder or depression, wherein reduced susceptibility is indicated when the allele of the polymorphic site at position 149585620 as numbered in FIG. 4 is 'T'.

As well as demonstrating an association between MR polymorphisms and an anxiety disorder or depression, the inventors have also shown that MR polymorphisms may impact on the efficacy of candidate treatments. Example 3 describes an in vitro transactivation assay in which the resultant MR gene haplotypes of rs2070951 and rs5522 were found to modulate cortisol-induced gene transcription. Example 4 shows how the cortisol awakening response varies according to MR polymorphisms in patients who are using selective serotonin reuptake inhibitors (SSRIs). Accordingly, the inventors believe that by identifying agents whose affect on the MR is dependent upon MR polymorphisms, treatment efficacy can be improved. For example, candidate treatments can be identified and optimum treatments can be aligned with patient genotypes.

Thus, a tenth aspect of the invention provides a method of selecting an agent that modulates at least one activity of an MR in a MR gene haplotype-dependent manner, comprising:
i) providing two or more MRs encodable by a respective two or more of an MR gene haplotype comprising rs2070951 and rs5522 with respective alleles 'G' and 'A', or an MR gene haplotype comprising rs2070951 and rs5522 with respective alleles 'C' and 'A', or an MR gene haplotype comprising rs2070951 and rs5522 with respective alleles 'C' and 'G', or an MR gene haplotype comprising rs2070951 and rs5522 with respective alleles 'G' and 'G';
ii) providing a test agent; and
iii) assessing whether the test agent modulates at least one activity of each MR in an MR gene haplotype-dependent manner.

It is appreciated that an agent that modulates at least one activity of an MR in an MR haplotype-dependent manner may be useful in combating an MR-related disorder. Thus, in one embodiment, the agent is one which is suitable for combating an MR-related disorder. By an 'MR-related disorder' we include any disorder that is associated with abnormal MR signalling. Examples of MR-related disorders include anxiety disorder and depression, and cardiovascular disease (e.g. high blood pressure) associated with MR-mutations (see Geller, 2005, Endocrinology 62: 513-520; Zennaro and Lombes, 2004, *Trends in Endocrinol and Metabol* 15: 264-270; and Fernandes-Rosa 2010, *J Endocrinol Invest* 33: 472-7, all of which are incorporated herein by reference).

In a preferred embodiment, the agent is one which is suitable for combating an anxiety disorder or depression, and so the method may be used to select an agent for combating anxiety disorder or depression. It is appreciated that anxiety disorder and depression are comorbid with other disorders, such that the inventors believe the method to be also useful in identifying treatments for disorders associated with an anxiety disorder or depression, generally referred to as stress-related disorders. Examples of such disorders include cardiovascular disease; metabolic disorder (e.g. metabolic syndrome); Fibromyalgia; Insomnia; Alzheimers disease; Somatic disorder; Bipolar disorder; Pain; Osteoporosis; and Immune disorders (see, for example, Sher Y et al, The impact of depression in heart disease. *Curr Psychiatry Rep.* 2010 June; 12(3):255-64. Review; Egede L E and Ellis C. Diabetes and depression: global perspectives. *Diabetes Res Clin Pract.* 2010 March; 87(3):302-12. Epub 2010 Feb. 23. Review.; Arnold L M. Strategies for managing fibromyalgia. *Am J Med.* 2009 December; 122(12 Suppl):S31-43. Review; Staner L. Comorbidity of insomnia and depression. *Sleep Med Rev.* 2010 February; 14(1):35-46. Epub 2009 Nov. 25. Review.; Caraci F et al. Depression and Alzheimer's disease: neurobiological links and common pharmacological targets. *Eur J Pharmacol.* 2010 Jan. 10; 626(1):64-71. Epub 2009 Oct. 18. Review.; Uzun S et al. Depressive disorders and comorbidity: somatic illness vs. side effect.

*Psychiatr Danub.* 2009 September; 21(3):391-8. Review; Robinson M J et al. Depression and pain. *Front Biosci.* 2009 Jun. 1; 14:503151. Review.; Wu Q et al. Depression and low bone mineral density: a meta-analysis of epidemiologic studies. *Osteoporos Int.* 2009 August; 20(8):130920. Epub 2009 Apr. 3. Review.; Marques-Deak A et al. 2005 March; 10(3):239-50. Review; Diagnostic & Statistical Manual-IV; all of which are incorporated herein by reference).

By 'encodable' we include the meaning that the two or more MRs are encoded by the MR gene haplotypes having the specific alleles mentioned in step (i). However, it is appreciated that since the rs5522 polymorphism results in an amino acid change in the MR protein sequence (ie. I180V), the two or more MRs may be encoded by any MR gene provided that it gives rise to an MR protein which has an isoleucine or valine amino acid at position 180.

By an MR gene haplotype comprising rs2070951 and rs5522 with respective alleles 'G' and 'A' we include the meaning of any MR gene provided that it has bases 'G' and 'A' at respective positions rs2070951 and rs5522. As will become apparent below, when providing an MR, encodable by an MR gene haplotype, involves providing a subject, or a cell from a subject, having that MR gene haplotype, the MR gene haplotype comprising rs2070951 and rs5522 with respective alleles 'G' and 'A', will typically correspond to haplotype 1 or 1A. However, when providing an MR involves providing an MR gene in vitro (e.g. produced using recombinant technology), it is appreciated that the MR gene may not correspond to haplotype 1 or 1A, so long as the MR gene has bases 'G' and 'A' at respective positions rs2070951 and rs5522. For example, in an embodiment, the MR gene haplotype comprising rs2070951 and rs5522 with respective alleles 'G' and 'A' has a polynucleotide sequence with at least 95% sequence identity (such as 95.5, 96.0, 96.5, 97.0, 97.5, 98.0, 98.5, 99.0 or 99.5% sequence identity) with the sequence listed in FIG. 19, and, in a particularly preferred embodiment, has the polynucleotide sequence listed in FIG. 19 where rs2070951 and rs5522 in FIG. 19 are 'G' and 'A' respectively.

By an MR gene haplotype comprising rs2070951 and rs5522 with respective alleles 'C' and 'A' we include the meaning of any MR gene provided that it has bases 'C' and 'A' at respective positions rs2070951 and rs5522. As will become apparent below, when providing an MR, encodable by an MR gene haplotype, involves providing a subject, or a cell from a subject, having that MR gene haplotype, the MR gene haplotype comprising rs2070951 and rs5522 with respective alleles 'C' and 'A', will typically correspond to haplotype 2 or 2A. However, when providing an MR involves providing an MR gene in vitro (e.g. produced using recombinant technology), it is appreciated that the MR gene may not correspond to haplotype 2 or 2A, so long as the MR gene has bases 'C' and 'A' at respective positions rs2070951 and rs5522. For example, in an embodiment, the MR gene haplotype comprising rs2070951 and rs5522 with respective alleles 'C' and 'A' has a polynucleotide sequence with at least 95% sequence identity (such as 95.5, 96.0, 96.5, 97.0, 97.5, 98.0, 98.5, 99.0 or 99.5% sequence identity) with the sequence listed in FIG. 19, and, in a particularly preferred embodiment, has the polynucleotide sequence listed in FIG. 19, when rs2070951 and rs5522 in FIG. 19 are 'C' and 'A' respectively.

By an MR gene haplotype comprising rs2070951 and rs5522 with respective alleles 'C' and 'G' we include the meaning of any MR gene provided that it has bases 'C' and 'G' at respective positions rs2070951 and rs5522. As will become apparent below, when providing an MR, encodable by an MR gene haplotype, involves providing a subject, or a cell from a subject, having that MR gene haplotype, the MR gene haplotype comprising rs2070951 and rs5522 with respective alleles 'C' and 'G', will typically correspond to haplotype 3 or 3A. However, when providing an MR involves providing an MR gene in vitro (e.g. produced using recombinant technology), it is appreciated that the MR gene may not correspond to haplotype 3 or 3A, so long as the MR gene has bases 'C' and 'G' at respective positions rs2070951 and rs5522. For example, in an embodiment, the MR gene haplotype comprising rs2070951 and rs5522 with respective alleles 'C' and 'G' has a polynucleotide sequence with at least 95% sequence identity (such as 95.5, 96.0, 96.5, 97.0, 97.5, 98.0, 98.5, 99.0 or 99.5% sequence identity) with the sequence listed in FIG. 19, and, in a particularly preferred embodiment, has the polynucleotide sequence listed in FIG. 19, when rs2070951 and rs5522 on FIG. 19 are 'C' and 'G' respectively By an MR gene haplotype comprising rs2070951 and rs5522 with respective alleles 'G' and 'G' we include the meaning of any MR gene provided that it has bases 'G' and 'G' at respective positions rs2070951 and rs5522. In an embodiment, the MR gene haplotype comprising rs2070951 and rs5522 with respective alleles 'G' and 'G' has a polynucleotide sequence with at least 95% sequence identity (such as 95.5, 96.0, 96.5, 97.0, 97.5, 98.0, 98.5, 99.0 or 99.5% sequence identity) with the sequence listed in FIG. 19, and, in a particularly preferred embodiment, has the polynucleotide sequence listed in FIG. 19, when rs2070951 and rs5522 in FIG. 19 are 'G' and 'G' respectively.

In an embodiment, step (i) comprises providing MRs with two different MR gene haplotypes.

For example, step (i) may comprise providing an MR encodable by an MR gene haplotype comprising rs2070951 and rs5522 with respective alleles 'G' and 'A', and an MR encodable by an MR gene haplotype comprising rs2070951 and rs5522 with respective alleles 'C' and 'A'.

In another example, step (i) may comprise providing an MR encodable by an MR gene haplotype comprising rs2070951 and rs5522 with respective alleles 'G' and 'A', and an MR encodable by an MR gene haplotype comprising rs2070951 and rs5522 with respective alleles 'C' and 'G'.

In another example, step (i) may comprise providing an MR encodable by an MR gene haplotype comprising rs2070951 and rs5522 with respective alleles 'G' and 'A', and an MR encodable by an MR gene haplotype comprising rs2070951 and rs5522 with respective alleles 'G' and 'G'.

In another example, step (i) may comprise providing an MR encodable by an MR gene haplotype comprising rs2070951 and rs5522 with respective alleles 'C' and 'A', and an MR encodable by an MR gene haplotype comprising rs2070951 and rs5522 with respective alleles 'C' and 'G'.

In another example, step (i) may comprise providing an MR encodable by an MR gene haplotype comprising rs2070951 and rs5522 with respective alleles 'C' and 'A', and an MR encodable by an MR gene haplotype comprising rs2070951 and rs5522 with respective alleles 'G' and 'G'.

In a further embodiment, step (i) comprises providing MRs with three different MR gene haplotypes.

As mentioned above, the inventors have identified three major MR haplotypes (e.g. haplotypes 1-3 or 1A-3A) which comprise rs2070951 and rs5522 with respective alleles 'G' and 'A', or 'C' and 'A', or 'C' and 'G'. Thus, in a preferred embodiment step (i) comprises providing an MR encodable by an MR gene haplotype comprising rs2070951 and rs5522 with respective alleles 'G' and 'A', and an MR encodable by an MR gene haplotype comprising rs2070951 and rs5522 with respective alleles 'C' and 'A', and an MR encodable by an MR gene haplotype comprising rs2070951 and rs5522 with respective alleles 'C' and 'G'. Since these haplotypes have alleles of rs2070951 and rs5522 corresponding to those of the three major haplotypes identified by the inventions, the inventors believe them to be of most clinical relevance and are therefore preferred.

In another example, step (i) may comprise providing an MR encodable by an MR gene haplotype comprising rs2070951 and rs5522 with respective alleles 'G' and 'A', and an MR encodable by an MR gene haplotype comprising rs2070951 and rs5522 with respective alleles 'C' and 'A', and an MR encodable by an MR gene haplotype comprising rs2070951 and rs5522 with respective alleles 'G' and 'G'.

In another example, step (i) may comprise providing an MR encodable by an MR gene haplotype comprising rs2070951 and rs5522 with respective alleles 'G' and 'A', and an MR encodable by an MR gene haplotype comprising rs2070951 and rs5522 with respective alleles 'C' and 'G', and an MR encodable by an MR gene haplotype comprising rs2070951 and rs5522 with respective alleles 'G' and 'G'.

In another example, step (i) may comprise providing an MR encodable by an MR gene haplotype comprising rs2070951 and rs5522 with respective alleles 'C' and 'A', and an MR encodable by an MR gene haplotype comprising rs2070951 and rs5522 with respective alleles 'C' and 'G', and an MR encodable by an MR gene haplotype comprising rs2070951 and rs5522 with respective alleles 'G' and 'G'.

In a further embodiment, step (i) comprises providing MRs with four different MR gene haplotypes. For example, step (i) may comprise providing an MR encodable by a MR gene haplotype comprising rs2070951 and rs5522 with respective alleles 'G' and 'A', and an MR encodable by an MR gene haplotype comprising rs2070951 and rs5522 with respective alleles 'C' and 'A', and an MR encodable by an MR gene haplotype comprising rs2070951 and rs5522 with respective alleles 'C' and 'G', and an MR encodable by a MR gene haplotype comprising rs2070951 and rs5522 with respective alleles 'G' and 'G'. Since these haplotypes have alleles of rs2070951 and rs5522 corresponding to all of the MR gene haplotypes identified by the inventors (three major haplotypes and one minor haplotype), when providing MRs in step (i) involves providing subjects, or cells from subjects, it is appreciated that step (i) typically involves providing MRs with four different MR gene haplotypes, provided of course that sufficient subjects are sampled.

In an embodiment, the test agent is an MR agonist or an MR antagonist. Examples of MR agonists include deoxycortisol, aldosterone, cortisol, corticosterone and fludrocortisone. Examples of MR antagonists include spironolactone and epleronone. Preferably, the test agent is an MR agonist.

It is appreciated that the test agent may be a steroid, a SSRI such as citalopram, paroxetine or venlafaxine, or a tricyclic antidepressant (TCA) such as amytriptyline or nortriptyline.

In one embodiment, the method is performed in vitro, as exemplified in Example 3. By in vitro we include cell-based assays. For example, the method may be performed in any cell line that can be easily manipulated within a laboratory e.g. Cos-1 cells or CV-1 cells.

When the method is performed in vitro, it is appreciated that the two or more MRs provided in step (i) may be produced using recombinant technology. Thus, rather than being MRs encoded by MR gene haplotypes 1, 1A, 2, 2A, 3, 3A or 4 defined above, the two or more MRs may be encoded by the same MR polynucleotide sequence with different alleles at positions rs2070951 and rs5522. Conveniently, the appropriate mutations are introduced using site-directed mutagenesis to produce expression vectors for the different MR types (see Example 3).

The recombinant MRs used in the method may comprise a GST portion or may be biotinylated or otherwise tagged, for example with a 6H is, HA, myc or other epitope tag, as known to those skilled in the art. This may be useful in purifying and/or detecting the MRs. Techniques for cloning, manipulation, modification and expression of nucleic acids, including protein engineering and site-directed mutagenesis and purification of expressed proteins, are very well known in the art and are described for example in Sambrook et al (2001).

Although less preferred, it is appreciated that the two or more MRs provided in step (i) may also be obtained by extracting endogenous MRs from cells of subjects whose MR haplotype is known. For example, to obtain an MR encoded by an MR gene haplotype comprising rs2070951 and rs5522 with respective alleles 'G' and 'A', endogenous MR may be extracted from the cells of subjects known to have that MR haplotype (e.g. haplotype 1 or 1A).

Preferably, the method, when performed in vitro, is cell-based. Thus, in a particularly preferred embodiment, the two or more MRs provided in step (i) are provided in two or more cells expressing the respective MRs. For example, expression constructs containing the different MR gene haplotypes may be transfected into different cells as is routine in the art and described in Example 3.

In an alternative embodiment, the method is performed in vivo, as exemplified by Example 4. Thus, providing two or more MRs in step (i) may involve providing two or more subjects known to have two or more of the different MR gene haplotypes.

In a further embodiment, the method is performed ex vivo. Thus, providing two or more MRs in step (i) may involve providing cells from two or more subjects known to have two or more of the different MR gene haplotypes. Conveniently, the cells are provided in a cellular sample taken from the subject such as a blood sample.

Typically, the subject is a human subject, preferably female.

Since the inventors have identified three major and one minor MR haplotype, in humans, when performing the method in vivo or ex vivo, providing two or more MRs in step (i) generally comprises providing two or more subjects (or cells from subjects) having the respective MR haplotype. Thus, to provide an MR encodable by an MR gene haplotype comprising rs2070951 and rs5522 with respective alleles 'G' and 'A', a subject or a cell from a subject having haplotype 1 or 1A is provided. To provide an MR encodable by an MR gene haplotype comprising rs2070951 and rs5522 with respective alleles 'C' and 'A', a subject or a cell from a subject having haplotype 2 or 2A is provided. To provide an MR encodable by an MR gene haplotype comprising rs2070951 and rs5522 with respective alleles 'C' and 'G', a subject or a cell from a subject having haplotype 3 or 3A is provided. To provide an MR encodable by an MR gene haplotype comprising rs2070951 and rs5522 with respective alleles 'G' and 'G', a subject or a cell from a subject having haplotype 4 is provided. Methods of assessing the MR haplotype status of a subject are as described above and are detailed in the Examples.

Preferably, the subjects are homozygotes for the desired haplotype (i.e. the subjects have two copies of the desired haplotype). However, it is appreciated that heterozygotes may be used, for example by using a subject homozygous for haplotype 1 and comparing it to a haplotype 1/haplotype 2 subject to determine the effect of haplotype 2.

Having provided the two or more MRs encodable by the respective MR gene haplotypes, and the test agent, the effect of the test agent on at least one activity of each MR must be assessed.

By "at least one activity of each MR", we include the ability of the MR to modulate the expression of a reporter polynucleotide operably linked to an MR responsive promoter. Thus, in one embodiment, step (iii) comprises assessing if the test agent modulates expression of a reporter polynucleotide operably linked to an MR responsive promoter, such as the tyrosine amino transferase triple hormone response (TAT3) element. The sequence of the rat TAT-GRE (glucocorticoid response element) is 5'-TGTACAggaTGT-TCT-3' (SEQ ID No: 7) (Holmbeck et al. (1998) *J Mol Biol* 281: 271-284). Other MR responsive promoters may include the GREs mentioned in Ziera et al (2009) *FASEB J* 23: 3936-3946. It will be appreciated that this lends itself to an in vitro transactivation assay which is the subject of Example 3, wherein the inventors demonstrate that cortisol induced MR signalling is dependent upon MR haplotype.

By a 'reporter polynucleotide' we include the meaning of a polynucleotide whose expression is detectable by means of a suitable assay. For example, the polynucleotide may be one whose expression can be detected directly, for instance by using RT-PCR, or may be one whose expression can be detected indirectly, for instance by the polynucleotide encoding a reporter protein. By 'reporter protein', we include the meaning of a protein that can be detected (directly or indirectly) by an appropriate assay.

In an embodiment, the reporter polynucleotide is one that encodes a reporter protein whose activity may easily be assayed, for example luciferase, β-galactosidase, chloramphenicol acetyl transferase (CAT) gene, or Green Fluorescent Protein (see, for example, Tan et al., 1996).

The reporter polynucleotide may be fatal to the cells, or alternatively may allow cells to survive under otherwise fatal conditions. Cell survival can then be measured, for example using colorimetric assays for mitochondrial activity, such as reduction of WST-1 (Boehringer). WST-1 is a formosan dye that undergoes a change in absorbance on receiving electrons via succinate dehydrogenase. Alternatively, the reporter polynucleotide, when expressed, may produce a readily detectable signal that can be measured.

By a reporter polynucleotide we also include a gene whose expression is controlled by MR, such as those described in Datson et al (2008) *Eur J Pharmacol* 583: 272298.

Several techniques are available in the art to detect and measure expression of a reporter polynucleotide which would be suitable for use in the present invention. Many of these are available in kits both for determining expression in vitro and in vivo.

For example, levels of mRNA transcribed from a reporter polynucleotide can be assayed using RT-PCR. The specific mRNA is reverse transcribed into DNA which is then amplified such that the final DNA concentration is proportional to the initial concentration of target mRNA.

Levels of expression can also be determined by measuring the concentration of protein encoded by the reporter polynucleotide. Assaying protein levels in a biological sample can occur using any suitable method. For example, protein concentration can be studied by a range of antibody based methods including immunoassays, such as ELISAs and radioimmunoassays. In one such assay, a protein-specific monoclonal antibody can be used both as an immunoadsorbent and as an enzyme-labelled probe to detect and quantify a specific protein. The amount of the protein present in the sample can be calculated by reference to the amount present in a standard preparation using a linear regression computer algorithm. In another ELISA assay, two distinct specific monoclonal antibodies can be used to detect the specific protein. In this assay, one of the antibodies is used as the immunoadsorbent (primary antibody) and the other as the enzyme-labelled probe (secondary antibody).

Suitable enzyme labels include those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels such as fluorescein and rhodamine, and biotin.

Levels of expression may be determined by assessing the function or activity of a protein encoded by the reporter polynucleotide. For example, if the reporter polynucleotide encodes an enzyme, assessing its expression may involve measuring the activity of the enzyme. Enzyme assays typically measure either the consumption of substrate or production of product over time. It is appreciated that a large range of methods exist for determining the concentrations of substrates and products such that many enzymes can be assayed in several different ways as is well known in the art (e.g. Bergmeyer (1974)).

Preferably, the reporter polynucleotide is a luciferase gene and expression of the gene is assessed using a luminometer. In a particularly preferred embodiment, the reporter gene operably linked to an MR responsive promoter is a luciferase gene operably linked to a TAT3 element. A variety of methods are known in the art to operably link polynucleotides, especially DNA, to other polynucleotides.

By "at least one activity of each MR" we also include the ability of the MR to bind to an MR binding partner. Thus, in one embodiment, step (iii) comprises assessing if the test agent modulates binding of the MR to an MR binding partner.

By a "MR binding partner" we include a molecule that binds to human MR, whose amino acid sequence is listed in FIG. 20. The binding partner may be a polypeptide, an antibody, a small molecule, a natural product, an affibody, a peptidomimetic, a nucleic acid, a peptide nucleic acid molecule, a lipid or a carbohydrate.

Particular examples of suitable MR binding particles include the co-activators SRC-1, P300/CBP, TIF2, RHA and ELL and the co-repressors SMRT, NcoR, PIAS and DAXX (see Young and Young (2009) *J Mol Endo* 43: 53-64).

As used herein, the term "antibody" includes but is not limited to polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Furthermore, the antibodies and fragments thereof may be humanised antibodies, which are now well known in the art (Janeway et al, 2001 *Immunobiology*, 5th ed., Garland Publishing).

Suitable antibodies which bind to the MR, or to specified portions thereof, can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol.* 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: "*Monoclonal Hybridoma Antibodies: Techniques and Application*", Hurrell (CRC Press, 1982); "*Monoclonal Antibodies: A Manual of Techniques*", H. Zola, CRC Press, 1987, ISBN: 0-84936-476-0; "*Antibodies: A Laboratory Manual*" 1st Edition, Harlow & Lane, Eds, Cold Spring Harbor Laboratory Press, New York, 1988. ISBN 0-87969-314-2; "*Using Antibodies: A Laboratory Manual*" 2nd Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., 1st Edition, —Wiley-VCH, Weinheim, 2007. ISBN: 3-527-31453-9.

The binding partner may comprise a detectable label. By "detectable label" we include any molecule which can be used to label the binding partner, for example by coupling that molecule to the binding partner such as in a conjugate. Suitable labels are known in the art and include but are not limited to enzymes, radiolabels, fluorogens, biotin, toxins, drugs, haptens, DNA, RNA, modified nucleotides (eg 2-o-methyl-RNA, LNA and PNA), polysaccharides, polypeptides, liposomes, chromophores, chemiluminescers, colored particles and colored microparticles, and the like.

Preferably, assessing if the test agent modulates binding of the MR to an MR binding partner, assesses binding of the MR present in a cell or cell extract, to an MR binding partner.

Binding can be assessed by standard binding assays known in the art. For example, the binding partner may be radio-labelled or fluorescently labelled, and incubated with the MR (e.g. present in whole cells) until equilibrium is reached. The amount of free binding partner vs bound binding partner must then be determined by separating the signal from bound vs free binding partner. In the case of a radioligand this can be done by centrifugation or filtration to separate bound ligand present on whole cells from free binding partner in solution. Alternatively a scintillation proximity assay is used. In this assay the MR is bound to a bead containing scintillant and a signal is only detected by the proximity of the radioligand bound to the MR immobilised on the bead.

Since the MR regulates the hypothalmic-pituitary-adrenal (HPA) axis, it will be appreciated that the method may involve assessing the MR's effect on the HPA axis. For example, the MR regulates the HPA axis (e.g. cortisol and adrenocortico trophic hormone (ACTH)) by both genomic and fast non-genomic mechanisms. The genomic effects are in part mediated by control of arginine vasopressin (AVP) and corticotropin releasing factor expression within the hypothalamus, both involved in ACTH release. The fast non-genomic effects are mediated by pre-synaptic enhancement of glutamate release and post-synaptic decrease of hyperpolarising potassium currents; both increasing neuronal responsiveness (Joels et al, 2008, TINS 31: 1-7).

Accordingly, by "at least one activity of each MR" we also include the effect of the MR on cortisol levels. Thus, in one embodiment, step (iii) comprises assessing if a test agent modulates the effect of MR on cortisol levels.

It will be appreciated that this lends itself to the method being performed in vivo. Thus, as described in Example 4, the method may comprise providing two or more subjects known to have two or more of the different MR gene haplotypes, administering a test agent to each subject, and assessing if the test agent modulates the effect of each MR on cortisol levels.

Conveniently, cortisol is assessed in a sample taken from a subject, such as a saliva sample, a blood sample, a blood plasma sample, a blood serum sample, a urine sample or a cerebro spinal fluid (CSF) sample.

Assays for cortisol are well known in the art and are described, for example, in Example 4.

Preferably, the method involves assessing the effect of a test agent on the cortisol awakening response (CAR). This is a distinct rise in cortisol levels directly after awakening which typically reaches its peak at 30 minutes and returns to baseline 60 minutes after awakening (Pruessner et al, 1997; Wust et al, 2000b; Wilhelm et al, 2007). Generally, the CAR is measured at four time points: at awakening (T1), and at 30 (T2), 45 (T3) and 60 (T4) minutes. Various aspects of the CAR may be assessed in the method of the invention including the course of the CAR, the area under the curve with respect to increase (AUCi) and the area under the curve with respect to ground (AUCg) (see Example 4).

By 'at least one activity of each MR' we also include the effect of the MR on ACTH levels. Thus, in one embodiment, step (iii) comprises assessing if a test agent modulates the effect of MR on ACTH levels. It will be appreciated that this also lends itself to the method being performed in vivo. Conveniently, ACTH is assessed in a sample taken from a subject such as a saliva sample, a blood sample, a blood plasma sample, a blood serum sample, a urine sample or CSF sample.

Assays for ACTH are well known in the art and are described, for example, in Example 3.

Other activities of the MR that may be assessed include assessing cardiovascular effects of the MR, such as water and electrolyte balance, and the effect of the MR on autonomic nervous system reactivity following a challenge, such as heart rate response to psychosocial stress (De Rijk (2006) JCEM 91: (12): 5083-9).

A test agent will modulate at least one activity of each MR in an MR gene haplotype-dependent manner if the assessed activity is significantly different between the MRs tested (ie, typically $p<0.05$). For example, if a test agent's effect on the expression of three MRs (encoded by three different MR haplotypes) is assessed, the effect will be dependent on MR gene haplotype if the MRs encoded by the different MR haplotypes are found to be expressed at different levels. Any suitable statistical test known in the art can be used to assess significance, including for example T-tests and multivariate analysis of variance (MANOVA) tests, as described in the Examples.

It is appreciated that it may be desirable to increase an identified MR gene haplotype dependent effect, for example where the test agent is one that changes the expression of MR or the protein efficacy of the MR in a way that is believed to be beneficial to patients. Thus, in one embodiment the method further comprises modifying a test agent which has been shown to modulate at least one activity of each MR in an MR gene haplotype-dependent manner, and testing the ability of the modified agent to modulate at least one activity of each MR in an MR gene haplotype-dependent manner.

An eleventh aspect of the invention provides a method of classifying a subject according to the effectiveness of a treatment regime for an MR-related disorder, the method comprising determining whether a subject has a haplotype comprising rs3216799, rs6814934, rs7658048, rs2070950 and rs2070951 with respective alleles '−CT', 'G', 'C', 'G' and 'G', or a haplotype comprising rs3216799, rs6814934, rs7658048, rs2070950 and rs2070951 with respective alleles '+CT', 'C', 'T', 'C' and 'C', or a haplotype comprising rs3216799, rs6814934, rs7658048, rs2070950 and rs2070951 with respective alleles '−CT', 'C', 'C', 'C' and 'C', or a haplotype comprising rs2070951 and rs5522 with respective alleles 'G' and 'G' and either (i) administering a treatment regime, and assessing the effectiveness of the treatment regime, or (ii) administering an appropriate treatment regime for that haplotype, wherein the subject is one that has an MR-related disorder.

Preferences for the MR-related disorder are as defined above in relation to the tenth aspect of the invention. Preferably, the MR-related disorder is anxiety disorder or depression, or a disorder associated with anxiety disorder or depression, including those defined above.

Preferences for the haplotype comprising rs3216799, rs6814934, rs7658048, rs2070950 and rs2070951 with respective alleles '−CT', 'G', 'C', 'G' and 'G', the haplotype comprising rs3216799, rs6814934, rs7658048, rs2070950 and rs2070951 with respective alleles 'C', 'T', 'C' and 'C', and the haplotype comprising rs3216799, rs6814934, rs7658048, rs2070950 and rs2070951 with respective alleles '−CT', 'C', 'C', 'C' and 'C' are as defined above, and include, for example, haplotypes 1-3, and haplotypes 1A-3A.

By treatment regime, we include any one or more of an anti-depressant, an anti-convulsant, a beta-blocker, cortisol, a cortisol agonist, a cortisol antagonist, or an agent that modulates MR-expression to the subject. Examples of agents that modulate MR-expression include antidepressants such as tricyclic antidepressants (TCAs) and selective serotonin reuptake inhibitor (SSRIs), which have been shown to increase MR expression (de Koet, DeRijk, Meijer, Clinical Practice article 08). Further examples include ACTH which has been shown to increase MR expression in an animal model; steroids (both natural and synthetic); progesterone; benzodiazephines; and estrogen. Alternatively, the treatment regime may comprise administering cognitive behavioural therapy or an exercise regime, or electoconvulsion therapy (ECT).

By assessing the effectiveness of the treatment regime we include the meaning of assessing how the regime affects the symptoms of the MR-related disorder (eg. anxiety disorder or depression or associated disorder) in the subject. For example, an effective treatment regime will reduce or alleviate the symptoms of the MR-related disorder (eg. anxiety disorder or depression or associated disorder) in a subject following administration, whereas an ineffective treatment regime will increase or worsen the symptoms of the MR related disorder (eg. anxiety disorder or depression or associated disorder) in a subject following administration, or else have unwanted side-effects. Techniques to monitor the symptoms of MR-related disorders such as anxiety disorder or depression are well known in the art, and include questionnaire based diagnoses as described in the Examples. Examples include the DSM-IV Composite International Diagnostic Interview (CIDI) version 2.1, the Mini International Neuropsychiatric Interview (MINI) and the Structured Clinical Interview (SCID). Personality can be determined by the NEO, which measures neuroticism, extraversion, openness to experience, agreeableness and conscientiousness. Other examples are NormQuest (Leiden University Medical Center) and Montgomery-Åsberg Depression Rating Scale (MADRS) (Penninx BWJH et al (2008) *In t Meth Psy Res* 17:121-140; Montgomery and Åsberg (1979) *Brit J Psy* 134:382-89).

Conveniently, the subject is one who has been diagnosed as having depression or anxiety disorder, for example using standard questionnaire investigations.

It is preferred if the subject's MR-related disorder (eg. anxiety disorder or depression) status is evaluated just prior to administration of the treatment regime so as to define a baseline which can be used to monitor the efficacy of the treatment. Preferably, the same technique is used to evaluate a subject's MR related disorder (eg. anxiety disorder or depression status) before and after administration of the treatment regime.

Preferably, the subject is a human, most preferably a female.

It is appreciated that in the context of option (i) of the method of the eleventh aspect of the invention, the method may be employed, for example, in the context of establishing whether a particular treatment is effective for a particular individual. Alternatively, the method may be employed, for example, in the context of a clinical trial of a candidate treatment, eg a drug, for an MR-related disorder (eg. depression or anxiety disorder). Thus, the method may be used to determine the optimal treatment for an MR-related disorder (eg. anxiety disorder or depression) in a subject with any given MR gene haplotype. In this latter embodiment, the method is typically performed on a population of subjects. For example, the method may be carried out on at least 10, 50, 100, 200, 300, 400, 500 subjects, or at least 1000 subjects, or at least 5000 subjects or more.

As is well known in the art, to control for the 'placebo effect', it may be desirable to substitute the compound for a placebo in a proportion of the subjects undergoing the clinical trial.

A candidate treatment may be administered as an individual dose or in several doses over a period of 1, 2, 3 or 4 weeks, 2, 4, 6, 6-12, 12-18 or 18-24 months, or several years, depending upon the candidate treatment and route of administration.

It is appreciated that in the context of option (ii) of the method of the eleventh aspect of the invention, having established which treatments are optimal for which MR haplotypes, it may be determined which of the haplotypes a subject has, and based on that assessment the optimum therapy to treat an MR-related disorder (eg. anxiety disorder or depression) in that subject administered.

Without wishing to be bound by any theory, the inventors believe that the effects of the MR haplotypes are additive, such that a subject with two different MR haplotypes is expected to receive an intermediate level of treatment relative to a subject that has two of the same MR haplotypes.

The invention provides a kit of parts for use in selecting an agent that modulates at least one activity of an MR in a MR gene haplotype-dependent manner, comprising two or more MRs encoded by a respective two or more of an MR gene haplotype comprising rs2070951 and rs5522 with respective alleles 'G' and 'A', or an MR gene haplotype comprising rs2070951 and rs5522 with respective alleles 'C' and 'A', or an MR gene haplotype comprising rs2070951 and rs5522 with respective alleles 'C' and 'G', or an MR gene haplotype comprising rs2070951 and rs5522 with respective alleles 'G' and 'G', or a respective two or more polynucleotides encoding said MRs. For example, the kit may be used to select an agent for combating an MR-related disorder such as anxiety disorder or depression, or a disorder associated with anxiety disorder or depression.

Preferences for the MRs (and combinations thereof) and the MR gene haplotypes are as defined above. In an embodiment, the kit of parts comprises any three or four MRs encoded by a respective three or four of an MR gene haplotype comprising rs2070951 and rs5522 with respective alleles 'G' and 'A', or an MR gene haplotype comprising rs2070951 and rs5522 with respective alleles 'C' and 'A', or an MR gene haplotype comprising rs2070951 and rs5522 with respective alleles 'C' and 'G', or an MR gene haplotype comprising rs2070951 and rs5522 with respective alleles 'G' and 'G', or a respective three or four polynucleotides encoding said MRs.

Preferably, the two or more MRs in the kit of parts are expressed in a respective two or more cells, such as a Cos-1 cell or a CV-1 cell.

In an embodiment, the kit of parts further comprises a reporter polynucleotide operably linked to an MR responsive promoter. Suitable reporter polynucleotides and MR responsive promoters are listed above. In a particularly preferred embodiment, the kit comprises a luciferase gene operably linked to a TAT3 element. Conveniently, the kit further comprises a means (e.g. substrate) for detecting the reporter polynucleotide.

It is appreciated that the kit of parts may be useful in performing the methods of the invention. For example, the kit of parts may be useful in a laboratory to test the effect of various test agents on the activity of the MRs in the kit. Based on the results, candidate drugs may then be indicated and aligned for particular MR genotypes, such that the genotype of a particular patient can be assessed and the appropriate drug administered.

The invention provides any novel method of assessing susceptibility to an anxiety disorder in a subject substantially as disclosed herein.

The invention provides any novel method of selecting an agent that modulates at least one activity of an MR in a MR gene haplotype-dependent manner substantially as disclosed herein.

The invention provides any novel method of classifying a subject according to the effectiveness of a treatment regime for an MR-related disorder (eg. anxiety disorder or depression) substantially as disclosed herein.

The invention provides any novel kit of parts substantially as herein disclosed.

The invention will now be described in more detail with the aid of the following Figures and Examples.

FIG. 1. LD plot of the eight genotyped MR SNPs, generated by Haploview. The SNPs are located in a region spanning 8 kb, starting in promoter region 2 and ending in exon 2. The magnitude of inter-marker LD scores is indicated in r2. All SNPs are enclosed in one haplotype bin. The SNP rs7671250 was highly linked to the functional MR I180V SNP (rs5522), and the SNP rs6814934 was highly linked to the functional MR −2G/C SNP (rs2070951).

FIG. 2. Schematic overview of the MR- and GR gene structures with their respective haplotypes and haplotype frequencies. The gene encoding the MR consists of ten exons, exon 1α, exon 1β, till exon 9. The exons 1α and 1β result in two mRNA splice variants, MRα and MRβ. The exons 1α and 1β, the first 2 nucleotides of exon 2, and part of exon 9 (UTR) are not translated into protein (light gray). The eight SNPs that were genotyped are indicated with arrows. The functional MR −2 G/C SNP (rs2070951) 10 is located in exon 2, two nucleotides before the first translation start site. The functional MR I180V SNP (rs5522) is located in exon 2 and results in an Isoleucine to Valine amino-acid change (DeRijk, Wust et al (2006)). Both SNPs are located in a haplotype bin that extends into the promoter region. Three main haplotypes were found (plus five minor haplotypes with frequencies smaller than 0.02, not presented here, that were pooled with haplotype 2 as they had the same alleles for the −2 G/C and 1180V SNPs). P1=promoter 1 in front of MR exon 1α, P2=promoter 2 in front of MR exon 1β, UTR=untranslated region. The gene encoding the GR consists of 17 exons, with the untranslated exons 1A-1H and 9a and 9P resulting in different mRNA splice variants. The five SNPs that were genotyped are indicated with arrows. Six haplotypes were found with frequencies similar as previously reported (van Rossum, Roks et al (2004); Derijk, van Leeuwen et al (2008)).

FIG. 3. Comparison of crude mean (±SEM) dispositional optimism scores for the three most frequent MR haplotypes, separately for women and men. Only in women haplotype 2 was associated with an increased mean optimism score of almost 2 points as compared to haplotypes 1 and 3. In men mean optimism scores were similar between haplotypes 1 to 3. The number of chromosomes per haplotype group is indicated. Note that the scale for optimism on the y-axis is from 10 to 15. ANOVA was used to yield p-values for the overall comparison between the three haplotypes.

FIG. 4. Nucleotide sequence of genomic region encompassing haplotype 3 (SEQ ID No: 1). Exons are marked in bold type and the positions of the eighteen SNPs within haplotype 2A are highlighted. The possible alleles of each SNP are also provided.

FIG. 5. (A) SNPs linked to the SNPs reported in our studies, based on the hapmap database, subjects from Europe: The SNPs related to our SNPs are positioned in block 2, SNPs 60-82; chr4:149532194 . . . 149632193. (B) Different alleles for 18 distinct SNPs in the MR gene that are linked to each other. There are three combinations of alleles that occur the most (haplotypes 1A-3A). The haplotype structure is based on SNPs used in the described association studies with optimism and LEIDS-R (rs3216799; rs7671250; rs6814934; rs7658048; rs2070950; rs2070951; rs5522; rs5525)+SNPs linked to those SNPs based on other Dutch cohorts (rs9992256; SNP x; rs2248038)+SNPs linked to those SNPs based on the hapmap database, subjects from Europe (rs2070949; rs11730626; rs11099695; rs11929719; rs2172002; rs4835519). Genotype data from the hapmap database were downloaded and analysed in the program Haploview (Barrett et al (2005) "Haploview: analysis and visualisation of LD and haplotype maps" *Bioinformatics* 21(2): 263-5) to reconstruct haplotypes based on genotype data from multiple subjects.

FIG. 6. Scores for the total LEIDS-R and its subscales for MR haplotypes 1-3 in the total group (n=140). P-values represent results for ANOVA. P-value for linear regression analysis for haplotype 2, while correcting for sex, age and emotional abuse, was <0.01 for the scale Rumination; p<0.05 for Total LEIDS.

Figure 7:
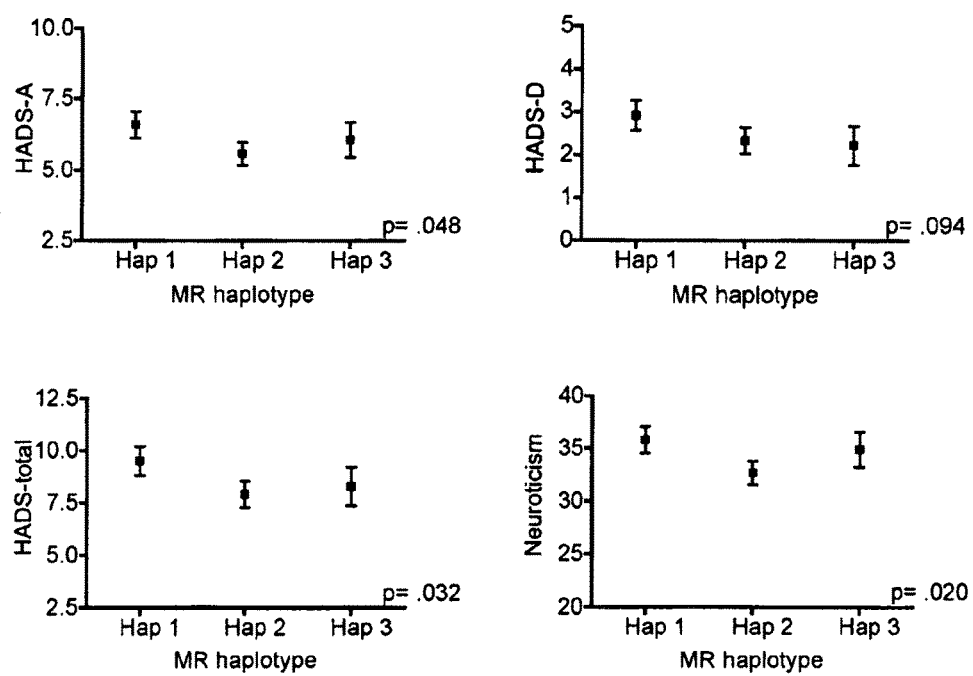

FIG. 7. Scores for neuroticism, symptoms for anxiety and depression in the total group. Scores for the HADS-A, HADS-D, total HADS and neuroticism (NEO-PI) for MR haplotypes 1-3 in the total group (n=140). P-values represent results for ANOVA. None of the scales gave a significant association with the haplotypes with linear regression analysis.

FIG. 8. Scores for the total LEIDS-R and its subscales for MR haplotypes 1-3 in females only (n=97). P-values represent results for ANOVA. P-value for linear regression analysis for haplotype 2, while correcting for age and emotional abuse, was <0.05 for the scales Aggression, Hopelessness, Risk aversion; p<0.001 for Rumination; p<0.01 for Total LEIDS.

Figure 9:
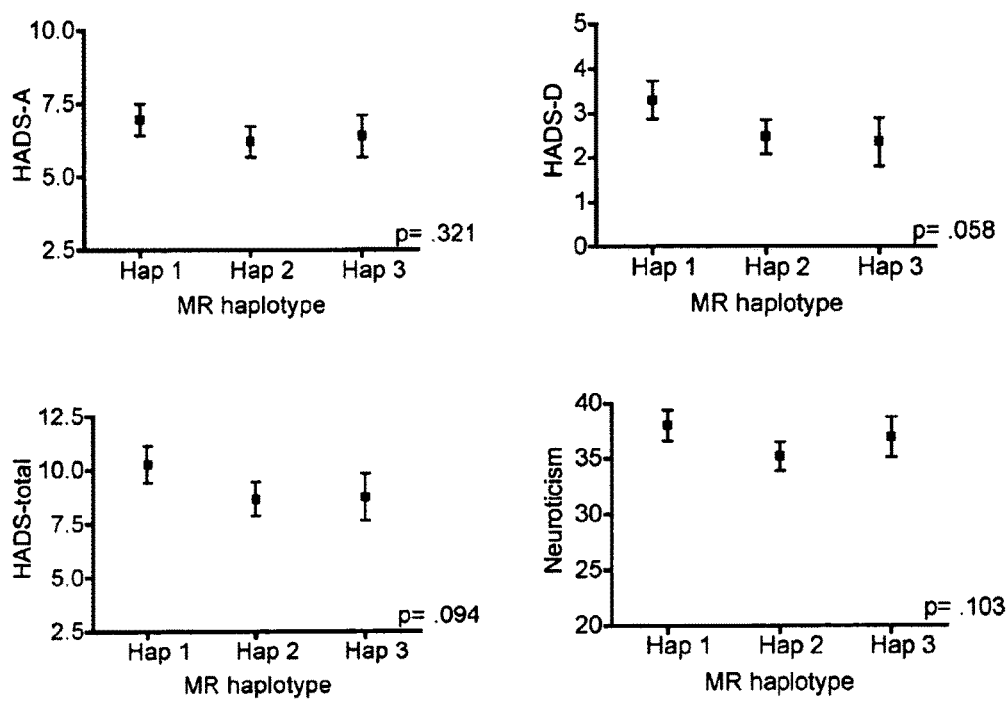

FIG. 9. Scores for the HADS-A, HADS-D, total HADS and neuroticism (NEO-PI) for MR haplotypes 1-3 in females only (n=97). P-values represent results for ANOVA. P-value for linear regression analysis for haplotype 2, while correcting for age and emotional abuse, was <0.05 for the scales HADS-D, HADS-total, Neuroticism.

FIG. 10. Scores for the total LEIDS-R and its subscales for MR haplotypes 1-3 in males only (n=43). P-values represent results for ANOVA. None of the scales gave a significant association with the haplotypes with linear regression analysis.

Figure 11:
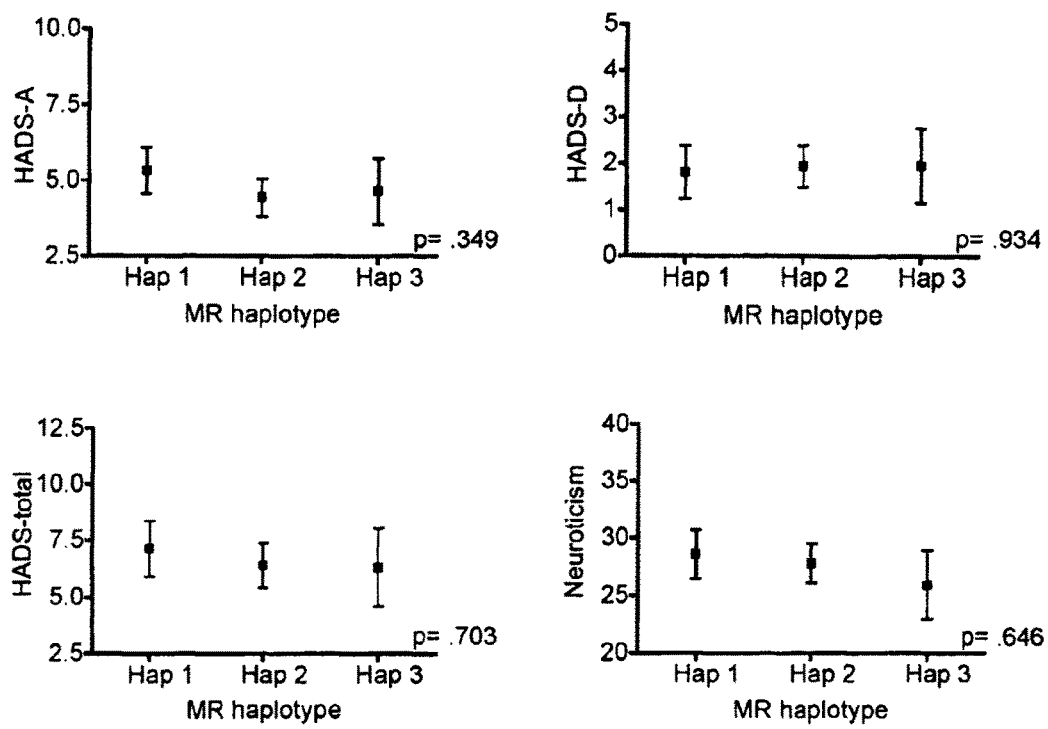

FIG. 11. Scores for neuroticism, anxiety and depression in male students. Scores for the HADS-A, HADS-D, total HADS and neuroticism (NEO-PI) for MR haplotypes 1-3 in males only (n=43). P-values represent results for ANOVA. None of the scales gave a significant association with the haplotypes with linear regression analysis.

Figure 12:
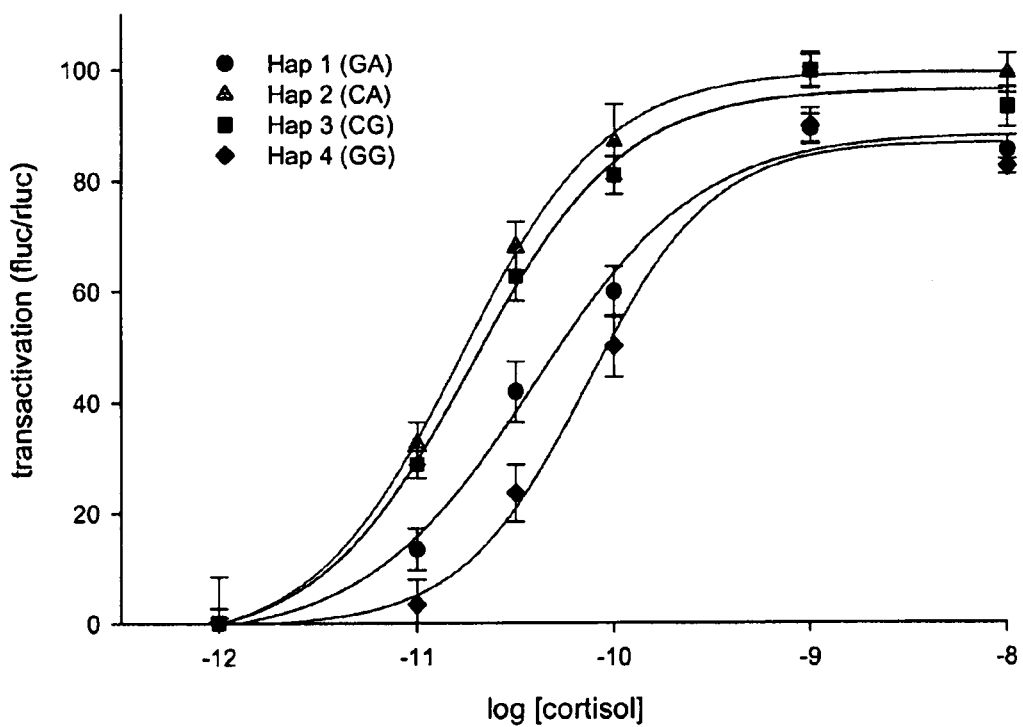

FIG. 12. Cortisol induced transactivation of the four MR haplotypes on a TAT-3 promoter in Cos-1 cells. Cortisol concentrations are indicated in log units and responses are displayed as reporter (fluc)/control (rluc) ratios. The four haplotypes showed significantly different responses (p<0.0001), with Hap 2 (triangle) being most efficient followed by respectively Hap 3 (square), Hap 1 (circle) and Hap 4 (diamond). The figure represents the data of three separate experiments, which did not show significant differences when compared to each other, and were therefore pooled.

Figure 13:
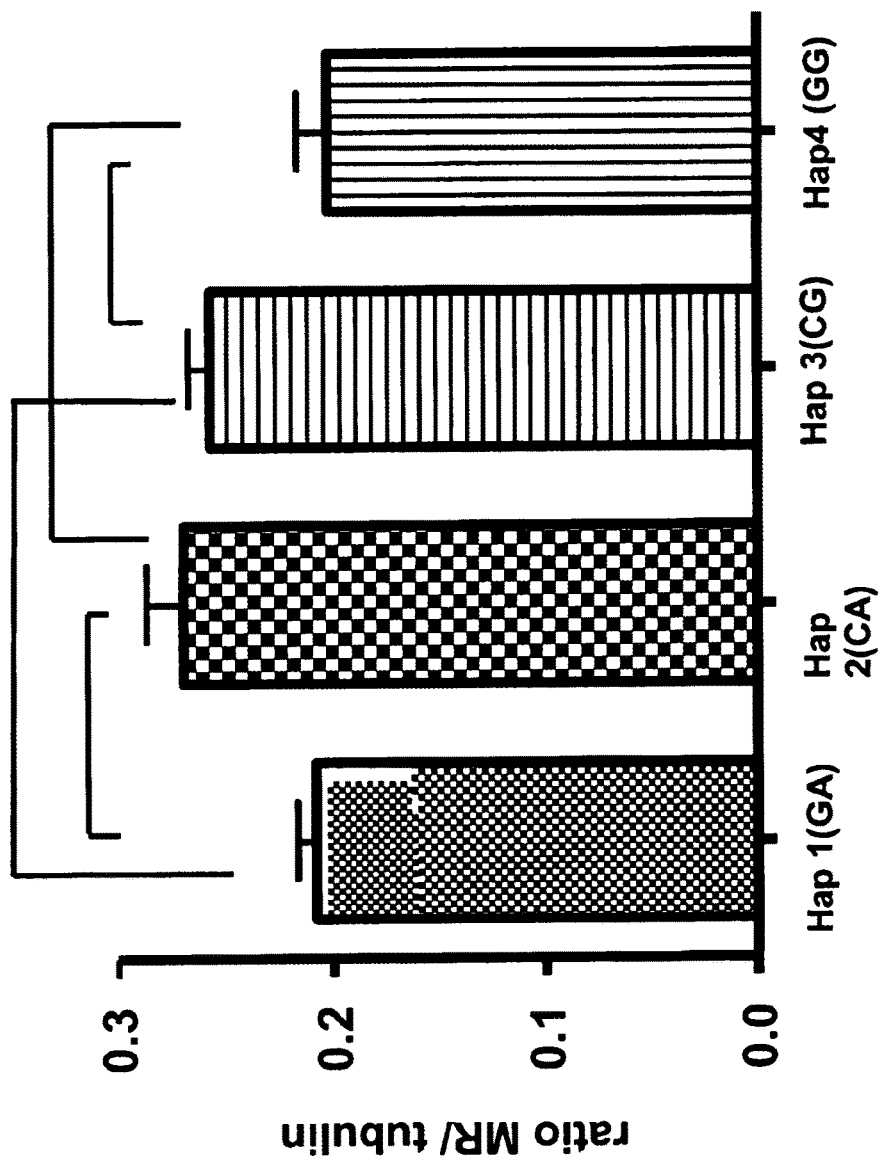

FIG. 13. MR protein expression measured in gray values on a western blot normalized against tubulin measured in gray values. The haplotypes Hap 2 and 3 had significantly higher MR expression than Hap 1 and 4 (*p<0.05) while there was no significant difference between Hap 1 and 4 and between Hap 2 and 3.

Figure 14:
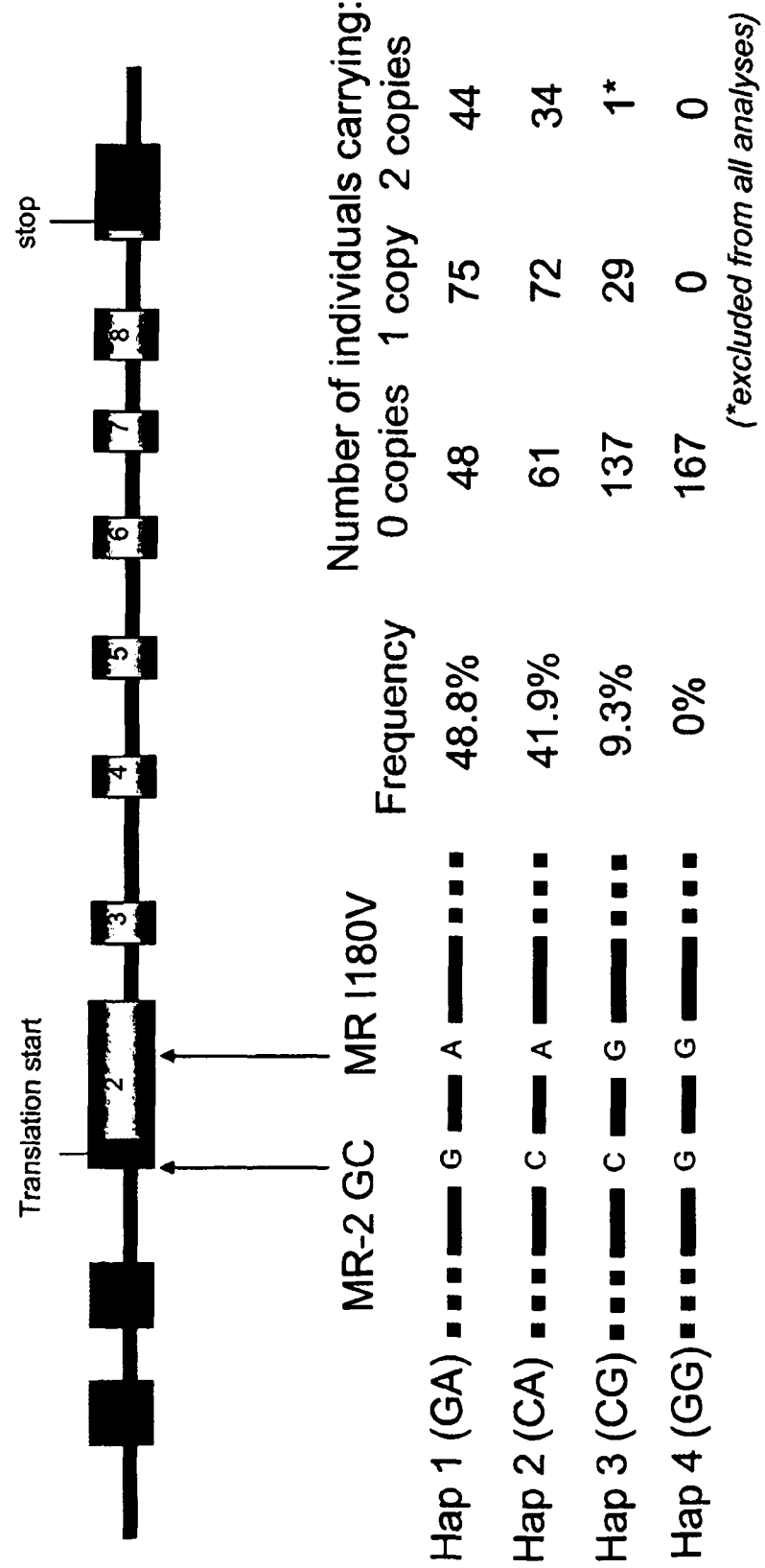

FIG. 14. Schematic overview of the human MR gene (not on scale) with the location of the MR SNPs MR-2G/C and MRI80V, the haplotypes and frequencies of the haplotypes formed by these SNPs. Dark gray boxes represent untranslated exonic regions, light gray boxes represent translated exonic regions and the black line represents the intronic regions of the gene. MR-2G/C is located in the untranslated exonic region just 2 nucleotides before the translation start and MRI180V is located in the translated region of exon 2. The frequency refers to the haplotype frequency observed in this cohort and the number of individuals in this cohort carrying 0, 1 (heterozygotes) or 2 (homozygotes) copies of a haplotype is indicated.

FIG. 15. ACTH, total plasma cortisol, salivary cortisol and heart rate responses to psychosocial stress (TSST) in subjects carrying 0, 1 or 2 copies of haplotype a) CA (haplotype 2), b) GA (haplotype 1) and c) CG (haplotype 3); data are expressed as mean±S.E.M.

Figure 16:
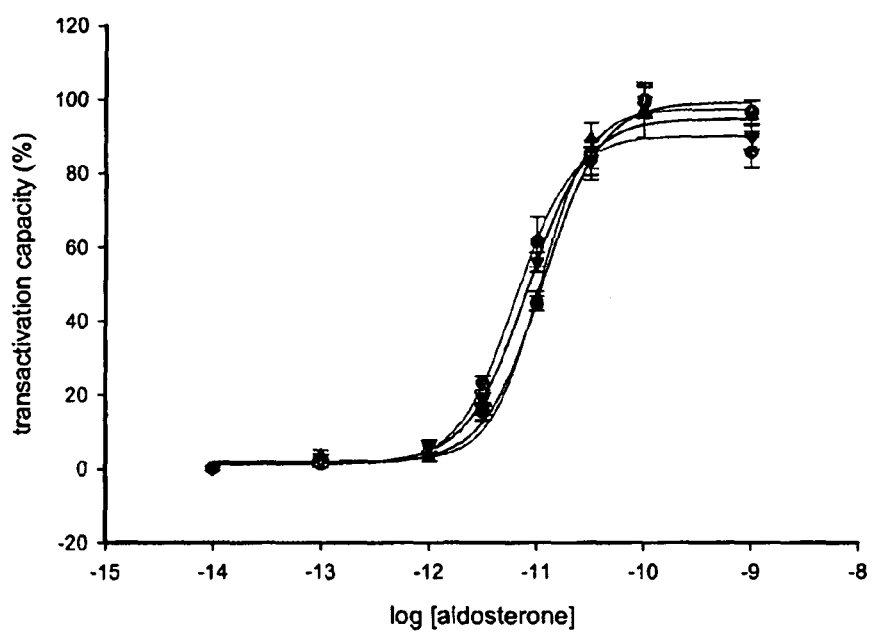

FIG. 16. Aldosterone induced transactivation of the four MR haplotypes on a TAT-3 promoter in Cos-1 cells. Aldosterone concentrations are indicated in log units and responses are displayed as reporter (fluc)/control (rluc) rations. The four haplotypes did not show significantly different responses. Diamonds=hap 1, Dots=hap 2, triangles point down=hap3, triangles point up=hap 4. The figure represents the data of three separate experiments, which did not show significant differences when compared to each other, and were therefore pooled. From FIGS. 12 and 16 it can be seen that differences among the genotypes are clear using cortisol but not using aldosterone as a ligand. Both are natural ligands for the MR. These data indicate that some drugs might result in different responses among the genotypes, while other drugs may not.

Figure 17:
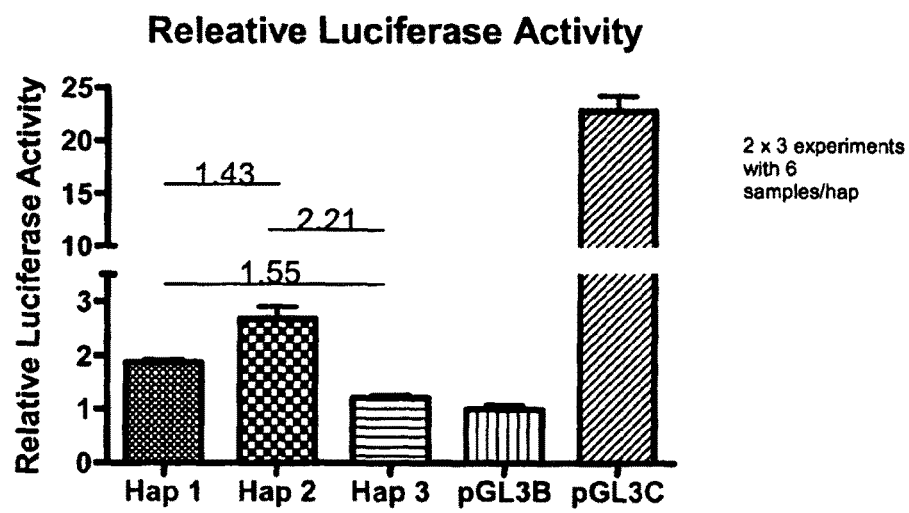

FIG. 17. Activity of the human MR promoter region associated with haplotype 1, 2 or 3. The pGL3-basic and pGL3-control constructs were taken along as respectively the negative and positive control. Results of the three independent assays with the two separate sets of plasmids were highly similar. The figure shows the results of a representative assay. Data are firefly signals divided by the Renilla signals, hereby controlling for cell death and variability in transfection efficiency. The activities of the constructs containing haplotype 1-3 are shown relative to the activity of the pGL3-basic plasmid, which activity was set to 1. Activities differed significantly between the three MR plasmids (ANOVA p<0.0001). Note the break in the y-axis.

Figure 18:
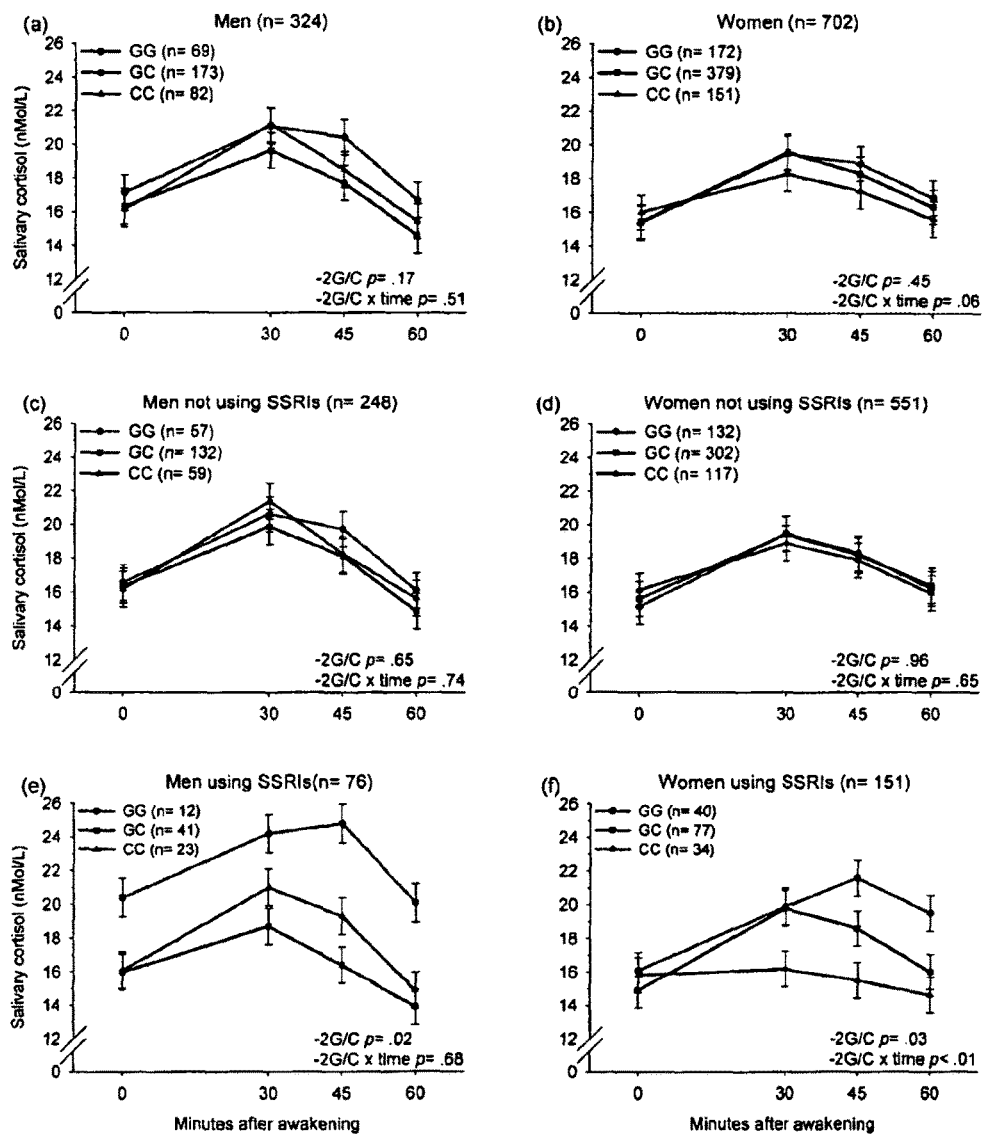

FIG. 18. Mean cortisol awakening response levels adjusted for age, smoking, awakening time and working on day of sampling. Error bars represent standard errors.

FIG. 19. Human MR sequence used to test in vitro functionality of four haplotypes (SEQ ID No: 8). Indicated are the rs2070951, the rs5522 and the rs5525, and the frequencies of their SNPs. Combinations of rs2070951 and rs5522 were generated in vitro using site-directed mutagenesis according to standard laboratory/manufacturer procedures. Haplotype 1 (depicted here, in vivo approx 50% frequency) consisted of rs2070951-G and rs5522-A; haplotype 2 (in vivo approx freq 35%) consisted of rs2070951-C and rs5522-A; haplotype 3 (in vivo approx freq 12%) consisted of rs2070951-C and rs5522-G and the rare haplotype 4 (in vivo freq less than 1/1000) consisted of rs2070951-G and rs5522-G.

FIG. 20. Amino acid sequence of human MR (SEQ ID No: 9). Also indicated is the position of the I180 V mutation.

EXAMPLE 1

A Mineralocorticoid Receptor Haplotype is Associated with Dispositional Optimism in Elderly Women but not in Men Summary The brain mineralocorticoid receptor (MR), together with the glucocorticoid receptor (GR), mediates the effects of the hormone cortisol on behaviour and cognition. We have tested the relation between MR gene variants and dispositional optimism. Dispositional optimism is defined as having generalized expectancy of positive outcomes for the future. It is a rather stable personality trait and might confer resilience against depression.

Eight single nucleotide polymorphisms (SNPs) in the MR gene, including two functional MR SNPs, were genotyped in 450 subjects aged 65-85 of the Dutch Arnhem Elderly Study. Six known GR haplotypes, constituted of five SNPs, were taken along. Participants completed a questionnaire on their subjective levels of dispositional optimism as part of the 'Scale of Subjective Well-being for Older persons' (SSWO). Haplotype reconstruction resulted in 3 main MR haplotypes with frequencies of 0.52, 0.36, and 0.12. MR haplotype 2 was associated with higher levels of optimism (15% increase) in women (p<0.001) but not in men (p=0.85; p=0.01 for interaction). The effect persisted after correction for several potential confounders and was estimated to explain 6% of the variance in optimism. The GR gene haplotypes had no influence on optimism scores. To conclude, our results suggest that MR haplotype 2 is associated with higher levels of dispositional optimism in women, which may establish resilience against stress and depression.

Introduction

The mineralocorticoid receptor (MR) is initially known for its function in the kidney, mediating aldosterone effects on salt status. Yet importantly, the MR is also expressed in the brain, mainly in limbic structures and frontal cortex. It has a ten-fold higher affinity for the hormone cortisol—the main corticosteroid—than its regulatory partner, the glucocorticoid receptor (GR). Central MR is involved in basal activity of the hypothalamic-pituitary-adrenal (HPA) axis, autonomic outflow and in physiological response to a stressor (De Kloet, Vreugdenhil et al (1998); de Kloet, Van Acker et al (2000)). In humans, associations have been found between MR- and GR gene variants and HPA activity (Derijk, van Leeuwen et al (2008)). A single nucleotide polymorphism (SNP) in the MR gene, the MR −2 G/C SNP, was associated with basal cortisol levels in elderly (Kuningas, de Rijk et al (2007)). In a study among healthy young males, another variant, the MR I180V SNP, modulated cortisol response after a psychosocial stressor (Trier Social Stress Test, TSST) (DeRijk, Wust et al (2006)). This same variant was also related to more feelings of depression in elderly (Kuningas, de Rijk et al (2007)). Moreover, associations between MR- and GR gene variants and stress-reactivity were found to be gender specific (Kumsta, Entringer et al (2007); Wust, Kumsta et al (2009)) (Nienke PNE09 in press). These gender specific effects of MR and GR gene variants might contribute to the differences in prevalence of depression between men and women.

In addition to regulation of the HPA axis, central corticosteroid receptors are responsible for the effects of cortisol on behaviour, learning and memory (Oitzl and de Kloet (1992); De Kloet, Vreugdenhil et al (1998)). Interestingly, based on studies with rodents the MR has been identified as a mediator of emotions and of explorative and coping behaviour (Oitzl and de Kloet (1992); Conrad, Lupien et al (1997); Rozeboom, Akil et al (2007)). Following an environmental demand the MR, but not the GR, regulates acute response selection, aimed to cope in an adaptive way. Also in humans cortisol and its receptors are necessary for learning and memory (Lupien, Wilkinson et al (2002)). However, it is unknown whether the MR and GR modulate human coping behaviour or psychological characteristics. This would be interesting to know, as psychological traits influence coping behaviour and eventually can establish resilience or vulnerability to psychopathology (Carver and Connor-Smith 2009).

Dispositional optimism is a positive personality characteristic that seems relatively stable over time and its heritability is estimated at 25-40% (Plomin, Scheier et al (1992); Scheier, Carver et al (1994); Giltay, Kamphuis et al (2006)). The construct of dispositional optimism was introduced in 1985 by Scheier and Carver and was described as having generally positive outcome expectancies (Scheier and Carver 1985). It is associated with enhanced goal engagement and self-regulatory flexibility when encountering environmental demands or stressful situations (Scheier, Weintraub et al (1986); Carver, Pozo et al (1993); Nes and Segerstrom (2006); Geers, Wellman et al (2009)). Eventually, this can be beneficial for physiological and psychological health. Dispositional optimism is associated with less distress and predicts lower risk for depression and all-cause and cardiovascular death (Plomin, Scheier et al (1992); Scheier and Carver (1992); Carver, Pozo et al (1993); Scheier, Carver et al (1994); Vickers and Vogeltanz (2000); Giltay, Geleijnse et al (2004); Giltay, Kamphuis et al (2006); Giltay, Zitman et al (2006)). Interestingly, variability in levels of optimism and positive affect seems to relate to differences in basal cortisol levels (Lai, Evans et al (2005); Steptoe, O'Donnell et al (2008)).

We hypothesised that the MR influences dispositional optimism, possibly modified by sex. In order to test this, we have analysed the association of eight MR gene variants, including two known functional MR SNPs, with optimism that was measured in subjects of the Arnhem elderly study cohort. Dispositional optimism was assessed with the 'Scale of Subjective Well-being for Older persons' (SSWO), a questionnaire measuring subjective wellbeing in elderly (Tempelman (1987)). In addition, genotypes for five common GR variants were determined.

Methods

Study Population

Our study population was based on the Arnhem Elderly Study, a population-based cohort study that started in 1991-1992. The study design and population characteristics have been described previously (van den Hombergh, Schouten et al (1995)). The subjects that we included in our research were part of a random sample that was followed for 9.1 years to assess the relation between a person's level of dispositional optimism and all-cause and cardiovascular mortality (Giltay, Geleijnse et al (2004)). This sample included men and women with an age between 65 to 85 years old who were independently living in the city of Arnhem, the Netherlands. Of this random sample of 1793 individuals, 1012 subjects gave an interview, 685 subjects underwent a physical examination, and 641 subjects gave a blood sample. Of the 641 blood samples, 499 (77.8%) DNA isolates were available for genotyping, which was successful for 473 (94.8%) DNA samples. The final subset of 450 subjects (optimism scores were missing for 23 subjects) did not differ from the initial group of 1012 subjects that gave an interview on sex, education, body mass index (BMI), or total number of chronic diseases. The included subjects were, however, significantly younger (mean age 73.7±5.7 vs. 75.2±5.7, p<0.001), more often together (60.9% vs. 54.1%, p=0.03), more often had a higher socioeconomic status (SES; 64.0% vs. 55.8%, p<0.01), more often suffered from cardio-vascular disease (CVD; 24.0% vs. 14.9%, p=0.01), and were more optimistic (mean score 13.40±4.68 vs. 12.36±4.91, p=0.001). When comparing the 450 subjects with the 49 subjects for whom we did not have a complete dataset, no significant differences were found for any of the sociodemographic or health factors. This study was approved by the Medical Ethics Committee of Wageningen University (Wageningen, the Netherlands). All participants provided written informed consent.

Assessment of Dispositional Optimism

Optimism was assessed using the Dutch Scale of Subjective Well-being for Older Persons (SSWO) developed by Groningen University (Groningen, the Netherlands) (Tempelman (1987)). The SSWO consists of five subscales including health, self-respect, morale, contacts, and optimism. Validity of the SSWO was previously assessed by comparing the results with objective measures of well-being (eg physical activity, mobility, use of health care, and activities of daily living) and the Hopkins Symptom Checklist (Tempelman (1987)). For each subscale an individual could indicate to what extent it conforms to a particular statement on a 3-point scale (from 0 to 2). The seven questions of the optimism subscale were: "I often feel that life is full of promises", "I still have positive expectations concerning my future", "There are many moments of happiness in my life", "I do not make any more future plans", "Happy laughter often occurs", "I still have many goals to strive for", and "Most of the time I am in good spirits" (our translations). The subscale had an adequate internal consistency (Cronbach's α: 0.76) and reliability (test-retest reliability coefficient: 0.76) (Tempelman (1987)). Questionnaires with missing data for the optimism subscale were excluded from the analyses. A mean item score for the optimism subscale was calculated and multiplied by 10, resulting in scores ranging from 0 to 20, with higher scores indicating a higher level of optimism.

Demographics, Health, and Blood Sampling

All data on demographics and health were assessed by trained interviewers (van den Hombergh, Schouten et al (1995); Giltay, Geleijnse et al (2004)). Dichotomous variables were created for sex (0=women; 1=men), marital status (0=living together as a married or unmarried couple; 1=otherwise), education (0=otherwise; 1=higher vocational or university), presence of CVD (0=absent; 1=present), and SES (0=housewives, unskilled and skilled workers, and lower employees; 1=small-business owners, employees, and higher professions; for married or widowed women SES was defined according to that of the husband). A variable for total number of chronic diseases coded for the total number of chronic disorders and illnesses of the respondent (0, 1, 2, 3, 4, or 5 or more from a list of 24; eg chronic gastric disease, cancer, thyroid disease). Body mass index (BMI) was calculated by dividing weight in kilograms (to the nearest 0.5 kg with the subject dressed but not wearing shoes) by height in meters squared (to the nearest 0.5 cm). A single blood sample was obtained from 641 subjects. Samples were stored at −80° C. until further analysis.

Genotyping

Genomic DNA was isolated from the blood samples according to standard procedures. Genotypes were determined for the functional MR −2G/C (rs2070951) and I180V (rs5522) SNPs. Two SNPs, the rs2070950 and rs5525, were included as additional control SNPs in case of genotyping failure for the −2 SNP or I180V SNP respectively. Four additional SNPs, with the accession numbers rs3216799 (an insertion-deletion polymorphism of two nucleotides, CT), rs7671250, rs6814934 and rs7678048, which are located in the MR promoter region, were assessed. In addition, genotypes for several common GR variants, the TthIIII (rs10052957), ER22EK (rs6189), N363S (rs6195), Bc/1 (rs41423247) and 9β (rs6198) SNPs, were assessed.

Genotyping was conducted using a Sequenom MassARRAY iPLEX assay (Sequenom, San Diego, Calif., USA). After a 'touchdown' polymerase chain reaction (PCR) and a primer extension reaction to introduce mass-differences between alleles, reaction products were desalted, processed and mass differences were detected using an Autoflex (Bruker, Wormer, Netherlands) MALDI-TOF Mass Spectrometer. Genotypes were assigned real-time using MassARRAY TYPER Analyzer 3.4 software (Sequenom, San Diego, Calif., USA). As quality control, 5 to 10% of the samples were genotyped in duplicate, and positive and negative controls that were included were consistent. Samples that failed for 50% of the SNPs or more were omitted from further analysis.

Statistical Analysis

Allele frequencies for the different SNPs were tested for Hardy-Weinberg Equilibrium (HWE) using HaploView (version 4.1 for Mac OSX) (Barrett, Fry et al (2005)). In addition, this program was used to test whether the SNPs for the MR gene were in linkage disequilibrium (LD) and to reconstruct haplotypes for the MR and GR genes. We used $r^2$ and $D^1$ to verify respectively the magnitude of inter-marker correlations and to define haplotype bins with the Solid Spine of LD method implemented in HaploView. Individual haplotypes were reconstructed in SNPHAP (version 1.3; available online at http://www-gene.cimr.cam.ac.uk/clayton/software/; last visited on Feb. 14, 2008). For the MR, haplotypes were reconstructed based on only the −2 G/C and I180V SNPs, which tag haplotypes 1–3 (five minor haplotypes with frequencies below 0.02 were pooled with haplotype 2 with a frequency of 0.32, resulting in a total frequency of 0.36). Samples with probabilities below 0.50 (n=1) were discarded. For the GR gene, haplotypes with a probability below 0.50 were also discarded (n=8); haplotypes with probabilities between 0.50 and 0.95 (n=10) or above 0.95 were weighted for their probabilities in the statistical analyses. Further analysis was performed in SPSS, version 16.0 for Mac OSX (SPSS Inc., Chicago, Ill., USA).

Association between dispositional optimism and sociodemographic or health factors was tested with regression analysis or an independent-samples t-test. Differences between men and women on these variables were tested using an independent-samples t-test or a $\chi^2$ test. The main aim was to test the influence of MR haplotypes on the level of optimism. To verify whether any of the MR or GR SNPs was associated with optimism scores, one-way ANOVA was used. Subsequently, differences between the MR haplotypes were tested using linear regression analysis. Next, analyses were repeated for the GR haplotypes. Furthermore, confounding effects of the GR haplotypes on the results with the MR haplotypes was verified. Comparison of mean optimism scores for the different MR diplotypes was conducted with one-way ANOVA, followed by a post-hoc Gabriel test. In a second regression analysis, we adjusted for potential confounding effects of sex (when appropriate), age, educational level, marital status, and SES in multivariable model 1, or additionally for CVD and total number of chronic diseases in model 2. All regression analyses were repeated while stratifying the data for sex. Finally, as the optimism scores showed a somewhat negatively skewed distribution, scores were inversed and log-transformed (to approach a normal distribution), and tests were repeated with these log-transformed data. A two-sided p-value<0.05 was considered statistically significant. As our main interest was the one test determining the association between the MR haplotypes and optimism, no Bonferroni correction was applied.

Results

Sample Characteristics

Data sets with optimism scores, genotypes, sociodemographic and health-related variables were available for 450 individuals (Table 1; note that for SES, BMI, total number of chronic diseases, and CVD several data points were missing). Increasing age, lower educational level, living alone, and more chronic disease were significantly associated with lower dispositional optimism scores (p's<0.05). No associations with optimism were found for SES, BMI, or CVD. There were important sex differences in sociodemographic and health-related variables (Table 1), but the mean optimism scores did not differ between men and women (p=0.78). One subject reported a depressive disorder.

MR and GR Haplotype Structure and Frequencies

All allele frequencies of the MR and GR SNPs were in HWE (p>0.10). For an overview of individual SNP genotype frequencies see Table 2. Allele frequencies of the MR −2G/C and 1180V SNPs were similar as previously reported (DeRijk, Wust et al (2006); Kuningas, de Rijk et al (2007)) Nienke PNE09 in press). Reconstruction of MR haplotypes resulted in one haplotype bin containing all eight genotyped SNPs (FIG. 1). The inter-marker correlation between the functional MR −2G/C (rs2070951) and 1180V (rs5522) SNPs was low ($r^2$=0.15), but these SNPs were in perfect LD with respectively the rs2070950 or rs5525 ($r^2$=1.0). Correlations between the SNPs in the promoter region and the −2G/C and 1180V SNPs ranged from 0.05 to 0.99 and D' LD values among all eight SNPs ranged from 0.86 to 1.0. FIG. 2 shows the structure of the three main MR haplotypes. For the GR gene inter-marker correlations ($r^2$) were between 0.0 and 0.45, D' LD values were between 0.08 and 1.0. Similar frequencies were found for the six haplotypes that previously have been described (FIG. 2).

Associations Between Individual MR or GR SNPs and Dispositional Optimism

For the eight MR SNPs, significant associations were found between dispositional optimism and the SNPs rs3216799, rs6814934, rs7658048, rs2070950 and rs2070951, with the highest significant associations found for the promoter SNPs rs3216799 and rs7658048 (Table 2). As sex differences exist for the effects of MR and GR SNPs on HPA activity, association analysis was repeated while stratifying for gender. Significant associations between optimism scores and the MR SNPs were found only in women, but not in men. No associations were found between dispositional optimism and any of the GR SNPs, not for the total group or for women or men separately.

Associations Between MR Haplotypes and Dispositional Optimism

We also tested associations between the naturally occurring MR haplotypes and the level of dispositional optimism. The MR haplotypes were significantly associated with dispositional optimism scores; haplotype 2 was associated with higher optimism when compared to the baseline haplotype 1 (Table 3). This haplotype 2 contains the functional −2 C-allele, while it does not contain the 180 V-allele. Importantly, we found a strong MR haplotype 2-by-sex interaction effect (p=0.01). Only in women, haplotype 2 was related to higher levels of optimism, while no significant effect was found in men (Table 3 and FIG. 3). Results were similar after adjustment for covariates in models 1 and 2, haplotype 2 giving an average increase per haplotype allele of 1.7 on a maximum score of 20 and explaining 6% of the variance in optimism ($\Delta R^2$=0.06, Table 3). Comparing the mean optimism scores for the six different MR diplotypes showed a clear and significant (one-way ANOVA, p=0.02) allele dose effect of haplotype 2 in women (data not shown). Post-hoc analysis revealed that the 2/2 diplotype was associated with significantly higher levels of dispositional optimism compared to the 1/1 diplotype, p<0.01; the 1/2 diplotype, p=0.01; and the 1/3 diplotype, p=0.01.

No association was found between dispositional optimism scores and the GR haplotypes (p=0.65 for the model for the total group), not in women (p=0.57), not in men (p=0.86;). In addition, including the GR haplotypes as confounders in the regression analysis for the MR haplotypes on optimism did not change the results. Finally: similar results were found when tests were repeated with the logarithmically transformed optimism data (data not shown).

The SSWO questionnaire actually consists of five subscales, namely health, self-respect, morale, contacts, and optimism. Association between the three MR haplotypes and these additional subscales was verified. Interestingly, also only in women haplotype 2 was associated with higher levels of self-respect, p<0.01; and the total SSWO score, p<0.001; a statistical trend was found for higher morale, p=0.06 and better health p=0.07.

TABLE 1

Sociodemographic and health factor measures according to sex in 450 elderly subjects

| Variable | | Total n | Total | Women | Men | p-value* |
|---|---|---|---|---|---|---|
| Gender | | 450 | 450 | 215 (47.8%) | 235 (52.2%) | |
| Age | | 450 | 73.7 ± 5.7 | 74.2 ± 5.9 | 73.2 ± 5.5 | 0.06 |
| Education level | Highschool or University | 450 | 91 (20.2%) | 26 (12.1%) | 65 (27.7%) | <.001 |
| | Otherwise | | 359 (79.8%) | 189 (87.9%) | 170 (72.3%) | |
| Marital status | Living together ((un)married couple) | 450 | 274 (60.9%) | 80 (37.2%) | 194 (82.6%) | <.001 |
| | Otherwise | | 176 (39.1%) | 135 (62.8%) | 41 (17.4%) | |
| Socioeconomic status | Low | 444 | 160 (36.0%) | 88 (41.7%) | 72 (30.9%) | 0.02 |
| | High | | 284 (64.0%) | 123 (58.3%) | 161 (69.1%) | |
| BMI | | 448 | 25.8 ± 3.9 | 26.3 ± 4.5 | 25.4 ± 3.1 | 0.01 |
| Total number of chronic diseases | 0 | 446 | 90 (20.2%) | 32 (15.0%) | 58 (25.0%) | 0.02 |
| | 1 | | 122 (27.4%) | 54 (25.2%) | 68 (29.3%) | |
| | 2 | | 100 (22.4%) | 51 (23.8%) | 49 (21.1%) | |
| | 3 | | 67 (15.0%) | 39 (18.2%) | 28 (12.1%) | |
| | 4 | | 30 (6.7%) | 14 (6.6%) | 16 (6.9%) | |
| | 5 or more | | 37 (8.3%) | 24 (11.2%) | 13 (5.6%) | |
| Cardiovascular disease | Absent | 446 | 339 (76.0%) | 171 (79.9%) | 168 (72.4%) | 0.06 |
| | Present | | 107 (24.0%) | 43 (20.1%) | 64 (27.6%) | |
| Dispositional optimism | | 450 | 13.40 ± 4.68 | 13.46 ± 4.69 | 13.34 ± 4.68 | 0.78 |

Data are mean ± SD or n (%).

*An independent-samples t-test or $\chi^2$ test was used to examine p-values for sex differences.

TABLE 2

Dispositional optimism scores according to genotypes for the different MR and GR SNPs in 450 elderly subjects

| MR SNP | Genotype | n (frequency) | Total (n = 450) Optimism (mean ± SD) | Test statistics[#] p-value | n (frequency) | Women (n = 215) Optimism (mean ± SD) | Test statistics[#] p-value | n (frequency) | Men (n = 235) Optimism (mean ± SD) | Test statistics[#] p-value |
|---|---|---|---|---|---|---|---|---|---|---|
| rs3216799 n = 416 | −/− | 195 (0.47) | 12.70 (4.81) | $F(1, 413) =$ 7.66 p = .01 | 84 (0.42) | 12.38 (4.59) | $F(1, 196) =$ 12.22 p = .001 | 111 (0.51) | 12.95 (4.97) | $F(1, 214) =$ 0.52 p = .47 |
|  | −/+CT | 173 (0.42) | 13.88 (4.36) |  | 97 (0.49) | 13.58 (4.61) |  | 76 (0.35) | 14.27 (4.02) |  |
|  | +CT/+CT | 48 (0.11) | 14.35 (5.15) |  | 18 (0.09) | 16.75 (4.27) |  | 30 (0.14) | 12.90 (5.16) |  |
| rs7671250 n = 449 | TT | 334 (0.74) | 13.49 (4.61) | $F(1, 446) =$ 0.60 p = .44 | 153 (0.72) | 13.58 (4.69) | $F(1, 211) =$ 0.46 p = .50 | 181 (0.77) | 13.43 (4.55) | $F(1, 232) =$ 0.19 p = .66 |
|  | TC | 110 (0.25) | 13.12 (4.90) |  | 58 (0.27) | 13.23 (4.76) |  | 52 (0.22) | 12.99 (5.09) |  |
|  | CC | 5 (0.01) | 12.86 (5.71) |  | 3 (0.01) | 11.90 (5.41) |  | 2 (0.01) | 14.29 (8.08) |  |
| rs6814934 n = 446 | GG | 125 (0.28) | 12.91 (4.53) | $F(1, 443) =$ 4.61 p = .03 | 51 (0.24) | 12.47 (4.27) | $F(1, 212) =$ 8.65 p < .01 | 74 (0.32) | 13.22 (4.71) | $F(1, 228) =$ 0.05 p = .82 |
|  | GC | 211 (0.47) | 13.33 (4.74) |  | 107 (0.50) | 13.10 (4.87) |  | 104 (0.45) | 13.57 (4.62) |  |
|  | CC | 110 (0.25) | 14.23 (4.62) |  | 57 (0.26) | 15.04 (4.37) |  | 53 (0.23) | 13.37 (4.76) |  |
| rs7658048 n = 445 | CC | 207 (0.47) | 12.82 (4.80) | $F(1, 442) =$ 6.28 p = .01 | 89 (0.42) | 12.42 (4.57) | $F(1, 209) =$ 14.92 p < .001 | 118 (0.51) | 13.11 (4.96) | $F(1, 230) =$ 0.00 p = .95 |
|  | CT | 187 (0.42) | 13.67 (4.42) |  | 103 (0.49) | 13.55 (4.69) |  | 84 (0.36) | 13.81 (4.08) |  |
|  | TT | 51 (0.11) | 14.43 (4.99) |  | 20 (0.09) | 17.14 (3.37) |  | 31 (0.13) | 12.67 (5.12) |  |
| rs2070950 n = 445 | GG | 123 (0.28) | 12.93 (4.56) | $F(1, 442) =$ 4.66 p = .03 | 51 (0.24) | 12.47 (4.27) | $F(1, 210) =$ 9.16 p < .01 | 72 (0.31) | 13.25 (4.76) | $F(1, 229) =$ 0.02 p = .88 |
|  | GC | 212 (0.47) | 13.20 (4.77) |  | 105 (0.49) | 13.02 (4.88) |  | 107 (0.46) | 13.38 (4.68) |  |
|  | CC | 110 (0.25) | 14.27 (4.63) |  | 57 (0.27) | 15.11 (4.39) |  | 53 (0.23) | 13.37 (4.76) |  |
| rs2070951 (−2 G/C) n = 444 | GG | 123 (0.28) | 12.81 (4.50) | $F(1, 441) =$ 5.70 p = .02 | 50 (0.24) | 12.34 (4.22) | $F(1, 210) =$ 10.05 p < .01 | 73 (0.32) | 13.13 (4.68) | $F(1, 228) =$ 0.12 p = .73 |
|  | GC | 210 (0.47) | 13.29 (4.74) |  | 105 (0.49) | 13.02 (4.88) |  | 105 (0.45) | 13.56 (4.60) |  |
|  | CC | 111 (0.25) | 14.27 (4.61) |  | 58 (0.27) | 15.10 (4.36) |  | 53 (0.23) | 13.37 (4.76) |  |
| rs5522 (I180V) n = 436 | AA | 331 (0.76) | 13.56 (4.60) | $F(1, 433) =$ 1.21 p = .27 | 156 (0.74) | 13.57 (4.72) | $F(1, 206) =$ 1.31 p = .25 | 175 (0.77) | 13.54 (4.51) | $F(1, 224) =$ 0.19 p = .67 |
|  | AG | 101 (0.23) | 12.94 (4.92) |  | 52 (0.25) | 13.02 (4.65) |  | 49 (0.22) | 12.86 (5.23) |  |
|  | GG | 4 (0.01) | 13.21 (7.13) |  | 1 (0.01) | 5.71 |  | 3 (0.01) | 15.71 (6.23) |  |
| rs5525 n = 449 | CC | 343 (0.76) | 13.51 (4.58) | $F(1, 446) =$ 0.85 p = .36 | 160 (0.75) | 13.61 (4.68) | $F(1, 211) =$ 1.08 p = .30 | 183 (0.78) | 13.43 (4.51) | $F(1, 232) =$ 0.08 p = .78 |
|  | CT | 101 (0.23) | 12.97 (4.95) |  | 52 (0.24) | 13.08 (4.72) |  | 49 (0.21) | 12.86 (5.23) |  |
|  | TT | 5 (0.01) | 13.43 (6.19) |  | 2 (0.01) | 10.00 (6.06) |  | 3 (0.01) | 15.71 (6.23) |  |
| GR SNP |  |  |  |  |  |  |  |  |  |  |
| rs10052957 (TthIII) n = 444 | CC | 218 (0.49) | 13.22 (4.57) | $F(1, 441) =$ 0.46 p = .50 | 104 (0.49) | 13.30 (4.58) | $F(1, 209) =$ 0.23 p = .63 | 114 (0.49) | 13.14 (4.59) | $F(1, 229) =$ 0.23 p = .64 |
|  | CT | 175 (0.39) | 13.61 (4.89) |  | 83 (0.39) | 13.56 (4.84) |  | 92 (0.40) | 13.65 (4.96) |  |
|  | TT | 51 (0.12) | 13.50 (4.54) |  | 25 (0.12) | 13.71 (4.98) |  | 26 (0.11) | 13.30 (4.16) |  |
| rs6189 (ER22/23EK) n = 450 | GG | 421 (0.93) | 13.41 (4.64) | $F(1, 447) =$ 0.13 p = .72 | 198 (0.92) | 13.41 (4.70) | $F(1, 213) =$ 0.36 p = .55 | 223 (0.95) | 13.41 (4.60) | $F(1, 232) =$ 1.17 p = .28 |
|  | GA | 27 (0.06) | 13.44 (5.29) |  | 17 (0.08) | 14.12 (4.65) |  | 10 (0.04) | 12.29 (6.23) |  |
|  | AA | 2 (0.01) | 10.71 (7.07) |  | 0 |  |  | 2 (0.01) | 10.71 (7.07) |  |
| rs6195 (N363S) n = 446 | AA | 418 (0.94) | 13.46 (4.67) | $F(1, 444) =$ 1.75 p = .19 | 202 (0.94) | 13.57 (4.70) | $F(1, 212) =$ 2.37 p = .13 | 216 (0.93) | 13.35 (4.65) | $F(1, 230) =$ 0.16 p = .69 |
|  | AG | 28 (0.06) | 12.24 (5.02) |  | 12 (0.06) | 11.43 (4.39) |  | 16 (0.07) | 12.86 (5.50) |  |
|  | GG | 0 |  |  | 0 |  |  | 0 |  |  |
| rs41423247 (BclI) n = 440 | CC | 169 (0.38) | 13.52 (4.48) | $F(1, 437) =$ 0.23 p = .63 | 78 (0.37) | 13.52 (4.46) | $F(1, 208) =$ 0.48 p = .49 | 91 (0.40) | 13.53 (4.52) | $F(1, 226) =$ 0.00 p = .99 |
|  | CG | 215 (0.49) | 13.38 (4.87) |  | 105 (0.50) | 13.74 (4.83) |  | 110 (0.48) | 13.04 (4.91) |  |
|  | GG | 56 (0.13) | 13.19 (4.74) |  | 28 (0.13) | 12.45 (4.70) |  | 28 (0.12) | 13.93 (4.76) |  |

TABLE 2-continued

Dispositional optimism scores according to genotypes for the different MR and GR SNPs in 450 elderly subjects

| MR SNP | Genotype | n (frequency) | Total (n = 450) Optimism (mean ± SD) | Test statistics[#] p-value | n (frequency) | Women (n = 215) Optimism (mean ± SD) | Test statistics[#] p-value | n (frequency) | Men (n = 235) Optimism (mean ± SD) | Test statistics[#] p-value |
|---|---|---|---|---|---|---|---|---|---|---|
| rs6198 (9β) n = 439 | AA | 303 (0.69) | 13.17 (4.57) | $F(1, 436) = 1.34$ p = .25 | 114 (0.68) | 13.08 (4.58) | $F(1, 208) = 2.03$ p = .16 | 159 (0.70) | 13.26 (4.58) | $F(1, 225) = 0.07$ p = .79 |
| | AG | 120(0.27) | 14.06 (4.76) | | 61 (0.29) | 14.40 (4.73) | | 59 (0.26) | 13.70 (4.80) | |
| | GG | 16 (0.04) | 12.86 (4.33) | | 6 (0.03) | 12.86 (3.94) | | 10 (0.04) | 12.86 (4.76) | |

Data are presented for the total group, as well as for women and men separately.
[#]One-way ANOVA F-values for linear trend (and their accompanying degrees of freedom) were used to examine p-values for association.

TABLE 3

Effects of MR haplotypes 1 to 3 on mean dispositional optimism scores in 450 elderly subjects

| | | MR haplotype 1 | MR haplotype 2 | MR haplotype 3 |
|---|---|---|---|---|
| Total (n = 450)[a] | | | | |
| Crude | ref. | | B = 0.90 (0.33); p = .01 | B = −0.08 (0.50); p = .88 |
| Mode 1 | ref. | | B = 0.81 (0.33); p = .01 | B = −0.26 (0.49); p = .60 |
| Mode 2 | ref. | | B = 0.72 (0.32); p = .03 | B = −0.13 (0.49); p = .79 |
| Women (n = 215)[b] | | | | |
| Crude | ref. | | B = 1.82 (0.48); p < .001 | B = −0.04 (0.69); p = .95 |
| Mode 1 | ref. | | B = 1.70 (0.48); p < .001 | B = −0.31 (0.70); p = .66 |
| Mode 2 | ref. | | B = 1.67 (0.47); p < .001 | B = −0.21 (0.69); p = .76 |
| Men (n = 235)[c] | | | | |
| Crude | ref. | | B = 0.14 (0.45); p = .75 | B = −0.13 (0.70); p = .85 |
| Mode 1 | ref. | | B = 0.08 (0.44); p = .87 | B = −0.13 (0.69); p = .86 |
| Mode 2 | ref. | | B = −0.09 (0.44); p = .85 | B = 0.67 (0.68); p = .92 |

Effects on mean dispositional optimism scores were compared between the three most frequent MR haplotypes, crude or adjusted for potential confounders, model 1 and 2. Model 1: adjusted for sex (when appropriate), age, education level, marital status, and SES. Model 2: data additionally adjusted for CVD and total number of chronic diseases. Linear regression analysis was used to yield B-coefficients and p-values. B-coefficients can be interpreted as the mean difference (SEM) in dispositional optimism score per haplotype allele when compared to the reference haplotype 1.
[a]Total: $R^2 = 0.02$; mode 1: $R^2 = 0.06$ for step 1, $\Delta R^2 = 0.02$ for step 2; mode 2: $R^2 = 0.06$ for step 1, $\Delta R^2 = 0.03$ for step 2, $\Delta R^2 = 0.01$ for step 3.
[b]Women: $R^2 = 0.07$; mode 1: $R^2 = 0.06$ for step 1, $\Delta R^2 = 0.06$ for step 2; mode 2: $R^2 = 0.06$ for step 1, $\Delta R^2 = 0.03$ for step 2, $\Delta R^2 = 0.06$ for step 3.
[c]Men: $R^2 < 0.01$, mode 1: $R^2 = 0.07$ for step 1, $\Delta R^2 < 0.01$ for step 2, mode 2: $R^2 = 0.06$ for step 1, $\Delta R^2 = 0.04$ for step 2, $\Delta R^2 < 0.01$ for step 3.

Discussion

We found that the MR haplotype 2, which consists of the C-allele of the functional −2 G/C SNP and extends into the promoter region, was highly significant associated with higher levels of dispositional optimism in elderly women but not in men. This was independent of several potential confounders. Importantly, we were also able to show that haplotype 2 was associated with optimism in a dose dependent manner, with women having a 2/2 diplotype reporting even higher optimism scores than women with only one haplotype 2 allele. No effect was found for the GR haplotypes. This is the first report on a MR gene variant that is associated with a positive psychological trait in humans.

MR haplotype 2 contains the functional −2 G/C SNP. The C-allele of this SNP increases MR expression and MR-driven gene transcription in vitro [Nienke PNE09 in press]

In addition, the −2 C-allele has been shown to associate with lower basal cortisol levels in elderly (Kuningas, de Rijk et al (2007)). Together with our results, this finding seems to fit with a study showing that higher levels of optimism associate with lower basal cortisol levels (Lai, Evans et al (2005)). It would be interesting to know whether the differences in optimism scores we found were also associated with variances in cortisol levels. Unfortunately, no cortisol data were assessed in the Arnhem elderly study. Furthermore, our results are also in line with a report showing that the MR 180 V-allele, or haplotype 3, associated with more depressive symptoms in a Dutch elderly cohort, the Leiden 85+ cohort (Kuningas, de Rijk et al (2007)). In our study this haplotype 3 (although carried by only 2 subjects) was associated with the lowest scores for optimism.

Only in women, MR haplotype 2 associated with higher levels of dispositional optimism. Sex differences have previously been reported for HPA responses to stress but also for personality traits (Kudielka and Kirschbaum (2005); Schmitt, Realo et al (2008)). A gene-by-sex interaction could contribute to this and indeed has been found for HPA axis functioning and personality (Lang, Hellweg et al (2008); Wust, Kumsta et al (2009)). Additionally, also in rodents sex-specific effects of genes are found, for example for the MR and its influence on behavioural stress response (Rozeboom, Akil et al (2007)). One of the possible explanations for this gene-by-sex interaction of the MR may be its interaction with sex steroids. Estrogens and progesterone modulate protein and mRNA expression of corticosteroid receptors (Castren, Patchev et al (1995); Turner (1997)). In addition, progesterone can also bind to the human MR (Quinkler, Meyer et al (2002)). However, all women were 65+ of age, which means they probably all have low levels of estradiol due to menopause. Still, when conducting certain cognitive tests, only in elderly women variability in endogenous estradiol levels has been reported to relate to differences in performance (Wolf and Kirschbaum (2002)).

No relation was found between the GR gene variants and optimism. Rodent studies have shown that both the MR and GR modulate anxiety- and depressive like behaviours, including learned helplessness (Urani, Chourbaji et al (2005); Rozeboom, Akil et al (2007)). Moreover, both the MR and GR are involved in behaviour and cognition. However, it seems that it is mainly the MR that is mediating choice of behavioural strategy, flexibility and reactivity (Oitzl and de Kloet (1992); Berger, Wolfer et al (2006); Brinks, van der Mark et al (2007)). When, for example after a training session rats are treated with a MR antagonist, they show an altered search-escape strategy in the Morris water maze. Blocking the GR had no such effect (Oitzl and de Kloet (1992)). To our knowledge there is only one study that reported an effect of MR blockage on cognitive flexibility in humans (Otte, Moritz et al (2007)). The importance of the GR for cognitive functioning during elevated levels of cortisol is generally accepted, but additional studies are warranted to elucidate the specific roles of the MR and GR in cognitive flexibility, coping behaviour and psychological traits.

To the best of our knowledge, this is the first study reporting on a gene variant that was associated with variability in the positive psychological trait dispositional optimism. Evidence is accumulating for optimism having influence on goal engagement and coping behaviour, indirectly enhancing a multitude of health outcomes, (Scheier, Weintraub et al (1986); Plomin, Scheier et al (1992); Scheier and Carver (1992); Carver, Pozo et al (1993); Scheier, Carver et al (1994); Vickers and Vogeltanz (2000); Giltay, Geleijnse et al (2004); Giltay, Kamphuis et al (2006); Giltay, Zitman et al (2006); Nes and Segerstrom (2006); Geers, Wellman et al (2009)). Hopelessness, on the other hand, has been reported to increase risk for disease and mortality and is positively associated to stress-related disorders like depression (Everson, Goldberg et al (1996); Joiner, Steer et al (2001)). Optimists seem more resilient against everyday challenges. People with high levels of optimism are better in tolerating stressful conditions and choose a coping strategy that is appropriate for the situation. For example, in a study following women that were diagnosed with breast cancer, the more optimistic women were able to accept their situation and used positive reframing and also humour to deal with it, leading to less distress (Carver, Pozo et al (1993)). Optimists are cognitively more flexible, seek and perceive more social support, and more often turn to religion or exercise (Scheier and Carver (1992); Carver, Pozo et al (1993); Scheier, Carver et al (1994); Southwick, Vythilingam et al (2005)). Moreover, optimists cope better maybe in part because they perceive information from their environment differently. Optimists are able to ignore negative stimuli better when it is not relevant and have more attention to positive stimuli (Isaacowitz (2005)). The identification of genes and biological mechanisms underlying traits that confer resilience against stress could provide important information for pharmaco- and cognitive therapy in patients with anxiety- and depressive disorders. The mechanism by which glucocorticoids and the MR affect optimism remains unclear. It has been postulated that people who are able to remain optimistic during challenging situations have a neurobiological system for reward and motivation that is hyperactive or resistant to change (Southwick, Vythilingam et al (2005)). Multiple studies have reported that glucocorticoids act on the brain reward system. An example is the effect of glucocorticoids on the motivation to take drugs, that is known to be mediated at least by the GR (Ambroggi, Turiault et al (2009)). Whether the MR is implicated in reward mechanisms needs further investigation.

We found an association between a MR gene variant and variability in optimism among elderly subjects. Multiple studies have reported on changes in emotional and cognitive functioning among older adults. Levels of optimism and positive effect but also cognitive functioning slowly decrease, while the prevalence of depressive symptoms and depressive disorder increases (de Beurs, Comijs et al (2005); Giltay, Zitman et al (2006); Kuningas, de Rijk et al (2007)). Malfunctioning of the HPA axis might be one of the underlying mechanisms. Expression of corticosteroid receptors in the brain changes during development, throughout adulthood and during aging (van Eekelen, Rots et al (1992); Schmidt, Enthoven et al (2003); Dalm, Enthoven et al (2005)). For example, expression of MR in the hippocampus is decreased in old rats. It is possible that MR gene variants play a modulating role, resulting in more or less decrease in MR expression, eventually leading to better or worse psychological functioning. As mentioned before, the −2 C-allele results in more expression of MR and a higher gene transactivation in vitro. Moreover, haplotype 2 also consists of two SNPs located in the promoter region for which the highest significant associations were found with optimism. It is very well possible that these SNPs have an additional and maybe even stronger effect on MR expression. Therefore, these promoter SNPs need to be tested for their effect on promoter activity.

To conclude, we found that the MR haplotype 2, including the functional −2 C-allele but not the 180 V-allele, was associated with higher levels of dispositional optimism in Dutch elderly females in a dose dependent manner. The results indicate that the MR modulates not only neuroendocrine- and autonomic response to a stressor but can also affect a positive psychological trait, which may determine resilience against stress and depression.

References for Example 1

Ambroggi, F., M. Turiault, et al (2009) "Stress and addiction: glucocorticoid receptor in dopaminoceptive neurons facilitates cocaine seeking." *Nat Neurosci* 12(3): 247-9.

Barrett, J. C., B. Fry, et al (2005) "Haploview: analysis and visualization of LD and haplotype maps." *Bioinformatics* 21(2): 263-5.

Berger, S., D. P. Wolfer, et al (2006) "Loss of the limbic mineralocorticoid receptor impairs behavioral plasticity." *Proc Natl Acad Sci USA* 103(1): 195-200.

Brinks, V., M. H. van der Mark, et al (2007) "Differential MR/GR activation in mice results in emotional states beneficial or impairing for cognition." *Neural Plast* 2007: 90163.

Carver, C. S. and J. Connor-Smith (2009) "Personality and Coping." *Annu Rev Psychol.*

Carver, C. S., C. Pozo, et al (1993) "How coping mediates the effect of optimism on distress: a study of women with early stage breast cancer." *J Pers Soc Psychol* 65(2): 375-90.

Castren, M., V. K. Patchev, et al (1995) "Regulation of rat mineralocorticoid receptor expression in neurons by progesterone." *Endocrinology* 136(9): 3800-6.

Conrad, C. D., S. J. Lupien, et al (1997) "The effects of type I and type II corticosteroid receptor agonists on exploratory behavior and spatial memory in the Y-maze." *Brain Res* 759(1): 76-83.

Dalm, S., L. Enthoven, et al (2005) "Age-related changes in hypothalamic-pituitary-adrenal axis activity of male C57BL/6J mice." *Neuroendocrinology* 81(6): 372-80.

de Beurs, E., H. Comijs, et al (2005) "Stability and change of emotional functioning in late life: modelling of vulnerability profiles." *J Affect Disord* 84(1): 53-62.

de Kloet, E. R., S. A. Van Acker, et al (2000) "Brain mineralocorticoid receptors and centrally regulated functions." *Kidney Int* 57(4): 1329-36.

De Kloet, E. R., E. Vreugdenhil, et al (1998) "Brain corticosteroid receptor balance in health and disease." *Endocr Rev* 19(3): 269-301.

Derijk, R. H., N. van Leeuwen, et al (2008) "Corticosteroid receptor-gene variants: modulators of the stress-response and implications for mental health." *Eur J Pharmacol* 585(2-3): 492-501.

DeRijk, R. H., S. Wust, et al (2006) "A common polymorphism in the mineralocorticoid receptor modulates stress responsiveness." *J Clin Endocrinol Metab* 91(12): 5083-9.

Everson, S. A., D. E. Goldberg, et al (1996) "Hopelessness and risk of mortality and incidence of myocardial infarction and cancer." *Psychosom Med* 58(2): 113-21.

Geers, A. L., J. A. Wellman, et al (2009) "Dispositional optimism and engagement: the moderating influence of goal prioritization." *J Pers Soc Psychol* 96(4): 913-32.

Giltay, E. J., J. M. Geleijnse, et al (2004) "Dispositional optimism and all-cause and cardiovascular mortality in a prospective cohort of elderly dutch men and women." *Arch Gen Psychiatry* 61(11): 1126-35.

Giltay, E. J., M. H. Kamphuis, et al (2006) "Dispositional optimism and the risk of cardiovascular death: the Zutphen Elderly Study." *Arch Intern Med* 166(4): 431-6.

Giltay, E. J., F. G. Zitman, et al (2006) "Dispositional optimism and the risk of depressive symptoms during 15 years of follow-up: the Zutphen Elderly Study." *J Affect Disord* 91(1): 45-52.

Isaacowitz, D. M. (2005) "The gaze of the optimist." *Pers Soc Psychol Bull* 31(3): 407-15.

Joiner, T. E., Jr., R. A. Steer, et al (2001) "Hopelessness depression as a distinct dimension of depressive symptoms among clinical and non-clinical samples." *Behav Res Ther* 39(5): 523-36.

Kudielka, B. M. and C. Kirschbaum (2005) "Sex differences in HPA axis responses to stress: a review." *Biol Psychol* 69(1): 113-32.

Kumsta, R., S. Entringer, et al (2007) "Sex specific associations between common glucocorticoid receptor gene variants and hypothalamus-pituitary-adrenal axis responses to psychosocial stress." *Biol Psychiatry* 62(8): 863-9.

Kuningas, M., R. H. de Rijk, et al (2007) "Mental performance in old age dependent on cortisol and genetic variance in the mineralocorticoid and glucocorticoid receptors." *Neuropsychopharmacology* 32(6): 1295-301.

Lai, J. C., P. D. Evans, et al (2005) "Optimism, positive affectivity, and salivary cortisol."*Br J Health Psychol* 10(Pt 4): 467-84.

Lang, U. E., R. Hellweg, et al (2008) "Gender-dependent association of a functional NGF polymorphism with anxiety-related personality traits." *Pharmacopsychiatry* 41(5): 196-9.

Lupien, S. J., C. W. Wilkinson, et al (2002) "The modulatory effects of corticosteroids on cognition: studies in young human populations." *Psychoneuroendocrinology* 27(3): 401-16.

Nes, L. S. and S. C. Segerstrom (2006) "Dispositional optimism and coping: a meta-analytic review." *Pers Soc Psychol Rev* 10(3): 235-51.

Oitzl, M. S. and E. R. de Kloet (1992) "Selective corticosteroid antagonists modulate specific aspects of spatial orientation learning." *Behav Neurosci* 106(1): 62-71.

Otte, C., S. Moritz, et al (2007) "Blockade of the mineralocorticoid receptor in healthy men: effects on experimentally induced panic symptoms, stress hormones, and cognition." *Neuropsychopharmacology* 32(1): 232-8.

Plomin, R., M. F. Scheier, et al (1992) "Optimism, pessimism and mental health: a twin/adoption analysis" *Person. individ. Diff.* 13(8): 921-930.

Quinkler, M., B. Meyer, et al (2002) "Agonistic and antagonistic properties of progesterone metabolites at the human mineralocorticoid receptor." *Eur J Endocrinol* 146(6): 789-99.

Rozeboom, A. M., H. Akil, et al (2007) "Mineralocorticoid receptor overexpression in forebrain decreases anxiety-like behavior and alters the stress response in mice." *Proc Natl Acad Sci USA* 104(11): 4688-93.

Scheier, M. F. and C. S. Carver (1985) "Optimism, coping, and health: assessment and implications of generalized outcome expectancies." *Health Psychol* 4(3): 219-47.

Scheier, M. F. and C. S. Carver (1992) "Effects of Optimism on Psychological and Physical Well-Being: Theoretical Overview and Empirical Update." *Cognit Therapy Res* 16(2): 201-228.

Scheier, M. F., C. S. Carver, at al (1994) "Distinguishing optimism from neuroticism (and trait anxiety, self-mastery, and self-esteem): a reevaluation of the Life Orientation Test." *J Pers Soc Psychol* 67(6): 1063-78.

Scheier, M. F., J. K. Weintraub, et al (1986) "Coping with stress: divergent strategies of optimists and pessimists." *J Pers Soc Psychol* 51(6): 1257-64.

Schmidt, M. V., L. Enthoven, et al (2003) "The postnatal development of the hypothalamic-pituitary-adrenal axis in the mouse." *Int J Dev Neurosci* 21(3): 125-32.

Schmitt, D. P., A. Realo, et al (2008) "Why can't a man be more like a woman? Sex differences in Big Five personality traits across 55 cultures." *J Pers Soc Psychol* 94(1): 168-82.

Southwick, S. M., M. Vythilingam, at al (2005) "The psychobiology of depression and resilience to stress: implications for prevention and treatment." *Annu Rev Clin Psychol* 1: 255-91.

Steptoe, A., K. O'Donnell, at al (2008) "Neuroendocrine and inflammatory factors associated with positive affect in healthy men and women: the Whitehall II study." *Am J Epidemiol* 167(1): 96-102.

Tempelman, C. J. J. (1987). "Welbevinden bij ouderen: konstruktie van een meetinstrument [Well-being in the elderly: development of the Scale Subjective Well-being Older Persons] [dissertation]. Groningen, the Netherlands: University of Groningen;"

Turner, B. B. (1997) "Influence of gonadal steroids on brain corticosteroid receptors: a minireview." *Neurochem Res* 22(11): 1375-85.

Urani, A., S. Chourbaji, et al (2005) "Mutant mouse models of depression: candidate genes and current mouse lines." *Neurosci Biobehav Rev* 29(4-5): 805-28.

van den Hombergh, C. E., E. G. Schouten, et al (1995) "Physical activities of noninstitutionalized Dutch elderly and characteristics of inactive elderly." *Med Sci Sports Exerc* 27(3): 334-9.

van Eekelen, J. A., N. Y. Rots, et al (1992) "The effect of aging on stress responsiveness and central corticosteroid receptors in the brown Norway rat." *Neurobiol Aging* 13(1): 159-70.

Vickers, K. S. and N. D. Vogeltanz (2000) "Dispositional optimism as a predictor of depressive symptoms over time" *Person. Individ. Diff.* 28: 259-272.

Wolf, O. T. and C. Kirschbaum (2002) "Endogenous estradiol and testosterone levels are associated with cognitive performance in older women and men." *Horm Behav* 41(3): 259-66.

Wust, S., R. Kumsta, et al (2009) "Sex-specific association between the 5-HTT gene-linked polymorphic region and basal cortisol secretion." *Psychoneuroendocrinology.*

EXAMPLE 2

Human Mineralocorticoid Receptor Gene Variants Modulate Cognitive Vulnerability for Depression The mineralocorticoid receptor (MR) plays a central role in the regulation of hypothalamic-pituitary-adrenal (HPA)

axis activity. Animal studies indicate that the MR mediates effects of cortisol on emotions and coping behaviour. We hypothesise that human MR-gene variants influence cognition and emotions. We have identified a MR haplotype (frequency 0.36) to relate to higher dispositional optimisim in elderly women, not in men (see Example 1).

In the present study 154 students (46 M/108 F; 23.9±5 yrs) completed a questionnaire that measures cognitive vulnerability to depression and that includes subscales for hopelessness, rumination and aggression (LEIDS-R—see Appendix; Van der Does, Behav Res & Therap 40:105-120, 2002); Leiden Index of Depression Sensitivity-Revised). Neuroticism was also measured (NEO-PI) as well as symptoms of depression (HADS-D). MR SNPs and haplotypes were assessed, resulting in three haplotypes with frequencies of 0.50; 0.35; 0.13.

Significant associations were found only in females between the haplotype with a frequency 0.35 and lower scores for hopelessness, aggression, risk aversion, neuroticism ($p<0.05$), and in particular for rumination ($p=0.001$), persisting after adjustment for age and emotional abuse during childhood. Excluding currently depressed participants (n=14) strengthened the results. Moreover, this haplotype significantly associated with less symptoms of depression ($p<0.05$). The results fit with our study showing an association between this haplotype and higher dispositional optimism (Example 1), also only in women. Together the data indicate that MR-gene variants modulate cognitive vulnerability for depression.

In the present study 154 Dutch students (46 M/108 F; 23.9±5 yrs) completed a questionnaire that was prepared to assess cognitive vulnerability to depression, the LEIDS-R (Leiden Index of Depression Sensitivity-Revised). This questionnaire measures cognitive reactivity to sad mood (Van der Does, A. J. W., 2002). The subjects have to read the instructions and indicate to what extend they agree with in total 34 statements. The scale includes 6 subscales, namely hopelessness/suicidality, acceptance/coping, aggression, control/perfectionism, risk aversion, and rumination. In addition, neuroticism was measured (NEO-PI) as well as symptoms of depression and anxiety (HADS-D and HADS-A). All students were genotyped for the MR SNPs −2G/C (rs2070951) and I180V (rs5522) and haplotypes were reconstructed.

FIGS. 6-11 show the results for the different scales (untransformed data) for the total group and for the females and males separately, excluding cases with current depression (n=14). P-values represent Analysis Of Variance (ANOVA) results, without correction for confounding effects of sex (when appropriate), age and emotional abuse. In addition, dummy variables were created for the haplotypes 1-3, followed by linear regression analysis to test association between the haplotypes, while correcting for the covariates. For this analysis, data for the subscales Acceptance/Coping, Aggression, Perfectionism/Control and Hopelessness were transformed (Square Root) to approach a normal distribution.

APPENDIX

APPENDIX

LEIDS-R Questionnaire

*Instructions*

Below are a number of statements that may apply to you to a lesser or greater extent.

Almost every statement concerns your thoughts about a certain matter *at times when you feel down or when you are in a low mood*. This does not mean a seriously depressed mood or true depression. Your task is to indicate the extent to which the statements apply to you when you feel somewhat sad.

*Try to imagine the following situation when filling out this questionnaire.*

It is certainly not a good day, but you don't feel truly down or depressed. Perhaps your mood is an early sign of something worse to come, but things might also improve in the next day or two.

On a scale ranging from 0 to 10 (0 = not at all sad; 10 = extremely sad; 6 and above = a truly depressed mood), you would choose a 3 or 4 to describe your mood.

The scale looks like this:

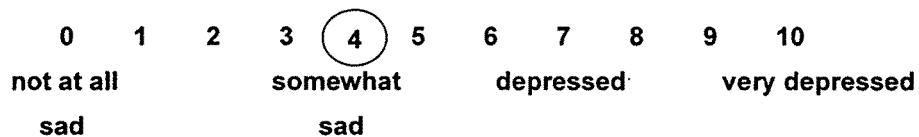

| 0 | 1 | 2 | 3 | 4 | 5 | 6 | 7 | 8 | 9 | 10 | not at all sad      somewhat sad      depressed      very depressed

Please try to imagine yourself in the above situation, for instance by thinking back to the last time you felt somewhat sad (score 3 or 4).

{Now take some time to imagine such a situation.}

*To what extent are you able to imagine such a situation?*
  ° well
  ° somewhat
  ° not at all Now proceed to the next question (even if you find it difficult to imagine yourself in such a situation).

|     |                                                                                              | This applies to me ..........: (please circle) | | | | |
| --- | --- | --- | --- | --- | --- | --- |
|     |                                                                                              | not at all | a bit | moderately | strongly | very strongly |
| 1.  | I can only think positive when I am in a good mood.                                         | 0 | 1 | 2 | 3 | 4 |
| 2.  | When in a low mood, I take fewer risks.                                                     | 0 | 1 | 2 | 3 | 4 |
| 3.  | When I feel sad, I spend more time thinking about what my moods reveal about me as a person. | 0 | 1 | 2 | 3 | 4 |
| 4.  | When in a sad mood, I am more creative than usual.                                          | 0 | 1 | 2 | 3 | 4 |
| 5.  | When I feel down, I more often feel hopeless about everything.                              | 0 | 1 | 2 | 3 | 4 |
| 6.  | When I feel down, I am more busy trying to keep images and thoughts at bay.                 | 0 | 1 | 2 | 3 | 4 |
| 7.  | In a sad mood, I do more things that I will later regret.                                   | 0 | 1 | 2 | 3 | 4 |
| 8.  | When I feel sad, I go out and do more pleasurable activities.                               | 0 | 1 | 2 | 3 | 4 |
| 9.  | When I feel sad, I feel as if I care less if I lived or died.                               | 0 | 1 | 2 | 3 | 4 |
| 10. | When I feel sad, I am more helpful.                                                         | 0 | 1 | 2 | 3 | 4 |
| 11. | When I feel sad, I am less inclined to express disagreement with someone else.              | 0 | 1 | 2 | 3 | 4 |
| 12. | When I feel somewhat depressed, I think I can permit myself fewer mistakes.                 | 0 | 1 | 2 | 3 | 4 |
| 13. | When I feel down, I more often feel overwhelmed by things.                                  | 0 | 1 | 2 | 3 | 4 |
| 14. | When in a low mood, I am more inclined to avoid difficulties or conflicts.                  | 0 | 1 | 2 | 3 | 4 |
| 15. | When I feel down, I have a better intuitive feeling for what people really mean.            | 0 | 1 | 2 | 3 | 4 |
| 16. | When in a sad mood, I become more bothered by perfectionism.                                | 0 | 1 | 2 | 3 | 4 |
| 17. | When I feel sad, I more often think that I can make no one happy.                           | 0 | 1 | 2 | 3 | 4 |
| 18. | When I feel bad, I feel more like breaking things.                                          | 0 | 1 | 2 | 3 | 4 |
| 19. | I work harder when I feel down.                                                             | 0 | 1 | 2 | 3 | 4 |
| 20. | When I feel sad, I feel less able to cope with everyday tasks and interests.                | 0 | 1 | 2 | 3 | 4 |
|     |                                                                                              | not at all | a bit | moderately | strongly | very strongly |

| | | not at all | a bit | moderately | strongly | very strongly |
|---|---|---|---|---|---|---|
| 21. | In a sad mood, I am bothered more by aggressive thoughts. | 0 | 1 | 2 | 3 | 4 |
| 22. | When I feel down, I more easily become cynical (blunt) or sarcastic. | 0 | 1 | 2 | 3 | 4 |
| 23. | When I feel down, I feel more like escaping everything. | 0 | 1 | 2 | 3 | 4 |
| 24. | When in a sad mood, I feel more like myself. | 0 | 1 | 2 | 3 | 4 |
| 25. | When I feel down, I more often neglect things. | 0 | 1 | 2 | 3 | 4 |
| 26. | When I feel sad, I do more risky things. | 0 | 1 | 2 | 3 | 4 |
| 27. | When I am sad, I have more problems concentrating. | 0 | 1 | 2 | 3 | 4 |
| 28. | When in a low mood, I am nicer than usual. | 0 | 1 | 2 | 3 | 4 |
| 29. | When I feel down, I lose my temper more easily. | 0 | 1 | 2 | 3 | 4 |
| 30. | When I feel sad, I feel more that people would be better off if I were dead. | 0 | 1 | 2 | 3 | 4 |
| 31. | When I feel down, I am more inclined to want to keep everything under control. | 0 | 1 | 2 | 3 | 4 |
| 32. | When I feel sad, I spend more time thinking about the possible causes of my moods. | 0 | 1 | 2 | 3 | 4 |
| 33. | When in a sad mood, I more often think about how my life could have been different. | 0 | 1 | 2 | 3 | 4 |
| 34. | When I feel sad, more thoughts of dying or harming myself go through my mind. | 0 | 1 | 2 | 3 | 4 |
| | | not at all | a bit | moderately | strongly | very strongly |

Statistical analysis of LEIDS-R questionnaire results

COMPUTE HOP = MEAN.4(leids5,leids9,leids17,leids30,leids34) * 5 .

COMPUTE ACC = MEAN.4(leids4,leids10,leids15,leids24,leids28) * 5 .

COMPUTE AGG = MEAN.5(leids7,leids18,leids21,leids22,leids26,leids29) * 6 .

COMPUTE CON = MEAN.5(leids3,leids8,leids12,leids16,leids19,leids31) * 6 .

COMPUTE RAV = MEAN.5(leids1,leids2,leids6,leids11,leids14,leids23)* 6 .

COMPUTE RUM = MEAN.5(leids13,leids20,leids25,leids27,leids32,leids33)* 6 .

EXECUTE .

COMPUTE LEIDSR = HOP + ACC + AGG + CON + RAV + RUM .

EXECUTE .

*******

In this syntax, subscales are computed with the MEAN function and multiplied by the number of items.

Of course, this is the same as summing the items - if there are no missing values.

This syntax allows one missing item per subscale (the missing value is replaced with the average item score for that particular subscale).

Labels:

HOP = hopelessness/suicidality

ACC = acceptance/coping

AGG = aggression

CON = control/perfectionism

HAV = risk aversion

RUM = rumination

EXAMPLE 3

Human Mineralocorticoid Receptor (MR) Gene Haplotypes Modulate MR Expression and Transactivation: Implication for the Stress Response Summary Stress causes activation of the hypothalamic-pituitary-adrenal (HPA) axis, resulting in secretion of corticosteroids which facilitate behavioural adaptation. These effects exerted by corticosteroids are mediated by two brain corticosteroid receptor types, the mineralocorticoid (MR) receptor, with a high affinity already occupied under basal conditions and the glucocorticoid receptor (GR), with a low affinity only activated during stress.

Here, we studied MR gene haplotypes constituted by the two single nucleotide polymorphisms MR-2G/C (rs2070951) and MRI180V (rs5522). In vitro the haplotypes showed differences in cortisol-induced gene transcription and protein expression, while the structural variant MRI180V did not affect ligand binding.

Moreover, in a well characterized cohort of 166 school teachers these haplotypes have been associated with perceived chronic stress (Trier Inventory for the Assessment of Chronic Stress, TICS) and, in a subgroup of 47 subjects, with ACTH, cortisol and heart rate responses to acute psychosocial stress (Trier Social Stress Test, TSST). MR haplotypes were significantly associated with the TICS scales "excessive demands at work" and "social overload". Subjects homozygous for haplotype MR-2C/MRI180, which in vitro showed highest expression and transactivational activity, displayed the highest salivary cortisol ($p<0.01$), plasma cortisol ($p<0.03$), plasma ACTH ($p<0.01$) and heartrate ($p<0.01$) responses.

It is concluded that the investigated MR haplotypes modulate cortisol-induced gene transcription in vitro. Moreover, these haplotypes may contribute to individual differences in perceived chronic stress as well as neuroendocrine and cardiovascular stress responses.

Introduction

Cortisol has profound effects in the brain, underlying behavioural adaptation to stress and feedback regulation of the hypothalamic-pituitary-adrenal (HPA) axis. These actions exerted by cortisol are mediated by a high affinity brain corticosteroid receptor, the mineralocorticoid receptor (MR) and a lower affinity glucocorticoid receptor (GR). The GR is widely expressed while the MR predominantly occurs in limbic brain areas including the hippocampus. Animal studies have shown that MR occupation is maintained at basal pulsatile cortisol levels, while the GR becomes only activated with rising cortisol levels in response to stress and at the peaks of the corticosterone pulses (Conway-Campbell et al., 2007; Lightman et al., 2008; Sarabdjitsingh et al., 2009). The MR and GR operate as transcription factors in the regulation of gene transcription, but recently these receptors were also found to mediate fast membrane-mediated actions (Di et al., 2003; Karst et al., 2005). Through the MR cortisol regulates basal HPA pulsatility (Atkinson et al., 2008) and the threshold or onset of the HPA axis response to stress (Arvat et al., 2001; Dodt et al., 1993; Ratka et al., 1989; Wellhoener et al., 2004), while the GR facilitates the suppression of stress-induced HPA activation and promotes adaptation.

Two functional single nucleotide polymorphisms (SNPs) in the MR have been previously identified, namely MR-2G/C (rs2070951) located 2 nucleotides before the translation startsite and MRI180V (rs5522), a SNP resulting in an amino acid change in the N-terminal domain of the protein. Both SNPs affect transactivation in vitro (DeRijk et al., 2006; van Leeuwen et al., 2010). MR-2G/C is located outside the coding region of the MR but inside the Kozac translation regulatory sequence, and is expected to influence brain function via changes in MR protein expression. The structural variant MRI180V was previously found to be associated with HPA axis and autonomic nervous system reactivity (DeRijk et al., 2006). This effect exerted by MRI180V may occur through differences in ligand binding, translocation to the nucleus, dimerization or recruitment of coactivators. Furthermore, these two SNPs in the MR are in linkage disequilibrium. (DeRijk et al., 2008). The in vitro and in vivo effects of these haplotypes are currently not known.

The main objective of the current study was to measure transactivation, ligand binding and protein expression of MRI180V, MR-2G/C and the resulting haplotypes. In addition, we sought to evaluate the association between these haplotypes and valid (endo)phenotypes for psychobiological stress regulation in a cohort that is independent of the samples that have previously been studied by our group (DeRijk et al., 2006; van Leeuwen et al., 2010). Therefore, we performed a genetic association analysis in a cohort of school teachers that has been characterized with the Trier Inventory for the Assessment of Chronic Stress (TICS) and the Trier Social Stress Test (TSST).

Materials and Methods
Functional Characterization In Vitro
Construction of the hMR Plasmids The expression plasmid containing human MR was obtained from Dr. R. Evans (gene expression laboratory and HHMI, The Salk Institute for Biological Studies, La Jolla, Calif.) and is described elsewhere (Arriza et al., 1987).

MR-2G/C (rs2070951) and MRI180V (rs5522) sites were mutated from G to C and from A to G, respectively using primers 5'-GGCCGAGGCAGCGATGGAGACCAAAG-3' (SEQ ID No: 10) and 5'-CGCTGCCTCGGCCCTTTG-GTCTCCAT-3' (SEQ ID No: 11) and primers 5'-GGCGT-CATGCGCGCCGTTGTTAAAAGCCCCTAT-3' (SEQ ID No: 12) and 5'-ATAGGGCTTTTAACAACGGCGCGCAT-GACGCC-3' (SEQ ID No: 13) and the Quick Change Site Directed Mutagenesis kit (Stratagene, La Jolla, Calif.), according to the manufacturer's protocol. After mutagenesis the hMR insert of the plasmid was sequenced to assure absence of other mutations.

Transactivation Assay

Cos-1 cells (African green monkey kidney cells) were cultured in DMEM high glucose supplemented with 10% FCS (Gibco, Paisley, UK). Cells were seeded in 24-well plates (Greiner Bio-One, Alphen a/d Rijn, The Netherlands) at $3\times10^4$ cells/well in DMEM supplemented with charcoal-stripped serum. The cells were transfected the next day using SuperFect (Qiagen, Venlo, The Netherlands). hMR plasmids and the reporter plasmid TAT3-Luc (tyrosine amino transferase triple hormone response element) were used at 100 ng/well. The control plasmid pCMV-R (Promega, Leiden, The Netherlands) coding for *Renilla* luciferase controlled by cytomegalovirus (CMV) promoter was used (10 ng/well). One day after transfection, the cells were treated with cortisol (Sigma-Aldrich, Zwijndrecht, the Netherlands) in concentrations ranging from 0 to $10^{-8}$ M. After 24 h of incubation the cells were harvested in passive lyses buffer (Promega) and firefly and *Renilla* luciferase activity was determined using a dual label reporter assay (Promega) and a luminometer (CENTRO XS3 LB960, Berthold, Bad Wildbad, Germany). Three separate experiments were performed and all three experiments were performed in triplicate.

Western Blot

For western blot Cos-1 cells were seeded in 6-well plates (Greiner Bio-One, Alphen a/d Rijn, The Netherlands) at $2\times10^5$ cells/well in DMEM supplemented with charcoal-stripped serum. The cells were transfected the next day using Trans-it Cos transfection reagent (Mirus, Madison, USA). Plasmids containing one of the hMR variants or no hMR (control) were used at 2 µg/well. Cells were harvested 48 hours after transfection. The primary antibody MR 1D5 (a generous gift by Gomez-Sanchez, Division of endocrinology, University of Mississippi, Jackson, Miss.) was diluted 1:1000 in 0.5% milk powder in Tris buffered saline and Tween 20 (TBST) and incubated for 1 h at room temperature (RT). The secondary antibody goat anti-mouse IgG HRP was used in 1:5000 dilutions in TBST with 0.5% milk for 1 h at RT. Tubulin was used as a control for the amount of cells and the monoclonal anti γ-Tubulin was used at a 1:1000 dilution (T6557; Sigma-Aldrich, Zwijndrecht, the Netherlands). The ECL detection system (GE healthcare, Diegem, Belgium) was used for detection. The differences in intensity of the MR bands were quantified with Image J (ImageJ, U.S. National Institutes of Health, Bethesda, Md., USA, http://rsb.info.nih.gov/ij/). Three separate experiments were performed.

Ligand Binding Assay

Cos-1 cells were seeded in 20 cm plates (Greiner Bio-One, Alphen a/d Rijn, The Netherlands) at $2\times10^6$ cells/plate in DMEM supplemented with 5% charcoal-stripped serum. Cells were transfected the next day using Mirus Transit-COS reagent according to the manufacturer's protocol (Sopachem, Ochten, The Netherlands) and hMR plasmids were used at 30 µg/plate. After 24 hours medium was replaced with serum free DMEM and after another 24 hours cells were pelleted. All further steps are carried out at 0° C. Cells were resuspended in 3.5 ml buffer (5 mM Tris-HCl (pH 7.4), 1 mM EDTA, 1 mM B-Mercaptoethanol, 10 mM Na-Molybdate, 5% glycerol) per plate and 3×15 seconds homogenised using an electric homogenizer (Pro200, Pro scientific, Oxford, Conn., USA). The homogenate was centrifuged (100.000×g, 2° C.) to obtain cytosol.

200 µl cytosol was incubated with [$^3$H]Cortisol (70 Ci/mmol, Amersham, Buckinghamshire, UK) to asses total binding or [$^3$H]Cortisol and a 500 fold excess of dexamethasone (Sigma-Aldrich, Zwijndrecht, the Netherlands) to asses non-specific binding. [$^3$H]Cortisol was used at 0.5 nM, 1 nM, 1.5 nM, 2.5 nM, 3.5 nM, 5 nM. After vortexing and 3 hours incubation on ice bound and free [$^3$H]Cortisol fractions were separated by Sephadex LH-20 as described previously (de Kloet et al., 1975). Fractions containing the receptor bound radioligand were collected, vortexed with 3 ml Ultima Gold scintillation fluid (Perkin Elmer, Waltham, Mass., USA) and radioactivity was measured in a liquid scintillation analyzer (1900CA Packard, Perkin Elmer). Three separate experiments were performed and all three experiments were performed in triplicate.

Statistical Analysis

The in vitro experiments were analyzed using GraphPad prism 4 (GraphPad software Inc, San Diego, Calif.). In the transactivation assays firefly/renilla luciferase ratios were normalized against the highest signal and background expression was subtracted. MR protein expression measured by western blot was normalized against γ-Tubulin. The differences between the four hMR variants were analyzed with one and two-way ANOVAs with Bonferroni posttests. In the radioligand binding assay one-binding-site curve fitting was used to determine the dissociation constant (Kd) and maximal binding (Bmax). The specific MR cortisol binding was obtained by subtracting the non-specific binding from the total binding. The difference in Kd and Bmax between MRI180 and MR180V was tested with a t-test. In vitro results are shown as the mean±SD.

Genetic Association Study

Recruitment

We approached teachers of all major school types in the region of Trier (Germany) and Luxembourg by means of personal visits in local schools and by newspaper announcements. Teachers were entered into the study if they reported to be free of psychiatric disorders, diabetes, pregnancy, and corticosteroid or psychotropic medication. Written informed consent was obtained from all participants and the protocol was approved by the ethics committee of the University of Trier and the Rheinland-Pfalz State Medical Association.

DNA Extraction and Genotyping

DNA was extracted from 10 ml peripheral venous blood following a standard method (Miller et al., 1988). Subjects were genotyped for the MR-2G/C and MRI180V SNPs by both matrix-assisted laser desorption/ionization time-of-flight (MALDI-TOF) mass spectrometry (MS), using the Sequenom MassARRAY™ methodology (Sequenom Inc., San Diego, Calif., USA) and by TaqMan pre-designed SNP genotyping assays, assay ID C12007869_20 and C1594392_10, respectively, in combination with TaqMan universal PCR master mix (Applied Biosystems, Nieuwekerk a/d IJssel, The Netherlands). Reaction components and amplification parameters were based on the manufacturer's instructions. Genotyping the samples with two different genotyping methods decreases method specific genotyping errors.

Assessment of Perceived Chronic Stress

Perceived chronic stress was measured using the short version of the Trier Inventory for the Assessment of Chronic Stress (TICS-S) (Schulz and Schlotz, 1999). The TICS covers nine dimensions of chronic stress, namely work overload, social overload, excessive demands at work, lack of social recognition, work discontent, social tension, performance pressure, social isolation and chronic worrying. For each item, the frequency of the experience in the last year had to be indicated on a 5-point rating scale, ranging from "never" to "very often."

Psychosocial Stress Protocol

The Trier Social Stress Test (TSST) consists of a three minutes preparation phase followed by a five minutes free speech phase (job interview) and a five minutes mental arithmetic task in front of a panel and a camera (for a detailed description of this protocol see (Kudielka et al., 2007b; Kudielka et al., 2007a). Test sessions were only run in the afternoon, starting between 15 h and 16 h. Participants were instructed to refrain from physical exercise, a heavy lunch and alcoholic beverages on test days. Premenopausal women not taking oral contraceptives were invited during the luteal phase of the menstrual cycle. The menstrual phase was estimated on the basis of the first day of last menses and the subject's usual cycle length. Only women with a regular cycle between 28 and 35 days were included and the luteal phase was defined as the last 14 days of the cycle. In the laboratory, at first an intravenous catheter was inserted in the antecubital vein of the dominant arm for later blood draws and subjects were instrumented with heart rate monitors. Heart rate was measured at 5 second intervals using a transmitter belt with a wrist receiver (Polar Sport Tester; Polar Electro, Büttelborn, Germany). After a rest period of 40 min following canula insertion and 10 min before the start of the stressor, subjects were asked to stand up. After TSST exposure subjects remained in an upright position for another 10 minutes.

Blood and Saliva Sampling

Blood samples for the assessment of ACTH and total plasma cortisol were collected in EDTA containing monovettes (Sarstedt, Nümbrecht, Germany) 1 min before as well as 1, 10, 20, 30 and 90 min after cessation of the TSST. In parallel, subjects obtained native saliva in 2 ml reaction tubes (Sarstedt, Nümbrecht, Germany) for later assessment of salivary cortisol. Additional saliva samples were obtained at 45 and 60 min after cessation of the TSST.

Biochemical Analysis

Salivary cortisol was measured by an in-house DELFIA (intra- and inter-assay variation ≤11.5%). Blood samples were instantaneously stored on ice and centrifuged at 4° C. for 15 min at 2000 g and pipetted into aliquots. Aliquots for the analysis of plasma cortisol as well as saliva samples were stored at −20° C. and aliquots for the analysis of ACTH were stored at −80° C. until assayed. ACTH and total plasma cortisol were measured by ELISA assays (plasma cortisol: IBL Hamburg, Germany, intra- and inter-assay variation 56.9%; ACTH: Biomerica Newport Beach, USA, intra- and inter-assay variation 56.0%).

Statistical Analysis

Haploview (Barrett et al., 2005) was used to calculate Hardy Weinberg equilibrium (HWE) and linkage disequilibrium among the two MR SNPs (estimated with D' and $r^2$). Haplotypes were estimated and assigned to each individual using SNPHAP (http://www-gene.cimr.cam.ac.uk/clayton/software/). In order to analyze the association between haplotypes and perceived chronic stress levels, we used the haplotype trend regression (HTR) approach as outlined by Zaykin et al (2002). Assuming additive effects of the haplotypes on the trait, the HTR approach tests for the contribution of individual haplotypes rather than haplotype pairs. We applied a permutational approach to obtain empirical p-values utilizing the HTR function of the R-package "gap", version 1.0-17 (R 2.7.2; http://www.R-project.org) with 10.000 simulations. HTR procedures provide a global p-value as well as p-values indicating the association between the trait and each haplotype. A two-stage strategy was applied to test for possible associations between haplotypes and neuroendocrine as well as autonomic TSST responses. First, the HTR approach was used as global significance test. Therefore, area under the response curve (AUC) measures were computed for salivary cortisol, plasma cortisol, ACTH and heart rate responses and entered into the HTR models. Secondly, post hoc tests were performed to further inspect the detected effects. To use the full information of the repeated measures design this was done with general linear models (GLMs) to assess the repeated measures effect time, the between-subjects effect haplotype as well as the interaction time x haplotype. In order to control for possible influences of gender, sex was included as additional predictor. Effect sizes were calculated for significant results by partial eta squared ($\eta^2$). Greenhouse-Geisser corrections were applied where appropriate, and only adjusted results are reported. GLM procedures were performed using the PASW statistical software package (Version 18.0). Unless otherwise stated, results are expressed as mean±standard error of the mean (S.E.M.). While cortisol, ACTH and heart rate values were log-transformed before statistical analyses to yield unskewed outcome variables, figures show untransformed means in order to provide a more naturalistic impression of endocrine levels.

Results

Functional Characterization In Vitro

All four MR haplotypes were tested in vitro. According to the observed frequency in the population (DeRijk et al., 2008) the haplotypes are referred to as Hap 1 (GA), constituted by MR-2 G and MRI180V A, Hap 2 (CA), constituted by MR-2 C and MRI180V A, Hap 3 (CG), constituted by MR-2C and MRI180V G and the in vivo rarely observed Hap 4 (GG), constituted by MR-2 G and MRI180V G.

Transactivation Assay

The four different MR haplotypes showed differential cortisol-induced luciferase transcription from a triple tyrosine amino transferase (TAT-3) promotor ($F_{3,26}$=42.7; p<0.0001; $\eta^2$=0.06; FIG. 12). The analysis of the dose response curves revealed a significant difference in the EC50 between the four MR haplotypes; Hap 1 (GA) EC50=3.9× $10^{-11}$, Hap 2 (CA) 1.7×$10^{-11}$, Hap 3 (CG) 1.9×$10^{-11}$ and Hap 4 (GG) 7.3×$10^{-11}$ ($F_{3,44}$=1651; p<0.0001; $\eta^2$=0.99) but no difference in the slope of the curves. Hap 1 (GA) and 4 (GG), the two haplotypes containing MR-2 G showed a significant lower maximal luciferase expression (Emax) than Hap 2 (CA) and 3 (CG), i.e. the two haplotypes containing MR-2 C ($F_{3,28}$=29.2; p<0.0001; $\eta^2$=0.76). Although the effect on transactivation was largest for the MR-2G/C SNP, MRI180V also influenced the transactivation with the A (MRI180) having a lower EC50 than the G (MR180V).

Western Blot

The MR haplotypes influenced MR protein expression in transfected COS-1 cells ($F_{3,4}$=7.07; p=0.03; $\eta^1$=0.80, FIG. 13). Post hoc analysis revealed that protein expression was only influenced by MR-2G/C and not by MRI180V. Hap 2 (CA) and 3 (CG), the two plasmids containing MR-2C, showed higher MR protein expression compared to Hap 1 (GA) and 4 (GG), the two plasmids containing MR-2 G (all combinations p<0.05), while there was no significant difference between Hap 1 and 4 and between Hap 2 and 3.

Ligand Binding

Cortisol binding to the MR (Kd and Bmax) was not influenced by MRI180V. The Kds of MRI180 and MR180V were not significantly different, being 0.86±0.20 and 0.93±0.16 nM, respectively. There was also no significant difference in Bmax, showing values of 6539±499 and 7112±371 binding sites/cell for the MRI180 and MR180V, respectively. As there was no significant difference between the three separate experiments, data of the three experiments were pooled for analysis.

Genetic Association Study

Genotypes and Haplotypes

The two employed genotyping methods yielded identical results. The distribution of both SNPs, MRI180V and MR-2G/C, did not deviate significantly from Hardy Weinberg equilibrium (HWE). The estimated linkage between MRI180V and MR-2G/C was D'=1 (conf bounds 0.63-1) and $r^2$=0.093. As expected, in this sample Hap 1 (GA) showed with 48.8% the highest frequency followed by Hap 2 (CA) with a frequency of 41.9% and Hap 3 (CG) with a frequency of 9.3%. Consistent with previous studies Hap 4 (GG) was not observed in this cohort (see FIG. 14). One subject showed the very rare genotype CGCG (i.e. homozygous for Hap 3) and was excluded from all association analyses.

Final Sample

The sample for the present analysis consisted of 166 healthy subjects (55 males and 111 females). Participants were between 23 to 63 years of age (mean age: 45.58±9.8) and had a mean body mass index (BMI) of 25.9±4.7. Fifteen of the subjects reported to be smokers. Questionnaire data from 163 to 166 participants (due to a different number of missing values across scales) could be analyzed.

Perceived Chronic Stress

HTR models revealed associations between the MR haplotype structure and perceived chronic stress assessed with the TICS in respect to four subscales, namely "social overload", "excessive demands at work", "social tension", and "social isolation" (Table 4). While global p-values were significant for "social overload" (F=3.21, p=0.042) and "excessive demands at work" (F=3.65, p=0.029), a trend was detected for "social tension" (F=2.39, p=0.095) and "social isolation" (F=2.63, p=0.076). Inspection of haplotype specific p-values for these four scales revealed that carriers of Hap 3 (CG) reported significantly more chronic stress in terms of "excessive demands at work" (F=7.27; p=0.008) and "social overload" (F=4.17; p=0.045) than non-carriers. Furthermore, individuals with two copies of Hap 1 (GA) reported more chronic stress in terms of "social isolation" (F=4.93; p=0.029) and "social tension" (F=4.80; p=0.032) than individuals with one copy or zero copies of Hap 1. The respective "social isolation" effect for Hap 2 (CA) was also significant (F=4.95; p=0.027), while the respective "social tension" effect (F=3.44; p=0.071) as well as the "social overload" effect (F=3.75; p=0.056) showed a trend, with individuals with zero copies having higher scores than individuals with one or two copies of Hap 2.

ACTH, Cortisol and Heart Rate Responses to Acute Psychosocial Stress

A subsample of 54 participants (20 males and 34 females) underwent the stress protocol. Because of the well-known intervening effects of oral contraceptive or sex steroid intake (Kirschbaum et al., 1999; Kudielka et al., 1999) as well as smoking (Rohleder and Kirschbaum, 2006) on acute HPA axis stress responses, we excluded three women taking oral contraceptives or receiving hormonal replacement therapy and two smokers from all further analyses. Two further subjects had missing data in the endocrine measures while six subjects had missing heart rate data due to technical problems. Thus, we included 47 subjects in the final analysis of endocrine and 41 subjects in the analysis of heart rate responses.

Despite the small size of this subsample MR haplotypes were significantly associated with neuroendocrine and autonomic TSST responses in a rather consistent way. Regarding the global test HTR procedures revealed significant associations between the investigated MR haplotype structure and the area under the curve measures for salivary cortisol responses (F=6.80; p=0.005), plasma cortisol responses (F=3.34; p=0.046), and ACTH responses (F=4.03; p=0.029). The respective effect for heart rate responses showed a trend towards statistical significance (F=2.37; p=0.109).

To use the full information of the repeated measures design, post hoc inspection of associations of specific hap-

TABLE 4

Association between subscales of the Trier Inventory for the assessment of chronic stress and MR haplotypes.

| | MR Haplotypes | 0 Copies | 1 Copy Mean (±Std) | 2 Copies | Global Test p [F] | Haplotype Specific Test p [F] |
|---|---|---|---|---|---|---|
| Work Overload | | | | | n.s. | |
| | GA | 2.22 (0.91) | 2.29 (0.81) | 2.41 (0.98) | | |
| | CA | 2.48 (0.94) | 2.21 (0.82) | 2.19 (0.89) | | |
| | CG | 2.26 (0.88) | 2.51 (0.88) | | | |
| Social Overload | | | | | .042 [3.21]* | |
| | GA | 1.93 (0.91) | 1.91 (0.94) | 2.10 (0.87) | | n.s. |
| | CA | 2.18 (0.96) | 1.84 (0.95) | 1.85 (0.90) | | .056 [3.75]+ |
| | CG | 1.90 (0.86) | 2.28 (0.91) | | | .045 [4.17]* |
| Excessive Demands at Work | | | | | .029 [3.65]* | |
| | GA | 1.35 (0.77) | 1.19 (0.79) | 1.29 (0.80) | | n.s. |
| | CA | 1.37 (0.86) | 1.18 (0.75) | 1.25 (0.73) | | n.s. |
| | CG | 1.19 (0.91) | 1.62 (0.79) | | | .008 [7.27]* |
| Lack of Social Recognition | | | | | n.s. | |
| | GA | 1.60 (0.99) | 1.63 (1.03) | 1.84 (1.10) | | |
| | CA | 1.73 (1.12) | 1.66 (1.02) | 1.61 (0.95) | | |
| | CG | 1.71 (1.02) | 1.50 (1.13) | | | |
| Work Discontent | | | | | n.s. | |
| | GA | 0.95 (0.90) | 0.99 (0.77) | 1.12 (0.76) | | |
| | CA | 1.06 (0.72) | 1.04 (0.86) | 0.87 (0.82) | | |
| | CG | 1.01 (0.80) | 1.00 (0.83) | | | |
| Social Tension | | | | | .095 [2.39]+ | |
| | GA | 1.13 (0.72) | 1.17 (0.72) | 1.45 (0.78) | | .032 [4.80]* |
| | CA | 1.44 (0.77) | 1.10 (0.72) | 1.21 (0.70) | | .071 [3.44]+ |
| | CG | 1.26 (0.74) | 1.16 (0.79) | | | n.s. |
| Performance Pressure | | | | | n.s. | |
| | GA | 1.84 (0.70) | 1.79 (0.74) | 1.89 (0.70) | | |
| | CA | 1.91 (0.77) | 1.77 (0.68) | 1.83 (0.70) | | |
| | CG | 1.82 (0.69) | 1.91 (0.84) | | | |
| Social Isolation | | | | | .076 [2.63]+ | |
| | GA | 1.28 (0.86) | 1.71 (0.95) | 1.73 (1.10) | | .029 [4.93]* |
| | CA | 1.73 (1.02) | 1.64 (0.95) | 1.25 (0.87) | | .027 [4.95]* |
| | CG | 1.59 (0.99) | 1.69 (0.88) | | | n.s. |
| Chronic Worrying | | | | | n.s. | |
| | GA | 1.89 (1.02) | 1.68 (0.84) | 1.78 (1.09) | | |
| | CA | 1.80 (1.04) | 1.74 (0.96) | 1.75 (0.83) | | |
| | CG | 1.70 (0.92) | 2.04 (1.15) | | | |

Figure 15A:
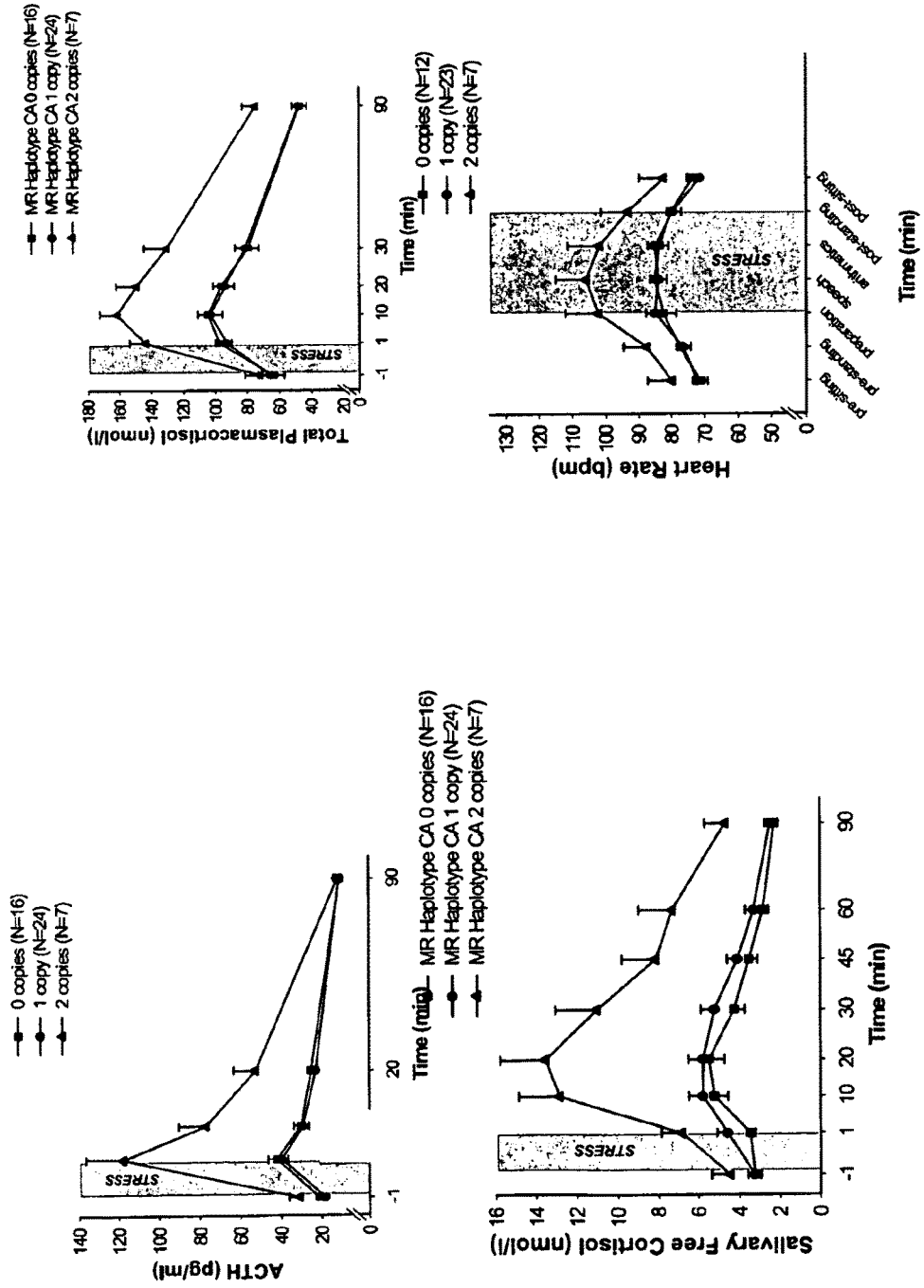
Figure 15B:
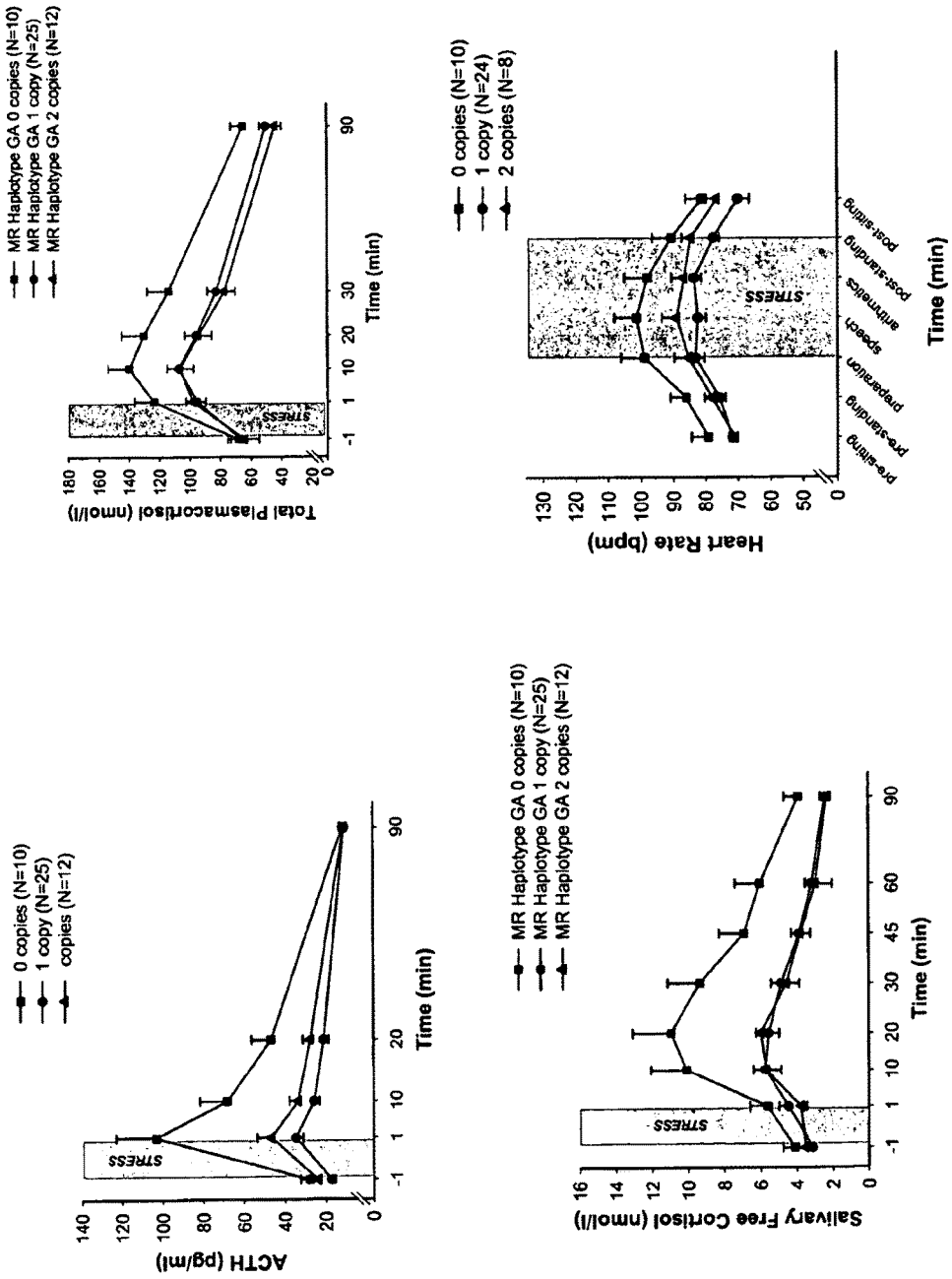
Figure 15C:
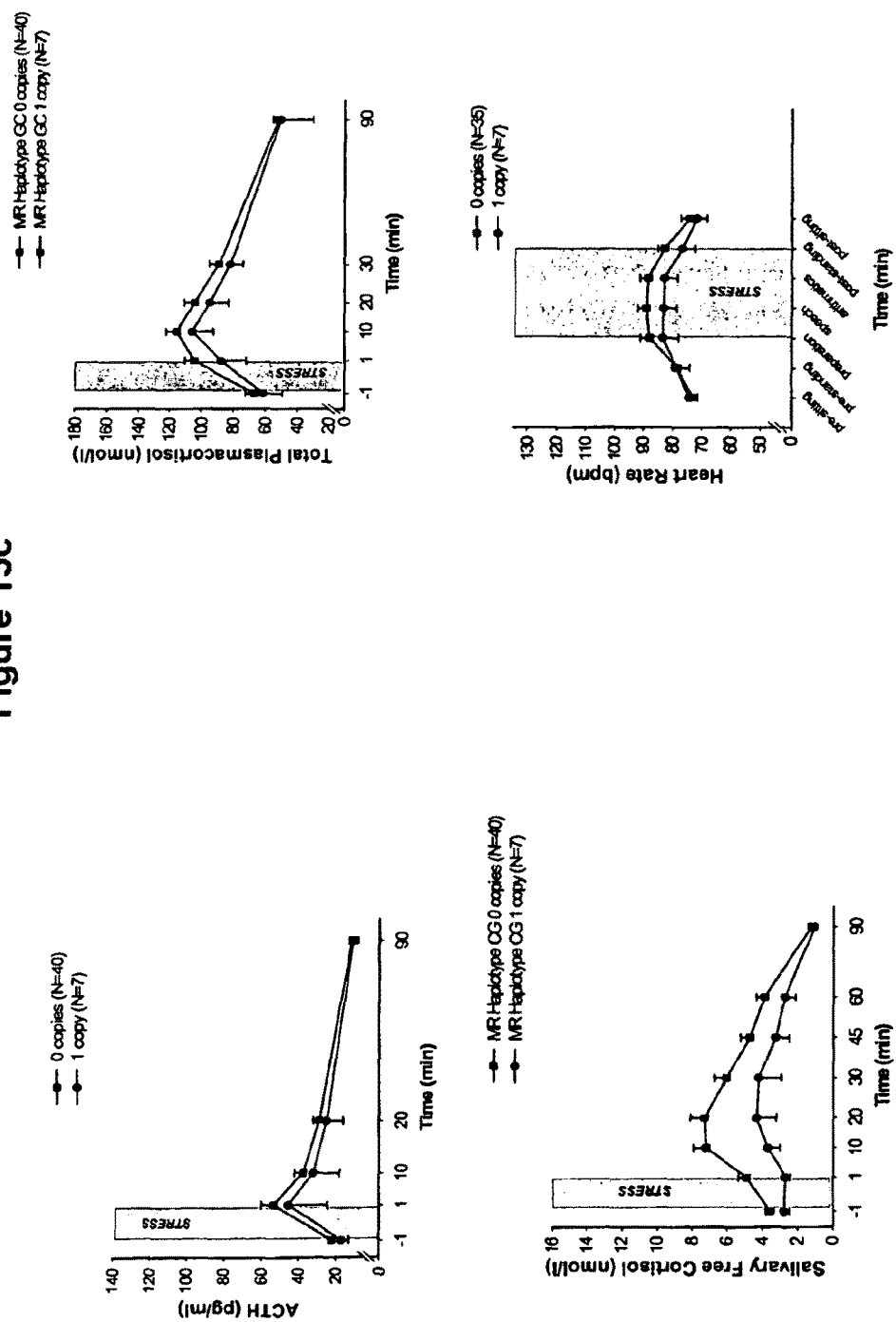

Table shows asymptotic F- and empirical p-values;
*p < .05,
+p < .10.

lotypes was done with general linear models. For Hap 2 (CA), significant main effects haplotype were observed for ACTH ($F_{2,41}=6.69$, p=0.003, $\eta^2=0.25$), plasma cortisol ($F_{2,41}=5.12$, p=0.010, $\eta^2=0.20$), salivary cortisol ($F_{2,41}=12.11$, p=0.000, $\eta^2=0.37$) as well as heart rate ($F_{2,35}=4.51$, p=0.018, $\eta^2=0.21$). Across all measures, individuals with two copies of Hap 2 showed a stronger response to the stressor than individuals with one copy or zero copies. In addition, significant time x haplotype interactions were found for ACTH ($F_{3.76,76.39}=4.58$, p=0.003, $\eta^2=0.18$) and salivary cortisol ($F_{6.89,141.17}=2.57$, p=0.017, $\eta^2=0.11$), while the respective interactions for plasma cortisol and heart rate were not significant (all p>0.14). Mean responses are shown in FIG. 15a.

A similar picture emerges for Hap 1 (GA), which is not surprising given that Hap 1 and Hap 2 are largely complimentary. Here, those individuals with zero copies of Hap 1 showed significantly elevated ACTH (main effect $F_{2,41}=7.73$, p=0.001, $\eta^2=0.27$), salivary cortisol (main effect $F_{2,41}=6.67$, p=0.003, $\eta^2=0.25$) and heart rate (main effect $F_{2,35}=4.96$, p=0.013, $\eta^2=0.22$) levels. The effect for plasma cortisol levels just missed the level of significance (main effect $F_{2,41}=2.90$, p=0.066). A significant time x haplotype emerged for ACTH ($F_{3.61,74.05}=4.68$, p=0.003, $\eta^2=0.19$) and a trend was observed for salivary cortisol ($F_{3.26,128.26}=1.91$, p=0.072), while the respective interactions for plasma cortisol and heart rate were not significant (all p>0.19, FIG. 15b). Finally, we did not detect a significant association between Hap 3 (GC) and neuroendocrine and autonomic TSST responses (p>0.10 for all main effects haplotype and p>0.15 for all interactions time x haplotype, FIG. 15c).

Discussion

Here we described neuroendocrine and behavioral consequences of two common functional polymorphisms in the human MR, MRI180V and MR-2G/C, both in vitro and in vivo. The haplotypes of the two SNPs showed differences in cortisol-induced transcription of the reporter gene. From protein analysis of the haplotypes it can be concluded that MR-2G/C changes protein expression while MRI180V did not have this effect. Furthermore, MRI180V did not affect ligand binding. Our data suggest that the haplotypes are associated with stress-induced HPA axis and autonomic responses following a psychosocial stress test. Moreover, the haplotypes might be associated with several aspects of perceived chronic stress.

Transactivation assays have been performed with the two MR SNPs individually (DeRijk et al., 2006; van Leeuwen et al., 2010). However, the combinations of the two SNPs, as occur in vivo as part of the observed haplotypes, have not been tested so far. Both haplotypes containing MR-2 C had a higher activity as compared to the two haplotypes containing MR-2 G. Moreover, statistical analysis did not reveal an interaction effect between the −2G/C and the MRI180V.

MRI180V produces an amino acid change in the N-terminal domain, which is involved in recruiting co-regulators that selectively modulate transcriptional activity of the MR. As shown in the current study, this effect was not mediated by differences in cortisol binding characteristics, since no differences in maximal binding capacity (Bmax) or dissociation constants (Kd) were observed between MRI180 and MR180V. This suggests that other factors such as differences in translocation to the nucleus, dimerization of the MR or binding of co-regulators might be responsible for the observed differences in transactivation.

In contrast to the MRI180V, the MR-2 G/C is not changing the primary structure of the receptor and is therefore less likely to have an effect on MR protein characteristics. In this study we showed that both haplotypes containing MR-2 C had a higher MR protein expression as compared to the two haplotypes containing MR-2 G while the MRI180V did not influence the protein expression. This finding explains the higher transactivational capacity of the two haplotypes containing MR-2 C, as occurring in haplotypes 2 and 3. In a supplementary part of the present study we investigated the association between these MR gene variants and subjectively perceived chronic stress and neuroendocrine as well as autonomic responses to acute experimental psychosocial stress. We selected a small but well characterized sample of healthy school teachers, since the teaching profession has been repeatedly described as a potentially stressful occupation (Guglielmi and Tatrow, 1998), which is reflected in high rates of early retirement among German school teachers (Weber, 2004). This cohort is independent of the samples in which the previously reported associations between MR gene polymorphisms and HPA axis regulation have been observed (DeRijk et al., 2006; van Leeuwen et al., 2010). This cohort has a rather modest sample size and this holds in particular for the subsample that was exposed to the TSST. However, given this limitation, the observed associations between MR gene haplotypes and biological stress responses have been remarkably consistent across the different indices.

Individuals carrying two copies of haplotype 2 (CA) showed higher salivary cortisol, plasma cortisol, ACTH as well as heart rate responses to acute psychosocial stress, compared to individuals with only one or zero copies of this haplotype. Despite the small sample, the global effect for salivary cortisol responses did survive bonferroni correction for multiple comparisons (corrected for four HTR procedures) and some of the GLM p-values are remarkably small. The distinct mean ACTH and cortisol response differences shown in FIGS. 15a and 15b were not caused by single subjects with extreme response patterns.

As a consequence of the sample size it was not possible to compute a separate analysis for males and females. We did, however, control for sex effects statistically, we did only include females who did not take oral contraceptives and premenopausal females were tested in the luteal phase of the menstrual cycle.

The association between MR gene haplotypes and perceived chronic stress could be investigated in a larger, but still modest sample of 166 subjects. Without correction for multiple testing haplotype 3 (CG) carriage was significantly related to higher levels of "excessive demands at work" and "social overload". Haplotype 1 (GA) was significantly related to higher "social isolation" and "social tension" scores. Consistently, haplotype 2 (CA) was also significantly related to "social isolation" scores and—on a trend level—to the subscales "social overload" and "social tension".

Combining the neuroendocrine and perceived chronic stress data, haplotype 2 appears to be associated with higher neuroendocrine stress-responses and better stress handling. A previous study showed that the MR −2 C variant associates with lower basal non-stress levels of cortisol in an elderly population (Kuningas et al., 2007). This suggests that a more reactive HPA axis with lower basal levels is beneficial for coping with stressors, as has been proposed (de Kloet et al., 2007). Moreover, the in vitro data show that haplotype 2 increases MR-expression, again adding to the notion that higher MR-expression is beneficial. This is further substantiated by animal research showing that increased MR-expression in the forebrain of mice results in less anxiety-like behavior (Rozeboom et al., 2007). With respect to the HPA axis response, the MR is involved in tonic inhibition of cortisol/corticosterone levels. Furthermore, during the ageing process, a loss of MR-expression in the brain is observed which coincides with less sensitivity towards ACTH in the Brown Norway rat (Van Eekelen et al., 1992). Also in MR forebrain knock out mice, less adaptation of the HPA axis response to stress is observed (Brinks et al., 2009). This indicates that higher MR-expression in the brain leads to a more dynamic HPA axis response with lower basal non-stress levels.

The precise mechanism how the putative increased MR-expression leads to a more reactive HPA axis responses and resilient behavior to stressors is unknown. MR-expression is essential for neuronal protection and stability of neuronal circuits (de Kloet et al., 2007; Lai et al., 2009). The recent discovery of a MR located in the membrane, in addition to the nuclear MR, has further implications (Karst et al., 2005). This low affinity membrane version of the MR becomes activated during stress-levels of cortisol and increases excitatory glutaminergic transmission while decreasing post-synaptic after-hyperpolarization (Joels et al., 2008). This rapid excitatory MR-mediated effect may very well underlie the non-genomic actions exerted by cortisol on neuroendocrine, emotional and cognitive processes (Brinks et al., 2009). Therefore, it will be a challenge for future research to dissociate during a psychosocial stressor the genomic and non-genomic effects mediated by the MR on processing of stressful information resulting in HPA axis reactivity and behavior. The MR haplotypes identified in this study may be very helpful in this respect.

In conclusion, in vitro assays demonstrate large differences in transactivation between the haplotypes. The molecular mechanism of these differences is only partly elucidated. In vivo, individuals with two copies of MR haplotype 2 (CA) had the most dynamic response to an acute psychosocial stressor, both the HPA axis and autonomic responses were higher in these individuals. Furthermore, our data suggest involvement of MR gene variants in perceived chronic stress, in which the haplotype 2 may be beneficial for coping with stressors. All together, it is concluded that these MR haplotypes may contribute to individual differences in the neuroendocrine response during coping with psychological stress.

References for Example 3

Arriza, J. L., Weinberger, C., Cerelli, G., Glaser, T. M., Handelin, B. L., Housman, D. E., Evans, R. M., 1987. Cloning of human mineralocorticoid receptor complementary DNA: structural and functional kinship with the glucocorticoid receptor. Science 237, 268-275.

Arvat, E., Maccagno, B., Giordano, R., Pellegrino, M., Broglio, F., Gianotti, L., Maccario, M., Camanni, F., Ghigo, E., 2001. Mineralocorticoid receptor blockade by canrenoate increases both spontaneous and stimulated adrenal function in humans. J. Clin. Endocrinol. Metab 86, 3176-3181.

Atkinson, H. C., Wood, S. A., Castrique, E. S., Kershaw, Y. M., Wiles, C. C. R., Lightman, S. L., 2008. Corticosteroids mediate fast feedback of the rat hypothalamic-pituitary-adrenal axis via the mineralocorticoid receptor. American Journal of Physiology-Endocrinology and Metabolism 294, E1011-E1022.

Barrett, J. C., Fry, B., Maller, J., Daly, M. J., 2005. Haploview: analysis and visualization of LD and haplotype maps. Bioinformatics 21, 263-265.

Brinks, V., Berger, S., Gass, P., de Kloet, E. R., Oitzl, M. S., 2009. Mineralocorticoid receptors in control of emotional arousal and fear memory. Horm. Behav. 56, 232-238.

Conway-Campbell, B. L., McKenna, M. A., Wiles, C. C., Atkinson, H. C., de Kloet, E. R., Lightman, S. L., 2007. Proteasome-dependent down-regulation of activated nuclear hippocampal glucocorticoid receptors determines dynamic responses to corticosterone. Endocrinology 148, 5470-5477.

de Kloet, R., DeRijk, R. H., Meijer, O. C., 2007. Therapy Insight: is there an imbalanced response of mineralocorticoid and glucocorticoid receptors in depression? Nature Clinical Practice Endocrinology & Metabolism 3, 168-179.

de Kloet, R., Wallach, G., Mcewen, B. S., 1975. Differences in corticosterone and dexamethasone binding to rat brain and pituitary. Endocrinology 96, 598-609.

DeRijk, R. H., van Leeuwen, N., Klok, M. D., Zitman, F. G., 2008. Corticosteroid receptor-gene variants: modulators of the stress-response and implications for mental health. Eur. J. Pharmacol. 585, 492-501.

DeRijk, R. H., Wüst, S., Meijer, O. C., Zennaro, M. C., Federenko, I. S., Hellhammer, D. H., Giacchetti, G., Vreugdenhil, E., Zitman, F. G., de Kloet, E. R., 2006. A common polymorphism in the mineralocorticoid receptor modulates stress responsiveness. Journal of Clinical Endocrinology and Metabolism 91, 5083-5089.

Di, S., Malcher-Lopes, R., Halmos, K. C., Tasker, J. G., 2003. Nongenomic glucocorticoid inhibition via endocannabinoid release in the hypothalamus: a fast feedback mechanism. J. Neurosci. 23, 4850-4857.

Dodt, C., Kern, W., Fehm, H. L., Born, J., 1993. Antimineralocorticoid canrenoate enhances secretory activity of the hypothalamus-pituitary-adrenocortical (HPA) axis in humans. Neuroendocrinology 58, 570-574.

Federenko, I. S., Schlotz, W., Kirschbaum, C., Bartels, M., Hellhammer, D. H., Wüst, S., 2006. The heritability of perceived stress. Psychological Medicine 36, 375-385.

Guglielmi, R. S., Tatrow, K., 1998. Occupational Stress, Burnout, and Health in Teachers: A Methodological and Theoretical Analysis. Review of Educational Research 69, 61-99.

Joëls, M., Karst, H., Derijk, R., de Kloet, E. R., 2008. The coming out of the brain mineralocorticoid receptor. Trends in Neurosciences 31, 1-7.

Karst, H., Berger, S., Turiault, M., Tronche, F., Schutz, G., Joëls, M., 2005. Mineralocorticoid receptors are indispensable for nongenomic modulation of hippocampal glutamate transmission by corticosterone. Proc. Natl. Acad. Sci. USA 102, 19204-19207.

Kirschbaum, C., Kudielka, B. M., Gaab, J., Schommer, N. C., Hellhammer, D. H., 1999. Impact of gender, menstrual cycle phase, and oral contraceptives on the activity of the hypothalamus-pituitary-adrenal axis. Psychosom. Med. 61, 154-162.

Kudielka, B. M., Hellhammer, D. H., Kirschbaum, C., 2007a. Ten years of research with the Trier Social Stress Test (TSST)—revisited. In: Harmon-Jones, E., Winkielman, P. (Eds.), Social Neuroscience. Guilford Press, New York, pp. 56-83.

Kudielka, B. M., Wüst, S., Kirschbaum, C., Hellhammer, D. H., 2007b. Trier Social Stress Test. In: Fink, G., Chrousos, G., Craig, I., de Kloet, E. R., Feuerstein, G., McEwen, B. S., Rose, N. R., Rubin, R. T., Steptoe, A. (Eds.), Encyclopedia of stress. Elsevier, Oxford, pp. 767-781.

Kudielka, B. M., Schmidt-Reinwald, A. K., Hellhammer, D. H., Kirschbaum, C., 1999. Psychological and endocrine responses to psychosocial stress and dexamethasone/corticotropin-releasing hormone in healthy postmenopausal women and young controls: The impact of age and a two-week estradiol treatment. Neuroendocrinology 70, 422-430.

Kuningas, M., de Rijk, R. H., Westendorp, R. G. J., Jolles, J., Slagboom, P. E., van Heemst, D., 2007. Mental performance in old age dependent on cortisol and genetic variance in the mineralocorticoid and glucocorticoid receptors. Neuropsychopharmacology 32, 1295-1301.

Lai, M., Bae, S. E., Bell, J. E., Seckl, J. R., Macleod, M. R., 2009. Mineralocorticoid receptor mRNA expression is increased in human hippocampus following brief cerebral ischaemia. Neuropathol. Appl. Neurobiol. 35, 156-164.

Lazarus, R. S., Launier, R., 1978. Stress-related transactions between person and environment. Perspectives in Interactional Psychology (ed. L. A. Pervin and M. Lewis) 287-327.

Lightman, S. L., Wiles, C. C., Atkinson, H. C., Henley, D. E., Russell, G. M., Leendertz, J. A., McKenna, M. A., Spiga, F., Wood, S. A., Conway-Campbell, B. L., 2008. The significance of glucocorticoid pulsatility. Eur. J. Pharmacol. 583, 255-262.

Mcewen, B. S., Stellar, E., 1993. Stress and the individual. Mechanisms leading to disease. Arch. Intern. Med. 153, 2093-2101.

Miller, S. A., Dykes, D. D., Polesky, H. F., 1988. A Simple Salting Out Procedure for Extracting Dna from Human Nucleated Cells. Nucleic Acids Research 16, 1215-1215.

Ratka, A., Sutanto, W., Bloemers, M., de Kloet, E. R., 1989. On the role of brain mineralocorticoid (type I) and glucocorticoid (type II) receptors in neuroendocrine regulation. Neuroendocrinology 50, 117-123.

Rohleder, N., Kirschbaum, C., 2006. The hypothalamic-pituitary-adrenal (HPA) axis in habitual smokers. Int. J. Psychophysiol. 59, 236-243.

Rozeboom, A. M., Akil, H., Seasholtz, A. F., 2007. Mineralocorticoid receptor overexpression in forebrain decreases anxiety-like behavior and alters the stress response in mice. Proc. Natl. Acad. Sci. U.SA 104, 4688-4693.

Sarabdjitsingh, R. A., Meijer, O. C., Schaaf, M. J., de Kloet, E. R., 2009. Subregion-specific differences in translocation patterns of mineralocorticoid and glucocorticoid receptors in rat hippocampus. Brain Res. 1249, 43-53.

Schulz, P., Schlotz, W., 1999. The Trier Inventory for the Assessment of Chronic Stress (TICS): Scale construction, statistical testing, and validation of the scale work overload. Diagnostica 45, 8-19.

Van Eekelen, J. A., Rots, N. Y., Sutanto, W., de Kloet, E. R., 1992. The effect of aging on stress responsiveness and central corticosteroid receptors in the brown Norway rat. Neurobiol. Aging 13, 159-170.

van Leeuwen, N., Kumsta, R., Entringer, S., de Kloet, E. R., Zitman, F. G., DeRijk, R. H., Wüst, S., 2010. Functional mineralocorticoid receptor (MR) gene variation influences the cortisol awakening response after dexamethasone. Psychoneuroendocrinology 35, 339-349.

Weber, A., 2004. Krankheitsbedingte Frühpensionierungen von Lehrkräften, Early retirement of teachers as a result of health problems. Psychosomatische Erkrankungen bei Lehrerinnen and Lehrern Hillert and E. Schmitz, Editors, 22-38.

Wellhoener, P., Born, J., Fehm, H. L., Dodt, C., 2004. Elevated resting and exercise-induced cortisol levels after mineralocorticoid receptor blockade with canrenoate in healthy humans. J. Clin. Endocrinol. Metab 89, 5048-5052.

Zaykin, D. V., Westfall, P. H., Young, S. S., Karnoub, M. A., Wagner, M. J., Ehm, M. G., 2002. Testing association of statistically inferred haplotypes with discrete and continuous traits in samples of unrelated individuals. Hum. Hered. 53, 79-91.

EXAMPLE 4

Common Functional Mineralocorticoid Receptor Polymorphisms Modulate the Cortisol Awakening Response: Interaction with SSRIs Summary Background:

Cortisol controls the activity of the hypothalamic-pituitary-adrenal (HPA) axis during stress and during the circadian cycle through central mineralocorticoid (MR) and glucocorticoid receptors (GR). Changes in MR and GR functioning, therefore, may affect HPA axis activity. In this study we examined the effect of common functional MR gene variants on the cortisol awakening response (CAR), which is often disturbed in stress-related disorders like depression.

Methods:

Common functional MR single nucleotide polymorphisms (SNPs; MR −2G/C and I180V) and haplotypes were tested for association with variability in the CAR in a large cohort (Netherlands Study of Depression and Anxiety, NESDA) of patients diagnosed with a lifetime major depressive disorder (MDD). Saliva cortisol measurements and genotypes could be obtained from a total of 1026 individuals, including 324 males and 702 females.

Results:

The MR −2C/C genotype was associated with an attenuated CAR increase in women ($p=0.03$) but not in men ($p=0.18$; $p=0.01$ for SNP-by-sex interaction). The MR I180V SNP had no significant effect on the CAR. Additional analysis revealed that effect of the −2G/C SNP on the CAR was due to an interaction with frequent use of selective serotonin reuptake inhibitors (SSRIs). Only in subjects using SSRIs (men and women) a prolonged CAR was observed in −2G/G carriers, while the CAR was completely flattened in women with the −2C/C genotype ($p<0.05$). The results were independent of multiple potential confounders and had an effect size of $r=0.14$–$0.27$.

Conclusions:

This study shows that the MR −2G/C SNP modulated the CAR only in the MDD patients using SSRIs, with a clear allele-dose effect only in women. This suggests that effect of SSRIs on cortisol regulation depends in part on MR genotype with possible implications for future treatment selection.

Introduction

Optimal regulation of cortisol levels by the hypothalamic-pituitary-adrenal (HPA) axis is crucial for physical and psychological responsiveness to everyday challenges and health (De Kloet et al., 1998). Hence, disturbances in activity of the HPA axis may develop into various disorders, including major depressive disorder (MDD) (Nestler et al., 2002), while normalization of HPA axis parameters preceding clinical relief is often observed (Barden et al., 1995; Zobel et al., 2004). These changes in HPA axis activity depend on the feedback action of cortisol, which is mediated by two brain corticosteroid receptors, i.e. the high affinity mineralocorticoid receptor (MR) and the low affinity glucocorticoid receptor (GR).

Due to its low affinity the GR only becomes activated when cortisol levels are high, as occurs during stress and at the peaks of the ultradian rhythm during the circadian cycle (de Kloet and Sarabdjitsingh, 2008). Through the GR, stress-induced cortisol levels are suppressed. The MR has a high affinity for cortisol and therefore remains already highly occupied throughout the day under non-stress, basal conditions. During the day the MR exerts a tonic inhibition on circulating cortisol levels (De Kloet et al., 1998). Administration of a MR antagonist to both animals and humans increases diurnal plasma corticosteroid levels by enhancing the amplitude of the corticosteroid pulses (Heuser et al., 2000; Atkinson et al., 2008). In addition, the MR potentiates the initial neuroendocrine stress reaction. In response to stress the MR and GR mediate in complementary fashion the action of cortisol from the initial stress reaction to the management of later adaptive phases. Recently, besides a cytoplasmic high affinity MR also a low affinity membrane MR was identified, however, the specific roles of these distinctly localized receptors in HPA axis activity still has to be assessed (Joels et al., 2008). What the specific roles of the MR and GR are in regulating the circadian peak is still unclear. Because of its high affinity it is likely that the MR is implicated. Moreover, the question remains whether cortisol levels at the circadian peak are high enough to actually bind to the GR. The present study focuses on the MR.

By examining the effect of common functional MR gene variants, we showed that MR genetic variability confers inter-individual differences in neuroendocrine regulation under both basal non-stress conditions and after stress (DeRijk et al., 2006; Kuningas et al., 2007; van Leeuwen et al., 2009). For the MR gene, two functional SNPs (MR I180V and −2G/C) have been described so far, both affecting MR expression and/or gene transactivation in cell lines. The V-allele of the MR I180V SNP results in a higher cortisol response to the Trier Social Stress Test (TSST) (DeRijk et al., 2006), which was accompanied by an increased heart rate response. In a different study, the C-allele of the MR −2G/C SNP was found to be associated with lower plasma cortisol levels in the morning among healthy elderly (Kuningas et al., 2007). These data indicate that both basal non-stress and stress-induced HPA regulation may vary in part due to differences in MR activity. As yet, it is still unclear to what extent the MR (and GR) influences the cortisol awakening response (CAR). In a recent study, both known MR SNPs were found to affect the CAR in healthy individuals, although effects were only significant after dexamethasone treatment and were sex dependent (van Leeuwen et al., 2009).

The CAR consists of a distinct rise in cortisol levels directly after awakening, which reaches peak levels at 30 min and returns to baseline levels 60 min after awakening (Pruessner et al., 1997; Wust et al., 2000b; Wilhelm et al., 2007). The CAR is considered as a response to awakening, superimposed on the ultradian rhythm during the circadian cycle (Kuehner et al., 2007). Because of its intra-individual stability, the CAR is thought of as a trait measure for HPA axis activity (Pruessner et al., 1997; Wust et al., 2000a) and appears to be influenced in part by genetic factors (Wust et al., 2000a). Sociodemographic, lifestyle and sleep factors, chronic stress and daily hassles all may modulate the CAR (Pruessner et al., 1997; Wust et al., 2000a; Wust et al., 2000b; Buchanan et al., 2004; Hellhammer et al., 2007; Fries et al., 2009; Vreeburg et al., 2009b).

Major depressive disorder (MDD) is in many cases associated with hyperactivity of the HPA axis (Nestler et al., 2002), including an enhanced CAR often found in both remitted and current depressed patients (Vreeburg et al., 2009a). Normalization of HPA axis reactivity often occurs after treatment with antidepressants (Barden et al., 1995; Zobel et al., 2004), while antidepressants themselves were found in animal studies and cell lines to increase the expression of both the MR and/or GR (Seckl and Fink, 1992; Holsboer and Barden, 1996; Bjartmar et al., 2000). Moreover, MR antagonists diminish, while MR agonists enhance the efficacy of a tricyclic antidepressant (TCA) or a selective serotonin reuptake inhibitor (SSRI) respectively (Holsboer, 1999; Otte et al., 2009). Collectively, these data imply an important role for the efficiency of MR signaling in changing HPA axis activity, pathogenesis and with consequences for treatment.

Here we tested the hypothesis that genetic variants of the MR gene relate to variability in the CAR in lifetime MDD patients. To address this hypothesis, the MR −2G/C and I180V SNPs were examined for association with the 1-hour cortisol awakening response in a large cohort of patients with a lifetime diagnosis of MDD (remitted and current). Subsequently, data were stratified for sex to assess sex-dependent effects. Finally, possible interaction effects with MR were tested for stressful life events and frequent use of SSRIs.

Materials and Methods

Study Population

Data were used from the Netherlands Study of Depression and Anxiety (NESDA), an eight-year longitudinal cohort study on the causes and course of depressive and anxiety disorders in people aged 18-65 years. For the NESDA study, a total of 2981 respondents were recruited from the general population and from primary care and specialized mental health care practices, including 2329 patients with a lifetime depressive and/or anxiety disorder and 652 subjects without a any (lifetime or current) depressive and/or anxiety disorder. Among those subjects a primary clinical diagnosis of psychotic disorder, obsessive-compulsive disorder, bipolar disorder, or severe addiction disorder, and not being fluent in Dutch was excluded. All participants provided written informed consent before inclusion. For details on the NESDA study see (Penninx et al., 2008).

In the present study patients were selected when they had a lifetime MDD diagnosis (n=1925), as assessed with the DSM-IV Composite International Diagnostic Interview (CIDI) version 2.1. Patients were excluded when they indicated not to be from western European ancestry (n=109), when taking corticosteroids (n=15) or when pregnant or breastfeeding (n=11). Of this subset of 1790 MDD patients, genotypes were available for 1572 individuals, which were assessed earlier as part of a large genome wide association (GWA) study for MDD, the GAIN-MDD study (Sullivan et al., 2009). Saliva cortisol data were available for 1091 of the 1572 genotyped MDD patients. When comparing this group of 1091 respondents with the subjects for which no genotypes or saliva data were available (n=699), they did not differ in sex. However, they were slightly older (43.6±12.4 vs. 39.6±12.2; p<0.001), were more educated (12.2±3.2 yrs vs. 11.6±3.2 yrs; p<0.001) and were more often currently depressed (54.3% vs. 45.7%; p<0.01). Finally, an additional group of 65 individuals was excluded because less than 2 valid CAR measurement points were available, leaving a final group of 1026 respondents. Of this final group of 1026 lifetime MDD patients, 555 (54.1%) had a current depression (depression diagnosis in the past 6 months) and 715 (69.7%) had a comorbid lifetime anxiety disorder. The present study combines remitted and current depressed patients as the previous analysis by Vreeburg et al. (Vreeburg et al., 2009a) showed that the CAR was similarly heightened in both groups when compared to the controls.

Sociodemographic, Sampling and Health Factors
Covariates

Multiple sociodemographic, sampling and health factors that were previously taken along as (possible) determinants of salivary cortisol were considered as potential covariates in the present study (Vreeburg et al., 2009a). These include: sex (1=men; 2=women), age (in years), education (years of attained education), time of awakening on sampling day, working on sampling day (0=not working; 1=working), sampling on a weekday vs. weekend day (0=weekend day; 1=weekday), season (0=dark months, that is October through February; 1=months with more daylight, that is March through September), average sleep duration during the last 4 weeks (0=more than 6 h sleep a night; 1=6 h of sleep or less a night), smoking status (0=no current smoker; 1=current smoker) and physical activity (which was assessed using the International Physical Activity Questionnaire and expressed as activity per 1000 MET-minutes, a metabolic equivalent of the number of calories spent per minute, per week).

Potential Moderators of Genetic Association

Based on literature, potential interaction effects with the MR gene were tested for sex (Carey et al., 1995; Turner, 1997; Kumsta et al., 2007; van Leeuwen et al., 2009), SSRIs (0=no frequent SSRI use; 1=frequent SSRI use; for at least 1 month) (Seckl and Fink, 1992; Bjartmar et al., 2000; Otte et al., 2009) and stress (Gesing et al., 2001; Bet et al., 2009), i.e. childhood trauma before age 16 (index score on the Netherlands Mental Health Survey and Incidence Study childhood trauma interview (de Graaf et al., 2004) assessing the frequency of emotional neglect, psychological neglect, physical abuse and sexual abuse experienced before the age of 16 years; median split, 0=no or infrequent trauma; 1=frequent trauma) and number of life events in the past year (including illness or death of family member among others; median split, 0=no life events; 1=1+life events). Multiple studies suggest an interaction between the MR gene and SSRIs or TCAs (Seckl and Fink, 1992; Holsboer and Barden, 1996; Holsboer, 1999; Bjartmar et al., 2000; Otte et al., 2009). Due to the low number of cases using TCAs (n=35) or other antidepressants that may modulate MR activity, an interaction effect with the MR could not be tested. Because of potential differential mechanisms we did not initially choose to test for an interaction effect between the MR and all antidepressants (benzodiazepines not included) combined.

Salivary Cortisol Measurements

At the baseline interview, the patients were instructed to collect saliva samples using salivettes (Sarstedt AG and Co, Nümbrecht, Germany) at home and on a regular (preferably working) day shortly after the interview. This is a minimally intrusive method to assess the free and active form of cortisol that has previously been shown to be a reliable measure of free cortisol in the blood (Kirschbaum and Hellhammer, 1994). Patients were instructed not to eat, drink, smoke or brush their teeth within the 15 min before sampling. The CAR was measured at 4 time points: at awakening (T1) and at 30 (T2), 45 (T3) and 60 (T4) minutes after awakening. Participants were instructed to store the salivettes in their refrigerator until returning them by mail. For details on cortisol measurements, see (Vreeburg et al., 2009a). In short, cortisol analysis was performed by competitive electrochemiluminescence immunoassay (E170; Roche, Basel, Switzerland). The functional detection limit was 0.07 µg/dL or 2 nMol/L and the intra-assay and inter-assay variability coefficients were below 10%.

Cortisol Awakening Response (CAR)

For genetic association analyses with the course of the CAR, at least 2 valid CAR measurement points had to be available, that is when collected within a margin of 5 min before or after the protocol time and when values were not more than 2 standard deviations (SDs) from the mean. With linear mixed model (LMM) analyses missing values could be interpolated, which was conducted for 24 subjects with 2 CAR measurement points, and 96 subjects with 3 CAR measurement points. For the remaining 906 subjects all 4 data points were available. Besides studying the course of the CAR with LMM analysis, also the area under the curve (AUC) with respect to the increase (AUCi) and with respect to the ground (AUCg) were used, calculated according to the formula's by (Pruessner et al., 2003). The AUCg is a measure for the total cortisol secretion during the first hour after awakening, while the AUCi is a measure for cortisol increase with respect to awakening (T0) and therefore is a measure of the dynamics of the CAR (Clow et al., 2004). For association analyses with the AUC subjects were included when all 4 1-hour awakening cortisol samples were available (n=906).

Genotyping

Genotyping of the patients was performed as part of a large GWA study, the GAIN-MDD study (Sullivan et al., 2009). Details on blood sampling and data collection can be found elsewhere (Boomsma et al., 2008). Individual genotyping was conducted by using the Perlegen GWAS platform (Mountain View, Calif., USA). The SNPs that were present on these arrays were selected to tag common variation in the HapMap European and Asian populations. For the MR gene the two common and functional MR −2G/C (rs2070951_GC) and I180V (rs5522_AG) SNPs were present. Based on DNA sequencing and haplotype reconstruction by our group it is known that, in the Dutch population, these two SNPs tag the three most common haplotypes located in exon 2 and extending into the promoter region (see Example 1).

Statistical Analyses

Allele frequencies for the different SNPs were tested for Hardy-Weinberg Equilibrium (HWE) using HaploView (version 4.1 for Mac OSX; available online at http://www-.broadinstitute.org/mpg/haploview; (Barrett et al., 2005). In addition, HaploView was used to assess inter-marker linkage disequilibrium (LD) scores (expressed as D' and $r^2$) between the MR SNPs and to reconstruct haplotypes. Individual haplotypes were reconstructed with SNPHAP (version 1.3; available online at http://www-gene.cimr.cam.ac.uk/clayton/software/snphap.txt). Further analysis was performed in SPSS, version 16.0 for Mac OSX (SPSS Inc., Chicago, Ill., USA).

Differences between men and women for the various characteristics were verified using an independent-samples t-test, a Mann-Whitney test or a 2-test. Before testing for sex differences, a square root transformation was used to reach a normal distribution for awakening time and physical activity. The 4 morning cortisol measures were positively skewed and therefore log-transformed data were used in Linear Mixed Models (LMM) analysis, for the AUCg and AUCi non-transformed values could be used. For the data shown in FIG. 1 values were back-transformed.

First, associations between the single MR SNPs and AUCg or AUCi as outcome variables were tested with AN(C)OVA. Linear regression analysis was used to analyze associations between MR haplotypes and the AUCg or AUCi. Putative covariates were entered first, followed by adding the haplotypes in the second step. Random coefficient analysis of the 4 morning cortisol values was conducted with the help of LMM analysis. This method can interpolate missing values and it keeps the correlation between repeated data into account (Gueorguieva and Krystal, 2004). The model included a random intercept, taking into account different intercepts for the different subjects, the SNPs or haplotypes, time points (T1, T2, T3 or T4) and all covariates were entered in the model as fixed factors. To examine whether the different genetic variants affected the course of cortisol levels after awakening we added a variant-by-time interaction term. Second, because of clear sex-dependent effects of MR (and GR) gene variants in earlier studies, interaction effects between the SNPs and sex were verified and association analysis was repeated in both sex strata (Kumsta et al., 2007; van Leeuwen et al., 2009). Third, an interaction effect was tested for the MR SNPs with SSRIs or stress, i.e. childhood trauma or recent life events. Due to low frequencies, no interaction effect could be tested for use of TCAs (n=35). A two-sided p-value below 0.05 was considered statistically significant. For significant findings effect sizes are given as $r=\sqrt{(t^2/t^2+df)}$. Our main interest was to determine the association between the MR –2G/C SNP and the CAR. Because of multiple testing a Bonferroni correction was applied where appropriate.

Results

Population Characteristics

Characteristics of the 1026 subjects are presented in Table 5. The mean age of this subpopulation was 43.5 years (SD=12.3, range 18-65) and 68.4% was female. Of the 1026 subjects 72.3% showed an increase in cortisol level in the first hour after awakening. The two sexes differed significantly in age, education level, smoking behaviour, sleep duration, current depression diagnosis and cortisol level at T2 and T4. No significant differences in demographics were found depending on the MR SNP genotypes or haplotypes.

Genotype and Haplotype Frequencies

Allele frequencies of the MR SNPs were in HWE, as assessed using HaploView. Frequencies for the MR –2G/C and I180V genotypes and haplotypes (Table 5) and the inter-marker LD scores (D'=1.0; $r^2$=0.14) were similar as previously described (Derijk, 2009; van Leeuwen et al., 2009). Concordant with previous results, three main haplotypes were found; haplotype 1 consisting of the –2 G-allele and the 180 I-allele (or A nucleotide; hap 1 freq.=0.50); haplotype 2 consisting of the –2 C-allele and the 180 I-allele (hap 2 freq.=0.38) and haplotype 3 consisting of the –2 C-allele and the 180 V-allele (or G nucleotide, hap 3 freq.=0.12). Notably, there were no individuals carrying a haplotype consisting of the G-allele of the –2G/C SNP combined with the V-allele (or G nucleotide) of the I180V SNP, in accordance with our previous observations this combination is very rare.

Associations Between MR Gene Variants and the CAR

Of the variables listed in Table 5 age, smoking, time of awakening, working on day of sampling and frequent TCA use were significant determinants of the CAR in the total group or in the women or men separately. Without or with adjustment for these covariates (except for TCAs, due to the small number; n=35) no effect was found for the –2G/C and I180V SNPs on the CAR in the total group.

However, a significant interaction effect was found for the –2G/C SNP with sex on the AUCi (p=0.01) and a trend was found for an interaction effect on the AUCg (p=0.08). Therefore, for further analysis data were stratified for sex. The course of the CAR over time (FIGS. 18A and B) was slightly modulated by the MR –2G/C SNP only in women, as reflected by a trend for an interaction effect with time (p=0.06; FIG. 18B) and/or an attenuated cortisol increase after awakening (AUCi) in carriers of the –2 C/C genotype (p=0.03; Table 6). No effect was observed for the total morning cortisol secretion, i.e. no significant association with the AUCg and/or no direct SNP effect in LMM analysis, only in men a trend was found for a lower AUCg in –2 C-allele carriers (p=0.06). In addition, no effect was observed for the I180V SNP, not in the men or women. In the women both the haplotypes 2 and 3 lowered (significant or trend) the AUCi compared to haplotype 1, explaining however, only 0.9% of the variance.

As a third step, interaction was verified with frequent use of SSRIs. No significant three-way (–2G/C-x-sex-x-SSRI) interaction effect was found (p=0.49 for AUCg; p=0.06 for AUCi). However, the effect found for the –2G/C SNP on the CAR in women was found to be due to an interaction with SSRI use (p=0.07 for the AUCg and p=0.05 for the AUCi). No significant interaction effect was found in men (p>0.3) or in the total group (men and women; p>0.10). Interestingly, subsequent stratification of the data for the use of SSRIs (FIGS. 18C to 18F) showed that the MR –2G/C SNP was associated with variability in the CAR only in the individuals (both men and women) using SSRIs (n=227, of whom 149 had a current MDD diagnosis). In the female SSRI users the –2G/C SNP clearly affected the course of the CAR throughout time, SNP-by-time interaction p=0.006 (after a Bonferoni correction for 6 tests, giving a new significance threshold of p=0.008, this is still significant; effect size r for AUCi: CC vs. GG r=0.27, p<0.01; CC vs. GC r=0.27, p<0.01). The –2G/C SNIP also had a direct effect on total morning cortisol secretion (p=0.03 in LMM analysis; AUCg: CC vs. GG r=0.23, p=0.01; CC vs. GC r=0.14, p=0.11). In the male SSRI users only a direct effect on total cortisol secretion was observed (p=0.02 in LMM analysis; AUCg: CC vs. GG r=0.21, p=0.11; CC vs. GC r=0.18, p=0.16). Notably, among the SSRI users the CAR was entirely blunted in female –2C/C carriers and was prolonged in male and female –2G/G carriers.

Additional correction for remitted vs. current depression did not change the results. LMM analysis in only the 906 subjects with all 4 CAR data point available gave similar (bit stronger) results. In addition, results did not change after excluding the subjects taking TCAs (n=35; of the subjects using SSRIs, n=227, only 2 were also taking TCAs). An interaction effect between the MR SNP and the use/no use of all antidepressants combined was verified but was not significant. No interaction effect was found between the MR –2G/C SNP and childhood trauma or recent life events. Finally, as earlier studies indicate that sex hormones can effect MR (and GR) mRNA and protein expression and protein binding (Carey et al., 1995; Turner, 1997), a possible interaction was verified between the –2G/C SNP and the use of oral contraceptives (OC) or menstrual phase, however, no significant interaction was observed.

TABLE 5

Sample characteristics of the total group and comparisons between men and women.

| Variable | Total n | Total group n = 1026 | Men n = 324 (31.6%) | Women n = 702 (68.4%) | p-value |
|---|---|---|---|---|---|
| Demographic | | | | | |
| Age, mean (SD), y | 1026 | 43.5 (12.3) | 45.3 (11.2) | 42.6 (12.8) | .001 |
| Education level, mean (SD), y | 1026 | 12.2 (3.2) | 11.9 (3.1) | 12.4 (3.2) | .02 |
| Health | | | | | |
| Smoking, % | 1026 | 36.7 | 41.0 | 34.8 | .05 |
| Physical activity, mean (SD) | 1026 | 3.7 (3.1) | 3.7 (3.2) | 3.7 (3.0) | .79 |
| Sampling factor | | | | | |
| Time of awakening, mean (SD) | 1026 | 07:31 (1 h, 13 min) | 07:30 (1 h, 12 min) | 07:31 (1 h, 13 min) | .71 |
| Working on day of sampling, % | 1026 | 57.5 | 59.9 | 56.4 | .30 |
| Sampling on a weekday, % | 1026 | 91.5 | 89.2 | 92.6 | .07 |
| Sampling in month with more daylight, % | 1026 | 58.0 | 58.3 | 57.8 | .88 |
| $\geq$6 h of sleep, % | 1026 | 29.5 | 34.0 | 27.5 | .04 |
| Frequent antidepressant use | | | | | |
| TCA, % | 1026 | 3.4 | 3.4 | 3.4 | .98 |
| SSRI, % | 1026 | 22.1 | 23.5 | 21.5 | .49 |
| Other, % | 1026 | 7.8 | 9.3 | 7.1 | .24 |
| Benzodiazepines, % | 1026 | 8.6 | 9.9 | 8.0 | .31 |
| Trauma | | | | | |
| Childhood trauma index score, regularly, % | 1022 | 48.5 | 45.5 | 49.9 | .19 |
| Life events in past year, 1 or more events, % | 1026 | 39.1 | 35.5 | 40.7 | .11 |
| Depression | | | | | |
| Current, % | 1026 | 54.1 | 59.6 | 51.6 | .02 |
| Comorbid anxiety disorder, % | 1026 | 69.7 | 67.6 | 70.7 | .33 |
| Cortisol | | | | | |
| CAR, mean (SD), nMol/L | | | | | |
| T1, at awakening | 1014 | 17.0 (6.8) | 17.8 (7.5) | 16.7 (6.4) | .07 |
| T2, 30 min after awakening | 1005 | 21.4 (9.3) | 22.6 (10.9) | 20.9 (8.5) | .03 |
| T3, 45 min after awakening | 1000 | 20.2 (9.8) | 20.7 (11.5) | 20.1 (9.0) | .88 |
| T4, 60 min after awakening | 1011 | 18.0 (9.7) | 16.9 (8.1) | 18.5 (10.3) | .03 |
| AUCg, mean (SD), nMol/L/h | 906 | 19.6 (7.1) | 20.2 (7.7) | 19.3 (6.8) | .10 |
| AUCi, mean (SD), nMol/L/h | 906 | 2.5 (6.3) | 2.2 (7.0) | 2.6 (5.9) | .31 |
| MR variants | | | | | |
| rs2070951 (−2) GG/CG/CC, freq. | 1026 | .23/.54/.23 | .21/.54/.25 | .24/.54/.22 | .30 |
| rs5522 (I180V) AA/GA/GG, freq. | 1026 | .78/.20/.02 | .75/.23/.02 | .79/.19/.02 | .30 |
| MR hap 1 G-A, freq. | 1026 | .50 | .48 | .52 | |
| MR hap 2 C-A, freq. | 1026 | .38 | .39 | .37 | .23 |
| MR hap 3 C-G, freq. | 1026 | .12 | .14 | .11 | |

Abbreviations: SD = standard deviation; MET = metabolic energy turnover; TCA = tricyclic antidepressant; SSRI = serotonin transporter reuptake inhibitor; CAR = cortisol awakening response; AUCg = area under the morning curve with respect to the ground (=(((T1 + T2)/2)*0.5) + (((T2 + T3)/2)*0.25) + (((T3 + T4)/2)*0.25)); AUCi = area under the morning curve with respect to the increase = (((T1 + T2)/2)*0.5) + (((T2 + T3)/2)*0.25) + (((T3 + T4)/2)*0.25)) − (T1*(0.5 + 0.25 + 0.25)) (Pruessner et al., 2003).

TABLE 6

Unadjusted and adjusted area under the curve cortisol values according to MR SNPs and haplotypes, F-statistics, standardized regression coefficients ($\beta$) and p-values.

| | | rs2070951 | | | rs5522 | | | MR haplotype 1-3 | |
|---|---|---|---|---|---|---|---|---|---|
| | | GG | GC | CC | AA | AG/GG | Constant | Hap 2 | Hap 3 |
| Women (n = 624) | AUCg, mean (SD) | 19.4 (6.5) | 19.4 (6.8) | 19.0 (7.2) | 19.5 (6.9) | 18.4 (6.3) | 19.5 (0.5) | 19.5 (0.4) | 18.5 (0.6) |
| | Unadjusted | F (1, 621) = 0.33; p = .56 | | | F (1, 622) = 2.77; p = .10 | | ref. | B = −0.00 (0.43); p = 1.0 | B = −0.99 (0.63); p = .12 |
| | Adjusted | F (2, 617) = 0.34; p = .71 | | | F (1, 618) = 2.29; p = .13 | | ref. | B = −0.10 (0.42); p = .80 | B = −0.94 (0.61); p = .13 |
| | Adjusted, no SSRI use | F (2, 489) = 0.07; p = .93 | | | F (1, 490) = 2.13; p = .15 | | ref. | B = 0.45 (0.48); p = .35 | B = −0.73 (0.68); p = .29 |
| | Adjusted, SSRI users | F (2, 121) = 3.55; p = .03 | | | F (1, 122) = 0.04; p = .84 | | ref. | B = −2.27 (0.83); p < .01 | B = −1.33 (1.37); p = .33 |
| Men (n = 282) | AUCg, mean (SD) | 22.0 (9.1) | 19.2 (7.0) | 20.6 (7.6) | 20.5 (7.9) | 19.3 (7.3) | 20.9 (0.8) | 20.4 (0.7) | 19.6 (1.0) |
| | Unadjusted | F (1, 279) = 0.99; p = .32 | | | F (1, 280) = 1.34; p = .25 | | ref. | B = −0.44 (0.72); p = .54 | B = −1.30 (1.01); p = .20 |
| | Adjusted | F (2, 275) = 2.86; p = .06 | | | F (1, 376) = 0.84; p = .36 | | ref. | B = −0.09 (0.71); p = .89 | B = −0.89 (1.00); p = .38 |

TABLE 6-continued

Unadjusted and adjusted area under the curve cortisol values according to MR SNPs and haplotypes, F-statistics, standardized regression coefficients (β) and p-values.

|  |  | rs2070951 | | | rs5522 | | | MR haplotype 1-3 | |
|---|---|---|---|---|---|---|---|---|---|
|  |  | GG | GC | CC | AA | AG/GG | Constant | Hap 2 | Hap 3 |
|  | Adjusted, no SSRI use | F (2, 214) = 0.99; p = .37 | | | F (1, 215) = 0.79; p = .38 | | ref. | B = 0.11 (0.81); p = .89 | B = −1.03 (1.17); p = .38 |
|  | Adjusted, SSRI users | F (2, 54) = 4.35; p = .02 | | | F (1, 55) = 0.13; p = .73 | | ref. | B = −1.18 (1.51); p = .44 | B = −1.24 (2.04); p = .54 |
| Women (n = 624) | AUCi, mean (SD) | 3.1 (6.0) | 2.9 (5.6) | 1.5 (6.4) | 2.8 (6.0) | 1.9 (5.4) | 3.4 (0.4) | 2.7 (0.4) | 2.3 (0.6) |
|  | Unadjusted | F (1, 621) = 4.88; p = .03 | | | F (1, 622) = 2.18; p = .14 | | ref. | B = −0.70 (0.38): p = .06 | B = −1.03 (0.55); p = .06 |
|  | Adjusted | F (2, 617) = 3.60; p = .03 | | | F (1, 618) = 1.94; p = .16 | | ref. | B = −0.77 (0.37); p = .04 | B = −1.03 (0.54); p = .06 |
|  | Adjusted, no SSRI use | F (2, 489) = 0.86; p = .42 | | | F (1, 490) = 2.23; p = .14 | | ref. | B = −0.35 (0.42); p = .41 | B = −0.91 (0.59); p = .13 |
|  | Adjusted, SSRI users | F (2, 121) = 6.31; p < .01 | | | F (1, 122) = 0.00; p = 1.0 | | ref. | B = −2.63 (0.79); p = .001 | B = −1.27 (1.31); p = .34 |
| Men (n = 282) | AUCi, mean (SD) | 2.8 (8.9) | 1.5 (5.5) | 3.1 (7.8) | 2.3 (7.2) | 1.8 (6.3) | 2.0 (0.8) | 2.2 (0.7) | 2.0 (0.9) |
|  | Unadjusted | F (1, 279) = 0.11; p = .74 | | | F (1, 280) = 0.31; p = .58 | | ref. | B = 0.28 (0.65); p = .67 | B = −0.02 (0.92); p = .99 |
|  | Adjusted | F (2, 275) = 1.74; p = .18 | | | F (1, 276) = 0.90; p = .77 | | ref. | B = 0.39 (0.65); p = .55 | B = 0.26 (0.93); p = .78 |
|  | Adjusted, no SSRI use | F (2, 214) = 0.76; p = .47 | | | F (1, 215) = 0.02; p = .89 | | ref. | B = −0.21 (0.74); p = .77 | B = −0.25 (1.06); p = .82 |
|  | Adjusted, SSRI users | F (2, 54) = 1.92; p = .16 | | | F (1, 55) = 1.03; p = .31 | | ref. | B = 2.89 (1.52); p = .06 | B = 0.63(2.06); p = .76 |

Adjusted = adjusted for age, smoking, awakening time, working on day of sampling and lifetime diagnosis of major depressive disorder.
Abbreviations:
AUCg = area under the morning curve with respect to the ground;
AUCi = area under the morning curve with respect to the increase:
SD = standard deviation;
SSRI = serotonin transporter reuptake inhibitor Discussion This study shows that the MR −2G/C SNP modulates the CAR in lifetime MDD patients depending on the use of SSRIs; a clear effect of the MR −2G/C SNP was found specifically in subjects (men and women) frequently using SSRIs. No effect of the MR SNPs on the CAR was found in subjects not using SSRIs. The results, therefore, suggest that MR gene variants can have substantial effects on HPA axis activity while interacting with other factors like use of SSRIs.

The current results are partly in line with a first report revealing that the MR −2 C-allele significantly associated with slightly lower morning cortisol levels among an elderly cohort consisting for 66% of women (Kuningas et al., 2007). Of note is that these results were based on a single morning blood sample for which no effect of time of awakening was taken into account. Earlier studies showed that cortisol levels measured at multiple time points in the morning are more reliable (Pruessner et al., 1997). The present results are also partly in line with a more recent study by our group. Among a group of healthy subjects (n=218) (van Leeuwen et al., 2009) showed that the CAR was lower in subjects with the MR −2C/C genotype. However, this association was not significant and was found only in men (n=93) and not in women (n=125; genotype-by-sex effect p=0.20). Together the results indicate that the MR −2 C-allele is related to a decrease in cortisol levels under specific conditions.

Since the MR is involved in tonic inhibition of basal corticosteroid levels, an increased expression of the MR protein is expected to result in lower cortisol levels. In accordance with this hypothesis and the above mentioned results, in cell lines the −2 C-allele results in increased expression of the MR protein, resulting in a higher capacity to activate target genes (van Leeuwen et al., 2009); N. van Leeuwen et al., unpublished observations). The −2G/C variant interferes with expression of the MR protein potentially at the translational level. Notably, MR expression is highly dynamic. Following exercise or an acute single psychological stressor, but also during ageing changes in MR expression can be observed, at least in the latter two conditions associated with changes in HPA axis reactivity (van Eekelen et al., 1991; Gesing et al., 2001; Chang et al., 2008). Based on the present and previous association studies (DeRijk et al., 2006; van Leeuwen et al., 2009) we hypothesize that only under challenging conditions (like stress or medication) the MR gene variants may affect HPA axis activity. Here, a clear effect of the MR −2G/C SNP was found only in the lifetime MDD patients frequently using SSRIs. Among those subjects, carriers of the MR −2 C-allele showed an attenuated CAR, with a clear allele-dose effect only in women. On the other hand, carriers (men and women) of the −2G/G genotype showed an extended CAR, with elevated cortisol levels even 60 min after awakening. In the previous study by (van Leeuwen et al., 2009) also a more distinct effect of the −2G/C SNP on the CAR was detected following pre-treatment with dexamethasone and in a sex-dependent manner. Finally, a significant effect of MR gene variants on ACTH, cortisol and heartbeat could be observed under psychosocial stress conditions (DeRijk et al., 2006) N. van Leeuwen et al., unpublished observations).

Importantly, the two functional MR SNPs described here are linked to multiple SNPs located in the MR gene promoter region. These promoter SNPs result in turn in differences in transcriptional activity, leading to differential mRNA and protein regulation (M. D. Klok et al., unpublished observations). Together the SNPs result in 3 major haplotypes (which are tagged by the −2G/C and I180V SNPs) with distinct genetic sequences, which can modulate MR expression and HPA activity in a context-dependent manner. Most likely, these SNPs located in the promoter region modulate effects of other factors like corticosteroids, sex steroids or antidepressants leading to gene-variant specific changes in MR regulation. Proof for possible interactions between the MR gene and sex steroids has been demonstrated for both estrogens and progesterone, which modulate mRNA and/or protein expression and binding of corticosteroid receptors (Carey et al., 1995; Turner, 1997). This could provide an explanation for the gender-dependent effects of the MR on the CAR.

Multiple indications for an interaction between MR signaling and the serotonin system exist. Changes in hippocampal MR expression in mice influence expression of the serotonin receptor 1A (5-HT1A) (Rozeboom et al., 2007). Moreover, the MR, GR and 5-HT1A receptors are co-expressed in specific cells of the hippocampus, while the level of MR occupation by cortisol affects the 5HT1A-receptor mediated hyperpolarization response (Joels and Van Riel, 2004). On the other hand, serotonin but also SSRIs increase MR and/or GR expression in vivo and in vitro (Seckl and Fink, 1991; Seckl and Fink, 1992; Robertson et al., 2005). Possibly, SSRIs affect MR expression directly or indirectly through 5-HT in a genotype-dependent manner, eventually leading to differential cortisol regulation.

Several lines of evidence suggest a role for the MR in the CAR. Highest MR mRNA expression levels have been measured in the human hippocampus, while much lower levels were detectable in other areas such as the amygdala, prefrontal cortex and anterior cingulate cortex (M. D. Klok et al., unpublished observations). A putative role for the hippocampus in the regulation of the CAR was previously demonstrated (Buchanan et al., 2004). In addition, the CAR was recently postulated to enable individuals to anticipate upcoming daily events, a process in which the hippocampus is central and in which the MR is involved (de Kloet et al., 2005; Fries et al., 2009). Moreover, the hippocampus is important for tonic inhibition of the HPA axis, which is MR mediated. Taken together, the data fit with a role of the MR, predominantly located in the hippocampus, in the control of the CAR.

The function and importance of the CAR for health and disease is still unclear. However, data indicate that small differences in the CAR can be of clinical relevance as they are associated with physiological and psychological disturbances (Fries et al., 2009; Vreeburg et al., 2009a). It was demonstrated that the CAR was elevated not only in current depressed patients but also in remitted depressed patients and in unaffected subjects with a parental history of depression or anxiety disorder, as assessed with the DSM-IV Composite International Diagnostic Interview (CIDI) (Vreeburg et al., 2009a); Vreeburg et al., unpublished observations). This suggests that an increased CAR in MDD patients is not only a state marker but represents in part a trait. Here, we identified a biological determinant of inter-individual variability in the CAR, possibly representing a vulnerability/protective factor for the pathophysiology or course of depressed mood. Moreover, the MR gene variants may underlie in part the development of particular symptoms of depression, not only problems with mood but also for example cognitive problems (Kuningas et al., 2007). Indeed, multiple studies have shown that MR activity influences cognitive flexibility in healthy individuals (Otte et al., 2007; Schwabe et al., 2009).

Normalization of the HPA axis, either by alleviation of hypercortisolism or a decrease of reactivity as measured by the Dex-CRH test, is predictive for clinical benefit (Barden et al., 1995; Zobel et al., 2004). In the present study, the SSRIs by themselves had no effect on the CAR. However, the MR-by-SSRI interaction effect on the CAR was remarkably distinct; depending on MR genotype, 25 percent of the women and men using SSRIs showed a small or even flattened CAR (−2 C-allele carriers), while another 25 percent of the patients (−2G/G carriers) frequently using SSRIs displayed a high CAR compared to the other genotype groups. This effect could indicate that some patients benefit from SSRI treatment when it comes to neuroendocrine normalization, while others experience deterioration depending on their MR genotype. The groups are too small to properly evaluate the course of the disorder in these subjects, although the present association found with cortisol also seemed to correlate with differences in depressive and anxiety symptoms (data not shown). A role of the MR in pharmacological treatment of depression was recently demonstrated in a study by (Otte et al., 2009) in which administration of a MR agonist accelerated the response of MDD patients to the SSRI escitalopram. The results complement the results of earlier studies showing that the MR antagonist spironolactone hampers the response to the TCA amitriptyline (Holsboer, 1999). It is plausible that these effects are also depending on MR genetic makeup.

To conclude, we have identified the MR as a possible modulator of the CAR in depressed patients. A clear effect of the functional MR −2G/C SNP on the CAR was found in the lifetime MDD patients frequently using SSRIs, with prolonged heightened early morning cortisol levels observed in MR −2G/G carriers and lower levels in −2 C-allele carriers. No effect was found in patients not using SSRIs. The finding of a MR genotype-by-SSRI interaction effect on the dynamics of the CAR could be of importance for future therapy selection and for development of novel pharmacological treatments.

References for Example 4

Atkinson, H. C., Wood, S. A., Castrique, E. S., Kershaw, Y. M., Wiles, C. C., Lightman, S. L., 2008. Corticosteroids mediate fast feedback of the rat hypothalamic-pituitary-adrenal axis via the mineralocorticoid receptor. Am J Physiol Endocrinol Metab 294, E1011-1022.

Barden, N., Reul, J. M., Holsboer, F., 1995. Do antidepressants stabilize mood through actions on the hypothalamic-pituitary-adrenocortical system? Trends Neurosci. 18, 6-11.

Barrett, J. C., Fry, B., Maller, J., Daly, M. J., 2005. Haploview: analysis and visualization of LD and haplotype maps. Bioinformatics 21, 263-265.

Bet, P. M., Penninx, B. W., Bochdanovits, Z., Uitterlinden, A. G., Beekman, A. T., van Schoor, N. M., Deeg, D. J., Hoogendijk, W. J., 2009. Glucocorticoid receptor gene polymorphisms and childhood adversity are associated with depression: New evidence for a gene-environment interaction. Am J Med Genet B Neuropsychiatr Genet 150B, 660-669.

Bjartmar, L., Johansson, I. M., Marcusson, J., Ross, S. B., Seckl, J. R., Olsson, T., 2000. Selective effects on NGFI-A, MR, GR and NGFI-B hippocampal mRNA expression after chronic treatment with different subclasses of antidepressants in the rat. Psychopharmacology (Berl). 151, 7-12.

Boomsma, al., Willemsen, G., Sullivan, P. F., Heutink, P., Meijer, P., Sondervan, D., Kluft, C., Smit, G., Nolen, W. A., Zitman, F. G., Smit, J. H., Hoogendijk, W. J., van Dyck, R., de Geus, E. J., Penninx, B. W., 2008. Genome-wide association of major depression: description of samples for the GAIN Major Depressive Disorder Study: NTR and NESDA biobank projects. Eur. J. Hum. Genet. 16, 335-342.

Buchanan, T. W., Kern, S., Allen, J. S., Tranel, D., Kirschbaum, C., 2004. Circadian regulation of cortisol after hippocampal damage in humans. Biol. Psychiatry 56, 651-656.

Carey, M. P., Deterd, C. H., de Koning, J., Helmerhorst, F., de Kloet, E. R., 1995. The influence of ovarian steroids on hypothalamic-pituitary-adrenal regulation in the female rat. J. Endocrinol. 144, 311-321.

Chang, Y. T., Chen, Y. C., Wu, C. W., Yu, L., Chen, H. I., Jen, C. J., Kuo, Y. M., 2008. Glucocorticoid signaling and exercise-induced downregulation of the mineralocorticoid receptor in the induction of adult mouse dentate neurogenesis by treadmill running. Psychoneuroendocrinology 33, 1173-1182.

Clow, A., Thorn, L., Evans, P., Hucklebridge, F., 2004. The awakening cortisol response: methodological issues and significance. Stress 7, 29-37.

de Graaf, R., Biji, R. V., Ten Have, M., Beekman, A. T., Vollebergh, W. A., 2004. Pathways to comorbidity: the transition of pure mood, anxiety and substance use disorders into comorbid conditions in a longitudinal population-based study. J. Affect. Disord. 82, 461-467.

de Kloet, E. R., Joels, M., Holsboer, F., 2005. Stress and the brain: from adaptation to disease. Nat Rev Neurosci 6, 463-475.

de Kloet, E. R., Sarabdjitsingh, R. A., 2008. Everything has rhythm: focus on glucocorticoid pulsatility. Endocrinology 149, 3241-3243.

De Kloet, E. R., Vreugdenhil, E., Oitzl, M. S., Joels, M., 1998. Brain corticosteroid receptor balance in health and disease. Endocr. Rev. 19, 269-301.

Derijk, R. H., 2009. Single nucleotide polymorphisms related to HPA axis reactivity. Neuroimmunomodulation 16, 340-352.

DeRijk, R. H., Wust, S., Meijer, O. C., Zennaro, M. C., Federenko, I. S., Helihammer, D. H., Giacchetti, G., Vreugdenhil, E., Zitman, F. G., de Kloet, E. R., 2006. A common polymorphism in the mineralocorticoid receptor modulates stress responsiveness. J. Clin. Endocrinol. Metab. 91, 5083-5089.

Fries, E., Dettenborn, L., Kirschbaum, C., 2009. The cortisol awakening response (CAR): facts and future directions. Int. J. Psychophysiol. 72, 67-73.

Gesing, A., Bilang-Bleuel, A., Droste, S. K., Linthorst, A. C., Holsboer, F., Reul, J. M., 2001. Psychological stress increases hippocampal mineralocorticoid receptor levels: involvement of corticotropin-releasing hormone. J. Neurosci. 21, 4822-4829.

Gueorguieva, R., Krystal, J. H., 2004. Move over ANOVA: progress in analyzing repeated-measures data and its reflection in papers published in the Archives of General Psychiatry. Arch. Gen. Psychiatry 61, 310-317.

Hellhammer, J., Fries, E., Schweisthal, O. W., Schlotz, W., Stone, A. A., Hagemann, D., 2007. Several daily measurements are necessary to reliably assess the cortisol rise after awakening: state- and trait components. Psychoneuroendocrinology 32, 80-86.

Heuser, I., Deuschle, M., Weber, B., Stalla, G. K., Holsboer, F., 2000. Increased activity of the hypothalamus-pituitary-adrenal system after treatment with the mineralocorticoid receptor antagonist spironolactone. Psychoneuroendocrinology 25, 513-518.

Holsboer, F., 1999. The rationale for corticotropin-releasing hormone receptor (CRH-R) antagonists to treat depression and anxiety. J. Psychiatr. Res. 33, 181-214.

Holsboer, F., Barden, N., 1996. Antidepressants and hypothalamic-pituitary-adrenocortical regulation. Endocr. Rev. 17, 187-205.

Joels, M., Karst, H., DeRijk, R., de Kloet, E. R., 2008. The coming out of the brain mineralocorticoid receptor. Trends Neurosci. 31, 1-7.

Joels, M., Van Riel, E., 2004. Mineralocorticoid and glucocorticoid receptor-mediated effects on serotonergic transmission in health and disease. Ann. N.Y. Acad. Sci. 1032, 301-303.

Kirschbaum, C., Hellhammer, D. H., 1994. Salivary cortisol in psychoneuroendocrine research: recent developments and applications. Psychoneuroendocrinology 19, 313-333.

Kuehner, C., Holzhauer, S., Huffziger, S., 2007. Decreased cortisol response to awakening is associated with cognitive vulnerability to depression in a sample of young adults. Psychoneuroendocrinology 32, 199-209.

Kumsta, R., Entringer, S., Koper, J. W., van Rossum, E. F., Hellhammer, D. H., Wust, S., 2007. Sex specific associations between common glucocorticoid receptor gene variants and hypothalamus-pituitary-adrenal axis responses to psychosocial stress. Biol. Psychiatry 62, 863-869.

Kuningas, M., de Rijk, R. H., Westendorp, R. G., Jolles, J., Slagboom, P. E., van Heemst, D., 2007. Mental performance in old age dependent on cortisol and genetic variance in the mineralocorticoid and glucocorticoid receptors. Neuropsychopharmacology 32, 1295-1301.

Nestler, E. J., Barrot, M., DiLeone, R. J., Eisch, A. J., Gold, S. J., Monteggia, L. M., 2002. Neurobiology of depression. Neuron 34, 13-25.

Otte, C., Hinkelmann, K., Moritz, S., Yassouridis, A., Jahn, H., Wiedemann, K., Kellner, M., 2009. Modulation of the mineralocorticoid receptor as add-on treatment in depression: A randomized, double-blind, placebo-controlled proof-of-concept study. J. Psychiatr. Res.

Otte, C., Moritz, S., Yassouridis, A., Koop, M., Madrischewski, A. M., Wiedemann, K., Kellner, M., 2007. Blockade of the mineralocorticoid receptor in healthy men: effects on experimentally induced panic symptoms, stress hormones, and cognition. Neuropsychopharmacology 32, 232-238.

Penninx, B. W., Beekman, A. T., Smit, J. H., Zitman, F. G., Nolen, W. A., Spinhoven, P., Cuijpers, P., De Jong, P. J., Van Marwijk, H. W., Assendelft, W. J., Van Der Meer, K., Verhaak, P., Wensing, M., De Graaf, R., Hoogendijk, W. J., Ormel, J., Van Dyck, R., 2008. The Netherlands Study of Depression and Anxiety (NESDA): rationale, objectives and methods. Int J Methods Psychiatr Res 17, 121-140.

Pruessner, J. C., Kirschbaum, C., Meinlschmid, G., Hellhammer, D. H., 2003. Two formulas for computation of the area under the curve represent measures of total hormone concentration versus time-dependent change. Psychoneuroendocrinology 28, 916-931.

Pruessner, J. C., Wolf, O. T., Hellhammer, D. H., Buske-Kirschbaum, A., von Auer, K., Jobst, S., Kaspers, F., Kirschbaum, C., 1997. Free cortisol levels after awakening: a reliable biological marker for the assessment of adrenocortical activity. Life Sci. 61, 2539-2549.

Robertson, D. A., Beattie, J. E., Reid, I. C., Balfour, D. J., 2005. Regulation of corticosteroid receptors in the rat brain: the role of serotonin and stress. Eur. J. Neurosci. 21, 1511-1520.

Rozeboom, A. M., Akil, H., Seasholtz, A. F., 2007. Mineralocorticoid receptor overexpression in forebrain decreases anxiety-like behavior and alters the stress response in mice. Proc. Natl. Acad. Sci. U.S.A. 104, 4688-4693.

Schwabe, L., Oitzl, M. S., Richter, S., Schachinger, H., 2009. Modulation of spatial and stimulus-response learning strategies by exogenous cortisol in healthy young women. Psychoneuroendocrinology 34, 358-366.

Seckl, J. R., Fink, G., 1991. Use of in situ hybridization to investigate the regulation of hippocampal corticosteroid receptors by monoamines. J. Steroid Biochem. Mol. Biol. 40, 685-688.

Seckl, J. R., Fink, G., 1992. Antidepressants increase glucocorticoid and mineralocorticoid receptor mRNA expression in rat hippocampus in vivo. Neuroendocrinology 55, 621-626.

Sullivan, P. F., de Geus, E. J., Willemsen, G., James, M. R., Smit, J. H., Zandbelt, T., Arolt, V., Baune, B. T., Blackwood, D., Cichon, S., Coventry, W. L., Domschke, K., Farmer, A., Fava, M., Gordon, S. D., He, Q., Heath, A. C., Heutink, P., Holsboer, F., Hoogendijk, W. J., Hottenga, J. J., Hu, Y., Kohli, M., Lin, D., Lucae, S., Macintyre, D. J., Maier, W., McGhee, K. A., McGuffin, P., Montgomery, G. W., Muir, W. J., Nolen, W. A., Nothen, M. M., Perlis, R. H., Pirlo, K., Posthuma, D., Rietschel, M., Rizzu, P., Schosser, A., Smit, A. B., Smoller, J. W., Tzeng, J. Y., van Dyck, R., Verhage, M., Zitman, F. G., Martin, N. G., Wray, N. R., Boomsma, D. I., Penninx, B. W., 2009. Genome-wide association for major depressive disorder: a possible role for the presynaptic protein piccolo. Mol. Psychiatry 14, 359-375.

Turner, B. B., 1997. Influence of gonadal steroids on brain corticosteroid receptors: a minireview. Neurochem. Res. 22, 1375-1385.

van Eekelen, J. A., Rots, N. Y., Sutanto, W., Oitzl, M. S., de Kloet, E. R., 1991. Brain corticosteroid receptor gene expression and neuroendocrine dynamics during aging. J. Steroid Biochem. Mol. Biol. 40, 679-683.

van Leeuwen, N., Kumsta, R., Entringer, S., de Kloet, E. R., Zitman, F. G., Derijk, R. H., Wust, S., 2009. Functional mineralocorticoid receptor (MR) gene variation influences the cortisol awakening response after dexamethasone. Psychoneuroendocrinology.

Vreeburg, S. A., Hoogendijk, W. J., van Pelt, J., Derijk, R. H., Verhagen, J. C., van Dyck, R., Smit, J. H., Zitman, F. G., Penninx, B. W., 2009a. Major depressive disorder and hypothalamic-pituitary-adrenal axis activity: results from a large cohort study. Arch. Gen. Psychiatry 66, 617-626.

Vreeburg, S. A., Kruijtzer, B. P., van Pelt, J., van Dyck, R., DeRijk, R. H., Hoogendijk, W. J., Smit, J. H., Zitman, F. G., Penninx, B. W., 2009b. Associations between sociodemographic, sampling and health factors and various salivary cortisol indicators in a large sample without psychopathology. Psychoneuroendocrinology 34, 1109-1120.

Wilhelm, I., Born, J., Kudielka, B. M., Schlotz, W., Wust, S., 2007. Is the cortisol awakening rise a response to awakening? Psychoneuroendocrinology 32, 358-366.

Wust, S., Federenko, I., Hellhammer, D. H., Kirschbaum, C., 2000a. Genetic factors, perceived chronic stress, and the free cortisol response to awakening. Psychoneuroendocrinology 25, 707-720.

Wust, S., Wolf, J., Hellhammer, D. H., Federenko, I., Schommer, N., Kirschbaum, C., 2000b. The cortisol awakening response—normal values and confounds. Noise Health 2, 79-88.

Zobel, A. W., Schulze-Rauschenbach, S., von Widdern, O. C., Metten, M., Freymann, N., Grasmader, K., Pfeiffer, U., Schnell, S., Wagner, M., Maier, W., 2004. Improvement of working but not declarative memory is correlated with HPA normalization during antidepressant treatment. J. Psychiatr. Res. 38, 377-383.

EMBODIMENTS OF INVENTION

1. A method of assessing the susceptibility of a subject to, or aiding the diagnosis of, an anxiety disorder or depression, the method comprising genotyping any one or more single nucleotide polymorphisms (SNPs) selected from the group consisting of rs3216799, rs6814934, rs7658048, rs2070950 and rs2070951, and/or one or more polymorphic sites which are in linkage disequilibrium with any one or more SNPs selected from the group consisting of rs3216799, rs6814934, rs7658048, rs2070950 and rs2070951, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more 'C', 'T', 'C' and 'C' alleles of the one or more SNPs.

2. A method according to Embodiment 1, wherein genotyping any one or more SNPs selected from the group consisting of rs3216799, rs6814934, rs7658048, rs2070950 and rs2070951, and/or one or more polymorphic sites which are in linkage disequilibrium with any one or more SNPs selected from the group consisting of rs3216799, rs6814934, rs7658048, rs2070950 and rs2070951, comprises contacting a sample of nucleic acid from the subject with one or more nucleic acid molecules that hybridise selectively to a genomic region encompassing any one or more SNPs selected from the group consisting of rs3216799, rs6814934, rs7658048, rs2070950 and rs2070951, and/or a genomic region encompassing one or more polymorphic sites which are in linkage disequilibrium with any one or more SNPs selected from the group consisting of rs3216799, rs6814934, rs7658048, rs2070950 and rs2070951.

3. A method according to Embodiment 1 or 2, wherein the subject is a female human.

4. A method according to any of Embodiments 1-3, wherein the one or more polymorphic sites which are in linkage disequilibrium with any one or more SNPs selected from the group consisting of rs3216799, rs6814934, rs7658048, rs2070950 and rs2070951, are within the mineralocorticoid receptor (MR) gene.

5. A method according to any of Embodiments 1-4, wherein the one or more polymorphic sites which are in linkage disequilibrium with any one or more SNPs selected from the group consisting of rs3216799, rs6814934, rs7658048, rs2070950 and rs2070951, are SNPs selected from the group consisting of rs5522, rs5525 and rs7671250, wherein reduced susceptibility is indicated when the allele of one or more of rs5522, rs5525 and rs7671250 is respectively 'A', 'C' and 'T'.

6. A method according to any of Embodiments 1-5, wherein the one or more polymorphic sites are SNPs selected from the group consisting of rs7671250, rs5522, rs5525, rs4835519, rs2172002, rs11929719, rs11099695, rs11730626, rs2070949, rs2248038, rs9992256, rs5520 and SNP x at position 149585620 in the MR gene as numbered in FIG. 4.

7. A method according to any of Embodiments 1-6, wherein a further genetic locus associated with an anxiety disorder or depression is analysed in the subject.

8. A method according to Embodiment 7, wherein the further genetic locus is any one or more of the glucocorticoid receptor (GR) gene, a heat shock protein gene, the P-glycoprotein gene and the corticotropin releasing hormone receptor-1 (CRHR-1) gene.

9. A method according to any of Embodiments 1-8, wherein one or more of the age, sex, body mass index (BMI), smoking status, childhood trauma status, or stress status of the subject is considered.

10. A method according to Embodiment 2, wherein the sample of nucleic acid from the subject is subjected to a nucleic acid amplification before contacting with one or more nucleic acid molecules that hybridise selectively to the any one or more SNPs selected from the group consisting of rs3216799, rs6814934, rs7658048, rs2070950 and rs2070951, and/or to one or more polymorphic sites which are in linkage disequilibrium with any one or more SNPs selected from the group consisting of rs3216799, rs6814934, rs7658048, rs2070950 and rs2070951.

11. Use of one or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 for assessing the susceptibility of a subject to, or aiding the diagnosis of, an anxiety disorder or depression, wherein reduced susceptibility is indicated when the allele of the one or more SNPs is respectively one or more of '+CT', 'C', 'T' 'C' and 'C', and/or when the allele of the one or more polymorphic sites is one that is in linkage disequilibrium with the respective one or more '+CT', 'C', 'T', 'C' and 'C' alleles of the one or more SNPs 12. One or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 for use in assessing the susceptibility of a subject to, or aiding the diagnosis of, an anxiety disorder or depression, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more '+CT', 'C', 'T', 'C' and 'C' alleles of the one or more SNPs.

13. Use of one or more nucleic acid molecules that hybridise selectively to a genomic region encompassing any one or more SNPs selected from the group consisting of rs3216799, rs6814934, rs7658048, rs2070950 and rs2070951, and/or to a genomic region encompassing one or more polymorphic sites which are in linkage disequilibrium with any one or more SNPs selected from the group consisting of rs3216799, rs6814934, rs7658048, rs2070950 and rs2070951 in the manufacture of a reagent for assessing the susceptibility of a subject to, or aiding the diagnosis of, an anxiety disorder or depression, wherein reduced susceptibility is indicated when the allele of the one or more SNPs is respectively one or more of '+CT', 'C', 'T', 'C' and 'C', and/or when the allele of the one or more polymorphic sites is one that is in linkage disequilibrium with the respective one or more '+CT', 'C', 'T', 'C' and 'C' alleles of the one or more SNPs.

14. A kit of parts for use in assessing the susceptibility of a subject to, or aiding the diagnosis of, an anxiety disorder or depression, the kit comprising one or more nucleic acid molecules that hybridise selectively to a genomic region encompassing any two or more SNPs selected from the group consisting of rs3216799, rs6814934, rs7658048, rs2070950 and rs2070951, and/or that hybridise selectively to a genomic region encompassing two or more polymorphic sites in linkage disequilibrium with any one or more SNPs selected from the group consisting of rs3216799, rs6814934, rs7658048, rs2070950 and rs2070951.

15. A kit of parts for use in assessing the susceptibility of a subject to, or aiding the diagnosis of, an anxiety disorder or depression, the kit comprising one or more nucleic acid molecules that hybridise selectively to a genomic region encompassing any one or more SNPs selected from the group consisting of rs3216799, rs6814934, rs7658048, rs2070950 and rs2070951, and that hybridise selectively to a genomic region encompassing one or more polymorphic sites in linkage disequilibrium with any one or more SNPs selected from the group consisting of rs3216799, rs6814934, rs7658048, rs2070950 and rs2070951.

16. A solid substrate for use in assessing the susceptibility of a subject to, or aiding the diagnosis of, an anxiety disorder or depression, the solid substrate having attached thereto one or more nucleic acid molecules that hybridise selectively to a genomic region encompassing any two or more SNPs selected from the group consisting of rs3216799, rs6814934, rs7658048, rs2070950 and rs2070951, and/or that hybridise selectively to a genomic region encompassing two or more polymorphic sites in linkage disequilibrium with any one or more SNPs selected from the group consisting of rs3216799, rs6814934, rs7658048, rs2070950 and rs2070951.

17. A solid substrate for use in assessing the susceptibility of a subject to, or aiding the diagnosis of, an anxiety disorder or depression, the solid substrate having attached thereto one or more nucleic acid molecules that hybridise selectively to a genomic region encompassing any one or more SNPs selected from the group consisting of rs3216799, rs6814934, rs7658048, rs2070950 and rs2070951, and that hybridise selectively to a genomic region encompassing one or more polymorphic sites in linkage disequilibrium with any one or more SNPs selected from the group consisting of rs3216799, rs6814934, rs7658048, rs2070950 and rs2070951.

18. A kit of parts according to Embodiment 14 or 15, or solid substrate according to Embodiment 16 or 17, wherein the polymorphic sites in linkage disequilibrium with any one or more SNPs selected from the group consisting of rs3216799, rs6814934, rs7658048, rs2070950 and rs2070951, are SNPs selected from the group consisting of rs5522, rs5525 and rs7671250.

19. A kit of parts according to Embodiment 14 or 15, or solid substrate according to Embodiment 16 or 17, wherein the polymorphic sites in linkage disequilibrium with any one or more SNPs selected from the group consisting of rs3216799, rs6814934, rs7658048, rs2070950 and rs2070951, are SNPs selected from the group consisting of rs7671250, rs5522, rs5525, rs4835519, rs2172002, rs11929719, rs11099695, rs11730626, rs2070949, rs2248038, rs9992256, rs5520 and SNP x at position 149585620 in the MR gene as numbered in FIG. 4.

20. A kit of parts according to any of Embodiments 14, 15, 18 and 19, or a solid substrate according to any of Embodiments 16-19, further comprising a nucleic acid molecule that hybridises selectively to a further genetic locus associated with an anxiety disorder or depression.

21. A kit of parts or solid substrate according to Embodiment 20, wherein the further genetic locus is any one or more of the glucocorticoid receptor (GR) gene, a heat shock protein gene, the P-glycoprotein gene and the corticotropin releasing hormone receptor-1 (CRHR-1) gene.

22. A method of recording data on the susceptibility of a subject to an anxiety disorder or depression, the method comprising carrying out the method of any of Embodiments 1-10 and recording the results on a data carrier.

23. A method of preparing a data carrier containing data on the susceptibility of a subject to an anxiety disorder or depression, the method comprising carrying out the method of Embodiment 22.

24. A method according to Embodiment 22 or 23 wherein the data is recorded in electronic form.

25. A method of combating an anxiety disorder or depression in a subject, the method comprising assessing the susceptibility of a subject to, or aiding the diagnosis of, an anxiety disorder or depression according to any of Embodiments 1-10 and depending upon the outcome of the assessment treating the subject.

26. A method according to Embodiment 25, wherein treating the subject comprises administering any one or more of an anti-depressant, an anti-convulsant, a beta-blocker, cortisol, a cortisol agonist, a cortisol antagonist, an MR agonist, an MR antagonist or an agent that modulates MR-expression to the subject.

27. A compound for use in combating an anxiety disorder or depression in a subject who has been assessed as having, or having an increased likelihood of developing, an anxiety disorder or depression according to any of Embodiments 1-10, the compound being selected from an anti-depressant, an anti-convulsant, a beta-blocker, cortisol, a cortisol agonist, a cortisol antagonist, an MR agonist, an MR antagonist or an agent that modulates MR-expression.

28. Use of a compound in the manufacture of a medicament for combating an anxiety disorder or depression in a subject who has been assessed as having, or having an increased likelihood of developing, an anxiety disorder or depression according to any of Embodiments 1-10, the compound being selected from an anti-depressant, an anti-convulsant, a beta-blocker, cortisol, a cortisol agonist, a cortisol antagonist, an MR agonist, an MR antagonist, or an agent that modulates MR-expression.

29. A method according to any of Embodiments 1-10 and 22-26, a use according to any of Embodiments 11, 13 and 28, a nucleic acid according to Embodiment 12, a kit of parts according to any of Embodiments 14, 15 and 18-21, a solid substrate according to any of Embodiments 16-21, and a compound according to Embodiment 27, wherein the anxiety disorder is any of substance-induced anxiety disorder, generalised anxiety, panic disorder, acute stress disorder, post-traumatic stress disorder, adjustment disorder with anxious features, social phobia, obsessive-compulsive disorder or specific phobias.

30. Any novel method of assessing susceptibility to, or aiding diagnosis of, an anxiety disorder or depression in a subject as herein disclosed.

31. Any novel kit of parts as herein disclosed.

---

The invention claimed is:

1. A method for treating a subject suffering from depression, the method comprising performing an assay to genotype nucleic acid from the subject for the alleles present at single nucleotide polymorphisms rs2070951 and rs5522, detecting that the subject is homozygous for "C" at rs2070951 and "A" at rs5522, and then beginning treatment of the depression by administering an SSRI to the subject.

2. A method according to claim 1, wherein the subject is a female human.

* * * * *

UNITED STATES PATENT AND TRADEMARK OFFICE
CERTIFICATE OF CORRECTION

PATENT NO.        : 9,644,240 B2  
APPLICATION NO. : 13/503424  
DATED             : May 9, 2017  
INVENTOR(S)       : de Rijk et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this

Twenty-fifth Day of September, 2018

Andrei Iancu
*Director of the United States Patent and Trademark Office*